US012692311B2

(12) United States Patent
Arathoon et al.

(10) Patent No.: US 12,692,311 B2
(45) Date of Patent: Jul. 28, 2026

(54) ANTI-MDR1 ANTIBODIES AND USES THEREOF

(71) Applicant: William Robert Arathoon Living Trust Dated August 29, 2016, Tiburon, CA (US)

(72) Inventors: William Robert Arathoon, Tiburon, CA (US); Raffaella Briante, Burlingame, CA (US); Suchismita Mohanty, San Bruno, CA (US); Paul David Ponath, San Francisco, CA (US); Qianting Zhai, South San Francisco, CA (US); Pingping Zhang, Cupertino, CA (US)

(73) Assignee: William Robert Arathoon Living Trust Dated August 29, 2016, Tiburon, CA (US)

( * ) Notice: Subject to any disclaimer, the term of this patent is extended or adjusted under 35 U.S.C. 154(b) by 971 days.

(21) Appl. No.: 17/793,804

(22) PCT Filed: Jan. 28, 2021

(86) PCT No.: PCT/US2021/015534
§ 371 (c)(1),
(2) Date: Jul. 19, 2022

(87) PCT Pub. No.: WO2021/155028
PCT Pub. Date: Aug. 5, 2021

(65) Prior Publication Data
US 2023/0203156 A1      Jun. 29, 2023

Related U.S. Application Data

(60) Provisional application No. 63/085,818, filed on Sep. 30, 2020, provisional application No. 62/967,470, filed on Jan. 29, 2020.

(51) Int. Cl.
*C07K 16/28* (2006.01)
*A61K 31/337* (2006.01)
(Continued)

(52) U.S. Cl.
CPC ........ *C07K 16/2803* (2013.01); *A61K 31/337* (2013.01); *A61K 39/3955* (2013.01);
(Continued)

(58) Field of Classification Search
None
See application file for complete search history.

(56) References Cited

U.S. PATENT DOCUMENTS

| | | | |
|---|---|---|---|
| 5,948,647 A | 9/1999 | Ring | |
| 5,959,084 A | 9/1999 | Ring et al. | |

(Continued)

FOREIGN PATENT DOCUMENTS

| | | |
|---|---|---|
| CA | 2025695 | 9/1991 |
| EP | 3243840 | 11/2017 |

(Continued)

OTHER PUBLICATIONS

Chen et al., Enhancement and destruction of antibody function by somatic mutation: unequal occurrence is controlled by V gene combinatorial associations. Embo J. Jun. 15, 1995;14(12):2784-94. (Year: 1995).*

(Continued)

*Primary Examiner* — Aurora M Fontainhas
*Assistant Examiner* — Selam Berhane
(74) *Attorney, Agent, or Firm* — Shweta Chandra; Bozicevic, Field & Francis LLP

(57) ABSTRACT

Provided are antibodies that target the cellular efflux pump MDR1. Also provided are pharmaceutical compositions, nucleic acids, recombinant expression vectors, cells, and kits that include or encode such antibodies. Methods of using the
(Continued)

antibodies for detecting presence or absence of MDR1 expression in cells, e.g., tumor cells, level of MDR1 expression, and/or inhibiting MDR1 function are also disclosed. In addition, multi-specific antibodies that bind to MDR1 and a tumor associated antigen are provided. Also provided are methods for treating a subject for a cancer that include administering to the subject an anti-MDR1 antibody as disclosed herein or a multi-specific antibody that targets both MDR1 and a tumor associated antigen.

16 Claims, 31 Drawing Sheets

Specification includes a Sequence Listing.

(51) Int. Cl.

| | |
|---|---|
| *A61K 39/00* | (2006.01) |
| *A61K 39/395* | (2006.01) |
| *A61K 45/06* | (2006.01) |
| *A61P 35/00* | (2006.01) |

(52) U.S. Cl.
CPC .............. *A61K 45/06* (2013.01); *A61P 35/00* (2018.01); *C07K 16/28* (2013.01); *A61K 2039/505* (2013.01); *C07K 2317/31* (2013.01)

(56) References Cited

U.S. PATENT DOCUMENTS

| | | | |
|---|---|---|---|
| 9,017,675 B2 | 4/2015 | Liu et al. | |
| 2015/0216970 A1 | 8/2015 | Grogan et al. | |
| 2017/0355756 A1 * | 12/2017 | Julien ..................... | C07K 16/18 |
| 2019/0031782 A1 | 1/2019 | Xu et al. | |
| 2022/0204627 A1 | 6/2022 | Arathoon et al. | |
| 2025/0051471 A1 | 2/2025 | Arathoon et al. | |

FOREIGN PATENT DOCUMENTS

| | | | | |
|---|---|---|---|---|
| JP | H03254691 | 11/1991 | | |
| JP | H10506881 | 7/1998 | | |
| JP | 2013534409 | 9/2013 | | |
| JP | 2019514846 | 6/2019 | | |
| WO | WO 1996004313 | 2/1996 | | |
| WO | WO 2006108070 | 10/2006 | | |
| WO | WO-2008068048 A2 * | 6/2008 | .............. | A61P 31/10 |
| WO | WO 2011143624 | 11/2011 | | |
| WO | WO 2018099978 | 6/2018 | | |
| WO | WO 2019080883 | 5/2019 | | |
| WO | WO 2020206033 | 10/2020 | | |

OTHER PUBLICATIONS

Koenig et al., Mutational landscape of antibody variable domains reveals a switch modulating the interdomain conformational dynamics and antigen binding. PNAS Jan. 24, 2017 114 (4) E486-E495; first published Jan. 5, 2017. (Year: 2017).*

Kussie, Paul H., "A Single Engineered Amino Acid Substitution Changes Antibody Fine Specificity", 1994, Journal of Immunology 152(1): pp. 146-152. (Year: 1994).*

Edwards et al., The remarkable flexibility of the human antibody repertoire; isolation of over one thousand different antibodies to a single protein, BLyS. J Mol Biol. Nov. 14, 2003;334(1):103-118. (Year: 2003).*

Chung-Pu et al., (2018) "Human ATP-binding cassette transporters ABCB1 and ABCG2 confer resistance to histone deacetylase 6 inhibitor ricolinostat (ACY-1215) in cancer cell lines", Biochemical Pharmacology, 155:316-325.

Cianfriglia et al., (2002) "Monoclonal Antibodies as a Tool for Structure-Function Studies of the MDR1-P-Glycoprotein", Current Protein and Peptide Science, 3(5):513-530.

Füredi et al., (2016) "Identification and Validation of Compounds Selectively Killing Resistant Cancer: Delineating Cell Line-Specific Effects from P-Glycoprotein-Induced Toxicity", Molecular Cancer Therapeutics, 16(1):45-56.

Gao et al., (2004) "Efficient inhibition of multidrug-resistant human tumors with a recombinant bispecific anti-P-glycoprotein x anti-CD3 diabody", Leukemia, 18(3):513-520.

Jackman et al., (2010) "Development of a Two-part Strategy to Identify a Therapeutic Human Bispecific Antibody That Inhibits IgE Receptor Signaling", Journal of Biological Chemistry, 285(27):20850-20859.

Kazuhiko et al., (2012) "Single nucleotide polymorphism of multidrug-resistance 1 and anti- multidrug-resistance 1 single chain antibody treatment for the pancreatic cancer cell line.", Hepato-Gastroenterology, 59(113):272-275.

Klein et al., (2012) "Progress in overcoming the chain association issue in bispecific heterodimeric IgG antibodies", MABS, 4(6):653-663.

Krah et al., (2017) "Generation of human bispecific common light chain antibodies by combining animal immunization and yeast display", Protein Engineering, Design and Selection, 30(4):291-301.

Maurizio Cianfriglia, (2013) "The biology of MDR1-P-glycoprotein (MDR1-Pgp) in designing functional antibody drug conjugates (ADCs): the experience of gemtuzumab ozogamicin", Ann Ist Super Sanità, 49(2):150-168.

Okochi et al., (1997) "Monoclonal antibodies specific for P-glycoprotein", Leukemia, 11(7):1119-1123.

Shiraiwa et al., (2019) "Engineering a bispecific antibody with a common light chain: Identification and optimization of an anti-CD3 epsilon and anti-GPC3 bispecific antibody, ERY974", Methods, 154:10-20.

Van Blarcom et al., (2017) "Productive common light chain libraries yield diverse panels of high affinity bispecific antibodies", MABS, 10(2):256-268.

Desmyter, et al., "Camelid nanobodies: killing two birds with one stone", Current Opinion in Structural Biology, 2015, 32: 1-8.

Dondelinger, et al., "Understanding the significance and implications of antibody numbering and antigen-binding surface/residue definition", Frontiers in Immunology, 2018, 9(2278): 1-15.

Iizuka, et al., "Study on the influence of relative dose intensity on neo adjuvant chemotherapy and adjuvant chemotherapy for breast cancer", Iyaku Yakugaku (Medical and Pharmaceutical Science), Aug. 10, 2019, 45(8): 485-490. (With English Abstract Only).

Iwahashi, et al., "Specific targeting and killing activities of anti-P-glycoprotein monoclonal antibody MRK16 directed against intrinsically multidrug-resistant human colorectal carcinoma cell lines in the nude mouse model", Cancer Research, Nov. 15, 1993, 53(22): 5475-5482.

Janeway, et al., "B cells undergo a strictly programmed series of gene rearrangements in the bone marrow", Immuno Biology: The immune system in Health and Disease, 5th edition, 2001, Section 7-8., 17 pages.

Kawasumi, "(17) Vinorelbine", Professional Cancer Nursing, 2015, 5(2): 138-139. (Official Copy Only).

Kellner, et al., "Modulating cytotoxic effector functions by Fc engineering to improve cancer therapy", Transfusion Medicine and Hemotherapy, Sep. 8, 2017, 44(5): 10 pages.

Krah, et al., "Engineering IgG-like bispecific antibodies—an overview", Antibodies, 2018, 7(3)28: 1-10.

Kwak, et al., "Selective inhibition of MDR1 (ABCB1) by HM30181 increases oral bioavailability and therapeutic efficacy of paclitaxel", European Journal of Pharmacology, Feb. 2010, 627(1-3): 92-98.

Lin, et al., "Improved affinity of a chicken single-chain antibody to avian infectious bronchitis virus by site-directed mutagenesis of complementarity-determining region H3", African Journal of Biotechnology, Dec. 12, 2011, 10(79): 18294-18302.

Lydard, et al., "D3: Generation of diversity", Section D—Antibodies, 2011, pp. 76-85.

Schurch, "Therapeutic antibodies for myeloid neoplasms-current developments and future directions", Frontiers in Oncology, May 18, 2018, 8(152): 34 pages.

(56)     References Cited

OTHER PUBLICATIONS

Shimizu, "Biomarkers development of PARP inhibitors", Cancer Molecular Targeted Therapy, 2016, 14(1): 112-115. (With English Abstract Only).

Szakacs, et al., "Targeting multidrug resistance in cancer", Nature Reviews Drug Discovery, 2006, 5(3): 219-234.

Wang, et al., "Cetuximab enhanced the efficacy of chemotherapeutic agent in ABCB1/P-glycoprotein-overexpressing cancer cells.", Oncotarget, 2015, 6(38): 40850-40865.

Zhang, et al., "The development of bispecific antibodies and their applications in tumor immune escape", Experimental Hematology and Oncology, 2017, 6(12): 6 pages.

\* cited by examiner

| Ab | EC50 (nM) |
|---|---|
| B1-178 | 16.6 |
| B1-184 | 4.3 |
| B1-188 | 14.1 |
| B1-193B | 18.7 |
| B1-197 | 6.8 |
| B1-198 | 14.8 |
| B1-201 | 8.0 |
| B1-207 | 4.3 |
| B1-223 | 4.6 |
| B1-28 | 4.8 |
| B1-85 | 9.2 |
| B1-99 | 88.2 |
| B1-27 | 34.0 |
| B1-39 | 14.2 |
| B1-30 | 8.5 |

Effect of anti-MDR1 antibodies and paclitaxel on MES-SA-DX5 model

- Isotype 3 mg/kg
- Isotype 3mg/kg + Paclitaxel 20 mg/kg
- KNJY B1-129 3mg/kg
- KNJY B1-129 3 mg/kg+ Paclitaxel 20 mg/kg
- KNJY B1-261 3mg/kg
- KNJY B1-261 3 mg/kg+ Paclitaxel 20 mg/kg
- KNJY B1-223 3mg/kg
- KNJY B1-223 3 mg/kg+ Paclitaxel 20 mg/kg
- 15D3 hybridoma 3mg/kg
- 15D3 hybridoma 3 mg/kg+ Paclitaxel 20 mg/kg
- DX5 -B1 KO Isotype 3 mg/kg
- DX5 B1 KO Isotype 3mg/kg + Paclitaxel 20 mg/kg B1 knock-out in drug resistant tumors induces chemosensitivity to paclitaxel Nude mice model NSG mice model

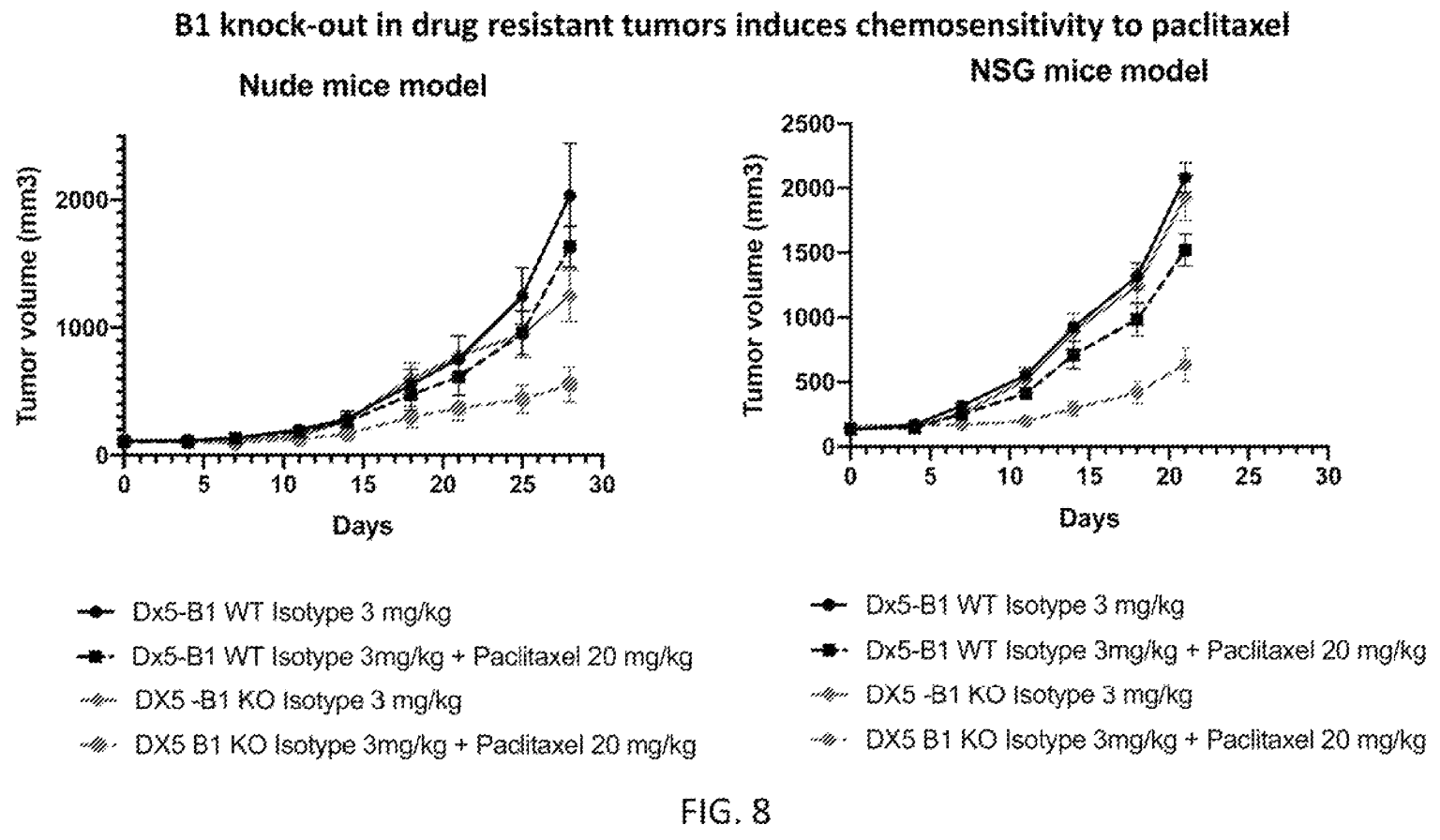

- Dx5-B1 WT Isotype 3 mg/kg
- Dx5-B1 WT Isotype 3mg/kg + Paclitaxel 20 mg/kg
- DX5 -B1 KO Isotype 3 mg/kg
- DX5 B1 KO Isotype 3mg/kg + Paclitaxel 20 mg/kg

FIG. 8

| Antibody Name | ECD1 | ECD4 | others |
|---|---|---|---|
| KB1.228A | - | + | - |
| KB1.99 | - | + | - |
| KB1.197A | - | + | - |
| KB1.277B | - | + | - |
| KB1.178 | - | + | - |
| KB1.193B | - | + | - |
| KB1.277B | - | + | - |
| KB1.228 | - | + | - |
| KB1.177 | - | + | - |
| KB1.278 | - | + | - |
| KB1.39 | - | + | - |
| KB1.272 | - | + | - |
| KB1.197 | - | + | - |
| KB1.275 | - | + | - |
| KB1.276 | - | + | - |
| KB1.264 | - | + | - |
| KB1.269A | - | + | + |
| KB1-1404 | - | + | + |
| KB1_27 | - | + | + |
| KB1.89 | - | + | + |
| KB1.261 | - | + | + |
| KB1.263 | - | + | + |
| KB1.225 | - | + | + |
| KB1_95 | - | + | +/- |
| KB1.28 | - | + | |
| KPA01 | - | + | |
| KPA08 | - | + | |
| KB1-1401 | - | + | |
| KB1.228b | + | + | - |
| KB1.198 | + | + | - |
| KB1.223 | + | + | - |
| KB1.219 | + | + | - |
| KB1.184 | + | + | - |
| KB1_207 | + | + | - |
| KB1_201 | + | + | - |
| KB1.129 | + | + | - |
| KB1.273 | + | + | - |
| KB1.236 | + | + | - |
| KB1.217 | +/- | + | - |
| KB1.179 | +/- | + | - |
| KB1.30 | +/- | + | + |
| KB1.188 | +/- | + | +/- |

FIG. 9

FIG. 10A
293T-hB1-ox
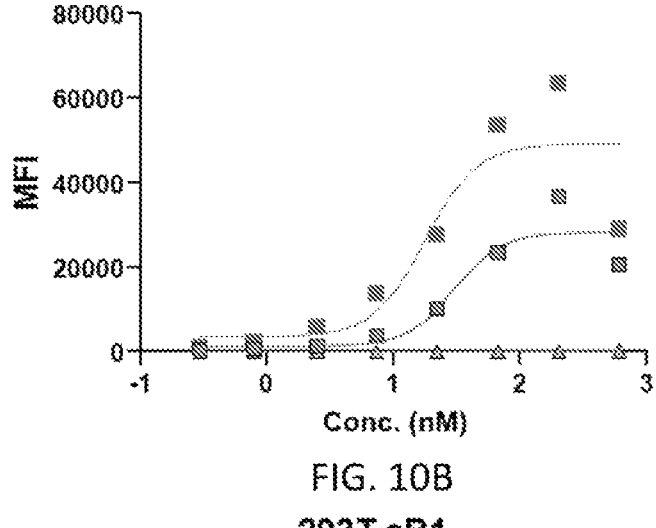
FIG. 10B
293T-cB1
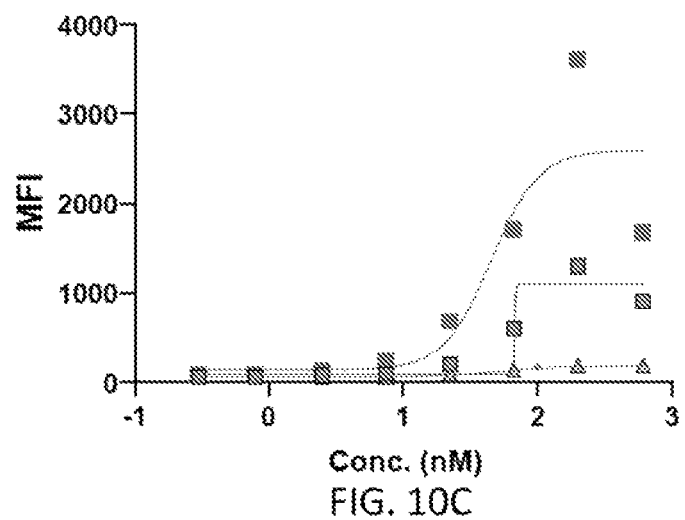
FIG. 10C
| Antibody | KD (hB1, nM) | KD (cB1, nM) | KD ratio cB1/hB1 |
|---|---|---|---|
| KB1.129 | 17 | 44 | 2.6 |
| KB1.129.hz1 | 30 | 66 | 7.2 |
| KB1.129.hz2 | N.D. | N.D. | N.D. |

Bis Ab Titration (C6-hKT14)
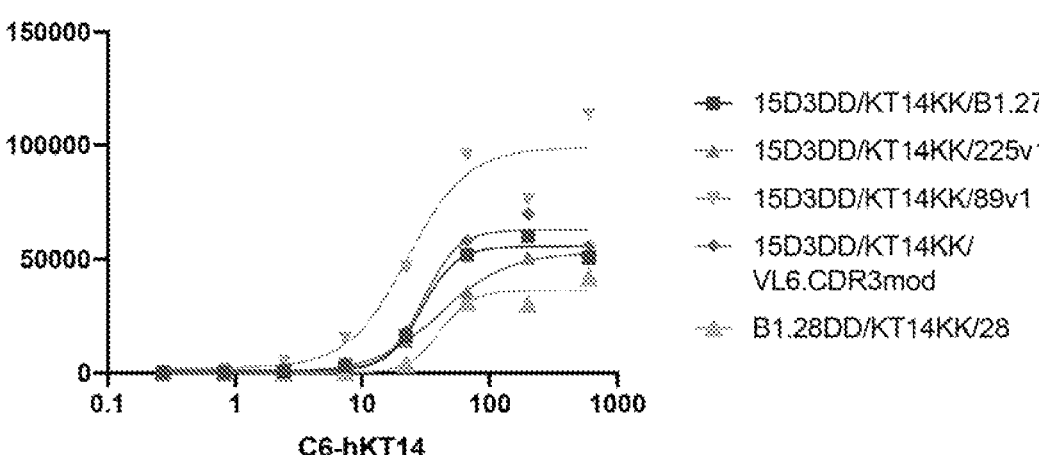
Legend:
- 15D3DD/KT14KK/B1.27
- 15D3DD/KT14KK/225v1
- 15D3DD/KT14KK/89v1
- 15D3DD/KT14KK/ VL6.CDR3mod
- B1.28DD/KT14KK/28
Bis Ab Titration (C6-cKT14)
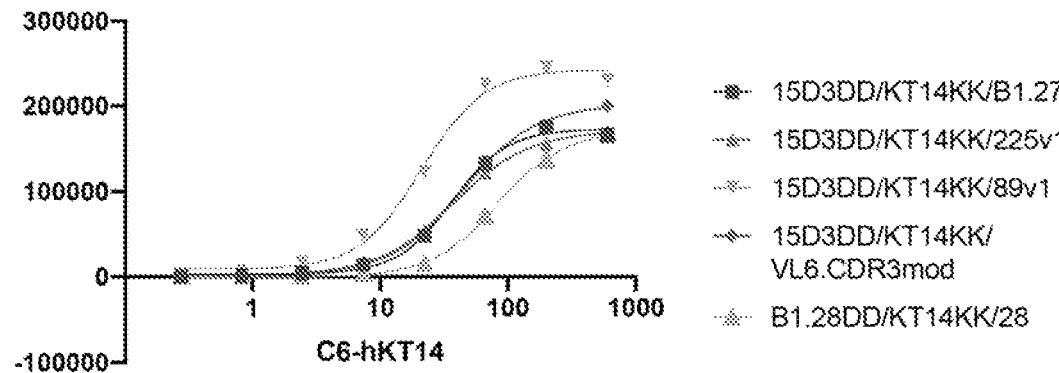
Legend:
- 15D3DD/KT14KK/B1.27
- 15D3DD/KT14KK/225v1
- 15D3DD/KT14KK/89v1
- 15D3DD/KT14KK/ VL6.CDR3mod
- B1.28DD/KT14KK/28
| Antibody | Octet KD (nM) | hKT14 Cell EC50 (nM) | cKT14 Cell EC50 (nM) |
|---|---|---|---|
| 15D3DD/KT14KK/B1.27 | 34 | 29 | 36 |
| 15D3DD/KT14KK/225v1 | 11 | 42 | 37 |
| 15D3DD/KT14KK/89v1 | 27 | 23 | 21 |
| 15D3DD/KT14KK/VL6.CDR3mod | 39 | 30 | 44 |
| B1.28DD/KT14KK/28 | NA | 40 | 83 |
FIG. 15

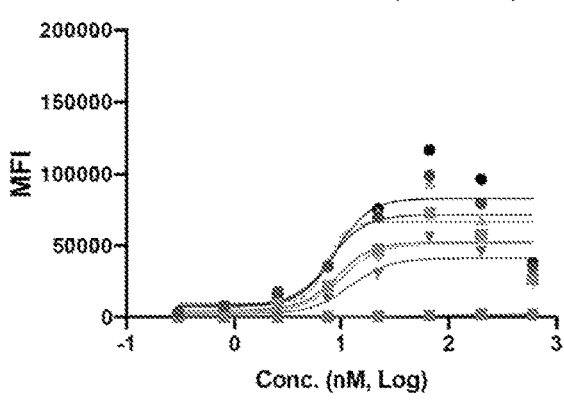

BisAb Titration (C6-hB1)

- 15D3 hmz DD IgG1-KT14KK-28.huL1
- 15D3 hmz DD IgG1-KT14KK-28.huL2
- 15D3 hmz DD IgG1-KT14KK-28.huL3
- 15D3 hmz DD IgG1-KT14KK-B1V6.CDR3v1.hmzLC
- 15D3 hmz DD IgG1-KT14KK-B1V6.CDR3v2.hmzLC
- 15D3 hmz DD IgG1-KT14KK-B1V6.CDR3v3.hmzLC
- hIgG isotype

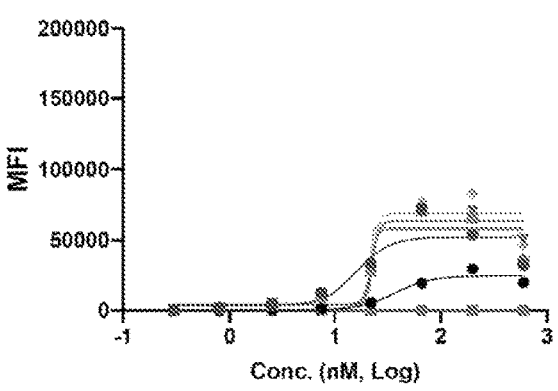

Bis Ab Titration (C6-hKT14)

- 15D3 hmz DD IgG1-KT14KK-28.huL1
- 15D3 hmz DD IgG1-KT14KK-28.huL2
- 15D3 hmz DD IgG1-KT14KK-28.huL3
- 15D3 hmz DD IgG1-KT14KK-B1V6.CDR3v1.hmzLC
- 15D3 hmz DD IgG1-KT14KK-B1V6.CDR3v2.hmzLC
- 15D3 hmz DD IgG1-KT14KK-B1V6.CDR3v3.hmzLC
- hIgG isotype

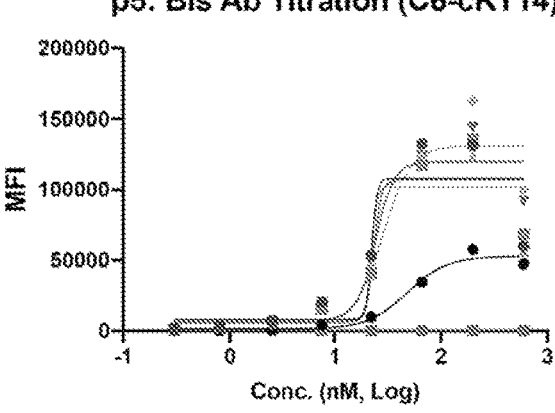

p5: Bis Ab Titration (C6-cKT14)

- 15D3 hmz DD IgG1-KT14KK-28.huL1
- 15D3 hmz DD IgG1-KT14KK-28.huL2
- 15D3 hmz DD IgG1-KT14KK-28.huL3
- 15D3 hmz DD IgG1-KT14KK-B1V6.CDR3v1.hmzLC
- 15D3 hmz DD IgG1-KT14KK-B1V6.CDR3v2.hmzLC
- 15D3 hmz DD IgG1-KT14KK-B1V6.CDR3v3.hmzLC
- hIgG isotype

FIG. 17A

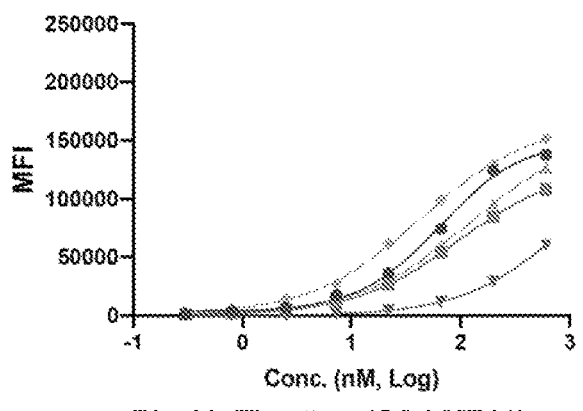

BisAb Titration (C6-hB1)

- 15D3 VH hu/KT14/MRK16v5 LC
- 15D3 VH hu/KT14/B1.28.huL2
- 15D3 VH hu/KT14/B1VL6/CDR3v2 hmzLC
- B1_28 VH humaniz /KT14/MRK16v4 LC
- 15D3hu/KT14/89v1huL1

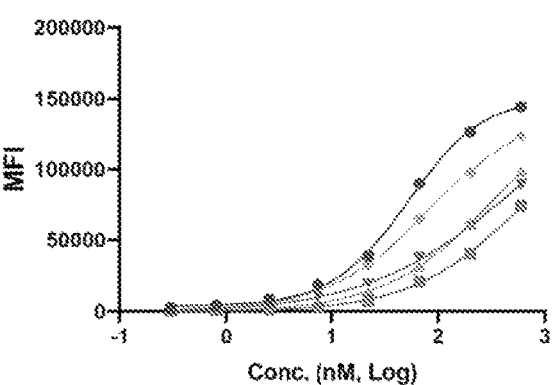

Bis Ab Titration (C6-hKT14)

- 15D3 VH hu/KT14/MRK16v5 LC
- 15D3 VH hu/KT14/B1.28.huL2
- 15D3 VH hu/KT14/B1VL6/CDR3v2 hmzLC
- B1_28 VH humaniz /KT14/MRK16v4 LC
- 15D3hu/KT14/89v1huL1

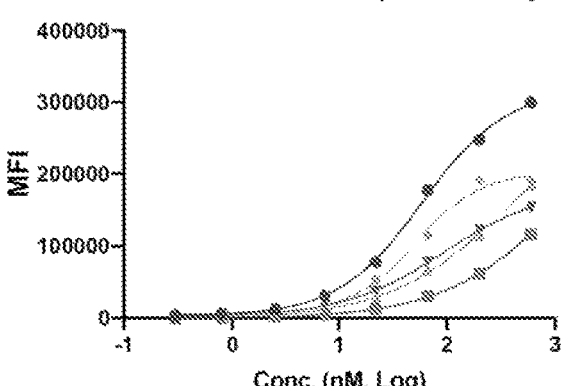

Bis Ab Titration (C6-cKT14)

- 15D3 VH hu/KT14/MRK16v5 LC
- 15D3 VH hu/KT14/B1.28.huL2
- 15D3 VH hu/KT14/B1VL6/CDR3v2 hmzLC
- B1_28 VH humaniz /KT14/MRK16v4 LC
- 15D3hu/KT14/89v1huL1

| | | | |
|---|---|---|---|
| 15D3 VH hu/KT14/MRK16v5 LC | 65 | 53 | 60 |
| 15D3 VH hu/KT14/B1.28.huL2 | 97 | 655 | 1184 |
| 15D3 VH hu/KT14/B1VL6/CDR3v2 hmzLC | 125 | 369 | 378 |
| B1_28 VH humaniz /KT14/MRK16v4 LC | 748 | 480 | 94 |
| 15D3hu/KT14/89v1huL1 | 43 | 85 | 51 |

FIG. 17B

| B1 antibody HC1 | Anti-CD47 HC2 | B1 antibody LC | CD47 ELISA | CD47 Binding on cells | B1 Binding on Cells |
|---|---|---|---|---|---|
| B1_129 DD | KT14 KK | B1_129 | ± | - | + |
| B1_129 DD | KT14 KK | KPB1 VL/CDR3 | + | + | + |
| B1_129 hmzKV3 DD | KT14 KK | KPB1 VL/CDR3 | + | + | + |
| B1_129 hmzKV3 DD | KT14 KK | B1_129 hmzKV3 | - | - | + |
| B1_129 hmzKV3 DD | KT14 KK | B1_129 hmzKV1 | - | - | + |
| B1_188 DD | KT14 KK | B1_188 | + | + | + |
| B1_188 DD | KT14 KK | MRK16 | + | + | + |
| B1_188 DD | KT14 KK | KPB1 VL/CDR3 | + | + | + |
| B1_223 DD | KT14 KK | KPB1 VL/CDR3 | + | + | + |
| B1_225 DD | KT14 KK | B1_225 | + | + | + |
| B1_225 DD | KT14 KK | MRK16 | + | + | + |
| B1_225 DD | KT14 KK | KPB1 VL/CDR3 | + | + | + |
| B1_226 DD | KT14 KK | B1_226 | + | + | + |
| B1_226 DD | KT14 KK | MRK16 | - | ± | + |
| B1_226 DD | KT14 KK | KPB1 VL/CDR3 | + | + | + |
| B1_261 DD | KT14 KK | B1_261 | ± | + | + |
| B1_261 DD | KT14 KK | MRK16 | + | + | + |
| B1_261 DD | KT14 KK | KPB1 VL/CDR3 | + | + | + |
| B1_261 VH3 DD | KT14 KK | B1_26 VH3 | + | - | + |
| B1_261 VH4 DD | KT14 KK | B1_261 VH4 | + | - | + |
| B1_261 VH4 DD | KT14 KK | MRK16 | + | + | + |
| B1_261 VH4 DD | KT14 KK | B1_129 hmzKV1 | - | - | + |
| B1_28 DD | KT14 KK | B1_28 | + | + | + |

FIG. 18A

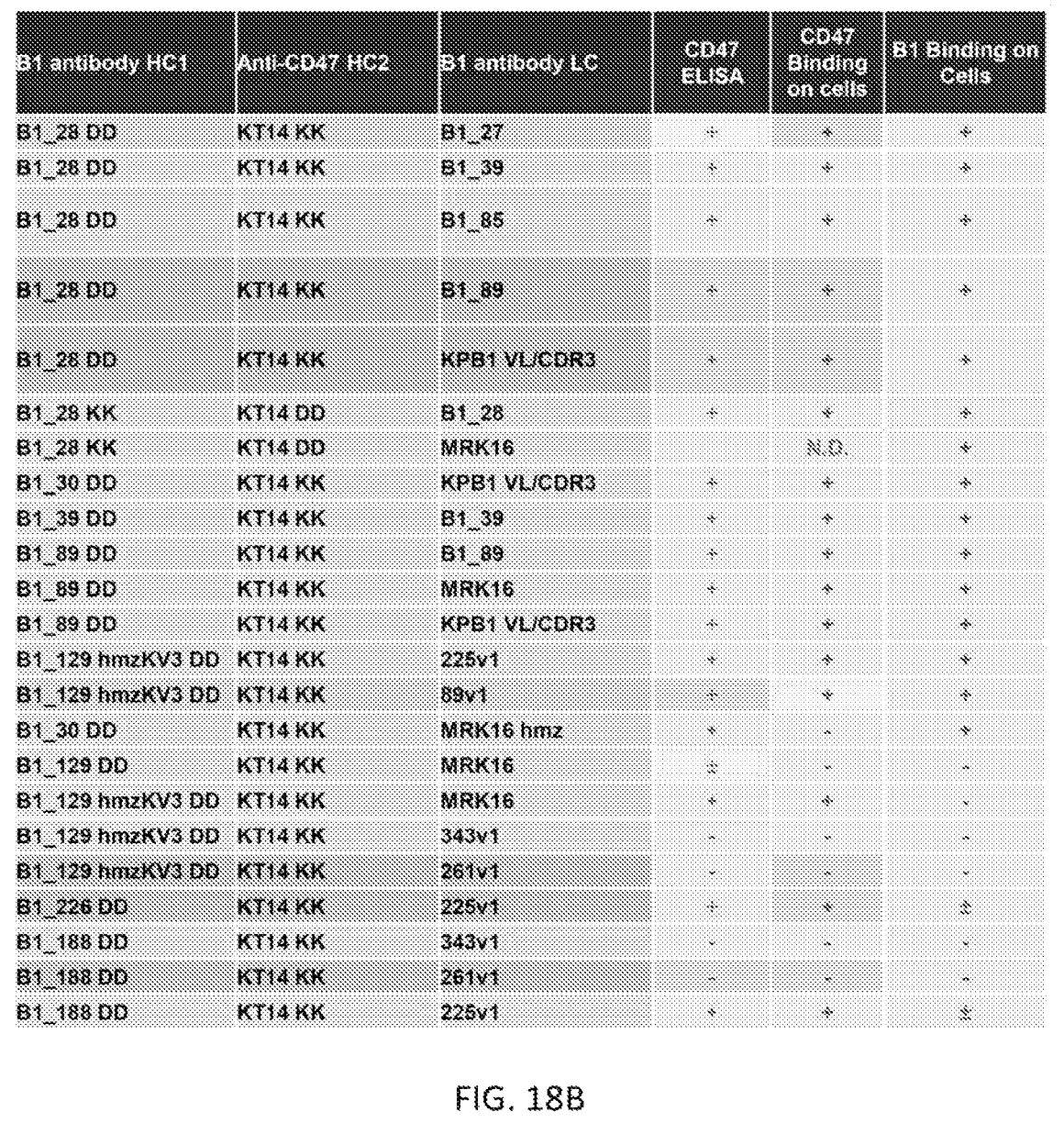

| B1 antibody HC1 | Anti-CD47 HC2 | B1 antibody LC | CD47 ELISA | CD47 Binding on cells | B1 Binding on Cells |
|---|---|---|---|---|---|
| B1_28 DD | KT14 KK | B1_27 | + | + | + |
| B1_28 DD | KT14 KK | B1_39 | + | + | + |
| B1_28 DD | KT14 KK | B1_85 | + | + | + |
| B1_28 DD | KT14 KK | B1_89 | + | + | + |
| B1_28 DD | KT14 KK | KPB1 VL/CDR3 | + | + | + |
| B1_28 KK | KT14 DD | B1_28 | + | + | + |
| B1_28 KK | KT14 DD | MRK16 | | N.D. | + |
| B1_30 DD | KT14 KK | KPB1 VL/CDR3 | + | + | + |
| B1_39 DD | KT14 KK | B1_39 | + | + | + |
| B1_89 DD | KT14 KK | B1_89 | + | + | + |
| B1_89 DD | KT14 KK | MRK16 | + | + | + |
| B1_89 DD | KT14 KK | KPB1 VL/CDR3 | + | + | + |
| B1_129 hmzKV3 DD | KT14 KK | 225v1 | + | + | + |
| B1_129 hmzKV3 DD | KT14 KK | 89v1 | + | + | + |
| B1_30 DD | KT14 KK | MRK16 hmz | + | - | - |
| B1_129 DD | KT14 KK | MRK16 | ± | - | - |
| B1_129 hmzKV3 DD | KT14 KK | MRK16 | + | + | - |
| B1_129 hmzKV3 DD | KT14 KK | 343v1 | - | - | - |
| B1_129 hmzKV3 DD | KT14 KK | 261v1 | - | - | - |
| B1_226 DD | KT14 KK | 225v1 | + | + | ± |
| B1_188 DD | KT14 KK | 343v1 | - | - | - |
| B1_188 DD | KT14 KK | 261v1 | - | - | - |
| B1_188 DD | KT14 KK | 225v1 | + | + | ± |

FIG. 18B

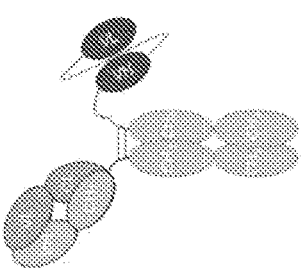
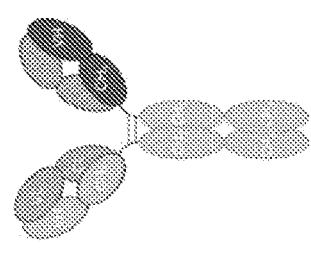
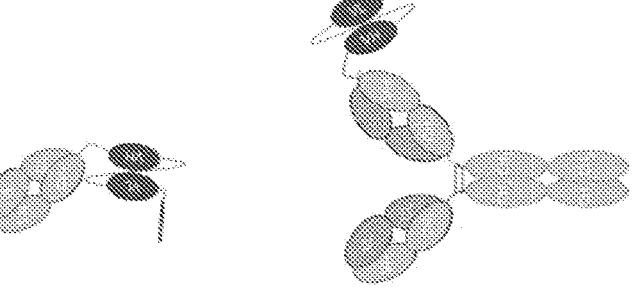
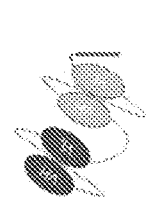
FIG. 19

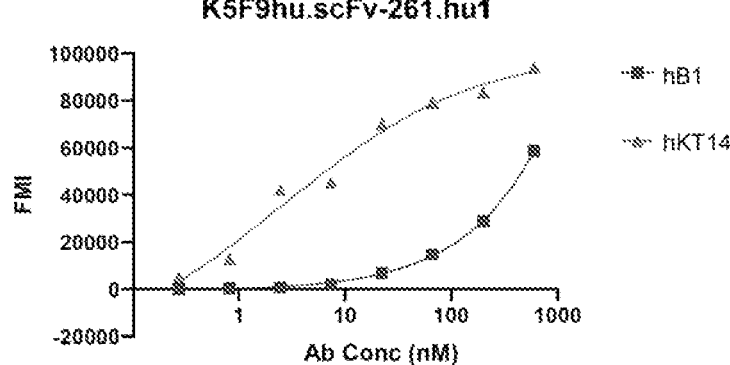
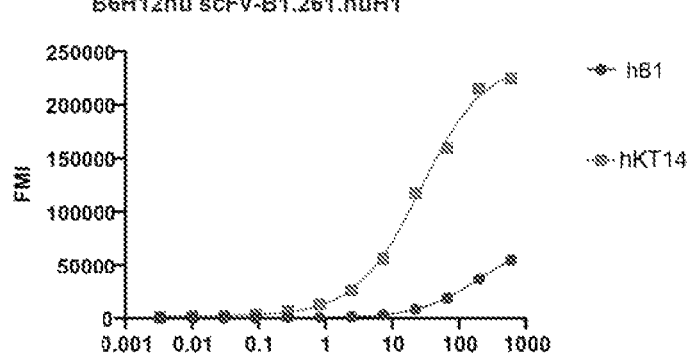
| | hB1 EC50 (nM) | hKT14 EC50 (nM) |
|---|---|---|
| KT14.5F9huscFv-B1.261.hu1 | >1000 | 2.7 |
| KT14.B6H12huscFv-B1.261.hu1 | 229 | 26 |
FIG. 22

Effect of anti-MDR1 and anti-CD47 bispecific antibodies and paclitaxel on MES-SA-DX5 model

- —◆— Isotype 3 mg/kg
- ─■─ Isotype 3mg/kg + Paclitaxel 20 mg/kg

- ─◆─ KNJY B1-188/KT14/MRK16 3mg/kg
- ─◆─ KNJY B1-188/KT14/MRK16  3 mg/kg+ Paclitaxel 20 mg/kg

- —◆— KNJY B1-225/KT14/MRK16 3mg/kg
- ─◆─ KNJY B1-225/KT14/MRK16 3 mg/kg+ Paclitaxel 20 mg/kg

- ─── KNJY 15D3/KT14/MRK16 3mg/kg
- ─── KNJY 15D3/KT14/MRK16 3 mg/kg+ Paclitaxel 20 mg/kg

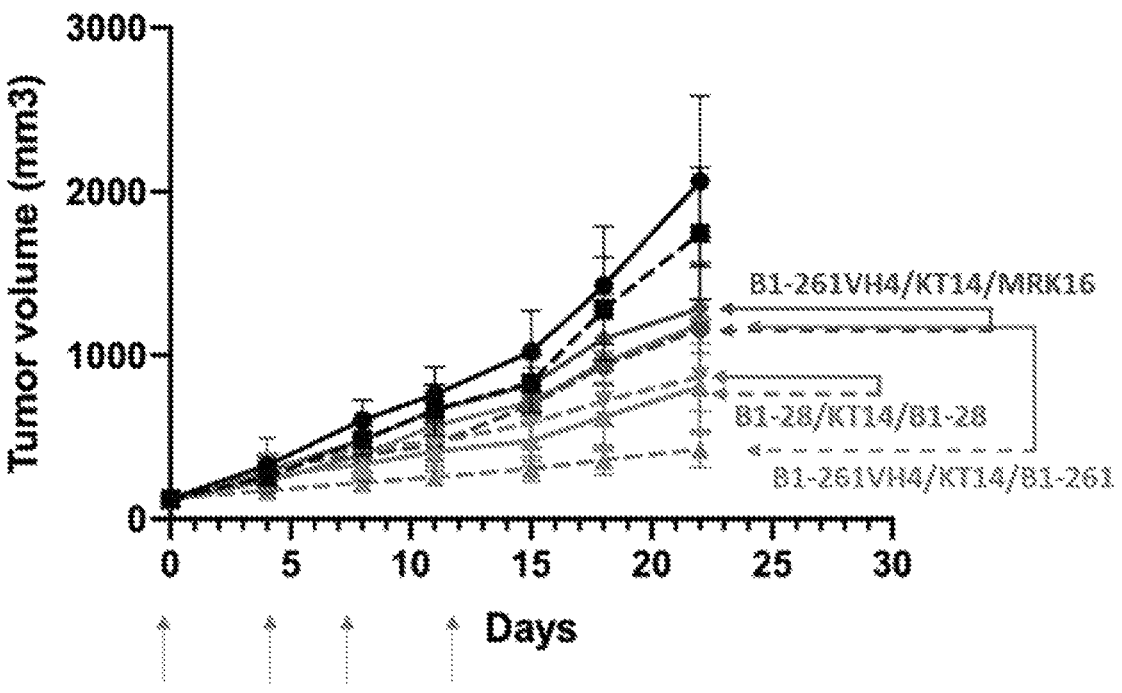

Effect of anti-MDR1 and anti-CD47 bispecific antibodies and paclitaxel on MES-SA-DX5 model

→ Isotype 3 mg/kg

-■- Isotype 3 mg/kg + Paclitaxel 20 mg/kg

→ KNJY B1 28 VH huIgG1 DD KT14 KK KNJY B1 28 VL pC1 neo 3 mg/kg

-●- KNJY B1 28 VH huIgG1 DD KT14 KK KNJY B1 28 VL pC1 neo 3 mg/kg+ Paclitaxel 20 mg/kg → KNJY B1-261 VH4 VH-HC DD/KT14 IgG1 KK/MRK16 LC humanized 3 mg/kg -●- KNJY B1-261 VH4 VH-HC DD/KT14 IgG1 KK/MRK16 LC humanized 3 mg/kg + Paclitaxel 20 mg/kg → KNJY B1-261 VH4 VH-HC DD/KT14 IgG1 KK/KNJY B1-261 VH4 VL-LC KK 3 mg/kg -●- KNJY B1-261 VH4 VH-HC DD/KT14 IgG1 KK/KNJY B1-261 VH4 VL-LC KK 3 mg/kg + Paclitaxel 20 mg/kg

FIG. 23B

Effect of anti-MDR1 and anti-CD47 bispecific antibodies and paclitaxel on MES-SA-DX5 model

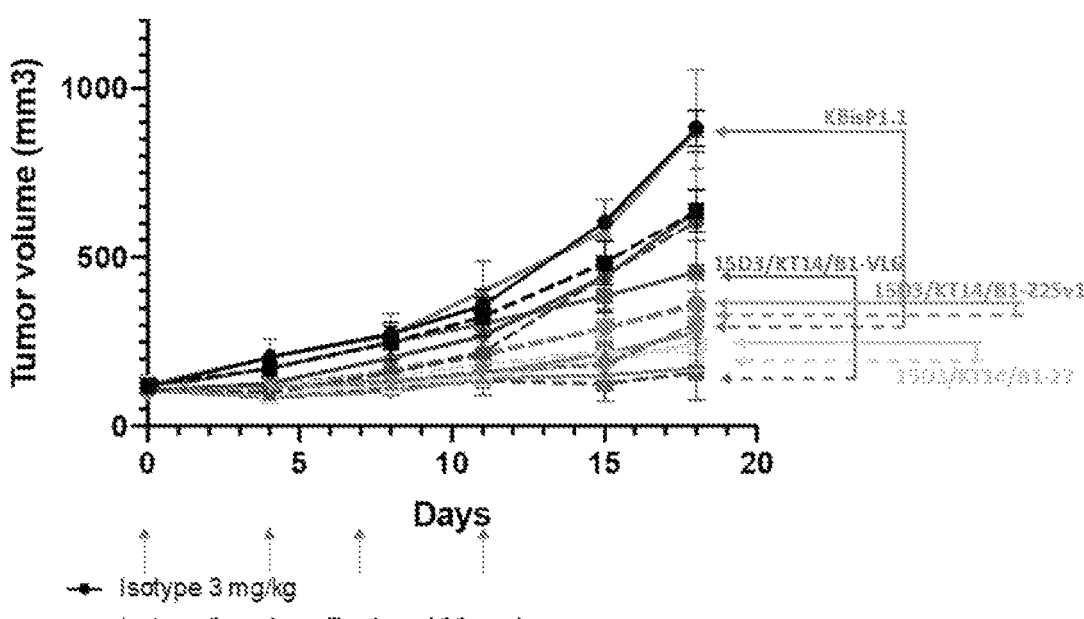

-■- Isotype 3 mg/kg
-■- Isotype 3 mg/kg + Paclitaxel 20 mg/kg

-❋- KBisP1.1 3 mg/kg
-❋- KBisP1.1 3 mg/kg+ Paclitaxel 20 mg/kg

-▼- 15D3 DD IgG1 KT14 VH KK IGG1 KNJY G2 343 VL hu IgG 3 mg/kg
-▼- 15D3 DD IgG1 KT14 VH KK IGG1 KNJY G2 343 VL hu IgG 3 mg/kg + Paclitaxel 20 mg/kg -◇- 15D3 DD IgG1 KT14 VH KK IGG1 KNJY B1 27 VL pClneo 3 mg/kg
-◆- 15D3 DD IgG1 KT14 VH KK IGG1 KNJY B1 27 VL pClneo 3 mg/kg + Paclitaxel 20 mg/kg -◆- 15D3 DD IgG1 KT14 VH KK IGG1 225v1 VL in huIgG1 LCK 3 mg/kg
-◆- 15D3 DD IgG1 KT14 VH KK IGG1 225v1 VL in huIgG1 LCK 3 mg/kg + Paclitaxel 20 mg/kg -◆- 15D3 DD IgG1 KT14 VH KK IGG1 89v1 VL in huIgG1 3 mg/kg
-◆- 15D3 DD IgG1 KT14 VH KK IGG1 89v1 VL in huIgG1 3 mg/kg + Paclitaxel 20 mg/kg -◆- 15D3 DD IgG1 KT14 VH KK IGG1 KPB1 VL6/CD3 mod 3 mg/kg
-◆- 15D3 DD IgG1 KT14 VH KK IGG1 KPB1 VL6/CD3 mod 3 mg/kg + Paclitaxel 20 mg/kg

FIG. 23C

| B1 antibody HC1 | Her2 antibody HC2 | LC | B1 Expressing Cells | Her2 ELISA | Her2 SKBR |
|---|---|---|---|---|---|
| B1_129 DD | KT1-2 KK | B1_129 | + | - | + |
| B1_188 DD | KT1 KK | MRK16 | + | + | + |
| B1_261 DD | KT1-2 KK | B1_261 | + | ± | + |
| B1_261 VH4 DD | KT1 KK | MRK16 | - | + | + |
| B1_261 VH4 DD | KT1 KK | B1_261 VH4 | + | + | + |
| B1_261 VH4 DD | KT1-2 KK | B1_261 VH4 | + | + | + |
| B1_261 VH4 DD | KT1-2 KK | B1_129 hmzKV1 | - | + | + |
| B1_129 DD | KT1-2 KK | MRK16 | - | - | - |
| B1_188 DD | KT1-2 KK | MRK16 | + | + | ± |
| B1_188 DD | KT1-2 KK | B1_188 | + | + | ± |
| B1_188 DD | KT1 DD | B1_188 | + | ± | ± |
| B1_223 DD | KT1 KK | B1_223 | + | + | ± |
| B1_223 DD | KT1 KK | MRK16 | + | + | ± |
| B1_223 DD | KT1-2 KK | MRK16 | + | - | ± |
| B1_223 DD | KT1-2 KK | B1_223 | + | - | ± |
| B1_225 DD | KT1-2 KK | MRK16 | + | - | ± |
| B1_226 DD | KT1-2 KK | MRK16 | + | - | ± |
| B1_226 DD | KT1-2 KK | B1_226 | + | - | - |
| B1_226 DD | KT1 DD | B1_226 | + | - | ± |
| B1_226 DD | KT1 DD | MRK16 | - | ± | - |
| B1_261 DD | KT1-2 KK | MRK16 | - | ± | - |
| B1_261 VH3 DD | KT1 KK | MRK16 | - | + | ± |
| B1_261 VH4 DD | KT1 KK | B1_129 hmzKV1 | + | | |
| B1_129 hmzKV3 DD | KT1 KK | MRK16 | - | - | - |
| B1_129 hmzKV3 DD | KT1 KK | B1_129 hmzKV3 | + | - | - |
| B1_129 hmzKV3 DD | KT1 KK | B1_129 hmzKV1 | + | - | - |
| B1_129 hmzKV3 DD | KT1-2 KK | MRK16 | - | - | - |
| B1_129 hmzKV3 DD | KT1-2 KK | B1_129 hmzKV3 | + | - | - |
| B1_129 hmzKV3 DD | KT1-2 KK | B1_129 hmzKV1 | + | - | - |

FIG. 24

| B1 antibody HC1 | Anti-PDL1 HC2 | LC | B1 Expressing Cells | PDL1 ELISA | PDL1 Expressing Cells |
|---|---|---|---|---|---|
| B1_188 DD | KT9 KK | B1_188 | - | + | + |
| B1_188 DD | KT9 KK | B1_188 | - | + | + |
| B1_261 VH3 DD | KT9 KK | B1_261 VH3 | + | + | + |
| B1_261 VH4 DD | KT9 KK | B1_261 VH4 | + | + | + |
| B1_261 VH4 DD | KT9 KK | B1_129 hmzKV1 | + | - | + |
| B1_261 VH4 DD | KT9 KK | MRK16 | + | + | + |
| B1_188 DD | KT9 KK | MRK16 | + | + | - |
| B1_188 DD | KT9 KK | MRK16 | + | + | - |
| B1_223 DD | KT9 KK | MRK16 | + | + | - |
| B1_226 DD | KT9 KK | B1_226 | + | + | - |
| B1_226 DD | KT9 KK | MRK16 | - | + | - |
| B1_226 DD | KT9 KK | B1_226 | ± | + | - |
| B1_226 DD | KT9 KK | MRK16 | - | + | - |
| B1_129 hmzKV3 DD | KT9 KK | MRK16 | - | - | - |
| B1_129 hmzKV3 DD | KT9 KK | B1_129 hmzKV3 | + | - | - |
| B1_129 hmzKV3 DD | KT9 KK | B1_129 hmzKV1 | + | - | - |

FIG. 25

SEQUENCE LISTING

<160> NUMBER OF SEQ ID NOS: 380

<210> SEQ ID NO 1
<211> LENGTH: 49
<212> TYPE: PRT
<213> ORGANISM: Homo sapiens

<400> SEQUENCE: 1

Met Met Leu Val Phe Gly Glu Met Thr Asp Ile Phe Ala Asn Ala Gly
1               5                   10                  15

Asn Leu Glu Asp Leu Met Ser Asn Ile Thr Asn Arg Ser Asp Ile Asn
            20                  25                  30

Asp Thr Gly Phe Phe Met Asn Leu Glu Glu Asp Met Thr Arg Tyr Ala
        35                  40                  45

Tyr

<210> SEQ ID NO 2
<211> LENGTH: 6
<212> TYPE: PRT
<213> ORGANISM: Homo sapiens

<400> SEQUENCE: 2

Thr Arg Gly Trp Lys Leu
1               5

<210> SEQ ID NO 3
<211> LENGTH: 14
<212> TYPE: PRT
<213> ORGANISM: Homo sapiens

<400> SEQUENCE: 3

```
Gly Thr Thr Leu Val Leu Ser Gly Glu Tyr Ser Ile Gly Gln
1               5                   10
```

```
<210> SEQ ID NO 4
<211> LENGTH: 24
<212> TYPE: PRT
<213> ORGANISM: Homo sapiens

<400> SEQUENCE: 4

Ser Lys Ile Ile Gly Val Phe Thr Arg Ile Asp Asp Pro Glu Thr Lys
1               5                   10                  15

Arg Gln Asn Ser Asn Leu Phe Ser
            20
```

```
<210> SEQ ID NO 5
<211> LENGTH: 16
<212> TYPE: PRT
<213> ORGANISM: Homo sapiens

<400> SEQUENCE: 5

Arg Phe Gly Ala Tyr Leu Val Ala His Lys Leu Met Ser Phe Glu Asp
1               5                   10                  15
```

```
<210> SEQ ID NO 6
<211> LENGTH: 118
<212> TYPE: PRT
<213> ORGANISM: Mus musculus

<400> SEQUENCE: 6

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
            35                  40                  45

Ala Thr Val Ser Ser Gly Gly Gly Asn Thr Tyr Tyr Pro Asp Ser Val
        50                  55                  60

Lys Gly Arg Phe Thr Ile Ser Arg Asp Asn Ala Lys Asn Asn Leu Tyr
65                  70                  75                  80

Leu Gln Met Ser Ser Pro Arg Ser Glu Asp Thr Ala Leu Tyr Tyr Cys
                85                  90                  95

Ala Arg Tyr Gly Asn Tyr Gly Trp Phe Thr Tyr Trp Gly Gln Gly Thr
            100                 105                 110

Leu Val Thr Val Ser Ser
        115
```

```
<210> SEQ ID NO 7
<211> LENGTH: 5
<212> TYPE: PRT
<213> ORGANISM: Mus musculus

<400> SEQUENCE: 7

Ser Tyr Thr Met Ser
1               5
```

```
<210> SEQ ID NO 8
<211> LENGTH: 17
<212> TYPE: PRT
<213> ORGANISM: Mus musculus

<400> SEQUENCE: 8
```

```
Thr Val Ser Ser Gly Gly Gly Asn Thr Tyr Tyr Pro Asp Ser Val Lys
1               5                   10                  15

Gly

<210> SEQ ID NO 9
<211> LENGTH: 9
<212> TYPE: PRT
<213> ORGANISM: Mus musculus

<400> SEQUENCE: 9

Tyr Gly Asn Tyr Gly Trp Phe Thr Tyr
1               5

<210> SEQ ID NO 10
<211> LENGTH: 112
<212> TYPE: PRT
<213> ORGANISM: Mus musculus

<400> SEQUENCE: 10

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Thr Gly Asn Thr Tyr Leu Asp Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Ser His Ile Pro Arg Thr Phe Gly Gly Gly Thr Lys Leu Glu Ile Lys
                100                 105                 110

<210> SEQ ID NO 11
<211> LENGTH: 16
<212> TYPE: PRT
<213> ORGANISM: Mus musculus

<400> SEQUENCE: 11

Arg Ser Ser Gln Asn Ile Val His Ser Thr Gly Asn Thr Tyr Leu Asp
1               5                   10                  15

<210> SEQ ID NO 12
<211> LENGTH: 7
<212> TYPE: PRT
<213> ORGANISM: Mus musculus

<400> SEQUENCE: 12

Lys Val Ser Asn Arg Phe Ser
1               5

<210> SEQ ID NO 13
<211> LENGTH: 9
<212> TYPE: PRT
<213> ORGANISM: Mus musculus

<400> SEQUENCE: 13

Phe Gln Gly Ser His Ile Pro Arg Thr
1               5
```

-continued

```
<210> SEQ ID NO 14
<211> LENGTH: 119
<212> TYPE: PRT
<213> ORGANISM: Mus musculus

<400> SEQUENCE: 14

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Gly Leu Tyr
            20                  25                  30

Thr Met Ser Trp Val Arg Gln Thr Pro Glu Arg Arg Leu Glu Trp Val
        35                  40                  45

Ala Thr Ile Ser Ser Gly Gly Ser Asn Thr Tyr Tyr Pro Asp Ser Val
    50                  55                  60

Lys Gly Arg Phe Thr Ile Ser Arg Asp Asn Ala Lys Asn Asn Leu Phe
65                  70                  75                  80

Leu Gln Met Asn Ser Leu Arg Ser Glu Asp Thr Ala Leu Tyr Tyr Cys
                85                  90                  95

Ala Arg Tyr Tyr Arg Tyr Asp Ala Trp Phe Ala Tyr Trp Gly Gln Gly
            100                 105                 110

Thr Leu Val Thr Val Ser Ser
        115

<210> SEQ ID NO 15
<211> LENGTH: 5
<212> TYPE: PRT
<213> ORGANISM: Mus musculus

<400> SEQUENCE: 15

Leu Tyr Thr Met Ser
1               5

<210> SEQ ID NO 16
<211> LENGTH: 17
<212> TYPE: PRT
<213> ORGANISM: Mus musculus

<400> SEQUENCE: 16

Thr Ile Ser Ser Gly Gly Ser Asn Thr Tyr Tyr Pro Asp Ser Val Lys
1               5                   10                  15

Gly

<210> SEQ ID NO 17
<211> LENGTH: 10
<212> TYPE: PRT
<213> ORGANISM: Mus musculus

<400> SEQUENCE: 17

Tyr Tyr Arg Tyr Asp Ala Trp Phe Ala Tyr
1               5                   10

<210> SEQ ID NO 18
<211> LENGTH: 112
<212> TYPE: PRT
<213> ORGANISM: Mus musculus

<400> SEQUENCE: 18

Asp Val Leu Leu Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
```

-continued

```
                 20                  25                  30

Thr Gly Asn Thr Tyr Leu Asp Trp Tyr Leu Gln Lys Pro Gly Gln Ser
             35                  40                  45

Pro Lys Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                 85                  90                  95

Ser His Ile Pro Arg Thr Phe Gly Gly Gly Thr Lys Leu Glu Ile Lys
                 100                 105                 110

<210> SEQ ID NO 19
<211> LENGTH: 119
<212> TYPE: PRT
<213> ORGANISM: Unknown
<220> FEATURE:
<223> OTHER INFORMATION: humanized sequence

<400> SEQUENCE: 19

Glu Val Gln Leu Val Glu Ser Gly Gly Gly Leu Val Lys Pro Gly Gly
1                5                  10                  15

Ser Leu Arg Leu Ser Cys Ala Ala Ser Gly Phe Thr Phe Gly Leu Tyr
                 20                  25                  30

Thr Met Ser Trp Val Arg Gln Ala Pro Gly Lys Gly Leu Glu Trp Val
             35                  40                  45

Ala Thr Ile Ser Ser Gly Gly Ser Asn Thr Tyr Tyr Pro Asp Ser Val
     50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                 85                  90                  95

Ala Arg Tyr Tyr Arg Tyr Asp Ala Trp Phe Ala Tyr Trp Gly Gln Gly
                 100                 105                 110

Thr Leu Val Thr Val Ser Ser
             115

<210> SEQ ID NO 20
<211> LENGTH: 112
<212> TYPE: PRT
<213> ORGANISM: Unknown
<220> FEATURE:
<223> OTHER INFORMATION: humanized sequence

<400> SEQUENCE: 20

Asp Val Val Leu Thr Gln Ser Pro Leu Ser Leu Pro Val Thr Leu Gly
1                5                  10                  15

Gln Pro Ala Ser Ile Ser Cys Arg Ser Ser Gln Asn Ile Val His Ser
                 20                  25                  30

Thr Gly Asn Thr Tyr Leu Asp Trp Tyr Gln Gln Arg Pro Gly Gln Ser
             35                  40                  45

Pro Arg Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Phe Gln Gly
                 85                  90                  95
```

Ser His Ile Pro Arg Thr Phe Gly Gln Gly Thr Lys Leu Glu Ile Lys
            100                 105                 110

<210> SEQ ID NO 21
<211> LENGTH: 112
<212> TYPE: PRT
<213> ORGANISM: Unknown
<220> FEATURE:
<223> OTHER INFORMATION: humanized sequence

<400> SEQUENCE: 21

Asp Val Val Leu Thr Gln Ser Pro Leu Ser Leu Pro Val Thr Pro Gly
1               5                   10                  15

Glu Pro Ala Ser Ile Ser Cys Arg Ser Ser Gln Asn Ile Val His Ser
            20                  25                  30

Thr Gly Asn Thr Tyr Leu Asp Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Ile Pro Arg Thr Phe Gly Gln Gly Thr Lys Leu Glu Ile Lys
            100                 105                 110

<210> SEQ ID NO 22
<211> LENGTH: 112
<212> TYPE: PRT
<213> ORGANISM: Unknown
<220> FEATURE:
<223> OTHER INFORMATION: humanized sequence

<400> SEQUENCE: 22

Glu Val Val Leu Thr Gln Ser Pro Ala Thr Leu Ser Leu Ser Pro Gly
1               5                   10                  15

Glu Arg Ala Thr Leu Ser Cys Arg Ser Ser Gln Asn Ile Val His Ser
            20                  25                  30

Thr Gly Asn Thr Tyr Leu Asp Trp Tyr Gln Gln Lys Pro Gly Gln Ser
            35                  40                  45

Pro Arg Leu Leu Ile Tyr Lys Val Ser Asn Arg Phe Ser Gly Val Pro
        50                  55                  60

Ala Arg Phe Ser Gly Ser Gly Ser Gly Thr Asp Phe Thr Leu Thr Ile
65                  70                  75                  80

Ser Ser Leu Glu Pro Glu Asp Phe Ala Val Tyr Tyr Cys Phe Gln Gly
                85                  90                  95

Ser His Ile Pro Arg Thr Phe Gly Gly Gly Thr Lys Leu Glu Ile Lys
            100                 105                 110

<210> SEQ ID NO 23
<211> LENGTH: 119
<212> TYPE: PRT
<213> ORGANISM: Mus musculus

<400> SEQUENCE: 23

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

-continued

```
Thr Met Ser Trp Val Arg Gln Thr Pro Glu Lys Arg Leu Glu Trp Val
        35                  40                  45

Ala Thr Ile Ser Ser Gly Gly Gly Asn Thr Tyr Tyr Pro Asp Ser Val
        50                  55                  60

Lys Gly Arg Phe Thr Ile Ser Arg Asp Asn Ala Lys Asn Asn Leu Tyr
65                      70                  75                  80

Leu Gln Met Ser Ser Leu Arg Ser Glu Asp Thr Ala Leu Tyr Tyr Cys
                85                  90                  95

Ala Arg Tyr Tyr Arg Tyr Asp Ala Trp Phe Ala Tyr Trp Gly Gln Gly
            100                 105                 110

Thr Leu Val Thr Val Ser Ala
        115
```

```
<210> SEQ ID NO 24
<211> LENGTH: 112
<212> TYPE: PRT
<213> ORGANISM: Mus musculus

<400> SEQUENCE: 24
```

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Thr Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                      70                  75                  80

Ser Arg Val Glu Thr Glu Asp Leu Gly Val Tyr Tyr Cys Phe Gln Gly
                85                  90                  95

Ser His Val Pro Arg Thr Phe Gly Gly Gly Thr Lys Leu Glu Ile Lys
            100                 105                 110
```

```
<210> SEQ ID NO 25
<211> LENGTH: 16
<212> TYPE: PRT
<213> ORGANISM: Mus musculus

<400> SEQUENCE: 25
```

```
Arg Ser Ser Gln Ser Ile Val His Ser Thr Gly Asn Thr Tyr Leu Glu
1               5                   10                  15
```

```
<210> SEQ ID NO 26
<211> LENGTH: 118
<212> TYPE: PRT
<213> ORGANISM: Mus musculus

<400> SEQUENCE: 26
```

```
Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Thr Val Ser Ser Gly Gly Gly Asn Thr Tyr Tyr Pro Asp Ser Val
        50                  55                  60

Lys Gly Arg Phe Thr Ile Ser Arg Asp Asn Ala Lys Asn Asn Leu Tyr
```

-continued

```
65                    70                    75                    80

Leu Gln Met Ser Ser Leu Arg Ser Glu Asp Thr Ala Leu Tyr Tyr Cys
                85                    90                    95

Ala Arg Tyr Gly Asn Tyr Gly Trp Phe Thr Tyr Trp Gly Gln Gly Thr
                100                   105                   110

Leu Val Thr Val Ser Ala
        115

<210> SEQ ID NO 27
<211> LENGTH: 112
<212> TYPE: PRT
<213> ORGANISM: Mus musculus

<400> SEQUENCE: 27

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Leu His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Ala Ser Gly Ser Gly Thr Asp Phe Thr Leu Lys Ile
65                  70                  75                  80

Ser Arg Val Glu Ala Glu Asp Leu Gly Ile Tyr Tyr Cys Phe Gln Gly
                85                  90                  95

Ser His Val Pro Arg Thr Phe Gly Gly Gly Thr Lys Leu Glu Ile Lys
            100                 105                 110

<210> SEQ ID NO 28
<211> LENGTH: 16
<212> TYPE: PRT
<213> ORGANISM: Mus musculus

<400> SEQUENCE: 28

Arg Ser Ser Gln Ser Ile Leu His Ser Asn Gly Asn Thr Tyr Leu Glu
1               5                   10                  15

<210> SEQ ID NO 29
<211> LENGTH: 119
<212> TYPE: PRT
<213> ORGANISM: Mus musculus

<400> SEQUENCE: 29

Glu Val Gln Leu Val Glu Ser Gly Gly Ala Leu Val Lys Pro Gly Gly
1               5                   10                  15

Ser Leu Lys Leu Ser Cys Ala Ala Ser Gly Phe Thr Phe Ser Asn Tyr
            20                  25                  30

Gly Val Ser Trp Val Arg Gln Thr Pro Glu Lys Arg Leu Glu Trp Val
        35                  40                  45

Ala Thr Ile Ser Ser Ser Gly Ser Tyr Thr Tyr Tyr Pro Asp Ile Val
    50                  55                  60

Arg Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Phe Tyr Tyr Cys
                85                  90                  95

Ala Arg Gly Tyr Gly Asn Phe Ala Trp Phe Ala Tyr Trp Gly Gln Gly
            100                 105                 110
```

```
Thr Leu Val Thr Val Ser Ala
        115

<210> SEQ ID NO 30
<211> LENGTH: 5
<212> TYPE: PRT
<213> ORGANISM: Mus musculus

<400> SEQUENCE: 30

Asn Tyr Gly Val Ser
1               5

<210> SEQ ID NO 31
<211> LENGTH: 17
<212> TYPE: PRT
<213> ORGANISM: Mus musculus

<400> SEQUENCE: 31

Thr Ile Ser Ser Ser Gly Ser Tyr Thr Tyr Tyr Pro Asp Ile Val Arg
1               5                   10                  15

Gly

<210> SEQ ID NO 32
<211> LENGTH: 10
<212> TYPE: PRT
<213> ORGANISM: Mus musculus

<400> SEQUENCE: 32

Gly Tyr Gly Asn Phe Ala Trp Phe Ala Tyr
1               5                   10

<210> SEQ ID NO 33
<211> LENGTH: 112
<212> TYPE: PRT
<213> ORGANISM: Mus musculus

<400> SEQUENCE: 33

Asp Ile Gln Met Thr Gln Ser Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Thr Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 34
<211> LENGTH: 119
<212> TYPE: PRT
<213> ORGANISM: Mus musculus

<400> SEQUENCE: 34

Lys Val Gln Leu Val Glu Ser Gly Gly Ala Leu Val Lys Pro Gly Gly
1               5                   10                  15
```

-continued

```
Ser Leu Lys Leu Ser Cys Ala Ala Ser Gly Phe Thr Phe Ser Asn Tyr
        20                  25                  30

Ala Met Ser Trp Val Arg Gln Thr Pro Glu Lys Arg Leu Glu Trp Val
        35                  40                  45

Ala Thr Ile Ser Ser Ser Gly Ser Tyr Thr Tyr Phe Pro Asp Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Leu Tyr Tyr Cys
                85                  90                  95

Ala Arg Tyr Gly Tyr Asp Glu Ala Trp Phe Ala Ser Trp Gly Gln Gly
            100                 105                 110

Thr Leu Val Thr Val Ser Ala
            115

<210> SEQ ID NO 35
<211> LENGTH: 5
<212> TYPE: PRT
<213> ORGANISM: Mus musculus

<400> SEQUENCE: 35

Asn Tyr Ala Met Ser
1               5

<210> SEQ ID NO 36
<211> LENGTH: 17
<212> TYPE: PRT
<213> ORGANISM: Mus musculus

<400> SEQUENCE: 36

Thr Ile Ser Ser Ser Gly Ser Tyr Thr Tyr Phe Pro Asp Ser Val Lys
1               5                   10                  15

Gly

<210> SEQ ID NO 37
<211> LENGTH: 10
<212> TYPE: PRT
<213> ORGANISM: Mus musculus

<400> SEQUENCE: 37

Tyr Gly Tyr Asp Glu Ala Trp Phe Ala Ser
1               5                   10

<210> SEQ ID NO 38
<211> LENGTH: 112
<212> TYPE: PRT
<213> ORGANISM: Mus musculus

<400> SEQUENCE: 38

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Ser
        20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Lys Arg Phe Ser Gly Val Pro
        50                  55                  60

Asp Arg Phe Ser Gly Ser Gly Ser Gly Thr Asp Phe Thr Leu Lys Ile
65                  70                  75                  80
```

-continued

```
Ser Arg Val Glu Ala Glu Asp Leu Gly Val Tyr Tyr Cys Phe Gln Gly
             85              90              95

Ser His Phe Pro Arg Thr Phe Gly Gly Gly Thr Lys Leu Glu Ile Lys
            100             105             110

<210> SEQ ID NO 39
<211> LENGTH: 16
<212> TYPE: PRT
<213> ORGANISM: Mus musculus

<400> SEQUENCE: 39

Arg Ser Ser Gln Thr Ile Val His Ser Asn Gly Asn Thr Tyr Leu Glu
1               5                  10                  15

<210> SEQ ID NO 40
<211> LENGTH: 7
<212> TYPE: PRT
<213> ORGANISM: Mus musculus

<400> SEQUENCE: 40

Lys Val Ser Lys Arg Phe Ser
1               5

<210> SEQ ID NO 41
<211> LENGTH: 9
<212> TYPE: PRT
<213> ORGANISM: Mus musculus

<400> SEQUENCE: 41

Phe Gln Gly Ser His Val Pro Arg Thr
1               5

<210> SEQ ID NO 42
<211> LENGTH: 9
<212> TYPE: PRT
<213> ORGANISM: Mus musculus

<400> SEQUENCE: 42

Phe Gln Gly Ser His Phe Pro Arg Thr
1               5

<210> SEQ ID NO 43
<211> LENGTH: 121
<212> TYPE: PRT
<213> ORGANISM: Mus musculus

<400> SEQUENCE: 43

Glu Val Ile Leu Val Glu Ser Gly Glu Gly Leu Val Lys Pro Gly Gly
1               5                  10                  15

Ser Leu Lys Val Ser Cys Ala Ala Ser Gly Phe Thr Phe Ser Asn Tyr
            20                  25                  30

Tyr Met Ser Trp Val Arg Gln Thr Pro Glu Lys Arg Leu Glu Leu Val
            35                  40                  45

Ala Ala Ile Asn Ser Asn Gly Gly Asn Thr Tyr Tyr Pro Asp Thr Val
        50                  55                  60

Lys Gly Arg Phe Thr Ile Ser Arg Asp Asn Ala Arg Asn Ile Leu Tyr
65                  70                  75                  80

Leu Gln Met Ser Ser Leu Lys Ser Glu Asp Thr Ala Leu Tyr Tyr Cys
                85                  90                  95

Ala Arg His Tyr Tyr Gly Tyr Glu Gly Trp Tyr Phe Asp Val Trp Gly
            100             105             110
```

-continued

```
Ala Gly Thr Thr Val Thr Val Ser Ser
        115                 120

<210> SEQ ID NO 44
<211> LENGTH: 5
<212> TYPE: PRT
<213> ORGANISM: Mus musculus

<400> SEQUENCE: 44

Asn Tyr Tyr Met Ser
1               5

<210> SEQ ID NO 45
<211> LENGTH: 17
<212> TYPE: PRT
<213> ORGANISM: Mus musculus

<400> SEQUENCE: 45

Ala Ile Asn Ser Asn Gly Gly Asn Thr Tyr Tyr Pro Asp Thr Val Lys
1               5                   10                  15

Gly

<210> SEQ ID NO 46
<211> LENGTH: 12
<212> TYPE: PRT
<213> ORGANISM: Mus musculus

<400> SEQUENCE: 46

His Tyr Tyr Gly Tyr Glu Gly Trp Tyr Phe Asp Val
1               5                   10

<210> SEQ ID NO 47
<211> LENGTH: 106
<212> TYPE: PRT
<213> ORGANISM: Mus musculus

<400> SEQUENCE: 47

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ser Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Pro Pro Thr
                85                  90                  95

Phe Gly Gly Gly Thr Lys Leu Glu Ile Lys
            100                 105

<210> SEQ ID NO 48
<211> LENGTH: 10
<212> TYPE: PRT
<213> ORGANISM: Mus musculus

<400> SEQUENCE: 48

Arg Ala Ser Ser Ser Val Ser Tyr Met His
1               5                   10
```

-continued

```
<210> SEQ ID NO 49
<211> LENGTH: 7
<212> TYPE: PRT
<213> ORGANISM: Mus musculus

<400> SEQUENCE: 49

Ala Thr Ser Asn Leu Ala Ser
1               5

<210> SEQ ID NO 50
<211> LENGTH: 9
<212> TYPE: PRT
<213> ORGANISM: Mus musculus

<400> SEQUENCE: 50

Gln Gln Trp Ser Ser Asn Pro Pro Thr
1               5

<210> SEQ ID NO 51
<211> LENGTH: 119
<212> TYPE: PRT
<213> ORGANISM: Mus musculus

<400> SEQUENCE: 51

Glu Val Gln Leu Val Glu Ser Gly Gly Ala Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Glu Arg Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Ile Ser Glu Asp Thr Ala Leu Tyr Tyr Cys
                85                  90                  95

Thr Arg Gly Tyr Gly Asn Phe Ala Trp Phe Ala Tyr Trp Gly His Gly
            100                 105                 110

Thr Leu Val Thr Val Ser Ala
        115

<210> SEQ ID NO 52
<211> LENGTH: 17
<212> TYPE: PRT
<213> ORGANISM: Mus musculus

<400> SEQUENCE: 52

Thr Ile Ser Ser Gly Gly Ser Tyr Thr Tyr Tyr Pro Asp Ser Val Lys
1               5                   10                  15

Gly

<210> SEQ ID NO 53
<211> LENGTH: 112
<212> TYPE: PRT
<213> ORGANISM: Mus musculus

<400> SEQUENCE: 53

Asp Val Val Met Thr Gln Thr Pro Leu Ser Leu Pro Val Ser Leu Gly
1               5                   10                  15

Asp Gln Val Ser Ile Ser Cys Arg Ser Ser Gln Ser Ile Val His Ser
            20                  25                  30
```

```
Tyr Gly Ser Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Ser His Ile Pro Tyr Thr Phe Gly Gly Gly Thr Lys Leu Glu Leu Lys
            100                 105                 110

<210> SEQ ID NO 54
<211> LENGTH: 16
<212> TYPE: PRT
<213> ORGANISM: Mus musculus

<400> SEQUENCE: 54

Arg Ser Ser Gln Ser Ile Val His Ser Tyr Gly Ser Thr Tyr Leu Glu
1               5                   10                  15

<210> SEQ ID NO 55
<211> LENGTH: 9
<212> TYPE: PRT
<213> ORGANISM: Mus musculus

<400> SEQUENCE: 55

Phe Gln Gly Ser His Ile Pro Tyr Thr
1               5

<210> SEQ ID NO 56
<211> LENGTH: 122
<212> TYPE: PRT
<213> ORGANISM: Mus musculus

<400> SEQUENCE: 56

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Ser Thr Tyr
            20                  25                  30

Val Ile His Trp Val Lys Gln Lys Pro Gly Gln Gly Leu Glu Trp Ile
        35                  40                  45

Gly Tyr Ile Tyr Pro Tyr Asn Asp Tyr Thr Lys Tyr Asn Glu Lys Phe
    50                  55                  60

Lys Asp Lys Ala Thr Leu Thr Ser Asp Lys Ser Ser Ser Thr Ala Tyr
65                  70                  75                  80

Met Glu Ile Arg Ser Leu Thr Ser Glu Asp Ser Ala Val Tyr Tyr Cys
                85                  90                  95

Ser Arg Ala Tyr Tyr Gly Asn Leu Val Gly Tyr Gly Val Asp Tyr Trp
            100                 105                 110

Gly Gln Gly Thr Ser Val Thr Val Ser Ser
            115                 120

<210> SEQ ID NO 57
<211> LENGTH: 5
<212> TYPE: PRT
<213> ORGANISM: Mus musculus

<400> SEQUENCE: 57

Thr Tyr Val Ile His
```

```
1                 5

<210> SEQ ID NO 58
<211> LENGTH: 17
<212> TYPE: PRT
<213> ORGANISM: Mus musculus

<400> SEQUENCE: 58

Tyr Ile Tyr Pro Tyr Asn Asp Tyr Thr Lys Tyr Asn Glu Lys Phe Lys
1               5                   10                  15

Asp

<210> SEQ ID NO 59
<211> LENGTH: 13
<212> TYPE: PRT
<213> ORGANISM: Mus musculus

<400> SEQUENCE: 59

Ala Tyr Tyr Gly Asn Leu Val Gly Tyr Gly Val Asp Tyr
1               5                   10

<210> SEQ ID NO 60
<211> LENGTH: 106
<212> TYPE: PRT
<213> ORGANISM: Mus musculus

<400> SEQUENCE: 60

Gln Ile Val Leu Thr Gln Ser Pro Ala Ile Leu Pro Ala Ser Pro Gly
1               5                   10                  15

Glu Lys Val Thr Met Thr Cys Arg Ala Ser Ser Ser Val Ser Phe Ile
            20                  25                  30

Tyr Trp Tyr Gln Gln Arg Pro Gly Ser Ser Pro Lys Pro Trp Ile Phe
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys His Gln Trp Gly Ser Asn Leu Pro Thr
                85                  90                  95

Phe Gly Gly Gly Thr Lys Leu Glu Ile Lys
            100                 105

<210> SEQ ID NO 61
<211> LENGTH: 10
<212> TYPE: PRT
<213> ORGANISM: Mus musculus

<400> SEQUENCE: 61

Arg Ala Ser Ser Ser Val Ser Phe Ile Tyr
1               5                   10

<210> SEQ ID NO 62
<211> LENGTH: 9
<212> TYPE: PRT
<213> ORGANISM: Mus musculus

<400> SEQUENCE: 62

His Gln Trp Gly Ser Asn Leu Pro Thr
1               5

<210> SEQ ID NO 63
```

```
<211> LENGTH: 122
<212> TYPE: PRT
<213> ORGANISM: Unknown
<220> FEATURE:
<223> OTHER INFORMATION: humanized sequence

<400> SEQUENCE: 63

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Thr Tyr
                20                  25                  30

Val Ile His Trp Val Arg Gln Ala Pro Gly Gln Gly Leu Glu Trp Ile
            35                  40                  45

Gly Tyr Ile Tyr Pro Tyr Asn Asp Tyr Thr Lys Tyr Asn Glu Lys Phe
        50                  55                  60

Lys Asp Arg Ala Thr Leu Thr Ser Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ser Arg Ala Tyr Tyr Gly Asn Leu Val Gly Tyr Gly Val Asp Tyr Trp
                100                 105                 110

Gly Gln Gly Thr Thr Val Thr Val Ser Ser
            115                 120

<210> SEQ ID NO 64
<211> LENGTH: 106
<212> TYPE: PRT
<213> ORGANISM: Unknown
<220> FEATURE:
<223> OTHER INFORMATION: humanized sequence

<400> SEQUENCE: 64

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Phe Ile
                20                  25                  30

Tyr Trp Tyr Gln Gln Lys Pro Gly Gln Ser Pro Arg Pro Trp Ile Phe
            35                  40                  45

Ala Thr Ser Asn Leu Ala Ser Gly Val Pro Ala Arg Phe Ser Gly Ser
        50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys His Gln Trp Gly Ser Asn Leu Pro Thr
                85                  90                  95

Phe Gly Gly Gly Thr Lys Leu Glu Ile Lys
            100                 105

<210> SEQ ID NO 65
<211> LENGTH: 106
<212> TYPE: PRT
<213> ORGANISM: Unknown
<220> FEATURE:
<223> OTHER INFORMATION: humanized sequence

<400> SEQUENCE: 65

Asp Ile Gln Leu Thr Gln Ser Pro Ser Ser Leu Ser Ala Ser Val Gly
1               5                   10                  15

Asp Arg Val Thr Ile Thr Cys Arg Ala Ser Ser Ser Val Ser Phe Ile
                20                  25                  30
```

-continued

```
Tyr Trp Tyr Gln Gln Lys Pro Gly Lys Ser Pro Lys Pro Trp Ile Phe
        35              40              45

Ala Thr Ser Asn Leu Ala Ser Gly Val Pro Ser Arg Phe Ser Gly Ser
    50              55              60

Gly Ser Gly Thr Asp Tyr Thr Leu Thr Ile Ser Ser Leu Gln Pro Glu
65              70              75              80

Asp Phe Ala Thr Tyr Tyr Cys His Gln Trp Gly Ser Asn Leu Pro Thr
                85              90              95

Phe Gly Gly Gly Thr Lys Leu Glu Ile Lys
            100             105

<210> SEQ ID NO 66
<211> LENGTH: 119
<212> TYPE: PRT
<213> ORGANISM: Mus musculus

<400> SEQUENCE: 66

Glu Val Met Leu Val Glu Ser Gly Gly Ala Leu Val Lys Pro Gly Gly
1               5               10              15

Ser Leu Lys Leu Ser Cys Ala Ala Ser Gly Phe Thr Phe Ser Asn Tyr
            20              25              30

Ala Met Ser Trp Val Arg Gln Thr Pro Glu Lys Arg Leu Glu Trp Val
        35              40              45

Ala Thr Ile Ser Ser Gly Gly Ser Tyr Thr Tyr Tyr Pro Asp Ser Val
    50              55              60

Lys Gly Arg Phe Thr Ile Ser Arg Asp Asn Ala Arg Asn Thr Leu Tyr
65              70              75              80

Leu Gln Met Ser Ser Leu Arg Ser Glu Asp Thr Ala Met Tyr Tyr Cys
                85              90              95

Ala Arg Gly Tyr Gly Asn Phe Ala Trp Phe Ala Tyr Trp Gly Gln Gly
            100             105             110

Thr Leu Val Thr Val Ser Ala
        115

<210> SEQ ID NO 67
<211> LENGTH: 112
<212> TYPE: PRT
<213> ORGANISM: Mus musculus

<400> SEQUENCE: 67

Asp Val Val Met Thr Gln Thr Pro Leu Ser Leu Pro Val Ser Leu Gly
1               5               10              15

Asp Gln Ala Ser Ile Ser Cys Arg Ser Ser Gln Ser Ile Val His Ser
            20              25              30

Asn Gly Asn Thr Tyr Leu Glu Trp Tyr Leu Gln Lys Pro Gly Gln Ser
        35              40              45

Pro Lys Leu Met Ile Tyr Lys Val Ser Asn Arg Phe Ser Gly Val Pro
    50              55              60

Asp Arg Phe Ser Gly Ser Gly Ser Gly Thr Asp Phe Thr Leu Lys Ile
65              70              75              80

Ser Arg Val Glu Ala Glu Asp Val Gly Val Tyr Tyr Cys Phe Gln Gly
                85              90              95

Ser His Val Pro Tyr Thr Phe Gly Gly Gly Thr Lys Leu Glu Ile Lys
            100             105             110

<210> SEQ ID NO 68
<211> LENGTH: 16
```

-continued

```
<212> TYPE: PRT
<213> ORGANISM: Mus musculus

<400> SEQUENCE: 68

Arg Ser Ser Gln Ser Ile Val His Ser Asn Gly Asn Thr Tyr Leu Glu
1               5                   10                  15

<210> SEQ ID NO 69
<211> LENGTH: 9
<212> TYPE: PRT
<213> ORGANISM: Mus musculus

<400> SEQUENCE: 69

Phe Gln Gly Ser His Val Pro Tyr Thr
1               5

<210> SEQ ID NO 70
<211> LENGTH: 118
<212> TYPE: PRT
<213> ORGANISM: Mus musculus

<400> SEQUENCE: 70

Glu Ala Gln Leu Val Glu Ser Gly Gly Ala Leu Val Lys Pro Gly Gly
1               5                   10                  15

Ser Leu Lys Leu Ser Cys Ser Ala Ser Gly Phe Thr Phe Ser Asn Tyr
            20                  25                  30

Ala Met Ser Trp Val Arg Gln Thr Pro Glu Lys Arg Leu Glu Trp Val
            35                  40                  45

Ala Thr Ile Ser Ser Gly Gly Thr Asn Thr Tyr Tyr Pro Gly Ser Val
        50                  55                  60

Lys Gly Arg Phe Thr Ile Ala Arg Asp Asn Ala Lys Asn Thr Leu Tyr
65                  70                  75                  80

Leu Leu Met Ser Ser Leu Arg Ser Glu Asp Thr Ala Leu Tyr Phe Cys
                85                  90                  95

Ala Arg Tyr Ser Asn Leu Ala Trp Phe Ala Ser Trp Gly Gln Gly Thr
            100                 105                 110

Leu Val Thr Val Ser Ala
        115

<210> SEQ ID NO 71
<211> LENGTH: 17
<212> TYPE: PRT
<213> ORGANISM: Mus musculus

<400> SEQUENCE: 71

Thr Ile Ser Ser Gly Gly Thr Asn Thr Tyr Tyr Pro Gly Ser Val Lys
1               5                   10                  15

Gly

<210> SEQ ID NO 72
<211> LENGTH: 9
<212> TYPE: PRT
<213> ORGANISM: Mus musculus

<400> SEQUENCE: 72

Tyr Ser Asn Leu Ala Trp Phe Ala Ser
1               5

<210> SEQ ID NO 73
<211> LENGTH: 112
<212> TYPE: PRT
```

<213> ORGANISM: Mus musculus

<400> SEQUENCE: 73

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Phe Leu Ile Ser Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Tyr Cys Phe Gln Gly
                85                  90                  95

Ser His Val Pro Tyr Thr Phe Gly Gly Gly Thr Lys Leu Glu Ile Lys
            100                 105                 110
```

<210> SEQ ID NO 74
<211> LENGTH: 118
<212> TYPE: PRT
<213> ORGANISM: Mus musculus

<400> SEQUENCE: 74

```
Gly Val Gln Leu Val Glu Ser Gly Gly Ala Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Thr Thr Leu Tyr
65                  70                  75                  80

Leu Gln Met Ser Gly Leu Arg Ser Glu Asp Thr Ala Leu Tyr Tyr Cys
                85                  90                  95

Ala Lys Tyr Ser Asn Tyr Gly Arg Phe Ala Ser Trp Gly Gln Gly Thr
            100                 105                 110

Leu Val Thr Val Ser Thr
        115
```

<210> SEQ ID NO 75
<211> LENGTH: 9
<212> TYPE: PRT
<213> ORGANISM: Mus musculus

<400> SEQUENCE: 75

```
Tyr Ser Asn Tyr Gly Arg Phe Ala Ser
1               5
```

<210> SEQ ID NO 76
<211> LENGTH: 112
<212> TYPE: PRT
<213> ORGANISM: Mus musculus

<400> SEQUENCE: 76

```
Asp Val Leu Met Thr Gln Thr Pro Leu Ser Leu Pro Val Ser Leu Gly
1               5                   10                  15
```

-continued

```
Asp Gln Ala Ser Ile Ser Cys Arg Ser Ser Gln Ser Ile Val His Ser
            20                  25                  30

Ser Gly Asn Thr Tyr Leu Glu Trp Tyr Leu Gln Lys Pro Gly Gln Ser
            35                  40                  45

Pro Arg Leu Leu Ile Tyr Lys Val Ser Asn Arg Phe Phe Gly Val Pro
            50                  55                  60

Asp Arg Ile Ser Gly Ser Gly Ser Gly Thr Asp Phe Thr Leu Arg Ile
65                  70                  75                  80

Ser Arg Val Glu Ala Glu Asp Leu Gly Val Tyr Tyr Cys Phe Gln Gly
                    85                  90                  95

Ser His Val Pro Tyr Thr Phe Gly Gly Gly Thr Lys Leu Glu Ile Lys
            100                 105                 110
```

<210> SEQ ID NO 77
<211> LENGTH: 16
<212> TYPE: PRT
<213> ORGANISM: Mus musculus

<400> SEQUENCE: 77

```
Arg Ser Ser Gln Ser Ile Val His Ser Ser Gly Asn Thr Tyr Leu Glu
1               5                   10                  15
```

<210> SEQ ID NO 78
<211> LENGTH: 7
<212> TYPE: PRT
<213> ORGANISM: Mus musculus

<400> SEQUENCE: 78

```
Lys Val Ser Asn Arg Phe Phe
1               5
```

<210> SEQ ID NO 79
<211> LENGTH: 112
<212> TYPE: PRT
<213> ORGANISM: Mus musculus

<400> SEQUENCE: 79

```
Asp Ile Gln Met Thr Gln Ser Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Thr Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                    85                  90                  95

Ser His Val Pro Phe Thr Phe Gly Ser Gly Thr Lys Leu Glu Ile Lys
            100                 105                 110
```

<210> SEQ ID NO 80
<211> LENGTH: 9
<212> TYPE: PRT
<213> ORGANISM: Mus musculus

<400> SEQUENCE: 80

```
Phe Gln Gly Ser His Val Pro Phe Thr
1               5
```

<210> SEQ ID NO 81
<211> LENGTH: 118
<212> TYPE: PRT
<213> ORGANISM: Mus musculus

<400> SEQUENCE: 81

Glu Val Gln Leu Val Glu Ser Gly Gly Ala Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Leu Ser Ser Gly Gly Thr Asn Thr Tyr Tyr Ser Asp Ser Val
    50                  55                  60

Lys Gly Arg Phe Thr Ile Ser Arg Asp Asn Val Lys Asn Thr Leu Tyr
65                  70                  75                  80

Leu Gln Met Ser Ser Leu Arg Ser Glu Asp Thr Ala Leu Tyr Tyr Cys
                85                  90                  95

Ala Arg Tyr Ser Asn Leu Ala Trp Phe Ala Tyr Trp Gly Gln Gly Thr
            100                 105                 110

Leu Val Thr Val Ser Ala
        115

<210> SEQ ID NO 82
<211> LENGTH: 17
<212> TYPE: PRT
<213> ORGANISM: Mus musculus

<400> SEQUENCE: 82

Thr Leu Ser Ser Gly Gly Thr Asn Thr Tyr Tyr Ser Asp Ser Val Lys
1               5                   10                  15

Gly

<210> SEQ ID NO 83
<211> LENGTH: 9
<212> TYPE: PRT
<213> ORGANISM: Mus musculus

<400> SEQUENCE: 83

Tyr Ser Asn Leu Ala Trp Phe Ala Tyr
1               5

<210> SEQ ID NO 84
<211> LENGTH: 112
<212> TYPE: PRT
<213> ORGANISM: Mus musculus

<400> SEQUENCE: 84

Asp Ile Val Met Thr Gln Ser Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Thr Gly Asn Thr Tyr Leu Glu Trp Tyr Leu Gln Lys Pro Gly Gln Ser
        35                  40                  45

Pro Lys Phe Leu Ile Ser Lys Val Ser Asn Arg Phe Ser Gly Val Pro
    50                  55                  60

Glu Arg Phe Ser Gly Ser Gly Ser Gly Thr Asp Phe Thr Leu Lys Ile
65                  70                  75                  80

-continued

```
Ser Arg Val Glu Ala Glu Asp Leu Gly Val Tyr Tyr Cys Phe Gln Gly
            85                  90                  95

Ser His Val Pro Tyr Thr Phe Gly Gly Gly Thr Lys Leu Glu Ile Lys
            100                 105                 110

<210> SEQ ID NO 85
<211> LENGTH: 119
<212> TYPE: PRT
<213> ORGANISM: Mus musculus

<400> SEQUENCE: 85

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
            35                  40                  45

Ala Thr Ile Ser Ser Gly Gly Gly Tyr Thr Tyr Tyr Pro Asp Ser Val
            50                  55                  60

Lys Gly Arg Phe Thr Ile Ser Arg Asp Asn Ala Arg Asn Thr Leu Tyr
65                  70                  75                  80

Leu Gln Met Ser Ser Leu Arg Ser Glu Asp Thr Ala Met Tyr Tyr Cys
            85                  90                  95

Ala Arg Gly Tyr Gly Asn Phe Ala Trp Phe Ala Tyr Trp Gly Gln Gly
            100                 105                 110

Thr Leu Val Thr Val Ser Ala
        115

<210> SEQ ID NO 86
<211> LENGTH: 17
<212> TYPE: PRT
<213> ORGANISM: Mus musculus

<400> SEQUENCE: 86

Thr Ile Ser Ser Gly Gly Gly Tyr Thr Tyr Tyr Pro Asp Ser Val Lys
1               5                   10                  15

Gly

<210> SEQ ID NO 87
<211> LENGTH: 119
<212> TYPE: PRT
<213> ORGANISM: Mus musculus

<400> SEQUENCE: 87

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
            35                  40                  45

Ala Thr Ile Ser Ser Gly Gly Gly Tyr Thr Tyr Tyr Pro Asp Ser Val
            50                  55                  60

Lys Gly Arg Phe Thr Ile Ser Arg Asp Asn Ala Arg Asn Thr Leu Tyr
65                  70                  75                  80

Leu Gln Met Ser Ser Leu Arg Ser Glu Asp Thr Ala Met Tyr Tyr Cys
            85                  90                  95

Ala Arg Gly Tyr Gly Asn Phe Ala Trp Phe Ala Tyr Trp Gly Gln Gly
```

```
            100                 105                 110

Thr Leu Val Thr Val Ser Ser
        115

<210> SEQ ID NO 88
<211> LENGTH: 118
<212> TYPE: PRT
<213> ORGANISM: Mus musculus

<400> SEQUENCE: 88

Glu Val Gln Leu Val Glu Ser Gly Gly Ala Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Leu Tyr Tyr Cys
                85                  90                  95

Ala Lys Tyr Ser Asn Tyr Gly Arg Phe Ala Tyr Trp Gly Gln Gly Thr
            100                 105                 110

Leu Val Thr Val Ser Ala
        115

<210> SEQ ID NO 89
<211> LENGTH: 9
<212> TYPE: PRT
<213> ORGANISM: Mus musculus

<400> SEQUENCE: 89

Tyr Ser Asn Tyr Gly Arg Phe Ala Tyr
1               5

<210> SEQ ID NO 90
<211> LENGTH: 112
<212> TYPE: PRT
<213> ORGANISM: Mus musculus

<400> SEQUENCE: 90

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Ile Val Asp Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Phe Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 91
```

-continued

```
<211> LENGTH: 16
<212> TYPE: PRT
<213> ORGANISM: Mus musculus

<400> SEQUENCE: 91

Arg Ser Ser Gln Ser Ile Val Asp Ser Asn Gly Asn Thr Tyr Leu Glu
1               5                   10                  15

<210> SEQ ID NO 92
<211> LENGTH: 118
<212> TYPE: PRT
<213> ORGANISM: Mus musculus

<400> SEQUENCE: 92

Glu Val Gln Leu Val Glu Ser Gly Gly Ala Leu Met Lys Pro Gly Gly
1               5                   10                  15

Ser Leu Lys Phe Ser Cys Ala Ala Ser Gly Phe Thr Phe Thr Asn Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Ser Asn Thr Tyr Tyr Ser Asp Ser Val
    50                  55                  60

Lys Gly Arg Phe Thr Ile Ser Arg Asp Asn Ala Lys Thr Thr Leu Tyr
65                  70                  75                  80

Leu Gln Met Ser Gly Leu Arg Ser Glu Asp Thr Ala Leu Tyr Tyr Cys
                85                  90                  95

Ala Lys Phe Ser Asn Phe Gly Arg Phe Ala Ser Trp Gly Gln Gly Thr
            100                 105                 110

Leu Val Thr Val Ser Ala
        115

<210> SEQ ID NO 93
<211> LENGTH: 17
<212> TYPE: PRT
<213> ORGANISM: Mus musculus

<400> SEQUENCE: 93

Thr Ile Ser Ser Gly Gly Ser Asn Thr Tyr Tyr Ser Asp Ser Val Lys
1               5                   10                  15

Gly

<210> SEQ ID NO 94
<211> LENGTH: 9
<212> TYPE: PRT
<213> ORGANISM: Mus musculus

<400> SEQUENCE: 94

Phe Ser Asn Phe Gly Arg Phe Ala Ser
1               5

<210> SEQ ID NO 95
<211> LENGTH: 112
<212> TYPE: PRT
<213> ORGANISM: Mus musculus

<400> SEQUENCE: 95

Asp Val Leu Met Thr Gln Thr Pro Leu Ser Leu Pro Val Ser Leu Gly
1               5                   10                  15

Asp Gln Ala Ser Ile Ser Cys Arg Phe Ser Gln Ser Ile Val His Ser
            20                  25                  30
```

```
Ser Gly Asn Thr Tyr Leu Glu Trp Tyr Leu Gln Lys Pro Gly Gln Ser
        35                  40                  45

Pro Arg Leu Leu Ile Tyr Lys Val Ser Asn Arg Phe Phe Gly Val Pro
    50                  55                  60

Asp Arg Ile Ser Gly Ser Gly Ser Gly Thr Asp Phe Thr Leu Arg Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110
```

<210> SEQ ID NO 96
<211> LENGTH: 16
<212> TYPE: PRT
<213> ORGANISM: Mus musculus

<400> SEQUENCE: 96

```
Arg Phe Ser Gln Ser Ile Val His Ser Ser Gly Asn Thr Tyr Leu Glu
1               5                   10                  15
```

<210> SEQ ID NO 97
<211> LENGTH: 118
<212> TYPE: PRT
<213> ORGANISM: Mus musculus

<400> SEQUENCE: 97

```
Glu Val Gln Leu Val Glu Ser Gly Gly Ala Leu Val Lys Pro Gly Gly
1               5                   10                  15

Ser Leu Lys Leu Ser Cys Ala Ala Ser Gly Phe Thr Phe Ser Asn Tyr
        20                  25                  30

Ala Met Ser Trp Val Arg Gln Thr Pro Glu Lys Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Leu Tyr Tyr Cys
                85                  90                  95

Thr Lys Tyr Ser Asn Tyr Gly Arg Phe Ala Tyr Trp Gly Gln Gly Thr
            100                 105                 110

Leu Val Thr Val Ser Thr
            115
```

<210> SEQ ID NO 98
<211> LENGTH: 112
<212> TYPE: PRT
<213> ORGANISM: Mus musculus

<400> SEQUENCE: 98

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
        20                  25                  30

Thr Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
```

-continued

```
65              70              75              80

Ser Arg Val Glu Ala Glu Asp Leu Gly Val Tyr Tyr Cys Phe Gln Gly
            85              90              95

Ser His Ile Pro Tyr Thr Phe Gly Gly Gly Thr Lys Leu Glu Ile Lys
            100             105             110

<210> SEQ ID NO 99
<211> LENGTH: 118
<212> TYPE: PRT
<213> ORGANISM: Mus musculus

<400> SEQUENCE: 99

Glu Val Gln Leu Val Glu Ser Gly Gly Ala Leu Val Lys Pro Gly Gly
1               5               10              15

Ser Leu Lys Leu Ser Cys Ala Ala Ser Gly Phe Thr Phe Ser Asn Tyr
            20              25              30

Ala Met Ser Trp Val Arg Gln Thr Pro Glu Lys Arg Leu Glu Trp Val
            35              40              45

Ala Thr Ile Ser Ser Val Gly Ser Tyr Thr Tyr Tyr Pro Asp Ser Val
        50              55              60

Lys Gly Arg Phe Thr Ile Ser Arg Asp Asn Ala Lys Thr Thr Leu Tyr
65              70              75              80

Leu Gln Met Ser Gly Leu Arg Ser Glu Asp Thr Ala Leu Tyr Tyr Cys
            85              90              95

Ala Lys Tyr Ser Asn Tyr Gly Arg Phe Ala Ser Trp Gly Gln Gly Thr
            100             105             110

Leu Val Thr Val Ser Thr
            115

<210> SEQ ID NO 100
<211> LENGTH: 17
<212> TYPE: PRT
<213> ORGANISM: Mus musculus

<400> SEQUENCE: 100

Thr Ile Ser Ser Val Gly Ser Tyr Thr Tyr Tyr Pro Asp Ser Val Lys
1               5               10              15

Gly

<210> SEQ ID NO 101
<211> LENGTH: 112
<212> TYPE: PRT
<213> ORGANISM: Mus musculus

<400> SEQUENCE: 101

Asp Val Leu Met Thr Gln Thr Pro Leu Ser Leu Pro Ala Ser Leu Gly
1               5               10              15

Asp Gln Ala Ser Ile Ser Cys Arg Ser Ser Gln Ser Ile Val His Ser
            20              25              30

Ser Gly Asn Thr Tyr Leu Glu Trp Tyr Leu Gln Lys Pro Gly Gln Ser
            35              40              45

Pro Arg Leu Leu Ile Tyr Lys Val Ser Asn Arg Phe Phe Gly Val Pro
        50              55              60

Asp Arg Ile Ser Gly Ser Gly Ser Gly Thr Asp Phe Thr Leu Arg Ile
65              70              75              80

Ser Arg Val Glu Ala Glu Asp Leu Gly Val Tyr Tyr Cys Phe Gln Gly
            85              90              95
```

-continued

```
Ser His Val Pro Tyr Thr Phe Gly Gly Gly Thr Lys Leu Glu Ile Glu
        100                     105                     110

<210> SEQ ID NO 102
<211> LENGTH: 118
<212> TYPE: PRT
<213> ORGANISM: Mus musculus

<400> SEQUENCE: 102

Glu Val Lys Leu Val Glu Ser Gly Gly Ala Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Thr Thr Leu Tyr
65                  70                  75                  80

Leu Gln Met Ser Gly Leu Arg Ser Glu Asp Thr Ala Leu Tyr Tyr Cys
                85                  90                  95

Ala Lys Phe Ser Asn Tyr Gly Arg Phe Ala Ser Trp Gly Gln Gly Thr
            100                 105                 110

Leu Val Thr Val Ser Ser
        115

<210> SEQ ID NO 103
<211> LENGTH: 9
<212> TYPE: PRT
<213> ORGANISM: Mus musculus

<400> SEQUENCE: 103

Phe Ser Asn Tyr Gly Arg Phe Ala Ser
1               5

<210> SEQ ID NO 104
<211> LENGTH: 112
<212> TYPE: PRT
<213> ORGANISM: Mus musculus

<400> SEQUENCE: 104

Asp Ile Gln Met Ile Gln Ser Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Ser Gly Asn Thr Tyr Leu Glu Trp Tyr Leu Gln Lys Pro Gly Gln Ser
        35                  40                  45

Pro Arg Leu Leu Ile Tyr Lys Val Ser Asn Arg Phe Phe Gly Val Pro
    50                  55                  60

Asp Arg Ile Ser Gly Ser Gly Ser Gly Thr Asp Phe Thr Leu Arg Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Leu Lys
            100                 105                 110

<210> SEQ ID NO 105
<211> LENGTH: 119
<212> TYPE: PRT
```

<213> ORGANISM: Mus musculus

<400> SEQUENCE: 105

Glu Val Gln Leu Val Glu Ser Gly Gly Ala Leu Val Lys Pro Gly Gly
1               5                   10                  15

Ser Leu Lys Leu Ser Cys Ala Ala Ser Gly Phe Thr Phe Ser Asn Tyr
            20                  25                  30

Gly Met Ser Trp Val Arg Gln Thr Pro Glu Lys Arg Leu Glu Trp Val
        35                  40                  45

Ala Thr Ile Ser Ser Gly Gly Ser Tyr Thr Tyr Tyr Pro Asp Thr Val
    50                  55                  60

Lys Gly Arg Phe Thr Ile Ser Arg Asp Asn Ala Lys Asn Thr Leu His
65                  70                  75                  80

Leu Gln Met Ser Ser Leu Arg Ser Glu Asp Thr Ala Leu Tyr Tyr Cys
                85                  90                  95

Ala Arg Arg Gly Thr Asn Asp Ala Trp Phe Gly Tyr Trp Gly Gln Gly
            100                 105                 110

Thr Leu Val Thr Val Ser Ala
        115

<210> SEQ ID NO 106
<211> LENGTH: 5
<212> TYPE: PRT
<213> ORGANISM: Mus musculus

<400> SEQUENCE: 106

Asn Tyr Gly Met Ser
1               5

<210> SEQ ID NO 107
<211> LENGTH: 17
<212> TYPE: PRT
<213> ORGANISM: Mus musculus

<400> SEQUENCE: 107

Thr Ile Ser Ser Gly Gly Ser Tyr Thr Tyr Tyr Pro Asp Thr Val Lys
1               5                   10                  15

Gly

<210> SEQ ID NO 108
<211> LENGTH: 10
<212> TYPE: PRT
<213> ORGANISM: Mus musculus

<400> SEQUENCE: 108

Arg Gly Thr Asn Asp Ala Trp Phe Gly Tyr
1               5                   10

<210> SEQ ID NO 109
<211> LENGTH: 113
<212> TYPE: PRT
<213> ORGANISM: Mus musculus

<400> SEQUENCE: 109

Asp Val Val Met Thr Gln Thr Pro Leu Ser Leu Pro Val Ser Leu Gly
1               5                   10                  15

Asp Gln Ala Ser Ile Ser Cys Arg Phe Ser Gln Ser Ile Val His Ser
            20                  25                  30

Asn Gly Asn Thr Tyr Leu Glu Trp Tyr Leu Gln Lys Pro Gly Gln Ser
        35                  40                  45

-continued

```
Pro Lys Leu Leu Ile Tyr Lys Val Ser Asn Arg Phe Phe Gly Val Pro
    50              55              60

Asp Arg Phe Ser Gly Ser Gly Ser Gly Thr Asp Phe Thr Leu Lys Ile
65              70              75              80

Ser Arg Val Glu Ala Glu Asp Leu Gly Val Tyr Phe Cys Phe Gln Gly
                85              90              95

Ser His Val Pro Gln Tyr Thr Phe Gly Gly Gly Thr Lys Leu Glu Ile
            100             105             110

Lys

<210> SEQ ID NO 110
<211> LENGTH: 16
<212> TYPE: PRT
<213> ORGANISM: Mus musculus

<400> SEQUENCE: 110

Arg Phe Ser Gln Ser Ile Val His Ser Asn Gly Asn Thr Tyr Leu Glu
1               5               10              15

<210> SEQ ID NO 111
<211> LENGTH: 10
<212> TYPE: PRT
<213> ORGANISM: Mus musculus

<400> SEQUENCE: 111

Phe Gln Gly Ser His Val Pro Gln Tyr Thr
1               5               10

<210> SEQ ID NO 112
<211> LENGTH: 118
<212> TYPE: PRT
<213> ORGANISM: Mus musculus

<400> SEQUENCE: 112

Glu Val Gln Leu Val Glu Ser Gly Gly Ala Leu Val Lys Pro Gly Gly
1               5               10              15

Ser Leu Lys Leu Ser Cys Ala Ala Ser Gly Phe Thr Phe Ser Asn Tyr
            20              25              30

Ala Met Ser Trp Val Arg Gln Thr Pro Glu Thr Arg Leu Glu Trp Val
        35              40              45

Ala Thr Ile Ser Ser Gly Gly Ser Tyr Thr Tyr Tyr Pro Asp Ser Val
    50              55              60

Lys Gly Arg Phe Thr Ile Ser Arg Asp Asn Ala Lys Asn Thr Leu Tyr
65              70              75              80

Leu Gln Met Ser Ser Leu Arg Ser Glu Asp Thr Ala Leu Tyr Tyr Cys
                85              90              95

Ala Arg Tyr Ser Asn Leu Ala Trp Phe Ala Tyr Trp Gly Gln Gly Thr
            100             105             110

Leu Val Thr Val Ser Ala
        115

<210> SEQ ID NO 113
<211> LENGTH: 112
<212> TYPE: PRT
<213> ORGANISM: Mus musculus

<400> SEQUENCE: 113

Asp Val Val Met Thr Gln Thr Pro Leu Ser Leu Pro Val Ser Leu Gly
1               5               10              15
```

-continued

```
Asp Gln Ala Ser Ile Ser Cys Arg Ser Ser Gln Ser Ile Val His Ser
            20                  25                  30

Asn Gly Asn Thr Tyr Leu Asp Trp Tyr Leu Gln Lys Pro Gly Gln Ser
            35                  40                  45

Pro Lys Phe Met Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110
```

<210> SEQ ID NO 114
<211> LENGTH: 112
<212> TYPE: PRT
<213> ORGANISM: Mus musculus

<400> SEQUENCE: 114

```
Asp Val Leu Met Thr Gln Thr Pro Leu Ser Leu Pro Ala Ser Leu Gly
1               5                   10                  15

Asp Gln Ala Ser Ile Ser Cys Arg Phe Ser Gln Ser Ile Val His Ser
            20                  25                  30

Ser Gly Asn Thr Tyr Leu Glu Trp Tyr Leu Gln Lys Pro Gly Gln Ser
            35                  40                  45

Pro Arg Leu Leu Ile Tyr Lys Val Ser Asn Arg Phe Phe Gly Val Pro
    50                  55                  60

Asp Arg Ile Ser Gly Ser Gly Ser Gly Thr Asp Phe Thr Leu Arg Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Glu
            100                 105                 110
```

<210> SEQ ID NO 115
<211> LENGTH: 118
<212> TYPE: PRT
<213> ORGANISM: Mus musculus

<400> SEQUENCE: 115

```
Glu Ala Gln Leu Val Glu Ser Gly Gly Ala Leu Val Lys Pro Gly Gly
1               5                   10                  15

Ser Leu Lys Leu Ser Cys Ser Ala Ser Gly Phe Thr Phe Ser Asn Tyr
            20                  25                  30

Ala Met Ser Trp Val Arg Gln Thr Pro Glu Lys Arg Leu Glu Trp Val
            35                  40                  45

Ala Thr Ile Ser Ser Gly Gly Thr Asn Thr Tyr Tyr Pro Gly Ser Val
    50                  55                  60

Lys Gly Arg Phe Thr Ile Ala Arg Asp Asn Ala Lys Asn Thr Leu Tyr
65                  70                  75                  80

Leu Leu Met Ser Ser Leu Arg Ser Glu Asp Thr Ala Leu Tyr Phe Cys
                85                  90                  95

Ala Lys Tyr Ser Asn Leu Ala Trp Phe Ala Ser Trp Gly Gln Gly Thr
            100                 105                 110

Leu Val Thr Val Ser Ala
            115
```

-continued

```
<210> SEQ ID NO 116
<211> LENGTH: 112
<212> TYPE: PRT
<213> ORGANISM: Mus musculus

<400> SEQUENCE: 116

Gln Ile Val Leu Thr Gln Ser Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Ile Gly Asn Thr Tyr Leu Glu Trp Tyr Leu Gln Lys Pro Gly Gln Ser
        35                  40                  45

Pro Lys Phe Leu Ile Ser Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 117
<211> LENGTH: 16
<212> TYPE: PRT
<213> ORGANISM: Mus musculus

<400> SEQUENCE: 117

Arg Ser Ser Gln Ser Leu Val His Ser Ile Gly Asn Thr Tyr Leu Glu
1               5                   10                  15

<210> SEQ ID NO 118
<211> LENGTH: 122
<212> TYPE: PRT
<213> ORGANISM: Mus musculus

<400> SEQUENCE: 118

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Val Val Ile Trp Ser Asp Gly Ser Thr Thr Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Ile Asp Asp Thr Ala Met Tyr Tyr Cys Ala
                85                  90                  95

Arg His Gly Arg Trp Leu Leu Gln Arg Gly Gly Ala Met Asp Tyr Trp
            100                 105                 110

Gly Gln Gly Thr Ser Val Thr Val Ser Ser
        115                 120

<210> SEQ ID NO 119
<211> LENGTH: 5
<212> TYPE: PRT
<213> ORGANISM: Mus musculus
```

-continued

<400> SEQUENCE: 119

Ser Tyr Gly Val His
1               5

<210> SEQ ID NO 120
<211> LENGTH: 16
<212> TYPE: PRT
<213> ORGANISM: Mus musculus

<400> SEQUENCE: 120

Val Ile Trp Ser Asp Gly Ser Thr Thr Tyr Asn Ser Ala Leu Lys Ser
1               5                   10                  15

<210> SEQ ID NO 121
<211> LENGTH: 14
<212> TYPE: PRT
<213> ORGANISM: Mus musculus

<400> SEQUENCE: 121

His Gly Arg Trp Leu Leu Gln Arg Gly Gly Ala Met Asp Tyr
1               5                   10

<210> SEQ ID NO 122
<211> LENGTH: 107
<212> TYPE: PRT
<213> ORGANISM: Mus musculus

<400> SEQUENCE: 122

Asp Val Val Met Thr Gln Ala Pro Lys Phe Met Ser Thr Ser Val Gly
1               5                   10                  15

Asp Arg Val Ser Val Thr Cys Arg Ala Ser Gln Asn Val Gly Ser Tyr
                20                  25                  30

Ile Ala Trp Tyr Gln Gln Lys Leu Gly Gln Ser Pro Lys Ala Leu Ile
            35                  40                  45

Tyr Ser Ala Ser Tyr Arg Cys Ser Gly Val Pro Asp Arg Phe Thr Gly
        50                  55                  60

Ser Gly Ala Gly Thr Asp Phe Thr Leu Thr Ile Arg Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Gly Gly Thr Lys Leu Glu Ile Lys
            100                 105

<210> SEQ ID NO 123
<211> LENGTH: 11
<212> TYPE: PRT
<213> ORGANISM: Mus musculus

<400> SEQUENCE: 123

Arg Ala Ser Gln Asn Val Gly Ser Tyr Ile Ala
1               5                   10

<210> SEQ ID NO 124
<211> LENGTH: 7
<212> TYPE: PRT
<213> ORGANISM: Mus musculus

<400> SEQUENCE: 124

Ser Ala Ser Tyr Arg Cys Ser
1               5

<210> SEQ ID NO 125
<211> LENGTH: 9
<212> TYPE: PRT
<213> ORGANISM: Mus musculus

<400> SEQUENCE: 125

Gln Gln Tyr Asn Ser Tyr Pro Leu Thr
1               5

<210> SEQ ID NO 126
<211> LENGTH: 122
<212> TYPE: PRT
<213> ORGANISM: Mus musculus

<400> SEQUENCE: 126

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Val Val Ile Trp Ser Asp Gly Ser Thr Thr Tyr Asn Ser Ala Leu Lys
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg His Gly Arg Trp Leu Leu Gln Arg Gly Gly Ala Met Asp Tyr Trp
            100                 105                 110

Gly Gln Gly Thr Met Val Thr Val Ser Ser
        115                 120

<210> SEQ ID NO 127
<211> LENGTH: 107
<212> TYPE: PRT
<213> ORGANISM: Mus musculus

<400> SEQUENCE: 127

Asp Val Gln Met Thr Gln Ser Pro Ser Ser Leu Ser Ala Ser Val Gly
1               5                   10                  15

Asp Arg Val Thr Ile Thr Cys Arg Ala Ser Gln Asn Val Gly Ser Tyr
            20                  25                  30

Ile Ala Trp Tyr Gln Gln Lys Pro Gly Lys Ser Pro Lys Ala Leu Ile
        35                  40                  45

Tyr Ser Ala Ser Tyr Arg Ser Ser Gly Val Pro Ser Arg Phe Ser Gly
    50                  55                  60

Ser Gly Ala Gly Thr Asp Phe Thr Leu Thr Ile Ser Ser Leu Gln Pro
65                  70                  75                  80

Glu Asp Phe Ala Thr Tyr Phe Cys Gln Gln Tyr Asn Ser Tyr Pro Leu
                85                  90                  95

Thr Phe Gly Gly Gly Thr Lys Leu Glu Ile Lys
            100                 105

<210> SEQ ID NO 128
<211> LENGTH: 7
<212> TYPE: PRT
<213> ORGANISM: Mus musculus

<400> SEQUENCE: 128

```
Ser Ala Ser Tyr Arg Ser Ser
1               5

<210> SEQ ID NO 129
<211> LENGTH: 122
<212> TYPE: PRT
<213> ORGANISM: Mus musculus

<400> SEQUENCE: 129

Glu Val Gln Leu Val Glu Ser Gly Gly Gly Leu Ile Gln Pro Gly Gly
1               5                   10                  15

Ser Leu Arg Leu Ser Cys Ala Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Val Val Ile Trp Ser Asp Gly Ser Thr Thr Tyr Asn Ser Ala Leu Lys
    50                  55                  60

Ser Arg Leu Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
            85                  90                  95

Arg His Gly Arg Trp Leu Leu Gln Arg Gly Gly Ala Met Asp Tyr Trp
            100                 105                 110

Gly Gln Gly Thr Met Val Thr Val Ser Ser
        115                 120

<210> SEQ ID NO 130
<211> LENGTH: 122
<212> TYPE: PRT
<213> ORGANISM: Mus musculus

<400> SEQUENCE: 130

Gln Val Gln Met Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Val Val Ile Trp Ser Asp Gly Ser Thr Thr Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Ile Asp Asp Thr Ala Met Tyr Tyr Cys Ala
            85                  90                  95

Arg His Gly Arg Trp Leu Leu Gln Arg Gly Gly Ala Met Asp Tyr Trp
            100                 105                 110

Gly Gln Gly Thr Ser Val Thr Val Ser Ser
        115                 120

<210> SEQ ID NO 131
<211> LENGTH: 107
<212> TYPE: PRT
<213> ORGANISM: Mus musculus

<400> SEQUENCE: 131

Asp Val Val Met Thr Gln Thr Pro Ser Phe Met Ser Thr Ser Val Gly
1               5                   10                  15

Asp Arg Val Ser Val Thr Cys Arg Ala Ser Gln Asn Val Gly Ser Tyr
```

-continued

```
             20              25              30

Val Ala Trp Tyr Gln Gln Lys Leu Gly Gln Ser Pro Lys Ala Leu Ile
         35              40              45

Tyr Ser Ala Ser Tyr Arg Cys Ser Gly Val Pro Asp Arg Phe Thr Gly
     50              55              60

Ser Gly Ala Gly Thr Asp Phe Thr Leu Thr Ile Arg Asn Val Gln Ser
65              70              75              80

Glu Asp Leu Ala Glu Tyr Phe Cys Gln Gln Tyr Asn Ser Tyr Pro Leu
             85              90              95

Thr Phe Gly Gly Gly Thr Lys Leu Glu Ile Lys
         100             105

<210> SEQ ID NO 132
<211> LENGTH: 11
<212> TYPE: PRT
<213> ORGANISM: Mus musculus

<400> SEQUENCE: 132

Arg Ala Ser Gln Asn Val Gly Ser Tyr Val Ala
1               5               10

<210> SEQ ID NO 133
<211> LENGTH: 118
<212> TYPE: PRT
<213> ORGANISM: Mus musculus

<400> SEQUENCE: 133

Glu Val Lys Leu Val Glu Ser Gly Gly Gly Leu Val Lys Pro Gly Gly
1               5               10              15

Ser Leu Lys Leu Ser Cys Ala Ala Ser Gly Phe Thr Phe Ser Asn Tyr
             20              25              30

Gly Met Ser Trp Val Arg Gln Thr Pro Glu Lys Arg Leu Glu Trp Val
         35              40              45

Ala Ala Ile Ser Ser Asn Gly Ala Tyr Thr Tyr Phe Pro Asp Thr Val
     50              55              60

Lys Gly Arg Phe Thr Ile Ser Arg Asp Asn Ala Lys Asn Thr Leu Tyr
65              70              75              80

Leu Gln Met Asn Ser Leu Arg Ser Glu Asp Thr Ala Leu Tyr Tyr Cys
             85              90              95

Thr Arg Arg Gly Trp Asp Thr Trp Phe Ala Tyr Trp Gly Gln Gly Thr
         100             105             110

Leu Val Thr Val Ser Ser
     115

<210> SEQ ID NO 134
<211> LENGTH: 17
<212> TYPE: PRT
<213> ORGANISM: Mus musculus

<400> SEQUENCE: 134

Ala Ile Ser Ser Asn Gly Ala Tyr Thr Tyr Phe Pro Asp Thr Val Lys
1               5               10              15

Gly

<210> SEQ ID NO 135
<211> LENGTH: 9
<212> TYPE: PRT
<213> ORGANISM: Mus musculus
```

<400> SEQUENCE: 135

Arg Gly Trp Asp Thr Trp Phe Ala Tyr
1               5

<210> SEQ ID NO 136
<211> LENGTH: 112
<212> TYPE: PRT
<213> ORGANISM: Mus musculus

<400> SEQUENCE: 136

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Thr Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 137
<211> LENGTH: 16
<212> TYPE: PRT
<213> ORGANISM: Mus musculus

<400> SEQUENCE: 137

Arg Ser Ser Gln Asn Ile Val His Ser Thr Gly Asn Thr Tyr Leu Glu
1               5                   10                  15

<210> SEQ ID NO 138
<211> LENGTH: 9
<212> TYPE: PRT
<213> ORGANISM: Mus musculus

<400> SEQUENCE: 138

Phe Gln Gly Ser His Val Pro Trp Thr
1               5

<210> SEQ ID NO 139
<211> LENGTH: 118
<212> TYPE: PRT
<213> ORGANISM: Mus musculus

<400> SEQUENCE: 139

Glu Val Lys Leu Val Glu Ser Gly Gly Ala Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Ser Asn Thr Tyr Tyr Pro Asp Ser Val
    50                  55                  60

Met Gly Arg Phe Thr Ile Ser Arg Asp Asn Ala Lys Asn Thr Leu Tyr
65                  70                  75                  80

-continued

```
Leu Gln Met Ser Ser Leu Arg Ser Glu Asp Thr Ala Leu Tyr Tyr Cys
                85              90                  95

Ala Arg Tyr Ser Asn Tyr Gly Trp Phe Ala Tyr Trp Gly Gln Gly Thr
            100             105             110

Leu Val Thr Val Ser Ser
        115

<210> SEQ ID NO 140
<211> LENGTH: 17
<212> TYPE: PRT
<213> ORGANISM: Mus musculus

<400> SEQUENCE: 140

Thr Ile Ser Ser Gly Gly Ser Asn Thr Tyr Tyr Pro Asp Ser Val Met
1               5                   10                  15

Gly

<210> SEQ ID NO 141
<211> LENGTH: 9
<212> TYPE: PRT
<213> ORGANISM: Mus musculus

<400> SEQUENCE: 141

Tyr Ser Asn Tyr Gly Trp Phe Ala Tyr
1               5

<210> SEQ ID NO 142
<211> LENGTH: 112
<212> TYPE: PRT
<213> ORGANISM: Mus musculus

<400> SEQUENCE: 142

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20              25                  30

Asn Gly Asn Thr Tyr Leu Glu Trp Tyr Leu Gln Lys Pro Gly Gln Ser
        35              40                  45

Pro Lys Leu Leu Ile Tyr Lys Val Ser Asn Arg Phe Ser Gly Val Pro
    50              55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85              90                  95

Ser Leu Val Pro Arg Thr Phe Gly Gly Gly Thr Lys Leu Glu Ile Lys
            100             105             110

<210> SEQ ID NO 143
<211> LENGTH: 9
<212> TYPE: PRT
<213> ORGANISM: Mus musculus

<400> SEQUENCE: 143

Phe Gln Gly Ser Leu Val Pro Arg Thr
1               5

<210> SEQ ID NO 144
<211> LENGTH: 119
<212> TYPE: PRT
<213> ORGANISM: Mus musculus
```

<400> SEQUENCE: 144

Glu Val Gln Leu Val Glu Ser Gly Gly Ala Ser Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Ser Tyr Thr Tyr Tyr Leu Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Leu Tyr Tyr Cys
                85                  90                  95

Ala Arg Tyr Tyr Val Tyr Asp Ala Trp Phe Ala Tyr Trp Gly Gln Gly
            100                 105                 110

Thr Leu Val Thr Val Ser Ala
        115

<210> SEQ ID NO 145
<211> LENGTH: 17
<212> TYPE: PRT
<213> ORGANISM: Mus musculus

<400> SEQUENCE: 145

Thr Ile Ser Ser Gly Gly Ser Tyr Thr Tyr Tyr Leu Asp Ser Val Lys
1               5                   10                  15

Gly

<210> SEQ ID NO 146
<211> LENGTH: 10
<212> TYPE: PRT
<213> ORGANISM: Mus musculus

<400> SEQUENCE: 146

Tyr Tyr Val Tyr Asp Ala Trp Phe Ala Tyr
1               5                   10

<210> SEQ ID NO 147
<211> LENGTH: 112
<212> TYPE: PRT
<213> ORGANISM: Mus musculus

<400> SEQUENCE: 147

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Thr Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Phe Tyr Cys Phe Gln Gly
                85                  90                  95

Ser His Val Pro Arg Thr Phe Gly Gly Gly Thr Lys Leu Glu Ile Lys
            100                 105                 110

<210> SEQ ID NO 148
<211> LENGTH: 120
<212> TYPE: PRT
<213> ORGANISM: Mus musculus

<400> SEQUENCE: 148

```
Glu Val Met Leu Val Glu Ser Gly Gly Ala Leu Val Lys Pro Gly Gly
1               5                   10                  15

Ser Leu Lys Leu Ser Cys Val Val Ser Gly Phe Thr Phe Ser Asn Tyr
            20                  25                  30

Ala Met Ser Trp Val Arg Arg Thr Pro Glu Lys Arg Leu Glu Trp Val
        35                  40                  45

Ala Thr Ile Ser Ser Asp Gly Thr Tyr Thr Tyr Tyr Pro Phe Ser Val
    50                  55                  60

Lys Gly Arg Phe Thr Ile Ser Arg Asp Asn Ala Arg Asn Ile Leu Tyr
65                  70                  75                  80

Leu Gln Met Ser Ser Leu Arg Ser Glu Asp Thr Ala Met Tyr Tyr Cys
                85                  90                  95

Gly Arg Gln Gly His Trp Gly Arg Thr Trp Phe Ala Tyr Trp Gly Gln
            100                 105                 110

Gly Thr Thr Leu Thr Val Ser Ser
        115                 120
```

<210> SEQ ID NO 149
<211> LENGTH: 17
<212> TYPE: PRT
<213> ORGANISM: Mus musculus

<400> SEQUENCE: 149

```
Thr Ile Ser Ser Asp Gly Thr Tyr Thr Tyr Tyr Pro Phe Ser Val Lys
1               5                   10                  15

Gly
```

<210> SEQ ID NO 150
<211> LENGTH: 11
<212> TYPE: PRT
<213> ORGANISM: Mus musculus

<400> SEQUENCE: 150

```
Gln Gly His Trp Gly Arg Thr Trp Phe Ala Tyr
1               5                   10
```

<210> SEQ ID NO 151
<211> LENGTH: 108
<212> TYPE: PRT
<213> ORGANISM: Mus musculus

<400> SEQUENCE: 151

```
Glu Asn Val Leu Thr Gln Ser Pro Ala Ile Met Ser Ala Ser Pro Gly
1               5                   10                  15

Glu Lys Val Thr Met Thr Cys Arg Ala Ser Ser Ser Val Ser Ser Ser
            20                  25                  30

Tyr Leu His Trp Phe Gln Gln Lys Ser Gly Ala Ser Pro Lys Leu Trp
        35                  40                  45

Ile Tyr Ser Thr Ser Ser Leu Ala Ser Gly Val Pro Ser Arg Phe Ser
    50                  55                  60

Gly Ser Gly Trp Gly Thr Ser Tyr Ser Leu Thr Ile Ser Ser Val Glu
65                  70                  75                  80
```

-continued

```
Gly Glu Asp Gly Ala Thr Tyr Tyr Cys Gln Gln Tyr Ser Gly Tyr Pro
                85                  90                  95

Leu Thr Phe Gly Ala Gly Thr Lys Leu Glu Leu Lys
            100                 105

<210> SEQ ID NO 152
<211> LENGTH: 12
<212> TYPE: PRT
<213> ORGANISM: Mus musculus

<400> SEQUENCE: 152

Arg Ala Ser Ser Ser Val Ser Ser Ser Tyr Leu His
1               5                   10

<210> SEQ ID NO 153
<211> LENGTH: 7
<212> TYPE: PRT
<213> ORGANISM: Mus musculus

<400> SEQUENCE: 153

Ser Thr Ser Ser Leu Ala Ser
1               5

<210> SEQ ID NO 154
<211> LENGTH: 9
<212> TYPE: PRT
<213> ORGANISM: Mus musculus

<400> SEQUENCE: 154

Gln Gln Tyr Ser Gly Tyr Pro Leu Thr
1               5

<210> SEQ ID NO 155
<211> LENGTH: 122
<212> TYPE: PRT
<213> ORGANISM: Mus musculus

<400> SEQUENCE: 155

Gln Val Gln Leu Gln Gln Ser Gly Pro Glu Leu Val Lys Thr Gly Ala
1               5                   10                  15

Ser Val Lys Ile Ser Cys Lys Ala Ser Gly Tyr Ser Phe Ser Asn Tyr
                20                  25                  30

Tyr Ile His Trp Val Lys Gln Ser His Gly Lys Ser Leu Glu Trp Ile
            35                  40                  45

Gly Phe Ile Ser Cys Tyr Asn Gly Ala Thr Phe Tyr Asn Gln Lys Phe
        50                  55                  60

Lys Gly Lys Ala Thr Phe Thr Val Asp Thr Ser Ser Ser Thr Ala Tyr
65                  70                  75                  80

Met Lys Phe Asn Ser Leu Thr Phe Glu Asp Ser Ala Val Tyr Tyr Cys
                85                  90                  95

Ala Arg Leu Pro Ile Gln Phe Gly Asn Phe Tyr Pro Met Asp Tyr Trp
            100                 105                 110

Gly Gln Gly Thr Ser Val Thr Val Ser Ser
            115                 120

<210> SEQ ID NO 156
<211> LENGTH: 5
<212> TYPE: PRT
<213> ORGANISM: Mus musculus

<400> SEQUENCE: 156
```

```
Asn Tyr Tyr Ile His
1               5

<210> SEQ ID NO 157
<211> LENGTH: 17
<212> TYPE: PRT
<213> ORGANISM: Mus musculus

<400> SEQUENCE: 157

Phe Ile Ser Cys Tyr Asn Gly Ala Thr Phe Tyr Asn Gln Lys Phe Lys
1               5                   10                  15

Gly

<210> SEQ ID NO 158
<211> LENGTH: 13
<212> TYPE: PRT
<213> ORGANISM: Mus musculus

<400> SEQUENCE: 158

Leu Pro Ile Gln Phe Gly Asn Phe Tyr Pro Met Asp Tyr
1               5                   10

<210> SEQ ID NO 159
<211> LENGTH: 108
<212> TYPE: PRT
<213> ORGANISM: Mus musculus

<400> SEQUENCE: 159

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Pro Thr Phe Gly Ala Gly Thr Lys Leu Glu Leu Lys
            100                 105

<210> SEQ ID NO 160
<211> LENGTH: 12
<212> TYPE: PRT
<213> ORGANISM: Mus musculus

<400> SEQUENCE: 160

Thr Ala Ser Ser Ser Val Ser Ser Ser Tyr Leu His
1               5                   10

<210> SEQ ID NO 161
<211> LENGTH: 7
<212> TYPE: PRT
<213> ORGANISM: Mus musculus

<400> SEQUENCE: 161

Ser Thr Ser Asn Leu Ala Ser
1               5
```

-continued

```
<210> SEQ ID NO 162
<211> LENGTH: 9
<212> TYPE: PRT
<213> ORGANISM: Mus musculus

<400> SEQUENCE: 162

His Gln Tyr His Arg Ser Pro Pro Thr
1               5

<210> SEQ ID NO 163
<211> LENGTH: 118
<212> TYPE: PRT
<213> ORGANISM: Mus musculus

<400> SEQUENCE: 163

Glu Val Met Leu Val Glu Ser Gly Gly Ala Leu Val Lys Pro Gly Gly
1               5                   10                  15

Ser Leu Lys Val Ser Cys Ala Ala Ser Gly Phe Thr Phe Ser Asn Tyr
            20                  25                  30

Ala Met Ser Trp Val Arg Gln Ser Pro Glu Met Arg Leu Glu Trp Val
        35                  40                  45

Ala Thr Ile Ser Ser Gly Gly Thr Asn Thr Tyr Tyr Pro Asp Ser Val
    50                  55                  60

Lys Gly Arg Phe Thr Ile Ser Arg Asp Asn Ala Arg Asn Thr Leu Tyr
65                  70                  75                  80

Leu Gln Met Ser Ser Leu Arg Ser Lys Asp Thr Ala Met Tyr Tyr Cys
                85                  90                  95

Ala Arg Tyr Ser Asn Tyr Gly Trp Phe Pro Tyr Trp Gly Gln Gly Thr
            100                 105                 110

Thr Leu Thr Val Ser Ser
        115

<210> SEQ ID NO 164
<211> LENGTH: 17
<212> TYPE: PRT
<213> ORGANISM: Mus musculus

<400> SEQUENCE: 164

Thr Ile Ser Ser Gly Gly Thr Asn Thr Tyr Tyr Pro Asp Ser Val Lys
1               5                   10                  15

Gly

<210> SEQ ID NO 165
<211> LENGTH: 9
<212> TYPE: PRT
<213> ORGANISM: Mus musculus

<400> SEQUENCE: 165

Tyr Ser Asn Tyr Gly Trp Phe Pro Tyr
1               5

<210> SEQ ID NO 166
<211> LENGTH: 112
<212> TYPE: PRT
<213> ORGANISM: Mus musculus

<400> SEQUENCE: 166

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Ser
            20                  25                  30
```

-continued

Asp Gly Tyr Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
                100                 105                 110

<210> SEQ ID NO 167
<211> LENGTH: 16
<212> TYPE: PRT
<213> ORGANISM: Mus musculus

<400> SEQUENCE: 167

Arg Ser Ser Gln Thr Ile Val His Ser Asp Gly Tyr Thr Tyr Leu Glu
1                   5                   10                  15

<210> SEQ ID NO 168
<211> LENGTH: 120
<212> TYPE: PRT
<213> ORGANISM: Mus musculus

<400> SEQUENCE: 168

Glu Val Lys Leu Val Glu Ser Gly Gly Ala Leu Val Lys Pro Gly Gly
1                   5                   10                  15

Ser Leu Lys Leu Ser Cys Ala Ala Ser Gly Phe Thr Phe Arg Asn Tyr
                20                  25                  30

Ala Met Ser Trp Val Arg Gln Thr Pro Glu Lys Arg Leu Glu Trp Val
        35                  40                  45

Ala Thr Ile Ser Ser Asp Gly Ser Tyr Thr Tyr His Pro Asp Ser Val
        50                  55                  60

Lys Gly Arg Phe Thr Ile Ser Arg Asp Asn Ala Arg Asn Thr Leu Tyr
65                  70                  75                  80

Leu Gln Met Ser Ser Leu Arg Ser Glu Asp Thr Ala Met Tyr Ser Cys
                85                  90                  95

Thr Arg Gln Gly Asn Trp Gly Arg Thr Trp Phe Thr Tyr Trp Gly Gln
                100                 105                 110

Gly Thr Leu Val Thr Val Ser Ser
        115                 120

<210> SEQ ID NO 169
<211> LENGTH: 17
<212> TYPE: PRT
<213> ORGANISM: Mus musculus

<400> SEQUENCE: 169

Thr Ile Ser Ser Asp Gly Ser Tyr Thr Tyr His Pro Asp Ser Val Lys
1                   5                   10                  15

Gly

<210> SEQ ID NO 170
<211> LENGTH: 11
<212> TYPE: PRT
<213> ORGANISM: Mus musculus

<400> SEQUENCE: 170

-continued

```
Gln Gly Asn Trp Gly Arg Thr Trp Phe Thr Tyr
1               5                   10

<210> SEQ ID NO 171
<211> LENGTH: 108
<212> TYPE: PRT
<213> ORGANISM: Mus musculus

<400> SEQUENCE: 171

Gln Ile Val Leu Thr Gln Ser Pro Ala Ile Met Ser Ala Ser Pro Gly
1               5                   10                  15

Glu Lys Val Thr Met Thr Cys Arg Ala Ser Ser Ser Val Ser Ser Ser
                20                  25                  30

Tyr Leu His Trp Tyr Gln Gln Lys Ser Gly Ala Ser Pro Lys Leu Trp
            35                  40                  45

Ile Tyr Ser Thr Ser Ser Leu Ala Ser Gly Val Pro Ala Arg Phe Ser
        50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Leu Thr Phe Gly Ala Gly Thr Lys Leu Glu Leu Lys
            100                 105

<210> SEQ ID NO 172
<211> LENGTH: 118
<212> TYPE: PRT
<213> ORGANISM: Mus musculus

<400> SEQUENCE: 172

Glu Val Ile Leu Val Glu Ser Gly Gly Ala Leu Val Lys Pro Gly Gly
1               5                   10                  15

Ser Leu Lys Val Ser Cys Ala Ala Ser Gly Phe Thr Phe Ser Asn Tyr
                20                  25                  30

Gly Met Ser Trp Val Arg Gln Ser Pro Glu Lys Arg Leu Glu Trp Val
            35                  40                  45

Ala Thr Ile Ser Ser Gly Gly Thr Asn Thr Tyr Tyr Pro Asp Ser Val
        50                  55                  60

Lys Gly Arg Phe Thr Ile Ser Arg Asp Asn Ala Arg Asn Thr Leu Tyr
65                  70                  75                  80

Leu Gln Met Ser Ser Leu Arg Ser Lys Asp Thr Ala Met Tyr Tyr Cys
                85                  90                  95

Gly Arg Tyr Ser Asn Tyr Gly Trp Phe Ala Tyr Trp Gly Gln Gly Thr
                100                 105                 110

Leu Val Thr Val Ser Ala
        115

<210> SEQ ID NO 173
<211> LENGTH: 112
<212> TYPE: PRT
<213> ORGANISM: Mus musculus

<400> SEQUENCE: 173

Asp Ile Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Thr
                20                  25                  30
```

```
Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110
```

```
<210> SEQ ID NO 174
<211> LENGTH: 16
<212> TYPE: PRT
<213> ORGANISM: Mus musculus

<400> SEQUENCE: 174

Arg Ser Ser Gln Ser Ile Val His Thr Asn Gly Asn Thr Tyr Leu Glu
1               5                   10                  15
```

```
<210> SEQ ID NO 175
<211> LENGTH: 122
<212> TYPE: PRT
<213> ORGANISM: Mus musculus

<400> SEQUENCE: 175

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Phe Met Asn Trp Val Met Gln Ser His Gly Lys Ser Leu Glu Trp Ile
        35                  40                  45

Gly Arg Ile Asn Pro Tyr Asn Gly Asp Thr Phe Tyr Asn Gln Lys Phe
    50                  55                  60

Lys Gly Lys Ala Thr Leu Thr Val Asp Lys Ser Ser Gly Thr Ala His
65                  70                  75                  80

Met Glu Leu Arg Ser Leu Ala Ser Glu Asp Ser Ala Val Tyr Tyr Cys
                85                  90                  95

Ala Arg Cys Tyr Tyr Tyr Gly Ser Ser Ser Tyr Gly Met Asp Tyr Trp
            100                 105                 110

Gly Gln Gly Thr Ser Val Thr Val Ser Ser
            115                 120
```

```
<210> SEQ ID NO 176
<211> LENGTH: 5
<212> TYPE: PRT
<213> ORGANISM: Mus musculus

<400> SEQUENCE: 176

Gly Tyr Phe Met Asn
1               5
```

```
<210> SEQ ID NO 177
<211> LENGTH: 17
<212> TYPE: PRT
<213> ORGANISM: Mus musculus

<400> SEQUENCE: 177

Arg Ile Asn Pro Tyr Asn Gly Asp Thr Phe Tyr Asn Gln Lys Phe Lys
1               5                   10                  15
```

-continued

Gly

<210> SEQ ID NO 178
<211> LENGTH: 13
<212> TYPE: PRT
<213> ORGANISM: Mus musculus

<400> SEQUENCE: 178

Cys Tyr Tyr Tyr Gly Ser Ser Ser Tyr Gly Met Asp Tyr
1               5               10

<210> SEQ ID NO 179
<211> LENGTH: 111
<212> TYPE: PRT
<213> ORGANISM: Mus musculus

<400> SEQUENCE: 179

Gln Ile Val Leu Thr Gln Ser Pro Ala Ser Leu Ala Val Ser Leu Gly
1               5               10              15

Gln Arg Ala Thr Ile Ser Cys Arg Ala Ser Glu Ser Val His Asn Tyr
            20              25              30

Gly Val Ser Phe Met Asn Trp Phe Gln Gln Arg Pro Gly Gln Pro Pro
        35              40              45

Lys Leu Leu Ile His Ala Ala Ser His Gln Gly Ser Gly Val Pro Ala
    50              55              60

Arg Phe Thr Gly Ser Gly Ser Gly Thr Asp Phe Ser Leu Asn Ile His
65              70              75              80

Pro Met Glu Glu Asp Asp Ile Ala Met Tyr Phe Cys Gln Gln Ser Lys
                85              90              95

Glu Val Pro Leu Thr Phe Gly Ala Gly Thr Lys Leu Lys Leu Lys
            100             105             110

<210> SEQ ID NO 180
<211> LENGTH: 15
<212> TYPE: PRT
<213> ORGANISM: Mus musculus

<400> SEQUENCE: 180

Arg Ala Ser Glu Ser Val His Asn Tyr Gly Val Ser Phe Met Asn
1               5               10              15

<210> SEQ ID NO 181
<211> LENGTH: 7
<212> TYPE: PRT
<213> ORGANISM: Mus musculus

<400> SEQUENCE: 181

Ala Ala Ser His Gln Gly Ser
1               5

<210> SEQ ID NO 182
<211> LENGTH: 9
<212> TYPE: PRT
<213> ORGANISM: Mus musculus

<400> SEQUENCE: 182

Gln Gln Ser Lys Glu Val Pro Leu Thr
1               5

<210> SEQ ID NO 183
<211> LENGTH: 261

```
<212> TYPE: PRT
<213> ORGANISM: Rattus norvegicus

<400> SEQUENCE: 183

Val Gln Leu Lys Glu Ser Gly Pro Gly Leu Val Lys Pro Ser Gln Ser
1               5                   10                  15

Leu Ser Leu Thr Cys Ser Val Thr Gly Phe Ser Ile Thr Ser Gly Tyr
                20                  25                  30

Gly Trp Asn Trp Ile Arg Lys Phe Pro Gly Asn Lys Leu Glu Trp Met
            35                  40                  45

Gly Phe Ile Asn Ser Ala Gly Ser Thr Asn Tyr Asn Pro Pro Leu Lys
        50                  55                  60

Ser Gln Ile Ser Ile Thr Arg Asp Thr Ser Lys Asn Gln Phe Phe Leu
65                  70                  75                  80

His Leu Thr Ser Val Thr Pro Glu Asp Thr Ala Thr Tyr Tyr Cys Ala
                85                  90                  95

Arg Trp Gly His Thr Leu Gly Val Thr Arg Asp Phe Trp Tyr Phe Asp
            100                 105                 110

Phe Trp Gly Pro Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
                195                 200                 205

Val Asn His Lys Pro Ser Asn Thr Lys Val Asp Lys Arg Val Glu Pro
        210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser
            260

<210> SEQ ID NO 184
<211> LENGTH: 6
<212> TYPE: PRT
<213> ORGANISM: Unknown
<220> FEATURE:
<223> OTHER INFORMATION: Mus musculus or Rattus norvegicus

<400> SEQUENCE: 184

Ser Gly Tyr Gly Trp Asn
1               5

<210> SEQ ID NO 185
<211> LENGTH: 16
<212> TYPE: PRT
<213> ORGANISM: Rattus norvegicus

<400> SEQUENCE: 185

Phe Ile Asn Ser Ala Gly Ser Thr Asn Tyr Asn Pro Pro Leu Lys Ser
1               5                   10                  15
```

-continued

<210> SEQ ID NO 186
<211> LENGTH: 16
<212> TYPE: PRT
<213> ORGANISM: Rattus norvegicus

<400> SEQUENCE: 186

Trp Gly His Thr Leu Gly Val Thr Arg Asp Phe Trp Tyr Phe Asp Phe
1               5                   10                  15

<210> SEQ ID NO 187
<211> LENGTH: 211
<212> TYPE: PRT
<213> ORGANISM: Rattus norvegicus

<400> SEQUENCE: 187

Met Thr Gln Ser Pro Ser Ser Leu Pro Ala Ser Leu Gly Glu Ser Val
1               5                   10                  15

Thr Ile Ile Cys Arg Ala Ser Gln Gly Ile Ser Asn Asn Leu Asn Trp
                20                  25                  30

Tyr Arg Gln Lys Pro Asp Gly Thr Ile Lys Pro Leu Ile Tyr Tyr Thr
            35                  40                  45

Ser Ile Leu Gln Ser Gly Val Pro Ser Ser Phe Ser Gly Ser Arg Ser
        50                  55                  60

Gly Thr Asp Tyr Ser Leu Thr Ile Ser Ser Leu Glu Pro Glu Asp Phe
65                  70                  75                  80

Ala Met Tyr Tyr Cys Gln Gln Asp Ala Ser Phe Pro Trp Thr Phe Gly
                85                  90                  95

Gly Gly Thr Lys Leu Glu Leu Lys Arg Thr Val Ala Ala Pro Ser Val
                100                 105                 110

Phe Ile Phe Pro Pro Ser Asp Glu Gln Leu Lys Ser Gly Thr Ala Ser
            115                 120                 125

Val Val Cys Leu Leu Asn Asn Phe Tyr Pro Arg Glu Ala Lys Val Gln
        130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
            195                 200                 205

Gly Glu Cys
    210

<210> SEQ ID NO 188
<211> LENGTH: 11
<212> TYPE: PRT
<213> ORGANISM: Unknown
<220> FEATURE:
<223> OTHER INFORMATION: Mus musculus or Rattus norvegicus

<400> SEQUENCE: 188

Arg Ala Ser Gln Gly Ile Ser Asn Asn Leu Asn
1               5                   10

<210> SEQ ID NO 189
<211> LENGTH: 7
<212> TYPE: PRT

```
<213> ORGANISM: Unknown
<220> FEATURE:
<223> OTHER INFORMATION: Mus musculus or Rattus norvegicus

<400> SEQUENCE: 189

Tyr Thr Ser Ile Leu Gln Ser
1               5

<210> SEQ ID NO 190
<211> LENGTH: 9
<212> TYPE: PRT
<213> ORGANISM: Unknown
<220> FEATURE:
<223> OTHER INFORMATION: Mus musculus or Rattus norvegicus

<400> SEQUENCE: 190

Gln Gln Asp Ala Ser Phe Pro Trp Thr
1               5

<210> SEQ ID NO 191
<211> LENGTH: 305
<212> TYPE: PRT
<213> ORGANISM: Rattus norvegicus

<400> SEQUENCE: 191

Glu Val Gln Leu Val Glu Ser Gly Gly Gly Leu Val Gln Pro Gly Arg
1               5                   10                  15

Ser Leu Lys Leu Ser Cys Val Ala Ser Gly Phe Thr Phe Asn Asn Tyr
            20                  25                  30

Trp Met Thr Trp Ile Arg Gln Ala Pro Gly Lys Gly Leu Glu Trp Val
        35                  40                  45

Ala Ser Ile Thr Asn Ile Gly Gly Ser Thr Phe Tyr Pro Asp Ser Val
    50                  55                  60

Lys Gly Arg Phe Thr Ile Ser Arg Asp Asn Ala Lys Ser Thr Leu Tyr
65                  70                  75                  80

Leu Gln Met Asn Ser Leu Arg Ser Glu Asp Thr Ala Thr Tyr Tyr Cys
                85                  90                  95

Thr Arg His Tyr Tyr Ser Ser Tyr Ile Tyr Pro Thr Gly Gly Phe Ala
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
```

```
                260               265               270
Val Ser His Glu Asp Pro Glu Val Lys Phe Asn Trp Tyr Val Asp Gly
       275               280               285

Val Glu Val His Asn Ala Gln Thr Lys Pro Arg Glu Glu Gln Tyr Asn
   290               295               300

Ser
305
```

```
<210> SEQ ID NO 192
<211> LENGTH: 5
<212> TYPE: PRT
<213> ORGANISM: Unknown
<220> FEATURE:
<223> OTHER INFORMATION: Mus musculus or Rattus norvegicus

<400> SEQUENCE: 192

Asn Tyr Trp Met Thr
1                 5
```

```
<210> SEQ ID NO 193
<211> LENGTH: 17
<212> TYPE: PRT
<213> ORGANISM: Rattus norvegicus

<400> SEQUENCE: 193

Ser Ile Thr Asn Ile Gly Gly Ser Thr Phe Tyr Pro Asp Ser Val Lys
1                 5                  10                 15

Gly
```

```
<210> SEQ ID NO 194
<211> LENGTH: 15
<212> TYPE: PRT
<213> ORGANISM: Rattus norvegicus

<400> SEQUENCE: 194

His Tyr Tyr Ser Ser Tyr Ile Tyr Pro Thr Gly Gly Phe Ala Tyr
1                 5                  10                 15
```

```
<210> SEQ ID NO 195
<211> LENGTH: 212
<212> TYPE: PRT
<213> ORGANISM: Rattus norvegicus

<400> SEQUENCE: 195

Ile Val Met Thr Gln Ser Pro Thr Thr Ile Ala Ala Ser Pro Gly Glu
1                 5                  10                 15

Lys Val Thr Ile Thr Cys Arg Ala Ser Ser Ser Val Ser Tyr Met Tyr
                20                25                30

Trp Tyr Gln Gln Lys Ser Gly Ala Ser Pro Lys Leu Trp Leu Tyr Asp
        35                40                45

Thr Ser Lys Leu Ala Ser Gly Val Pro Asn Arg Phe Ser Gly Ser Gly
    50                55                60

Ser Gly Thr Ser Tyr Ser Leu Thr Ile Asn Thr Met Glu Thr Glu Asp
65                70                75                80

Ala Ala Thr Tyr Tyr Cys Gln Gln Trp Ser Ser Thr Pro Pro Thr Phe
                85                90                95

Gly Gly Gly Thr Lys Leu Glu Leu Lys Arg Thr Val Ala Ala Pro Ser
            100               105               110

Val Phe Ile Phe Pro Pro Ser Asp Glu Gln Leu Lys Ser Gly Thr Ala
        115               120               125
```

```
Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
                180                 185                 190

Glu Val Thr His Gln Gly Leu Ser Ser Pro Val Thr Lys Ser Phe Asn
            195                 200                 205

Arg Gly Glu Cys
    210
```

```
<210> SEQ ID NO 196
<211> LENGTH: 10
<212> TYPE: PRT
<213> ORGANISM: Unknown
<220> FEATURE:
<223> OTHER INFORMATION: Mus musculus or Rattus norvegicus

<400> SEQUENCE: 196

Arg Ala Ser Ser Ser Val Ser Tyr Met Tyr
1               5                   10
```

```
<210> SEQ ID NO 197
<211> LENGTH: 7
<212> TYPE: PRT
<213> ORGANISM: Unknown
<220> FEATURE:
<223> OTHER INFORMATION: Mus musculus or Rattus norvegicus

<400> SEQUENCE: 197

Asp Thr Ser Lys Leu Ala Ser
1               5
```

```
<210> SEQ ID NO 198
<211> LENGTH: 9
<212> TYPE: PRT
<213> ORGANISM: Rattus norvegicus

<400> SEQUENCE: 198

Gln Gln Trp Ser Ser Thr Pro Pro Thr
1               5
```

```
<210> SEQ ID NO 199
<211> LENGTH: 210
<212> TYPE: PRT
<213> ORGANISM: Rattus norvegicus

<400> SEQUENCE: 199

Met Thr Gln Ser Pro Ser Leu Leu Ser Ala Ser Val Gly Asp Arg Val
1               5                   10                  15

Thr Leu Thr Cys Lys Gly Ser Gln Asn Ile Asn Asn Phe Leu Ala Trp
            20                  25                  30

Tyr Gln Gln Lys Arg Gly Glu Ala Pro Lys Leu Leu Ile Tyr Lys Thr
        35                  40                  45

Asn Ser Leu His Thr Gly Ile Pro Ser Arg Phe Ser Gly Ser Gly Ser
    50                  55                  60

Gly Thr Glu Tyr Thr Leu Thr Ile Ser Ser Leu His Ser Glu Asp Leu
65                  70                  75                  80
```

```
Ala Thr Tyr Tyr Cys Tyr Gln Tyr Asn Asn Gly Tyr Thr Phe Gly Ala
                85                  90                  95

Gly Thr Lys Leu Glu Leu Lys Arg Thr Val Ala Ala Pro Ser Val Phe
            100                 105                 110

Ile Phe Pro Pro Ser Asp Glu Gln Leu Lys Ser Gly Thr Ala Ser Val
        115                 120                 125

Val Cys Leu Leu Asn Asn Phe Tyr Pro Arg Glu Ala Lys Val Gln Trp
    130                 135                 140

Lys Val Asp Asn Ala Leu Gln Ser Gly Asn Ser Gln Glu Ser Val Thr
145                 150                 155                 160

Glu Gln Asp Ser Lys Asp Ser Thr Tyr Ser Leu Ser Ser Thr Leu Thr
                165                 170                 175

Leu Ser Lys Ala Asp Tyr Glu Lys His Lys Val Tyr Ala Cys Glu Val
            180                 185                 190

Thr His Gln Gly Leu Ser Ser Pro Val Thr Lys Ser Phe Asn Arg Gly
        195                 200                 205

Glu Cys
    210
```

```
<210> SEQ ID NO 200
<211> LENGTH: 11
<212> TYPE: PRT
<213> ORGANISM: Rattus norvegicus

<400> SEQUENCE: 200

Lys Gly Ser Gln Asn Ile Asn Asn Phe Leu Ala
1               5                   10
```

```
<210> SEQ ID NO 201
<211> LENGTH: 7
<212> TYPE: PRT
<213> ORGANISM: Rattus norvegicus

<400> SEQUENCE: 201

Lys Thr Asn Ser Leu His Thr
1               5
```

```
<210> SEQ ID NO 202
<211> LENGTH: 8
<212> TYPE: PRT
<213> ORGANISM: Rattus norvegicus

<400> SEQUENCE: 202

Tyr Gln Tyr Asn Asn Gly Tyr Thr
1               5
```

```
<210> SEQ ID NO 203
<211> LENGTH: 290
<212> TYPE: PRT
<213> ORGANISM: Unknown
<220> FEATURE:
<223> OTHER INFORMATION: Mus musculus or Rattus norvegicus
<220> FEATURE:
<221> NAME/KEY: misc_feature
<222> LOCATION: (277)..(277)
<223> OTHER INFORMATION: Xaa can be any naturally occurring amino acid

<400> SEQUENCE: 203

Glu Val Gln Leu Leu Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30
```

```
Tyr Gly Trp Asn Trp Ile Arg Lys Phe Pro Gly Asn Lys Leu Glu Trp
        35              40              45

Met Gly Tyr Ile Asn Ser Ala Gly Ser Thr Asn Tyr Asn Pro Pro Leu
    50              55              60

Lys Ser Gln Ile Ser Ile Thr Arg Asp Thr Ser Lys Asn Gln Phe Phe
65              70              75              80

Leu Gln Leu Thr Ser Val Thr Thr Glu Asp Thr Ala Thr Tyr Tyr Cys
            85              90              95

Ala Arg Trp Gly His Thr Met Gly Thr Ile Arg Asp Phe Trp Tyr Phe
            100             105             110

Asp Phe Trp Gly Pro Gly Thr Met Val Thr Val Ser Ser Ala Ser Thr
            115             120             125

Lys Gly Pro Ser Val Phe Pro Leu Ala Pro Ser Ser Lys Ser Thr Ser
    130             135             140

Gly Gly Thr Ala Ala Leu Gly Cys Leu Val Lys Asp Tyr Phe Pro Glu
145             150             155             160

Pro Val Thr Val Ser Trp Asn Ser Gly Ala Leu Thr Ser Gly Val His
            165             170             175

Thr Phe Pro Ala Val Leu Gln Ser Ser Gly Leu Tyr Ser Leu Ser Ser
            180             185             190

Val Val Thr Val Pro Ser Ser Ser Leu Gly Thr Gln Thr Tyr Ile Cys
            195             200             205

Asn Val Asn His Lys Pro Ser Asn Thr Lys Val Asp Lys Arg Val Glu
    210             215             220

Pro Lys Ser Cys Asp Lys Thr His Thr Cys Pro Pro Cys Pro Ala Pro
225             230             235             240

Glu Leu Leu Gly Gly Pro Ser Val Phe Leu Phe Pro Pro Lys Pro Lys
            245             250             255

Asp Thr Leu Met Ile Ser Arg Thr Pro Glu Val Thr Cys Val Val Val
            260             265             270

Asp Val Ser His Xaa Asp Pro Glu Val Lys Phe Asn Trp Tyr Val Asp
    275             280             285

Gly Val
    290
```

```
<210> SEQ ID NO 204
<211> LENGTH: 16
<212> TYPE: PRT
<213> ORGANISM: Unknown
<220> FEATURE:
<223> OTHER INFORMATION: Mus musculus or Rattus norvegicus

<400> SEQUENCE: 204

Tyr Ile Asn Ser Ala Gly Ser Thr Asn Tyr Asn Pro Pro Leu Lys Ser
1               5               10              15

<210> SEQ ID NO 205
<211> LENGTH: 16
<212> TYPE: PRT
<213> ORGANISM: Rattus norvegicus

<400> SEQUENCE: 205

Trp Gly His Thr Met Gly Thr Ile Arg Asp Phe Trp Tyr Phe Asp Phe
1               5               10              15

<210> SEQ ID NO 206
<211> LENGTH: 125
```

<212> TYPE: PRT
<213> ORGANISM: Mus musculus

<400> SEQUENCE: 206

```
Glu Val Gln Leu Gln Glu Ser Gly Pro Gly Leu Val Lys Thr Ser Gln
1               5                   10                  15

Ser Leu Ser Leu Thr Cys Ser Val Thr Gly Phe Ser Ile Thr Ser Gly
            20                  25                  30

Phe Gly Trp Asn Trp Ile Arg Lys Phe Pro Gly Asn Lys Leu Glu Trp
        35                  40                  45

Met Gly Tyr Ile Asn Ser Ala Gly Ser Thr Asn Tyr Asn Pro Pro Leu
    50                  55                  60

Lys Ser Gln Ile Ser Ile Thr Arg Asp Thr Ser Lys Asn Gln Phe Phe
65                  70                  75                  80

Leu Gln Leu Thr Ser Val Thr Thr Glu Asp Thr Gly Thr Tyr Tyr Cys
                85                  90                  95

Ala Arg Trp Gly His Ser Met Gly Thr Thr Arg Asp Tyr Trp Tyr Phe
            100                 105                 110

Asp Phe Trp Gly Pro Gly Thr Met Val Thr Val Ser Ser
        115                 120                 125
```

<210> SEQ ID NO 207
<211> LENGTH: 6
<212> TYPE: PRT
<213> ORGANISM: Mus musculus

<400> SEQUENCE: 207

```
Ser Gly Phe Gly Trp Asn
1               5
```

<210> SEQ ID NO 208
<211> LENGTH: 16
<212> TYPE: PRT
<213> ORGANISM: Mus musculus

<400> SEQUENCE: 208

```
Trp Gly His Ser Met Gly Thr Thr Arg Asp Tyr Trp Tyr Phe Asp Phe
1               5                   10                  15
```

<210> SEQ ID NO 209
<211> LENGTH: 107
<212> TYPE: PRT
<213> ORGANISM: Mus musculus

<400> SEQUENCE: 209

```
Asp Ile Gln Met Thr Gln Ser Pro Ser Ser Leu Pro Ala Ser Leu Gly
1               5                   10                  15

Glu Arg Val Thr Ile Ile Cys Arg Ala Ser Gln Gly Ile Ser Asn Asn
            20                  25                  30

Leu Asn Trp Tyr Gln Gln Lys Pro Asp Gly Thr Ile Lys Pro Leu Ile
        35                  40                  45

Tyr Tyr Thr Ser Ile Leu Gln Ser Gly Val Pro Ser Ser Phe Ser Gly
    50                  55                  60

Ser Arg Ser Gly Thr Asp Tyr Ser Leu Thr Ile Ser Ser Leu Glu Pro
65                  70                  75                  80

Glu Asp Phe Thr Met Tyr Phe Cys Gln Gln Asp Ala Ser Phe Pro Trp
                85                  90                  95

Thr Phe Gly Gly Gly Thr Lys Leu Glu Leu Lys
            100                 105
```

```
<210> SEQ ID NO 210
<211> LENGTH: 124
<212> TYPE: PRT
<213> ORGANISM: Mus musculus

<400> SEQUENCE: 210

Glu Val Lys Leu Val Glu Ser Gly Gly Gly Leu Val Gln Pro Gly Arg
1               5                   10                  15

Ser Leu Lys Leu Ser Cys Leu Ala Ser Gly Phe Thr Phe Thr Asn Tyr
            20                  25                  30

Trp Met Thr Trp Val Arg Gln Ala Pro Gly Lys Gly Leu Glu Trp Val
        35                  40                  45

Ala Ser Ile Thr Asn Thr Gly Ala Ala Thr Phe Tyr Pro Asp Ser Val
    50                  55                  60

Lys Gly Arg Phe Thr Leu Ser Arg Asp Asn Ala Lys Ser Thr Leu Tyr
65                  70                  75                  80

Leu Gln Met Asn Ser Leu Arg Ser Glu Asp Thr Ala Thr Tyr Tyr Cys
                85                  90                  95

Thr Arg His Tyr Tyr Ser Ser Tyr Val Tyr Pro Thr Gly Gly Phe Ala
            100                 105                 110

Tyr Trp Gly Gln Gly Thr Leu Val Thr Val Ser Ser
        115                 120

<210> SEQ ID NO 211
<211> LENGTH: 17
<212> TYPE: PRT
<213> ORGANISM: Mus musculus

<400> SEQUENCE: 211

Ser Ile Thr Asn Thr Gly Ala Ala Thr Phe Tyr Pro Asp Ser Val Lys
1               5                   10                  15

Gly

<210> SEQ ID NO 212
<211> LENGTH: 15
<212> TYPE: PRT
<213> ORGANISM: Mus musculus

<400> SEQUENCE: 212

His Tyr Tyr Ser Ser Tyr Val Tyr Pro Thr Gly Gly Phe Ala Tyr
1               5                   10                  15

<210> SEQ ID NO 213
<211> LENGTH: 106
<212> TYPE: PRT
<213> ORGANISM: Mus musculus

<400> SEQUENCE: 213

Glu Ile Val Leu Thr Gln Ser Pro Thr Thr Ile Ala Ala Ser Pro Gly
1               5                   10                  15

Glu Lys Val Thr Ile Thr Cys Arg Ala Arg Ser Ser Val Ser Tyr Met
            20                  25                  30

Tyr Trp Tyr Gln Gln Lys Ser Gly Ala Thr Pro Lys Leu Cys Ile Tyr
        35                  40                  45

Asp Thr Ser Lys Leu Ala Ser Gly Val Pro Asn Arg Phe Ser Gly Ser
    50                  55                  60

Gly Ser Gly Thr Ser Tyr Ser Leu Thr Ile Asn Thr Met Glu Thr Glu
65                  70                  75                  80
```

Asp Ala Ala Thr Tyr Tyr Cys Gln Gln Trp Thr Thr Asn Pro Pro Thr
            85                  90                  95

Phe Gly Gly Gly Thr Lys Leu Glu Leu Lys
            100                 105

<210> SEQ ID NO 214
<211> LENGTH: 10
<212> TYPE: PRT
<213> ORGANISM: Mus musculus

<400> SEQUENCE: 214

Arg Ala Arg Ser Ser Val Ser Tyr Met Tyr
1               5                   10

<210> SEQ ID NO 215
<211> LENGTH: 9
<212> TYPE: PRT
<213> ORGANISM: Mus musculus

<400> SEQUENCE: 215

Gln Gln Trp Thr Thr Asn Pro Pro Thr
1               5

<210> SEQ ID NO 216
<211> LENGTH: 124
<212> TYPE: PRT
<213> ORGANISM: Mus musculus

<400> SEQUENCE: 216

Glu Val Gln Leu Val Glu Ser Gly Gly Gly Leu Val Gln Pro Gly Arg
1               5                   10                  15

Ser Leu Lys Leu Ser Cys Val Ala Ser Gly Phe Thr Phe Asn Asn Tyr
            20                  25                  30

Trp Met Thr Trp Ile Arg Gln Ala Pro Gly Lys Gly Leu Glu Trp Val
            35                  40                  45

Ala Ser Ile Thr His Thr Gly Gly Asn Thr Phe Tyr Pro Asp Ser Val
    50                  55                  60

Lys Gly Arg Phe Thr Ile Ser Arg Asp Asn Ala Lys Ser Thr Leu Tyr
65                  70                  75                  80

Leu Gln Met Asn Ser Leu Arg Ser Glu Asp Thr Ala Thr Tyr Tyr Cys
            85                  90                  95

Thr Arg His Tyr Tyr Ser Ser Tyr Val Tyr Pro Thr Gly Gly Phe Ala
            100                 105                 110

Tyr Trp Gly Gln Gly Thr Leu Val Thr Val Ser Ser
            115                 120

<210> SEQ ID NO 217
<211> LENGTH: 17
<212> TYPE: PRT
<213> ORGANISM: Mus musculus

<400> SEQUENCE: 217

Ser Ile Thr His Thr Gly Gly Asn Thr Phe Tyr Pro Asp Ser Val Lys
1               5                   10                  15

Gly

<210> SEQ ID NO 218
<211> LENGTH: 106
<212> TYPE: PRT
<213> ORGANISM: Mus musculus

<400> SEQUENCE: 218

Asp Ile Val Leu Thr Gln Ser Pro Thr Thr Ile Ala Ala Ser Pro Gly
1               5                   10                  15

Glu Lys Val Thr Ile Thr Cys Arg Ala Ser Ser Ser Val Ser Tyr Met
            20                  25                  30

Tyr Trp Tyr Gln Gln Lys Ser Gly Ala Ser Pro Lys Leu Trp Ile Tyr
        35                  40                  45

Asp Thr Ser Lys Leu Ala Ser Gly Val Pro Asn Arg Phe Ser Gly Ser
    50                  55                  60

Gly Ser Gly Thr Ser Tyr Ser Leu Thr Ile Asn Thr Met Glu Thr Glu
65                  70                  75                  80

Asp Ala Ala Thr Tyr Tyr Cys Gln Gln Trp Thr Ser Thr Pro Pro Thr
                85                  90                  95

Phe Gly Gly Gly Thr Lys Leu Glu Leu Lys
            100                 105

<210> SEQ ID NO 219
<211> LENGTH: 9
<212> TYPE: PRT
<213> ORGANISM: Mus musculus

<400> SEQUENCE: 219

Gln Gln Trp Thr Ser Thr Pro Pro Thr
1               5

<210> SEQ ID NO 220
<211> LENGTH: 16
<212> TYPE: PRT
<213> ORGANISM: Mus musculus

<400> SEQUENCE: 220

Tyr Ile Asn Ser Ala Gly Ser Thr Asn Tyr Asn Pro Pro Leu Lys Gly
1               5                   10                  15

<210> SEQ ID NO 221
<211> LENGTH: 16
<212> TYPE: PRT
<213> ORGANISM: Mus musculus

<400> SEQUENCE: 221

Trp Gly His Thr Met Gly Val Thr Arg Asp Phe Trp His Phe Asp Phe
1               5                   10                  15

<210> SEQ ID NO 222
<211> LENGTH: 107
<212> TYPE: PRT
<213> ORGANISM: Mus musculus

<400> SEQUENCE: 222

Asp Ile His Met Thr Gln Ser Pro Ser Ser Leu Pro Ala Ser Leu Gly
1               5                   10                  15

Glu Arg Val Thr Ile Ile Cys Arg Ala Ser Gln Gly Ile Ser Asn Asn
            20                  25                  30

Leu Asn Trp Tyr Gln Gln Lys Pro Asp Gly Ala Ile Lys Pro Leu Ile
        35                  40                  45

Tyr Tyr Thr Ser Ile Leu Gln Ser Gly Val Pro Ser Thr Phe Ser Gly
    50                  55                  60

Ser Arg Ser Gly Thr Asp Tyr Ser Leu Thr Ile Ser Ser Leu Gly Pro
65                  70                  75                  80

```
Glu Asp Phe Ala Met Tyr Tyr Cys Gln Gln Asp Ala Ser Phe Pro Trp
                85                  90                  95

Thr Phe Gly Gly Gly Thr Lys Leu Glu Leu Lys
            100                 105

<210> SEQ ID NO 223
<211> LENGTH: 125
<212> TYPE: PRT
<213> ORGANISM: Mus musculus

<400> SEQUENCE: 223

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Ala
            20                  25                  30

Tyr Gly Trp Asn Trp Ile Arg Lys Phe Pro Gly Asn Lys Leu Glu Trp
            35                  40                  45

Met Gly Tyr Ile Asn Ser Ala Gly Ser Thr Asn Tyr Asn Pro Pro Leu
    50                  55                  60

Lys Ser Gln Ile Ser Ile Thr Arg Asp Thr Ser Lys Asn Gln Phe Phe
65                  70                  75                  80

Leu Gln Leu Thr Ser Val Thr Thr Glu Asp Thr Ala Thr Tyr Tyr Cys
                85                  90                  95

Ala Arg Trp Gly His Thr Met Gly Val Thr Arg Asp Tyr Trp Tyr Phe
            100                 105                 110

Asp Phe Trp Gly Pro Gly Thr Met Val Thr Val Ser Ser
        115                 120                 125

<210> SEQ ID NO 224
<211> LENGTH: 6
<212> TYPE: PRT
<213> ORGANISM: Mus musculus

<400> SEQUENCE: 224

Ser Ala Tyr Gly Trp Asn
1               5

<210> SEQ ID NO 225
<211> LENGTH: 16
<212> TYPE: PRT
<213> ORGANISM: Mus musculus

<400> SEQUENCE: 225

Trp Gly His Thr Met Gly Val Thr Arg Asp Tyr Trp Tyr Phe Asp Phe
1               5                   10                  15

<210> SEQ ID NO 226
<211> LENGTH: 107
<212> TYPE: PRT
<213> ORGANISM: Mus musculus

<400> SEQUENCE: 226

Asp Ile Gln Leu Thr Gln Ser Pro Ser Ser Leu Pro Ala Ser Leu Gly
1               5                   10                  15

Glu Arg Val Thr Ile Ile Cys Arg Ala Ser Gln Gly Ile Ser Asn Asn
            20                  25                  30

Leu Asn Trp Tyr Gln Gln Lys Pro Asp Gly Thr Ile Lys Pro Leu Ile
            35                  40                  45

Tyr Tyr Thr Ser Ile Leu His Ser Gly Val Pro Ser Ser Phe Ser Gly
```

-continued

```
            50                  55                  60

Ser Arg Ser Gly Thr Asp Tyr Ser Leu Thr Ile Ser Ser Leu Glu Pro
65                  70                  75                  80

Glu Asp Phe Ala Met Tyr Tyr Cys Gln Gln Asp Ala Ser Phe Pro Trp
                85                  90                  95

Thr Phe Gly Gly Gly Thr Lys Leu Glu Leu Lys
            100                 105

<210> SEQ ID NO 227
<211> LENGTH: 7
<212> TYPE: PRT
<213> ORGANISM: Mus musculus

<400> SEQUENCE: 227

Tyr Thr Ser Ile Leu His Ser
1               5

<210> SEQ ID NO 228
<211> LENGTH: 117
<212> TYPE: PRT
<213> ORGANISM: Mus musculus

<400> SEQUENCE: 228

Glu Val Lys Leu Leu Glu Ser Gly Gly Gly Leu Val Gln Pro Gly Gly
1               5                   10                  15

Ser Met Arg Leu Ser Cys Ala Ala Ser Gly Phe Thr Phe Thr Asp Phe
                20                  25                  30

Tyr Met Asn Trp Ile Arg Gln Pro Ser Gly Lys Ala Pro Glu Trp Leu
            35                  40                  45

Gly Phe Ile Arg Asp Lys Val Asn Gly Tyr Thr Thr Val Tyr Asn Pro
        50                  55                  60

Ser Val Gln Gly Arg Phe Thr Phe Ser Arg Asp Asn Ser Lys Asn Ile
65                  70                  75                  80

Leu Tyr Leu Gln Met Asn Thr Leu Arg Gly Glu Asp Thr Ala Thr Tyr
                85                  90                  95

Tyr Cys Val Arg Asn Trp Ala Leu Asp Tyr Trp Gly Gln Gly Val Met
                100                 105                 110

Val Thr Val Ser Ser
        115

<210> SEQ ID NO 229
<211> LENGTH: 5
<212> TYPE: PRT
<213> ORGANISM: Mus musculus

<400> SEQUENCE: 229

Asp Phe Tyr Met Asn
1               5

<210> SEQ ID NO 230
<211> LENGTH: 19
<212> TYPE: PRT
<213> ORGANISM: Mus musculus

<400> SEQUENCE: 230

Phe Ile Arg Asp Lys Val Asn Gly Tyr Thr Thr Val Tyr Asn Pro Ser
1               5                   10                  15

Val Gln Gly
```

-continued

```
<210> SEQ ID NO 231
<211> LENGTH: 6
<212> TYPE: PRT
<213> ORGANISM: Mus musculus

<400> SEQUENCE: 231

Asn Trp Ala Leu Asp Tyr
1               5

<210> SEQ ID NO 232
<211> LENGTH: 107
<212> TYPE: PRT
<213> ORGANISM: Mus musculus

<400> SEQUENCE: 232

Asp Ile Gln Met Thr Gln Phe Pro Ser Phe Leu Phe Ala Ser Val Gly
1               5                   10                  15

Asp Arg Val Thr Ile Lys Cys Lys Ala Ser Gln Asn Ile Asn Lys Tyr
                20                  25                  30

Leu Asn Trp Tyr Gln Gln Lys Leu Gly Glu Ala Pro Lys Arg Leu Ile
            35                  40                  45

Tyr Asp Thr Asn Ser Leu Leu Thr Gly Ile Pro Ser Arg Phe Ser Gly
    50                  55                  60

Ser Gly Phe Gly Thr His Tyr Thr Leu Thr Ile Ser Ser Leu Gln Pro
65                  70                  75                  80

Glu Asp Val Ala Thr Tyr Phe Cys Gln Gln Tyr Asn Asn Trp Pro Tyr
                85                  90                  95

Thr Phe Gly Ala Gly Thr Lys Leu Glu Leu Lys
            100                 105

<210> SEQ ID NO 233
<211> LENGTH: 11
<212> TYPE: PRT
<213> ORGANISM: Mus musculus

<400> SEQUENCE: 233

Lys Ala Ser Gln Asn Ile Asn Lys Tyr Leu Asn
1               5                   10

<210> SEQ ID NO 234
<211> LENGTH: 7
<212> TYPE: PRT
<213> ORGANISM: Mus musculus

<400> SEQUENCE: 234

Asp Thr Asn Ser Leu Leu Thr
1               5

<210> SEQ ID NO 235
<211> LENGTH: 9
<212> TYPE: PRT
<213> ORGANISM: Mus musculus

<400> SEQUENCE: 235

Gln His Tyr Asn Asn Trp Pro Tyr Thr
1               5

<210> SEQ ID NO 236
<211> LENGTH: 115
<212> TYPE: PRT
<213> ORGANISM: Mus musculus

<400> SEQUENCE: 236
```

-continued

```
Glu Val Lys Leu Glu Glu Ser Gly Gly Gly Leu Val Gln Pro Gly Arg
1               5                   10                  15

Ser Leu Gln Leu Ser Cys Leu Ala Ser Gly Phe Thr Phe Arg Asn Tyr
                20                  25                  30

Gly Met Thr Trp Ile Arg Gln Ala Pro Gly Arg Gly Leu Glu Trp Val
            35                  40                  45

Ala Ser Ile Ser Ser Thr Gly Ser Tyr Ile Tyr Tyr Ala Asp Thr Met
        50                  55                  60

Arg Gly Arg Phe Thr Ile Ser Arg Glu Asp Ala Lys Asn Ala Leu Tyr
65                  70                  75                  80

Leu Arg Met Thr Ser Leu Arg Ser Glu Asp Thr Ala Leu Tyr Tyr Cys
                85                  90                  95

Thr Arg Gln Glu Gly Ala Ala Tyr Trp Gly Gln Gly Val Met Val Thr
                100                 105                 110

Val Ser Ser
        115

<210> SEQ ID NO 237
<211> LENGTH: 5
<212> TYPE: PRT
<213> ORGANISM: Mus musculus

<400> SEQUENCE: 237

Asn Tyr Gly Met Thr
1               5

<210> SEQ ID NO 238
<211> LENGTH: 6
<212> TYPE: PRT
<213> ORGANISM: Mus musculus

<400> SEQUENCE: 238

Gln Glu Gly Ala Ala Tyr
1               5

<210> SEQ ID NO 239
<211> LENGTH: 107
<212> TYPE: PRT
<213> ORGANISM: Mus musculus

<400> SEQUENCE: 239

Glu Ile Val Met Ile Gln Ser Pro Ser Ser Leu Ser Val Ser Leu Gly
1               5                   10                  15

Asp Ser Val Thr Ile Thr Cys Arg Ala Ser Gln Asp Val Gly Ile Tyr
                20                  25                  30

Val Asn Trp Phe Gln Gln Lys Pro Gly Lys Ser Pro Arg Arg Met Ile
            35                  40                  45

Tyr Arg Ala Thr Asn Leu Ala Asp Gly Val Pro Ser Arg Phe Ser Gly
        50                  55                  60

Ser Arg Ser Gly Ser Asp Tyr Ser Leu Thr Ile Ser Ser Leu Glu Ser
65                  70                  75                  80

Glu Asp Val Ala Ala Tyr His Cys Leu Gln Tyr Asn Lys Tyr Pro Tyr
                85                  90                  95

Thr Phe Gly Ala Gly Thr Lys Leu Glu Leu Lys
                100                 105

<210> SEQ ID NO 240
<211> LENGTH: 11
```

-continued

<212> TYPE: PRT
<213> ORGANISM: Mus musculus

<400> SEQUENCE: 240

Arg Ala Ser Gln Asp Val Gly Ile Tyr Val Asn
1               5               10

<210> SEQ ID NO 241
<211> LENGTH: 7
<212> TYPE: PRT
<213> ORGANISM: Mus musculus

<400> SEQUENCE: 241

Arg Ala Thr Asn Leu Ala Asp
1               5

<210> SEQ ID NO 242
<211> LENGTH: 9
<212> TYPE: PRT
<213> ORGANISM: Mus musculus

<400> SEQUENCE: 242

Leu Gln Tyr Asn Lys Tyr Pro Tyr Thr
1               5

<210> SEQ ID NO 243
<211> LENGTH: 117
<212> TYPE: PRT
<213> ORGANISM: Mus musculus

<400> SEQUENCE: 243

Glu Val Lys Leu Leu Glu Ser Gly Gly Gly Leu Val Gln Pro Gly Gly
1               5               10              15

Ser Met Arg Leu Ser Cys Ala Ala Ser Gly Phe Thr Phe Thr Asp Phe
                20              25              30

Tyr Met Asn Trp Ile Arg Gln Pro Ala Gly Lys Ala Pro Glu Trp Leu
            35              40              45

Gly Leu Ile Arg Ser Lys Ala Asn Gly Tyr Thr Thr Glu Tyr Asn Thr
    50              55              60

Ser Val Lys Gly Arg Phe Thr Ile Ser Arg Asp Asn Thr Gln Asn Met
65              70              75              80

Leu Tyr Leu Gln Met Asn Thr Leu Arg Ala Glu Asp Thr Ala Thr Tyr
                85              90              95

Tyr Cys Ala Arg Asn Tyr Tyr Phe Asp Tyr Trp Gly Gln Gly Thr Leu
            100             105             110

Val Thr Val Ser Ser
        115

<210> SEQ ID NO 244
<211> LENGTH: 19
<212> TYPE: PRT
<213> ORGANISM: Mus musculus

<400> SEQUENCE: 244

Leu Ile Arg Ser Lys Ala Asn Gly Tyr Thr Thr Glu Tyr Asn Thr Ser
1               5               10              15

Val Lys Gly

<210> SEQ ID NO 245
<211> LENGTH: 6
<212> TYPE: PRT

-continued

```
<213> ORGANISM: Mus musculus

<400> SEQUENCE: 245

Asn Tyr Tyr Phe Asp Tyr
1               5

<210> SEQ ID NO 246
<211> LENGTH: 107
<212> TYPE: PRT
<213> ORGANISM: Mus musculus

<400> SEQUENCE: 246

Asp Val Gln Met Thr Gln Ser Pro Ser Asn Leu Ala Ala Ser Pro Gly
1               5                   10                  15

Glu Ser Val Ser Ile Asn Cys Lys Ala Ser Lys Ser Ile Tyr Lys Tyr
            20                  25                  30

Leu Ala Trp Tyr Gln Gln Lys Pro Gly Lys Ala Asn Lys Leu Leu Ile
        35                  40                  45

Tyr Ser Gly Ser Thr Leu Gln Ser Gly Thr Pro Ser Arg Phe Ser Gly
    50                  55                  60

Ser Gly Ser Gly Thr Asp Phe Thr Leu Thr Ile Arg Asn Leu Glu Pro
65                  70                  75                  80

Glu Asp Phe Gly Leu Tyr Tyr Cys Gln Gln His Asn Glu Tyr Pro Tyr
                85                  90                  95

Thr Phe Gly Ala Gly Thr Lys Leu Glu Leu Lys
            100                 105

<210> SEQ ID NO 247
<211> LENGTH: 11
<212> TYPE: PRT
<213> ORGANISM: Mus musculus

<400> SEQUENCE: 247

Lys Ala Ser Lys Ser Ile Tyr Lys Tyr Leu Ala
1               5                   10

<210> SEQ ID NO 248
<211> LENGTH: 7
<212> TYPE: PRT
<213> ORGANISM: Mus musculus

<400> SEQUENCE: 248

Ser Gly Ser Thr Leu Gln Ser
1               5

<210> SEQ ID NO 249
<211> LENGTH: 9
<212> TYPE: PRT
<213> ORGANISM: Mus musculus

<400> SEQUENCE: 249

Gln Gln His Asn Glu Tyr Pro Tyr Thr
1               5

<210> SEQ ID NO 250
<211> LENGTH: 122
<212> TYPE: PRT
<213> ORGANISM: Mus musculus

<400> SEQUENCE: 250

Glu Val Lys Leu Leu Glu Ser Gly Gly Gly Leu Val Gln Pro Gly Arg
1               5                   10                  15
```

```
Ser Leu Lys Leu Ser Cys Val Ala Ser Gly Phe Thr Phe Asn Asn Tyr
         20              25              30

Tyr Met Ser Trp Thr Arg Gln Ala Pro Gly Lys Gly Leu Glu Trp Val
         35              40              45

Ala Ser Ile Thr Asn Ser Gly Gly Thr Thr Tyr Tyr Pro Gly Ser Val
    50              55              60

Lys Gly Arg Phe Thr Ile Ser Arg Asp Asn Ala Gln Asn Thr Leu Tyr
65              70              75              80

Leu Gln Met Asn Ser Leu Arg Ser Glu Asp Thr Ala Thr Tyr Tyr Cys
             85              90              95

Thr Arg Ala Trp Gly Gly Ser Tyr Leu His Trp Tyr Phe Asp Phe Trp
            100             105             110

Gly Pro Gly Thr Met Val Thr Val Ser Ser
        115             120
```

<210> SEQ ID NO 251
<211> LENGTH: 17
<212> TYPE: PRT
<213> ORGANISM: Mus musculus

<400> SEQUENCE: 251

```
Ser Ile Thr Asn Ser Gly Gly Thr Thr Tyr Tyr Pro Gly Ser Val Lys
1               5               10              15

Gly
```

<210> SEQ ID NO 252
<211> LENGTH: 13
<212> TYPE: PRT
<213> ORGANISM: Mus musculus

<400> SEQUENCE: 252

```
Ala Trp Gly Gly Ser Tyr Leu His Trp Tyr Phe Asp Phe
1               5               10
```

<210> SEQ ID NO 253
<211> LENGTH: 113
<212> TYPE: PRT
<213> ORGANISM: Mus musculus

<400> SEQUENCE: 253

```
Asp Ile Val Met Thr Gln Ser Pro Ser Ser Leu Ala Val Ser Ala Gly
1               5               10              15

Glu Thr Val Thr Ile Lys Cys Lys Ser Ser Gln Ser Leu Leu Tyr Ser
         20              25              30

Arg Asn Gln Lys Asn Tyr Leu Ala Trp Tyr Gln Gln Lys Pro Gly Gln
         35              40              45

Ser Pro Thr Leu Leu Ile Tyr Trp Ala Ser Thr Arg Gln Ser Gly Val
    50              55              60

Pro Asp Arg Phe Ile Gly Ser Gly Ser Gly Thr Asp Phe Thr Leu Thr
65              70              75              80

Ile Ser Ser Val Gln Ala Glu Asp Leu Ala Ile Tyr Tyr Cys Gln Gln
             85              90              95

Tyr Tyr Asp Thr Pro Tyr Thr Phe Gly Ala Gly Thr Lys Leu Glu Leu
            100             105             110

Lys
```

<210> SEQ ID NO 254

-continued

```
<211> LENGTH: 17
<212> TYPE: PRT
<213> ORGANISM: Mus musculus

<400> SEQUENCE: 254

Lys Ser Ser Gln Ser Leu Leu Tyr Ser Arg Asn Gln Lys Asn Tyr Leu
1               5                   10                  15

Ala

<210> SEQ ID NO 255
<211> LENGTH: 7
<212> TYPE: PRT
<213> ORGANISM: Mus musculus

<400> SEQUENCE: 255

Trp Ala Ser Thr Arg Gln Ser
1               5

<210> SEQ ID NO 256
<211> LENGTH: 9
<212> TYPE: PRT
<213> ORGANISM: Mus musculus

<400> SEQUENCE: 256

Gln Gln Tyr Tyr Asp Thr Pro Tyr Thr
1               5

<210> SEQ ID NO 257
<211> LENGTH: 122
<212> TYPE: PRT
<213> ORGANISM: Mus musculus

<400> SEQUENCE: 257

Glu Val Gln Ile Leu Glu Thr Gly Gly Gly Leu Val Gln Pro Gly Arg
1               5                   10                  15

Ser Leu Lys Leu Ser Cys Val Gly Ser Gly Phe Thr Phe Lys Asn Ser
            20                  25                  30

Trp Met Ser Trp Thr Arg Gln Ala Pro Gly Lys Gly Leu Glu Trp Val
        35                  40                  45

Ala Ser Ile Thr Asn Ser Gly Gly Thr Thr Tyr Tyr Pro Asp Ser Val
    50                  55                  60

Lys Gly Arg Phe Thr Ile Ser Arg Asp Asn Ala Gln Asn Thr Leu Tyr
65                  70                  75                  80

Leu Gln Met Asn Ser Leu Arg Ser Glu Asp Thr Ala Thr Tyr Tyr Cys
                85                  90                  95

Thr Arg Ala Trp Gly Gly Val Tyr Leu His Trp Tyr Phe Asp Phe Trp
            100                 105                 110

Gly Pro Gly Thr Met Val Thr Val Ser Ser
        115                 120

<210> SEQ ID NO 258
<211> LENGTH: 5
<212> TYPE: PRT
<213> ORGANISM: Mus musculus

<400> SEQUENCE: 258

Asn Ser Trp Met Ser
1               5

<210> SEQ ID NO 259
<211> LENGTH: 17
```

<212> TYPE: PRT
<213> ORGANISM: Mus musculus

<400> SEQUENCE: 259

Ser Ile Thr Asn Ser Gly Gly Thr Thr Tyr Tyr Pro Asp Ser Val Lys
1               5                   10                  15

Gly

<210> SEQ ID NO 260
<211> LENGTH: 13
<212> TYPE: PRT
<213> ORGANISM: Mus musculus

<400> SEQUENCE: 260

Ala Trp Gly Gly Val Tyr Leu His Trp Tyr Phe Asp Phe
1               5                   10

<210> SEQ ID NO 261
<211> LENGTH: 113
<212> TYPE: PRT
<213> ORGANISM: Mus musculus

<400> SEQUENCE: 261

Asp Ile Val Met Thr Gln Ser Pro Ser Ser Leu Ala Val Ser Ala Gly
1               5                   10                  15

Glu Thr Val Thr Ile Asn Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Lys Leu Leu Ile Tyr Trp Ala Ser Ala Arg Gln Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Ile Tyr Tyr Cys Gln Gln
                85                  90                  95

Tyr Tyr Asp Thr Pro Tyr Thr Phe Gly Ala Gly Thr Lys Leu Glu Ile
            100                 105                 110

Lys

<210> SEQ ID NO 262
<211> LENGTH: 17
<212> TYPE: PRT
<213> ORGANISM: Mus musculus

<400> SEQUENCE: 262

Lys Ser Ser Gln Ser Leu Leu Tyr Ser Gly Asn Gln Lys Asn Tyr Leu
1               5                   10                  15

Ala

<210> SEQ ID NO 263
<211> LENGTH: 7
<212> TYPE: PRT
<213> ORGANISM: Mus musculus

<400> SEQUENCE: 263

Trp Ala Ser Ala Arg Gln Ser
1               5

<210> SEQ ID NO 264
<211> LENGTH: 117

```
<212> TYPE: PRT
<213> ORGANISM: Mus musculus

<400> SEQUENCE: 264

Glu Val Gln Leu Val Glu Ser Gly Gly Gly Leu Val Gln Pro Gly Arg
1               5                   10                  15

Ser Leu Lys Leu Ser Cys Val Ala Ser Gly Phe Thr Phe Asn Asn Tyr
            20                  25                  30

Trp Met Thr Trp Ile Arg Gln Ala Pro Gly Lys Gly Leu Glu Trp Val
        35                  40                  45

Ala Ser Ile Ile Asn Thr Gly Gly Ser Thr Tyr Tyr Pro Asp Ser Val
    50                  55                  60

Lys Gly Arg Phe Thr Ile Ser Arg Asp Asn Ala Lys Ser Thr Leu Tyr
65                  70                  75                  80

Leu Gln Met Asn Ser Leu Arg Ser Glu Asp Thr Ala Thr Tyr Tyr Cys
                85                  90                  95

Thr Arg Glu Trp Thr Thr Val Gly Asp Tyr Trp Gly Gln Gly Val Met
            100                 105                 110

Val Thr Val Ser Ser
        115

<210> SEQ ID NO 265
<211> LENGTH: 17
<212> TYPE: PRT
<213> ORGANISM: Mus musculus

<400> SEQUENCE: 265

Ser Ile Ile Asn Thr Gly Gly Ser Thr Tyr Tyr Pro Asp Ser Val Lys
1               5                   10                  15

Gly

<210> SEQ ID NO 266
<211> LENGTH: 8
<212> TYPE: PRT
<213> ORGANISM: Mus musculus

<400> SEQUENCE: 266

Glu Trp Thr Thr Val Gly Asp Tyr
1               5

<210> SEQ ID NO 267
<211> LENGTH: 109
<212> TYPE: PRT
<213> ORGANISM: Mus musculus

<400> SEQUENCE: 267

Asp Ile Val Leu Thr Gln Ser Pro Ala Leu Ala Val Ser Leu Gly Gln
1               5                   10                  15

Arg Ala Thr Ile Ser Cys Lys Thr Asn Gln Asn Val Asp Tyr Tyr Gly
            20                  25                  30

Asn Ser Tyr Met His Trp Tyr Gln Gln Lys Pro Gly Gln Pro Lys
        35                  40                  45

Leu Leu Ile Tyr Leu Ala Ser Asn Leu Ala Ser Gly Ile Pro Ala Arg
    50                  55                  60

Phe Ser Gly Arg Gly Ser Gly Thr Asp Phe Thr Leu Thr Ile Asp Pro
65                  70                  75                  80

Val Glu Ala Asp Asp Thr Ala Thr Tyr Tyr Cys Gln Gln Ser Arg Asn
                85                  90                  95
```

```
Leu Arg Thr Phe Gly Gly Gly Thr Lys Leu Glu Leu Lys
            100                 105

<210> SEQ ID NO 268
<211> LENGTH: 15
<212> TYPE: PRT
<213> ORGANISM: Mus musculus

<400> SEQUENCE: 268

Lys Thr Asn Gln Asn Val Asp Tyr Tyr Gly Asn Ser Tyr Met His
1               5                   10                  15

<210> SEQ ID NO 269
<211> LENGTH: 7
<212> TYPE: PRT
<213> ORGANISM: Mus musculus

<400> SEQUENCE: 269

Leu Ala Ser Asn Leu Ala Ser
1               5

<210> SEQ ID NO 270
<211> LENGTH: 8
<212> TYPE: PRT
<213> ORGANISM: Mus musculus

<400> SEQUENCE: 270

Gln Gln Ser Arg Asn Leu Arg Thr
1               5

<210> SEQ ID NO 271
<211> LENGTH: 109
<212> TYPE: PRT
<213> ORGANISM: Mus musculus

<400> SEQUENCE: 271

Asp Ile Trp Met Thr Gln Ser Pro Ala Leu Ala Val Ser Leu Gly Gln
1               5                   10                  15

Arg Ala Thr Ile Ser Cys Lys Thr Asn Gln Asn Val Asp Tyr Tyr Gly
                20                  25                  30

Asn Ser Tyr Met His Trp Tyr Gln Gln Lys Pro Gly Gln Gln Pro Lys
            35                  40                  45

Leu Leu Ile Tyr Leu Ala Ser Asn Leu Ala Ser Gly Ile Pro Ala Arg
        50                  55                  60

Phe Ser Gly Arg Gly Ser Gly Thr Asp Phe Thr Leu Thr Ile Asp Pro
65                  70                  75                  80

Val Glu Ala Asp Asp Thr Ala Thr Tyr Tyr Cys Gln Gln Ser Arg Asn
                85                  90                  95

Leu Arg Thr Phe Gly Gly Gly Thr Lys Leu Glu Leu Lys
            100                 105

<210> SEQ ID NO 272
<211> LENGTH: 122
<212> TYPE: PRT
<213> ORGANISM: Mus musculus

<400> SEQUENCE: 272

Glu Val Gln Leu Val Glu Thr Gly Gly Gly Leu Val Gln Pro Gly Arg
1               5                   10                  15

Ser Leu Lys Leu Ser Cys Val Ala Ser Gly Phe Thr Phe Asn Asn Tyr
                20                  25                  30
```

-continued

```
Trp Met Ser Trp Thr Arg Gln Ala Pro Gly Lys Gly Leu Glu Trp Val
    35              40              45

Ala Ser Ile Thr Asn Ser Gly Gly Thr Thr Tyr Tyr Pro Asp Ser Val
    50              55              60

Lys Gly Arg Phe Thr Ile Ser Arg Asp Asn Ala Gln Asn Thr Leu Ser
65              70              75              80

Leu Gln Met Asn Ser Leu Arg Ser Glu Asp Thr Ala Thr Tyr Tyr Cys
            85              90              95

Thr Arg Ala Trp Gly Ala Val Tyr Leu His Trp Phe Phe Asp Phe Trp
            100             105             110

Gly Pro Gly Thr Met Val Thr Val Ser Ser
        115             120
```

<210> SEQ ID NO 273
<211> LENGTH: 5
<212> TYPE: PRT
<213> ORGANISM: Mus musculus

<400> SEQUENCE: 273

```
Asn Tyr Trp Met Ser
1               5
```

<210> SEQ ID NO 274
<211> LENGTH: 13
<212> TYPE: PRT
<213> ORGANISM: Mus musculus

<400> SEQUENCE: 274

```
Ala Trp Gly Ala Val Tyr Leu His Trp Phe Phe Asp Phe
1               5                   10
```

<210> SEQ ID NO 275
<211> LENGTH: 119
<212> TYPE: PRT
<213> ORGANISM: Mus musculus

<400> SEQUENCE: 275

```
Glu Val Lys Leu Leu Glu Ser Gly Gly Gly Leu Val Gln Pro Gly Gly
1               5                   10              15

Ser Met Arg Leu Ser Cys Ala Ala Ser Gly Phe Thr Phe Thr Asp Phe
            20              25              30

Tyr Met Asn Trp Ile Arg Gln Pro Ala Gly Lys Ala Pro Glu Trp Leu
        35              40              45

Gly Phe Ile Arg Asn Lys His Asn Gly Tyr Thr Thr Glu Tyr Asn Ser
    50              55              60

Ser Leu Lys Gly Arg Phe Thr Ile Ser Arg Asp Asn Thr Gln Asn Met
65              70              75              80

Val Tyr Leu Gln Met Asn Ile Leu Arg Ala Glu Asp Thr Ala Thr Tyr
            85              90              95

Tyr Cys Ala Arg Gly Gly Thr Thr Gly Thr Asp Tyr Trp Gly Gln Gly
            100             105             110

Val Met Val Thr Val Ser Ser
        115
```

<210> SEQ ID NO 276
<211> LENGTH: 19
<212> TYPE: PRT
<213> ORGANISM: Mus musculus

<400> SEQUENCE: 276

```
Phe Ile Arg Asn Lys His Asn Gly Tyr Thr Thr Glu Tyr Asn Ser Ser
1               5                   10                  15

Leu Lys Gly

<210> SEQ ID NO 277
<211> LENGTH: 8
<212> TYPE: PRT
<213> ORGANISM: Mus musculus

<400> SEQUENCE: 277

Gly Gly Thr Thr Gly Thr Asp Tyr
1               5

<210> SEQ ID NO 278
<211> LENGTH: 107
<212> TYPE: PRT
<213> ORGANISM: Mus musculus

<400> SEQUENCE: 278

Asp Ile Gln Met Thr Gln Ser Pro Ser Phe Leu Ser Ala Ser Val Gly
1               5                   10                  15

Asp Arg Val Thr Ile Asn Cys Lys Ala Ser Gln Asn Ile Tyr Lys Tyr
            20                  25                  30

Leu Asn Trp Tyr Gln Gln Lys Leu Gly Glu Ala Pro Lys Arg Leu Ile
        35                  40                  45

Tyr Asn Thr Lys Ser Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Gln Gln Tyr Asn Ser Trp Pro Tyr
                85                  90                  95

Thr Phe Gly Ala Gly Thr Lys Leu Glu Leu Lys
            100                 105

<210> SEQ ID NO 279
<211> LENGTH: 11
<212> TYPE: PRT
<213> ORGANISM: Mus musculus

<400> SEQUENCE: 279

Lys Ala Ser Gln Asn Ile Tyr Lys Tyr Leu Asn
1               5                   10

<210> SEQ ID NO 280
<211> LENGTH: 7
<212> TYPE: PRT
<213> ORGANISM: Mus musculus

<400> SEQUENCE: 280

Asn Thr Lys Ser Leu Gln Thr
1               5

<210> SEQ ID NO 281
<211> LENGTH: 9
<212> TYPE: PRT
<213> ORGANISM: Mus musculus

<400> SEQUENCE: 281

Gln Gln Tyr Asn Ser Trp Pro Tyr Thr
1               5
```

-continued

```
<210> SEQ ID NO 282
<211> LENGTH: 17
<212> TYPE: PRT
<213> ORGANISM: Mus musculus

<400> SEQUENCE: 282

Ser Ile Ser Ser Thr Gly Ser Tyr Ile Tyr Tyr Ala Asp Thr Met Arg
1               5                   10                  15

Gly

<210> SEQ ID NO 283
<211> LENGTH: 112
<212> TYPE: PRT
<213> ORGANISM: Artificial sequence
<220> FEATURE:
<223> OTHER INFORMATION: synthetic sequence

<400> SEQUENCE: 283

Asp Val Leu Met Thr Gln Thr Pro Val Ser Leu Ser Val Ser Leu Gly
1               5                   10                  15

Asp Gln Ala Ser Ile Ser Cys Arg Ser Ser Gln Ser Ile Val His Ser
            20                  25                  30

Thr Gly Asn Thr Tyr Leu Glu Trp Tyr Leu Gln Lys Pro Gly Gln Ser
        35                  40                  45

Pro Lys Leu Leu Ile Tyr Lys Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Ala
                85                  90                  95

Ser His Phe Pro Arg Thr Phe Gly Gly Gly Thr Lys Leu Glu Ile Lys
            100                 105                 110

<210> SEQ ID NO 284
<211> LENGTH: 112
<212> TYPE: PRT
<213> ORGANISM: Artificial sequence
<220> FEATURE:
<223> OTHER INFORMATION: synthetic sequence

<400> SEQUENCE: 284

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Thr Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Leu Glu Ala Glu Asp Leu Gly Val Tyr Tyr Cys Phe Gln Gly
                85                  90                  95

Ser His Phe Pro Arg Thr Phe Gly Gly Gly Thr Arg Leu Glu Ile Lys
            100                 105                 110

<210> SEQ ID NO 285
<211> LENGTH: 113
<212> TYPE: PRT
```

```
<213> ORGANISM: Artificial sequence
<220> FEATURE:
<223> OTHER INFORMATION: synthetic sequence

<400> SEQUENCE: 285

Asp Val Val Met Thr Gln Thr Pro Arg Ser Leu Pro Val Ser Leu Gly
1               5                   10                  15

Asp Gln Ala Ser Ile Ser Cys Arg Ser Ser Gln Ser Leu Leu His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
            85                  90                  95

Thr His Ile Pro Pro Trp Thr Phe Gly Gly Gly Thr Lys Leu Asp Ile
            100                 105                 110

Lys

<210> SEQ ID NO 286
<211> LENGTH: 119
<212> TYPE: PRT
<213> ORGANISM: Artificial sequence
<220> FEATURE:
<223> OTHER INFORMATION: synthetic sequence

<400> SEQUENCE: 286

Glu Val Ile Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Thr Ile Ser Ser Gly Gly Gly Asn Thr Tyr Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Arg Ser Glu Asp Thr Ala Leu Tyr Tyr Cys
            85                  90                  95

Ala Arg Tyr Tyr Arg Tyr Glu Ala Trp Phe Ala Ser Trp Gly Gln Gly
            100                 105                 110

Thr Leu Val Thr Val Ser Ala
        115

<210> SEQ ID NO 287
<211> LENGTH: 119
<212> TYPE: PRT
<213> ORGANISM: Artificial sequence
<220> FEATURE:
<223> OTHER INFORMATION: synthetic sequence

<400> SEQUENCE: 287

Glu Val Lys Val Val Glu Ser Gly Gly Val Leu Val Arg Pro Gly Gly
1               5                   10                  15

Ser Leu Lys Leu Ser Cys Ala Ala Ser Gly Phe Thr Phe Ser Arg Tyr
            20                  25                  30
```

-continued

```
Thr Met Ser Trp Val Arg Gln Thr Pro Glu Lys Arg Leu Glu Trp Val
    35                  40                  45

Ala Thr Ile Ser Ser Gly Gly Gly Asn Thr Tyr Tyr Pro Asp Ser Val
    50                  55                  60

Lys Gly Arg Phe Thr Val Ser Arg Asp Asn Ala Met Ser Ser Leu Tyr
65                  70                  75                  80

Leu Gln Met Ser Ser Leu Arg Ser Glu Asp Thr Ala Leu Tyr Tyr Cys
                85                  90                  95

Ala Arg Tyr Gly Ala Gly Asp Ala Trp Phe Ala Tyr Trp Gly Gln Gly
                100                 105                 110

Thr Leu Val Thr Val Ser Ser
        115

<210> SEQ ID NO 288
<211> LENGTH: 122
<212> TYPE: PRT
<213> ORGANISM: Artificial sequence
<220> FEATURE:
<223> OTHER INFORMATION: synthetic sequence

<400> SEQUENCE: 288

Ala Val Gln Leu Gln Gln Ser Gly Pro Glu Leu Val Lys Thr Gly Ala
1               5                   10                  15

Ser Val Lys Ile Ser Cys Lys Ala Ser Gly Tyr Ser Phe Ser Asn Tyr
                20                  25                  30

Tyr Ile His Trp Val Lys Gln Ser His Gly Lys Ser Leu Glu Trp Ile
        35                  40                  45

Gly Phe Ile Ser Cys Tyr Asn Gly Ala Thr Phe Tyr Asn Gln Lys Phe
        50                  55                  60

Lys Gly Lys Ala Thr Phe Thr Val Asp Thr Ser Ser Ser Thr Ala Tyr
65                  70                  75                  80

Met Lys Phe Asn Ser Leu Thr Phe Glu Asp Ser Ala Val Tyr Tyr Cys
                85                  90                  95

Ala Arg Leu Pro Ile Gln Phe Gly Asn Phe Tyr Pro Met Asp Tyr Trp
                100                 105                 110

Gly Gln Gly Thr Ser Val Thr Val Ser Ser
        115                 120

<210> SEQ ID NO 289
<211> LENGTH: 120
<212> TYPE: PRT
<213> ORGANISM: Artificial sequence
<220> FEATURE:
<223> OTHER INFORMATION: synthetic sequence

<400> SEQUENCE: 289

Leu Trp Val Pro Gly Ser Thr Gly Asp Val Leu Met Thr Gln Thr Pro
1               5                   10                  15

Leu Ser Leu Pro Val Ser Leu Gly Asp Gln Ala Ser Ile Ser Cys Arg
                20                  25                  30

Ser Ser Gln Ser Leu Val His Ser Asn Gly Asn Thr Tyr Leu Glu Trp
        35                  40                  45

Tyr Leu Gln Lys Pro Gly Gln Ser Pro Lys Leu Leu Ile Tyr Lys Val
        50                  55                  60

Ser Asn Arg Phe Ser Gly Val Pro Asp Arg Phe Ser Gly Ser Gly Ser
65                  70                  75                  80

Gly Thr Asp Phe Thr Leu Lys Ile Ser Arg Val Glu Ala Glu Asp Leu
                85                  90                  95
```

```
Gly Val Tyr Tyr Cys Phe Gln Gly Ser His Phe Pro Arg Thr Phe Gly
            100                 105                 110

Gly Gly Thr Lys Leu Glu Ile Lys
        115                 120

<210> SEQ ID NO 290
<211> LENGTH: 16
<212> TYPE: PRT
<213> ORGANISM: Artificial sequence
<220> FEATURE:
<223> OTHER INFORMATION: synthetic sequence

<400> SEQUENCE: 290

Arg Ser Ser Gln Ser Leu Val His Ser Asn Gly Asn Thr Tyr Leu Glu
1               5                   10                  15

<210> SEQ ID NO 291
<211> LENGTH: 119
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (57)..(57)
<223> OTHER INFORMATION: The amino acid at position 57 is N, Q or S

<400> SEQUENCE: 291

Glu Val Lys Val Val Glu Ser Gly Gly Val Leu Val Arg Pro Gly Gly
1               5                   10                  15

Ser Leu Lys Leu Ser Cys Ala Ala Ser Gly Phe Thr Phe Ser Arg Tyr
            20                  25                  30

Thr Met Ser Trp Val Arg Gln Thr Pro Glu Lys Arg Leu Glu Trp Val
        35                  40                  45

Ala Thr Ile Ser Ser Gly Gly Gly Xaa Thr Tyr Tyr Pro Asp Ser Val
    50                  55                  60

Lys Gly Arg Phe Thr Val Ser Arg Asp Asn Ala Met Ser Ser Leu Tyr
65                  70                  75                  80

Leu Gln Met Ser Ser Leu Arg Ser Glu Asp Thr Ala Leu Tyr Tyr Cys
                85                  90                  95

Ala Arg Tyr Gly Ala Gly Asp Ala Trp Phe Ala Tyr Trp Gly Gln Gly
            100                 105                 110

Thr Leu Val Thr Val Ser Ser
        115

<210> SEQ ID NO 292
<211> LENGTH: 119
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (57)..(57)
<223> OTHER INFORMATION: The amino acid at position 57 is N, Q or S and
      optionally Q or S

<400> SEQUENCE: 292

Glu Val Lys Val Val Glu Ser Gly Gly Val Leu Val Arg Pro Gly Gly
1               5                   10                  15

Ser Leu Lys Leu Ser Cys Ala Ala Ser Gly Phe Thr Phe Ser Arg Tyr
            20                  25                  30
```

-continued

```
Thr Met Ser Trp Val Arg Gln Thr Pro Glu Lys Arg Leu Glu Trp Val
        35                  40                  45

Ala Thr Ile Ser Ser Gly Gly Gly Xaa Thr Tyr Tyr Pro Asp Ser Val
        50                  55                  60

Lys Gly Arg Phe Thr Val Ser Arg Asp Asn Ala Met Ser Ser Leu Tyr
65                  70                  75                  80

Leu Gln Met Ser Ser Leu Arg Ser Glu Asp Thr Ala Leu Tyr Tyr Cys
                    85                  90                  95

Ala Arg Tyr Gly Ala Gly Asp Ala Trp Phe Ala Tyr Trp Gly Gln Gly
                100                 105                 110

Thr Leu Val Thr Val Ser Ser
        115
```

```
<210> SEQ ID NO 293
<211> LENGTH: 119
<212> TYPE: PRT
<213> ORGANISM: Artificial sequence
<220> FEATURE:
<223> OTHER INFORMATION: synthetic sequence

<400> SEQUENCE: 293

Glu Val Lys Val Val Glu Ser Gly Gly Val Leu Val Arg Pro Gly Gly
1                   5                   10                  15

Ser Leu Lys Leu Ser Cys Ala Ala Ser Gly Phe Thr Phe Ser Arg Tyr
                    20                  25                  30

Thr Met Ser Trp Val Arg Gln Thr Pro Glu Lys Arg Leu Glu Trp Val
        35                  40                  45

Ala Thr Ile Ser Ser Gly Gly Gly Asn Thr Tyr Tyr Pro Asp Ser Val
        50                  55                  60

Lys Gly Arg Phe Thr Val Ser Arg Asp Asn Ala Met Ser Ser Leu Tyr
65                  70                  75                  80

Leu Gln Met Ser Ser Leu Arg Ser Glu Asp Thr Ala Leu Tyr Tyr Cys
                    85                  90                  95

Ala Arg Tyr Gly Ala Gly Asp Ala Trp Phe Ala Tyr Trp Gly Gln Gly
                100                 105                 110

Thr Leu Val Thr Val Ser Ala
        115
```

```
<210> SEQ ID NO 294
<211> LENGTH: 117
<212> TYPE: PRT
<213> ORGANISM: Artificial sequence
<220> FEATURE:
<223> OTHER INFORMATION: synthetic sequence

<400> SEQUENCE: 294

Gln Val Gln Leu Val Gln Ser Gly Ala Glu Val Lys Lys Pro Gly Ala
1                   5                   10                  15

Ser Val Lys Val Ser Cys Lys Ala Ser Gly Tyr Thr Phe Thr Asn Tyr
                    20                  25                  30

Asn Met His Trp Val Arg Gln Ala Pro Gly Gln Arg Leu Glu Trp Met
        35                  40                  45

Gly Thr Ile Tyr Pro Gly Asn Asp Asp Thr Ser Tyr Asn Gln Lys Phe
        50                  55                  60

Lys Asp Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                    85                  90                  95
```

```
Ala Arg Gly Gly Tyr Arg Ala Met Asp Tyr Trp Gly Gln Gly Thr Leu
            100                 105                 110

Val Thr Val Ser Ser
        115

<210> SEQ ID NO 295
<211> LENGTH: 118
<212> TYPE: PRT
<213> ORGANISM: Artificial sequence
<220> FEATURE:
<223> OTHER INFORMATION: synthetic sequence

<400> SEQUENCE: 295

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Gly Tyr
            20                  25                  30

Gly Met Ser Trp Val Arg Gln Thr Pro Asp Lys Arg Leu Glu Trp Val
        35                  40                  45

Ala Thr Ile Thr Ser Gly Gly Thr Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Ile Asp Ser Leu Lys Ser Glu Asp Thr Ala Ile Tyr Phe Cys
                85                  90                  95

Ala Arg Ser Leu Ala Gly Asn Ala Met Asp Tyr Trp Gly Gln Gly Thr
            100                 105                 110

Ser Val Thr Val Ser Ser
        115

<210> SEQ ID NO 296
<211> LENGTH: 107
<212> TYPE: PRT
<213> ORGANISM: Artificial sequence
<220> FEATURE:
<223> OTHER INFORMATION: synthetic sequence

<400> SEQUENCE: 296

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Thr Ile Ser Asp Tyr
            20                  25                  30

Leu His Trp Tyr Gln Gln Lys Ser His Glu Ser Pro Arg Leu Leu Ile
        35                  40                  45

Lys Phe Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Gly Phe Pro Arg
                85                  90                  95

Thr Phe Gly Gly Gly Thr Lys Leu Glu Ile Lys
            100                 105

<210> SEQ ID NO 297
<211> LENGTH: 118
<212> TYPE: PRT
<213> ORGANISM: Artificial sequence
<220> FEATURE:
<223> OTHER INFORMATION: synthetic sequence
```

<400> SEQUENCE: 297

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Gly Met Ser Trp Val Arg Gln Ala Pro Gly Lys Gly Leu Glu Trp Val
        35                  40                  45

Ala Thr Ile Thr Ser Gly Gly Thr Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Gly Asn Ala Met Asp Tyr Trp Gly Gln Gly Thr
            100                 105                 110

Met Val Thr Val Ser Ser
        115
```

<210> SEQ ID NO 298
<211> LENGTH: 107
<212> TYPE: PRT
<213> ORGANISM: Artificial sequence
<220> FEATURE:
<223> OTHER INFORMATION: synthetic sequence

<400> SEQUENCE: 298

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Thr Ile Ser Asp Tyr
            20                  25                  30

Leu His Trp Tyr Gln Gln Lys Pro Gly Gln Ala Pro Arg Leu Leu Ile
        35                  40                  45

Lys Phe Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Gly Phe Pro Arg
                85                  90                  95

Thr Phe Gly Gln Gly Thr Lys Leu Glu Ile Lys
            100                 105
```

<210> SEQ ID NO 299
<211> LENGTH: 17
<212> TYPE: PRT
<213> ORGANISM: Artificial sequence
<220> FEATURE:
<223> OTHER INFORMATION: synthetic sequence

<400> SEQUENCE: 299

```
Thr Ile Thr Ser Gly Gly Thr Tyr Thr Tyr Tyr Pro Asp Ser Val Lys
1               5                   10                  15

Gly
```

<210> SEQ ID NO 300
<211> LENGTH: 9
<212> TYPE: PRT
<213> ORGANISM: Artificial sequence
<220> FEATURE:

```
<223> OTHER INFORMATION: synthetic sequence

<400> SEQUENCE: 300

Ser Leu Ala Gly Asn Ala Met Asp Tyr
1               5

<210> SEQ ID NO 301
<211> LENGTH: 5
<212> TYPE: PRT
<213> ORGANISM: Artificial sequence
<220> FEATURE:
<223> OTHER INFORMATION: synthetic sequence

<400> SEQUENCE: 301

Arg Tyr Thr Met Ser
1               5

<210> SEQ ID NO 302
<211> LENGTH: 17
<212> TYPE: PRT
<213> ORGANISM: Artificial sequence
<220> FEATURE:
<223> OTHER INFORMATION: synthetic sequence

<400> SEQUENCE: 302

Thr Ile Ser Ser Gly Gly Gly Asn Thr Tyr Tyr Pro Asp Ser Val Lys
1               5                   10                  15

Gly

<210> SEQ ID NO 303
<211> LENGTH: 17
<212> TYPE: PRT
<213> ORGANISM: Artificial sequence
<220> FEATURE:
<223> OTHER INFORMATION: synthetic sequence

<400> SEQUENCE: 303

Thr Ile Ser Ser Gly Gly Gly Gln Thr Tyr Tyr Pro Asp Ser Val Lys
1               5                   10                  15

Gly

<210> SEQ ID NO 304
<211> LENGTH: 17
<212> TYPE: PRT
<213> ORGANISM: Artificial sequence
<220> FEATURE:
<223> OTHER INFORMATION: synthetic sequence

<400> SEQUENCE: 304

Thr Ile Ser Ser Gly Gly Gly Ser Thr Tyr Tyr Pro Asp Ser Val Lys
1               5                   10                  15

Gly

<210> SEQ ID NO 305
<211> LENGTH: 10
<212> TYPE: PRT
<213> ORGANISM: Artificial sequence
<220> FEATURE:
<223> OTHER INFORMATION: synthetic sequence

<400> SEQUENCE: 305

Tyr Gly Ala Gly Asp Ala Trp Phe Ala Tyr
1               5                   10
```

```
<210> SEQ ID NO 306
<211> LENGTH: 5
<212> TYPE: PRT
<213> ORGANISM: Artificial sequence
<220> FEATURE:
<223> OTHER INFORMATION: synthetic sequence

<400> SEQUENCE: 306

Asn Tyr Asn Met His
1               5

<210> SEQ ID NO 307
<211> LENGTH: 17
<212> TYPE: PRT
<213> ORGANISM: Artificial sequence
<220> FEATURE:
<223> OTHER INFORMATION: synthetic sequence

<400> SEQUENCE: 307

Thr Ile Tyr Pro Gly Asn Asp Asp Thr Ser Tyr Asn Gln Lys Phe Lys
1               5                   10                  15

Asp

<210> SEQ ID NO 308
<211> LENGTH: 8
<212> TYPE: PRT
<213> ORGANISM: Artificial sequence
<220> FEATURE:
<223> OTHER INFORMATION: synthetic sequence

<400> SEQUENCE: 308

Gly Gly Tyr Arg Ala Met Asp Tyr
1               5

<210> SEQ ID NO 309
<211> LENGTH: 448
<212> TYPE: PRT
<213> ORGANISM: Artificial sequence
<220> FEATURE:
<223> OTHER INFORMATION: synthetic sequence

<400> SEQUENCE: 309

Glu Val Gln Leu Val Glu Ser Gly Gly Val Val Val Gln Pro Gly Gly
1               5                   10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
            35                  40                  45

Ala Thr Ile Ser Ser Gly Gly Gly Asn Thr Tyr Tyr Pro Asp Ser Val
        50                  55                  60

Lys Gly Arg Phe Thr Val Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Arg Tyr Gly Ala Gly Asp Ala Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160
```

-continued

```
Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Asp Thr Thr Pro Pro Val Leu
385                 390                 395                 400

Asp Ser Asp Gly Ser Phe Phe Leu Tyr Ser Asp Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 310
<211> LENGTH: 446
<212> TYPE: PRT
<213> ORGANISM: Artificial sequence
<220> FEATURE:
<223> OTHER INFORMATION: synthetic sequence

<400> SEQUENCE: 310

Gln Val Gln Leu Val Gln Ser Gly Ala Glu Val Lys Lys Pro Gly Ala
1                   5                   10                  15

Ser Val Lys Val Ser Cys Lys Ala Ser Gly Tyr Thr Phe Thr Asn Tyr
            20                  25                  30

Asn Met His Trp Val Arg Gln Ala Pro Gly Gln Arg Leu Glu Trp Met
            35                  40                  45

Gly Thr Ile Tyr Pro Gly Asn Asp Asp Thr Ser Tyr Asn Gln Lys Phe
            50                  55                  60

Lys Asp Arg Val Thr Ile Thr Ala Asp Thr Ser Ala Ser Thr Ala Tyr
65                  70                  75                  80
```

-continued

```
Met Glu Leu Ser Ser Leu Arg Ser Glu Asp Thr Ala Val Tyr Tyr Cys
            85                  90                  95

Ala Arg Gly Gly Tyr Arg Ala Met Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Lys Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Lys Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
            435                 440                 445

<210> SEQ ID NO 311
<211> LENGTH: 112
<212> TYPE: PRT
<213> ORGANISM: Artificial sequence
<220> FEATURE:
<223> OTHER INFORMATION: synthetic sequence

<400> SEQUENCE: 311
```

-continued

```
Asp Ile Val Met Thr Gln Ser Pro Leu Ser Leu Pro Val Ser Leu Gly
1               5                   10                  15

Asp Pro Ala Ser Ile Ser Cys Arg Ser Ser Gln Ser Leu Val His Ser
            20                  25                  30

Asn Gly Asn Thr Tyr Leu Glu Tyr Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Phe Pro Arg Thr Phe Gly Gly Gly Thr Lys Leu Glu Ile Lys
            100                 105                 110
```

<210> SEQ ID NO 312
<211> LENGTH: 112
<212> TYPE: PRT
<213> ORGANISM: Artificial sequence
<220> FEATURE:
<223> OTHER INFORMATION: synthetic sequence

<400> SEQUENCE: 312

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Ile Val Tyr Ser
            20                  25                  30

Asn Gly Asn Thr Tyr Leu Glu Trp Tyr Gln Gln Lys Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Ser His Phe Pro Arg Thr Phe Gly Gly Gly Thr Lys Leu Glu Ile Lys
            100                 105                 110
```

<210> SEQ ID NO 313
<211> LENGTH: 112
<212> TYPE: PRT
<213> ORGANISM: Artificial sequence
<220> FEATURE:
<223> OTHER INFORMATION: synthetic sequence

<400> SEQUENCE: 313

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Ala
```

-continued

```
                 85                90                95
Ser His Phe Pro Arg Thr Phe Gly Gly Gly Thr Lys Leu Glu Ile Lys
            100                105                110
```

<210> SEQ ID NO 314
<211> LENGTH: 118
<212> TYPE: PRT
<213> ORGANISM: Artificial sequence
<220> FEATURE:
<223> OTHER INFORMATION: synthetic sequence

<400> SEQUENCE: 314

```
Glu Val Gln Leu Val Glu Ser Gly Gly Gly Leu Val Gln Pro Gly Gly
1               5                10                15

Ser Leu Arg Leu Ser Cys Ala Ala Ser Gly Phe Thr Phe Ser Asp Ser
            20                25                30

Trp Ile His Trp Val Arg Gln Ala Pro Gly Lys Gly Leu Glu Trp Val
            35                40                45

Ala Trp Ile Ser Pro Tyr Gly Gly Ser Thr Tyr Tyr Ala Asp Ser Val
        50                55                60

Lys Gly Arg Phe Thr Ile Ser Ala Asp Thr Ser Lys Asn Thr Ala Tyr
65                70                75                80

Leu Gln Met Asn Ser Leu Arg Ala Glu Asp Thr Ala Val Tyr Tyr Cys
                85                90                95

Ala Arg Arg His Trp Pro Gly Gly Phe Asp Tyr Trp Gly Gln Gly Thr
            100                105                110

Leu Val Thr Val Ser Ser
        115
```

<210> SEQ ID NO 315
<211> LENGTH: 5
<212> TYPE: PRT
<213> ORGANISM: Artificial sequence
<220> FEATURE:
<223> OTHER INFORMATION: synthetic sequence

<400> SEQUENCE: 315

```
Asp Ser Trp Ile His
1               5
```

<210> SEQ ID NO 316
<211> LENGTH: 17
<212> TYPE: PRT
<213> ORGANISM: Artificial sequence
<220> FEATURE:
<223> OTHER INFORMATION: synthetic sequence

<400> SEQUENCE: 316

```
Trp Ile Ser Pro Tyr Gly Gly Ser Thr Tyr Tyr Ala Asp Ser Val Lys
1               5                10                15

Gly
```

<210> SEQ ID NO 317
<211> LENGTH: 9
<212> TYPE: PRT
<213> ORGANISM: Artificial sequence
<220> FEATURE:
<223> OTHER INFORMATION: synthetic sequence

<400> SEQUENCE: 317

```
Arg His Trp Pro Gly Gly Phe Asp Tyr
1               5
```

-continued

```
<210> SEQ ID NO 318
<211> LENGTH: 448
<212> TYPE: PRT
<213> ORGANISM: Artificial sequence
<220> FEATURE:
<223> OTHER INFORMATION: synthetic sequence

<400> SEQUENCE: 318

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365
```

```
Leu Val Lys Gly Phe Tyr Pro Ser Asp Ile Ala Val Glu Trp Glu Ser
    370                 375                 380
```

```
Asn Gly Gln Pro Glu Asn Asn Tyr Lys Thr Thr Pro Pro Val Leu Asp
385                 390                 395                 400
```

```
Ser Asp Gly Ser Phe Phe Leu Tyr Ser Lys Leu Thr Val Asp Lys Ser
                405                 410                 415
```

```
Arg Trp Gln Gln Gly Asn Val Phe Ser Cys Ser Val Met His Glu Ala
            420                 425                 430
```

```
Leu His Asn His Tyr Thr Gln Lys Ser Leu Ser Leu Ser Pro Gly Lys
        435                 440                 445
```

<210> SEQ ID NO 319
<211> LENGTH: 214
<212> TYPE: PRT
<213> ORGANISM: Artificial sequence
<220> FEATURE:
<223> OTHER INFORMATION: synthetic sequence

<400> SEQUENCE: 319

```
Asp Val Gln Met Thr Gln Ser Pro Ser Ser Leu Ser Ala Ser Val Gly
1               5                   10                  15
```

```
Asp Arg Val Thr Ile Thr Cys Arg Ala Ser Gln Asn Val Gly Ser Tyr
            20                  25                  30
```

```
Ile Ala Trp Tyr Gln Gln Lys Pro Gly Lys Ser Pro Lys Ala Leu Ile
        35                  40                  45
```

```
Tyr Ser Ala Ser Tyr Arg Ser Ser Gly Val Pro Ser Arg Phe Ser Gly
    50                  55                  60
```

```
Ser Gly Ala Gly Thr Asp Phe Thr Leu Thr Ile Ser Ser Leu Gln Pro
65                  70                  75                  80
```

```
Glu Asp Phe Ala Thr Tyr Phe Cys Gln Gln Tyr Asn Ser Tyr Pro Leu
                85                  90                  95
```

```
Thr Phe Gly Gly Gly Thr Lys Leu Glu Ile Lys Arg Thr Val Ala Ala
            100                 105                 110
```

```
Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
        195                 200                 205
```

```
Phe Asn Arg Gly Glu Cys
    210
```

<210> SEQ ID NO 320
<211> LENGTH: 450
<212> TYPE: PRT
<213> ORGANISM: Artificial sequence
<220> FEATURE:
<223> OTHER INFORMATION: synthetic sequence

<400> SEQUENCE: 320

```
Glu Val Gln Leu Val Glu Ser Gly Gly Gly Leu Val Gln Pro Gly Gly
```

```
1                 5                    10                   15
Ser Leu Arg Leu Ser Cys Ala Ala Ser Gly Phe Asn Ile Lys Asp Thr
            20                   25                   30

Tyr Ile His Trp Val Arg Gln Ala Pro Gly Lys Gly Leu Glu Trp Val
            35                   40                   45

Ala Arg Ile Tyr Pro Thr Asn Gly Tyr Thr Arg Tyr Ala Asp Ser Val
            50                   55                   60

Lys Gly Arg Phe Thr Ile Ser Ala Asp Thr Ser Lys Asn Thr Ala Tyr
65                   70                   75                   80

Leu Gln Met Asn Ser Leu Arg Ala Glu Asp Thr Ala Val Tyr Tyr Cys
                    85                   90                   95

Ser Arg Trp Gly Gly Asp Gly Phe Tyr Ala Met Asp Tyr Trp Gly Gln
            100                  105                  110

Gly Thr Leu Val Thr Val Ser Ser Ala Ser Thr Lys Gly Pro Ser Val
            115                  120                  125

Phe Pro Leu Ala Pro Ser Ser Lys Ser Thr Ser Gly Gly Thr Ala Ala
            130                  135                  140

Leu Gly Cys Leu Val Lys Asp Tyr Phe Pro Glu Pro Val Thr Val Ser
145                  150                  155                  160

Trp Asn Ser Gly Ala Leu Thr Ser Gly Val His Thr Phe Pro Ala Val
                    165                  170                  175

Leu Gln Ser Ser Gly Leu Tyr Ser Leu Ser Ser Val Val Thr Val Pro
                    180                  185                  190

Ser Ser Ser Leu Gly Thr Gln Thr Tyr Ile Cys Asn Val Asn His Lys
                    195                  200                  205

Pro Ser Asn Thr Lys Val Asp Lys Lys Val Glu Pro Lys Ser Cys Asp
            210                  215                  220

Lys Thr His Thr Cys Pro Pro Cys Pro Ala Pro Glu Leu Leu Gly Gly
225                  230                  235                  240

Pro Ser Val Phe Leu Phe Pro Pro Lys Pro Lys Asp Thr Leu Met Ile
                    245                  250                  255

Ser Arg Thr Pro Glu Val Thr Cys Val Val Val Asp Val Ser His Glu
            260                  265                  270

Asp Pro Glu Val Lys Phe Asn Trp Tyr Val Asp Gly Val Glu Val His
            275                  280                  285

Asn Ala Lys Thr Lys Pro Arg Glu Glu Gln Tyr Asn Ser Thr Tyr Arg
            290                  295                  300

Val Val Ser Val Leu Thr Val Leu His Gln Asp Trp Leu Asn Gly Lys
305                  310                  315                  320

Glu Tyr Lys Cys Lys Val Ser Asn Lys Ala Leu Pro Ala Pro Ile Glu
                    325                  330                  335

Lys Thr Ile Ser Lys Ala Lys Gly Gln Pro Arg Glu Pro Gln Val Tyr
                    340                  345                  350

Thr Leu Pro Pro Ser Arg Glu Glu Met Thr Lys Asn Gln Val Ser Leu
            355                  360                  365

Thr Cys Leu Val Lys Gly Phe Tyr Pro Ser Asp Ile Ala Val Glu Trp
            370                  375                  380

Glu Ser Asn Gly Gln Pro Glu Asn Asn Tyr Lys Thr Thr Pro Pro Val
385                  390                  395                  400

Leu Asp Ser Asp Gly Ser Phe Phe Leu Tyr Ser Lys Leu Thr Val Asp
                    405                  410                  415

Lys Ser Arg Trp Gln Gln Gly Asn Val Phe Ser Cys Ser Val Met His
            420                  425                  430
```

-continued

Glu Ala Leu His Asn His Tyr Thr Gln Lys Ser Leu Ser Leu Ser Pro
        435                 440                 445

Gly Lys
    450

<210> SEQ ID NO 321
<211> LENGTH: 7
<212> TYPE: PRT
<213> ORGANISM: Artificial sequence
<220> FEATURE:
<223> OTHER INFORMATION: synthetic sequence

<400> SEQUENCE: 321

Gly Phe Asn Ile Lys Asp Thr
1               5

<210> SEQ ID NO 322
<211> LENGTH: 6
<212> TYPE: PRT
<213> ORGANISM: Artificial sequence
<220> FEATURE:
<223> OTHER INFORMATION: synthetic sequence

<400> SEQUENCE: 322

Tyr Pro Thr Asn Gly Tyr
1               5

<210> SEQ ID NO 323
<211> LENGTH: 11
<212> TYPE: PRT
<213> ORGANISM: Artificial sequence
<220> FEATURE:
<223> OTHER INFORMATION: synthetic sequence

<400> SEQUENCE: 323

Trp Gly Gly Asp Gly Phe Tyr Ala Met Asp Tyr
1               5                   10

<210> SEQ ID NO 324
<211> LENGTH: 448
<212> TYPE: PRT
<213> ORGANISM: Artificial sequence
<220> FEATURE:
<223> OTHER INFORMATION: synthetic sequence

<400> SEQUENCE: 324

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

-continued

```
Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445
```

```
<210> SEQ ID NO 325
<211> LENGTH: 7
<212> TYPE: PRT
<213> ORGANISM: Artificial sequence
<220> FEATURE:
<223> OTHER INFORMATION: synthetic sequence

<400> SEQUENCE: 325

Gly Phe Thr Phe Thr Asp Tyr
1               5

<210> SEQ ID NO 326
<211> LENGTH: 6
<212> TYPE: PRT
<213> ORGANISM: Artificial sequence
```

```
<220> FEATURE:
<223> OTHER INFORMATION: synthetic sequence

<400> SEQUENCE: 326

Asn Pro Asn Ser Gly Gly
1               5

<210> SEQ ID NO 327
<211> LENGTH: 10
<212> TYPE: PRT
<213> ORGANISM: Artificial sequence
<220> FEATURE:
<223> OTHER INFORMATION: synthetic sequence

<400> SEQUENCE: 327

Asn Leu Gly Pro Ser Phe Tyr Phe Asp Tyr
1               5                   10

<210> SEQ ID NO 328
<211> LENGTH: 7
<212> TYPE: PRT
<213> ORGANISM: Artificial sequence
<220> FEATURE:
<223> OTHER INFORMATION: synthetic sequence

<400> SEQUENCE: 328

Lys Ile Ser Asn Arg Phe Ser
1               5

<210> SEQ ID NO 329
<211> LENGTH: 9
<212> TYPE: PRT
<213> ORGANISM: Artificial sequence
<220> FEATURE:
<223> OTHER INFORMATION: synthetic sequence

<400> SEQUENCE: 329

Phe Gln Ala Ser His Phe Pro Arg Thr
1               5

<210> SEQ ID NO 330
<211> LENGTH: 1280
<212> TYPE: PRT
<213> ORGANISM: Homo sapiens

<400> SEQUENCE: 330

Met Asp Leu Glu Gly Asp Arg Asn Gly Gly Ala Lys Lys Lys Asn Phe
1               5                   10                  15

Phe Lys Leu Asn Asn Lys Ser Glu Lys Asp Lys Lys Glu Lys Lys Pro
                20                  25                  30

Thr Val Ser Val Phe Ser Met Phe Arg Tyr Ser Asn Trp Leu Asp Lys
            35                  40                  45

Leu Tyr Met Val Val Gly Thr Leu Ala Ala Ile Ile His Gly Ala Gly
        50                  55                  60

Leu Pro Leu Met Met Leu Val Phe Gly Glu Met Thr Asp Ile Phe Ala
65                  70                  75                  80

Asn Ala Gly Asn Leu Glu Asp Leu Met Ser Asn Ile Thr Asn Arg Ser
                85                  90                  95

Asp Ile Asn Asp Thr Gly Phe Phe Met Asn Leu Glu Glu Asp Met Thr
            100                 105                 110

Arg Tyr Ala Tyr Tyr Tyr Ser Gly Ile Gly Ala Gly Val Leu Val Ala
        115                 120                 125
```

-continued

```
Ala Tyr Ile Gln Val Ser Phe Trp Cys Leu Ala Ala Gly Arg Gln Ile
    130                 135                 140

His Lys Ile Arg Lys Gln Phe Phe His Ala Ile Met Arg Gln Glu Ile
145                 150                 155                 160

Gly Trp Phe Asp Val His Asp Val Gly Glu Leu Asn Thr Arg Leu Thr
                165                 170                 175

Asp Asp Val Ser Lys Ile Asn Glu Gly Ile Gly Asp Lys Ile Gly Met
                180                 185                 190

Phe Phe Gln Ser Met Ala Thr Phe Phe Thr Gly Phe Ile Val Gly Phe
                195                 200                 205

Thr Arg Gly Trp Lys Leu Thr Leu Val Ile Leu Ala Ile Ser Pro Val
    210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
                245                 250                 255

Val Leu Ala Ala Ile Arg Thr Val Ile Ala Phe Gly Gly Gln Lys Lys
                260                 265                 270

Glu Leu Glu Arg Tyr Asn Lys Asn Leu Glu Glu Ala Lys Arg Ile Gly
                275                 280                 285

Ile Lys Lys Ala Ile Thr Ala Asn Ile Ser Ile Gly Ala Ala Phe Leu
    290                 295                 300

Leu Ile Tyr Ala Ser Tyr Ala Leu Ala Phe Trp Tyr Gly Thr Thr Leu
305                 310                 315                 320

Val Leu Ser Gly Glu Tyr Ser Ile Gly Gln Val Leu Thr Val Phe Phe
                325                 330                 335

Ser Val Leu Ile Gly Ala Phe Ser Val Gly Gln Ala Ser Pro Ser Ile
                340                 345                 350

Glu Ala Phe Ala Asn Ala Arg Gly Ala Ala Tyr Glu Ile Phe Lys Ile
                355                 360                 365

Ile Asp Asn Lys Pro Ser Ile Asp Ser Tyr Ser Lys Ser Gly His Lys
    370                 375                 380

Pro Asp Asn Ile Lys Gly Asn Leu Glu Phe Arg Asn Val His Phe Ser
385                 390                 395                 400

Tyr Pro Ser Arg Lys Glu Val Lys Ile Leu Lys Gly Leu Asn Leu Lys
                405                 410                 415

Val Gln Ser Gly Gln Thr Val Ala Leu Val Gly Asn Ser Gly Cys Gly
                420                 425                 430

Lys Ser Thr Thr Val Gln Leu Met Gln Arg Leu Tyr Asp Pro Thr Glu
                435                 440                 445

Gly Met Val Ser Val Asp Gly Gln Asp Ile Arg Thr Ile Asn Val Arg
    450                 455                 460

Phe Leu Arg Glu Ile Ile Gly Val Val Ser Gln Glu Pro Val Leu Phe
465                 470                 475                 480

Ala Thr Thr Ile Ala Glu Asn Ile Arg Tyr Gly Arg Glu Asn Val Thr
                485                 490                 495

Met Asp Glu Ile Glu Lys Ala Val Lys Glu Ala Asn Ala Tyr Asp Phe
                500                 505                 510

Ile Met Lys Leu Pro His Lys Phe Asp Thr Leu Val Gly Glu Arg Gly
                515                 520                 525

Ala Gln Leu Ser Gly Gly Gln Lys Gln Arg Ile Ala Ile Ala Arg Ala
    530                 535                 540

Leu Val Arg Asn Pro Lys Ile Leu Leu Leu Asp Glu Ala Thr Ser Ala
```

-continued

```
545                 550                 555                 560

Leu Asp Thr Glu Ser Glu Ala Val Val Gln Val Ala Leu Asp Lys Ala
                565                 570                 575

Arg Lys Gly Arg Thr Thr Ile Val Ile Ala His Arg Leu Ser Thr Val
                580                 585                 590

Arg Asn Ala Asp Val Ile Ala Gly Phe Asp Asp Gly Val Ile Val Glu
            595                 600                 605

Lys Gly Asn His Asp Glu Leu Met Lys Glu Lys Gly Ile Tyr Phe Lys
        610                 615                 620

Leu Val Thr Met Gln Thr Ala Gly Asn Glu Val Glu Leu Glu Asn Ala
625                 630                 635                 640

Ala Asp Glu Ser Lys Ser Glu Ile Asp Ala Leu Glu Met Ser Ser Asn
                645                 650                 655

Asp Ser Arg Ser Ser Leu Ile Arg Lys Arg Ser Thr Arg Arg Ser Val
                660                 665                 670

Arg Gly Ser Gln Ala Gln Asp Arg Lys Leu Ser Thr Lys Glu Ala Leu
            675                 680                 685

Asp Glu Ser Ile Pro Pro Val Ser Phe Trp Arg Ile Met Lys Leu Asn
        690                 695                 700

Leu Thr Glu Trp Pro Tyr Phe Val Val Gly Val Phe Cys Ala Ile Ile
705                 710                 715                 720

Asn Gly Gly Leu Gln Pro Ala Phe Ala Ile Ile Phe Ser Lys Ile Ile
                725                 730                 735

Gly Val Phe Thr Arg Ile Asp Asp Pro Glu Thr Lys Arg Gln Asn Ser
                740                 745                 750

Asn Leu Phe Ser Leu Leu Phe Leu Ala Leu Gly Ile Ile Ser Phe Ile
            755                 760                 765

Thr Phe Phe Leu Gln Gly Phe Thr Phe Gly Lys Ala Gly Glu Ile Leu
        770                 775                 780

Thr Lys Arg Leu Arg Tyr Met Val Phe Arg Ser Met Leu Arg Gln Asp
785                 790                 795                 800

Val Ser Trp Phe Asp Asp Pro Lys Asn Thr Thr Gly Ala Leu Thr Thr
                805                 810                 815

Arg Leu Ala Asn Asp Ala Ala Gln Val Lys Gly Ala Ile Gly Ser Arg
                820                 825                 830

Leu Ala Val Ile Thr Gln Asn Ile Ala Asn Leu Gly Thr Gly Ile Ile
            835                 840                 845

Ile Ser Phe Ile Tyr Gly Trp Gln Leu Thr Leu Leu Leu Leu Ala Ile
        850                 855                 860

Val Pro Ile Ile Ala Ile Ala Gly Val Val Glu Met Lys Met Leu Ser
865                 870                 875                 880

Gly Gln Ala Leu Lys Asp Lys Lys Glu Leu Glu Gly Ser Gly Lys Ile
                885                 890                 895

Ala Thr Glu Ala Ile Glu Asn Phe Arg Thr Val Val Ser Leu Thr Gln
            900                 905                 910

Glu Gln Lys Phe Glu His Met Tyr Ala Gln Ser Leu Gln Val Pro Tyr
            915                 920                 925

Arg Asn Ser Leu Arg Lys Ala His Ile Phe Gly Ile Thr Phe Ser Phe
        930                 935                 940

Thr Gln Ala Met Met Tyr Phe Ser Tyr Ala Gly Cys Phe Arg Phe Gly
945                 950                 955                 960

Ala Tyr Leu Val Ala His Lys Leu Met Ser Phe Glu Asp Val Leu Leu
                965                 970                 975
```

-continued

```
Val Phe Ser Ala Val Val Phe Gly Ala Met Ala Val Gly Gln Val Ser
            980                 985                 990

Ser Phe Ala Pro Asp Tyr Ala Lys  Ala Lys Ile Ser Ala  Ala His Ile
        995                 1000                1005

Ile Met  Ile Ile Glu Lys Thr  Pro Leu Ile Asp Ser  Tyr Ser Thr
    1010                1015                1020

Glu Gly  Leu Met Pro Asn Thr  Leu Glu Gly Asn Val  Thr Phe Gly
    1025                1030                1035

Glu Val  Val Phe Asn Tyr Pro  Thr Arg Pro Asp Ile  Pro Val Leu
    1040                1045                1050

Gln Gly  Leu Ser Leu Glu Val  Lys Lys Gly Gln Thr  Leu Ala Leu
    1055                1060                1065

Val Gly  Ser Ser Gly Cys Gly  Lys Ser Thr Val Val  Gln Leu Leu
    1070                1075                1080

Glu Arg  Phe Tyr Asp Pro Leu  Ala Gly Lys Val Leu  Leu Asp Gly
    1085                1090                1095

Lys Glu  Ile Lys Arg Leu Asn  Val Gln Trp Leu Arg  Ala His Leu
    1100                1105                1110

Gly Ile  Val Ser Gln Glu Pro  Ile Leu Phe Asp Cys  Ser Ile Ala
    1115                1120                1125

Glu Asn  Ile Ala Tyr Gly Asp  Asn Ser Arg Val Val  Ser Gln Glu
    1130                1135                1140

Glu Ile  Val Arg Ala Ala Lys  Glu Ala Asn Ile His  Ala Phe Ile
    1145                1150                1155

Glu Ser  Leu Pro Asn Lys Tyr  Ser Thr Lys Val Gly  Asp Lys Gly
    1160                1165                1170

Thr Gln  Leu Ser Gly Gly Gln  Lys Gln Arg Ile Ala  Ile Ala Arg
    1175                1180                1185

Ala Leu  Val Arg Gln Pro His  Ile Leu Leu Leu Asp  Glu Ala Thr
    1190                1195                1200

Ser Ala  Leu Asp Thr Glu Ser  Glu Lys Val Val Gln  Glu Ala Leu
    1205                1210                1215

Asp Lys  Ala Arg Glu Gly Arg  Thr Cys Ile Val Ile  Ala His Arg
    1220                1225                1230

Leu Ser  Thr Ile Gln Asn Ala  Asp Leu Ile Val Val  Phe Gln Asn
    1235                1240                1245

Gly Arg  Val Lys Glu His Gly  Thr His Gln Gln Leu  Leu Ala Gln
    1250                1255                1260

Lys Gly  Ile Tyr Phe Ser Met  Val Ser Val Gln Ala  Gly Thr Lys
    1265                1270                1275

Arg Gln
    1280
```

```
<210> SEQ ID NO 331
<211> LENGTH: 1276
<212> TYPE: PRT
<213> ORGANISM: Mus musculus

<400> SEQUENCE: 331

Met Glu Leu Glu Glu Asp Leu Lys Gly Arg Ala Asp Lys Asn Phe Ser
1               5                   10                  15

Lys Met Gly Lys Lys Ser Lys Lys Glu Lys Lys Glu Lys Lys Pro Ala
            20                  25                  30

Val Ser Val Leu Thr Met Phe Arg Tyr Ala Gly Trp Leu Asp Arg Leu
```

-continued

```
            35                  40                  45
Tyr Met Leu Val Gly Thr Leu Ala Ala Ile Ile His Gly Val Ala Leu
    50                  55                  60

Pro Leu Met Met Leu Ile Phe Gly Asp Met Thr Asp Ser Phe Ala Ser
65                  70                  75                  80

Val Gly Asn Val Ser Lys Asn Ser Thr Asn Met Ser Glu Ala Asp Lys
                85                  90                  95

Arg Ala Met Phe Ala Lys Leu Glu Glu Glu Met Thr Thr Tyr Ala Tyr
            100                 105                 110

Tyr Tyr Thr Gly Ile Gly Ala Gly Val Leu Ile Val Ala Tyr Ile Gln
            115                 120                 125

Val Ser Phe Trp Cys Leu Ala Ala Gly Arg Gln Ile His Lys Ile Arg
    130                 135                 140

Gln Lys Phe Phe His Ala Ile Met Asn Gln Glu Ile Gly Trp Phe Asp
145                 150                 155                 160

Val His Asp Val Gly Glu Leu Asn Thr Arg Leu Thr Asp Asp Val Ser
            165                 170                 175

Lys Ile Asn Glu Gly Ile Gly Asp Lys Ile Gly Met Phe Phe Gln Ala
            180                 185                 190

Met Ala Thr Phe Phe Gly Gly Phe Ile Ile Gly Phe Thr Arg Gly Trp
            195                 200                 205

Lys Leu Thr Leu Val Ile Leu Ala Ile Ser Pro Val Leu Gly Leu Ser
    210                 215                 220

Ala Gly Ile Trp Ala Lys Ile Leu Ser Ser Phe Thr Asp Lys Glu Leu
225                 230                 235                 240

His Ala Tyr Ala Lys Ala Gly Ala Val Ala Glu Glu Val Leu Ala Ala
            245                 250                 255

Ile Arg Thr Val Ile Ala Phe Gly Gly Gln Lys Lys Glu Leu Glu Arg
            260                 265                 270

Tyr Asn Asn Asn Leu Glu Glu Ala Lys Arg Leu Gly Ile Lys Lys Ala
            275                 280                 285

Ile Thr Ala Asn Ile Ser Met Gly Ala Ala Phe Leu Leu Ile Tyr Ala
    290                 295                 300

Ser Tyr Ala Leu Ala Phe Trp Tyr Gly Thr Ser Leu Val Ile Ser Lys
305                 310                 315                 320

Glu Tyr Ser Ile Gly Gln Val Leu Thr Val Phe Phe Ser Val Leu Ile
            325                 330                 335

Gly Ala Phe Ser Val Gly Gln Ala Ser Pro Asn Ile Glu Ala Phe Ala
            340                 345                 350

Asn Ala Arg Gly Ala Ala Tyr Glu Val Phe Lys Ile Ile Asp Asn Lys
            355                 360                 365

Pro Ser Ile Asp Ser Phe Ser Lys Ser Gly His Lys Pro Asp Asn Ile
    370                 375                 380

Gln Gly Asn Leu Glu Phe Lys Asn Ile His Phe Ser Tyr Pro Ser Arg
385                 390                 395                 400

Lys Glu Val Gln Ile Leu Lys Gly Leu Asn Leu Lys Val Lys Ser Gly
            405                 410                 415

Gln Thr Val Ala Leu Val Gly Asn Ser Gly Cys Gly Lys Ser Thr Thr
            420                 425                 430

Val Gln Leu Met Gln Arg Leu Tyr Asp Pro Leu Asp Gly Met Val Ser
    435                 440                 445

Ile Asp Gly Gln Asp Ile Arg Thr Ile Asn Val Arg Tyr Leu Arg Glu
    450                 455                 460
```

-continued

```
Ile Ile Gly Val Val Ser Gln Glu Pro Val Leu Phe Ala Thr Thr Ile
465                 470             475             480

Ala Glu Asn Ile Arg Tyr Gly Arg Glu Asp Val Thr Met Asp Glu Ile
                485             490             495

Glu Lys Ala Val Lys Glu Ala Asn Ala Tyr Asp Phe Ile Met Lys Leu
            500             505             510

Pro His Gln Phe Asp Thr Leu Val Gly Glu Arg Gly Ala Gln Leu Ser
            515             520             525

Gly Gly Gln Lys Gln Arg Ile Ala Ile Ala Arg Ala Leu Val Arg Asn
        530             535             540

Pro Lys Ile Leu Leu Leu Asp Glu Ala Thr Ser Ala Leu Asp Thr Glu
545             550             555             560

Ser Glu Ala Val Val Gln Ala Ala Leu Asp Lys Ala Arg Glu Gly Arg
                565             570             575

Thr Thr Ile Val Ile Ala His Arg Leu Ser Thr Val Arg Asn Ala Asp
            580             585             590

Val Ile Ala Gly Phe Asp Gly Gly Val Ile Val Glu Gln Gly Asn His
        595             600             605

Asp Glu Leu Met Arg Glu Lys Gly Ile Tyr Phe Lys Leu Val Met Thr
        610             615             620

Gln Thr Ala Gly Asn Glu Ile Glu Leu Gly Asn Glu Ala Cys Lys Ser
625             630             635             640

Lys Asp Glu Ile Asp Asn Leu Asp Met Ser Ser Lys Asp Ser Gly Ser
                645             650             655

Ser Leu Ile Arg Arg Arg Ser Thr Arg Lys Ser Ile Cys Gly Pro His
            660             665             670

Asp Gln Asp Arg Lys Leu Ser Thr Lys Glu Ala Leu Asp Glu Asp Val
        675             680             685

Pro Pro Ala Ser Phe Trp Arg Ile Leu Lys Leu Asn Ser Thr Glu Trp
        690             695             700

Pro Tyr Phe Val Val Gly Ile Phe Cys Ala Ile Ile Asn Gly Gly Leu
705             710             715             720

Gln Pro Ala Phe Ser Val Ile Phe Ser Lys Val Val Gly Val Phe Thr
            725             730             735

Asn Gly Gly Pro Pro Glu Thr Gln Arg Gln Asn Ser Asn Leu Phe Ser
            740             745             750

Leu Leu Phe Leu Ile Leu Gly Ile Ile Ser Phe Ile Thr Phe Phe Leu
            755             760             765

Gln Gly Phe Thr Phe Gly Lys Ala Gly Glu Ile Leu Thr Lys Arg Leu
        770             775             780

Arg Tyr Met Val Phe Lys Ser Met Leu Arg Gln Asp Val Ser Trp Phe
785             790             795             800

Asp Asp Pro Lys Asn Thr Thr Gly Ala Leu Thr Thr Arg Leu Ala Asn
            805             810             815

Asp Ala Ala Gln Val Lys Gly Ala Thr Gly Ser Arg Leu Ala Val Ile
        820             825             830

Phe Gln Asn Ile Ala Asn Leu Gly Thr Gly Ile Ile Ile Ser Leu Ile
        835             840             845

Tyr Gly Trp Gln Leu Thr Leu Leu Leu Ala Ile Val Pro Ile Ile
        850             855             860

Ala Ile Ala Gly Val Val Glu Met Lys Met Leu Ser Gly Gln Ala Leu
865             870             875             880
```

-continued

```
Lys Asp Lys Lys Glu Leu Glu Gly Ser Gly Lys Ile Ala Thr Glu Ala
            885                 890                 895

Ile Glu Asn Phe Arg Thr Val Val Ser Leu Thr Arg Glu Gln Lys Phe
            900                 905                 910

Glu Thr Met Tyr Ala Gln Ser Leu Gln Ile Pro Tyr Arg Asn Ala Met
        915                 920                 925

Lys Lys Ala His Val Phe Gly Ile Thr Phe Ser Phe Thr Gln Ala Met
    930                 935                 940

Met Tyr Phe Ser Tyr Ala Ala Cys Phe Arg Phe Gly Ala Tyr Leu Val
945                 950                 955                 960

Thr Gln Gln Leu Met Thr Phe Glu Asn Val Leu Leu Val Phe Ser Ala
                965                 970                 975

Ile Val Phe Gly Ala Met Ala Val Gly Gln Val Ser Ser Phe Ala Pro
            980                 985                 990

Asp Tyr Ala Lys Ala Thr Val Ser Ala Ser His Ile Ile Arg Ile Ile
        995                 1000                1005

Glu Lys Thr Pro Glu Ile Asp Ser Tyr Ser Thr Gln Gly Leu Lys
    1010                1015                1020

Pro Asn Met Leu Glu Gly Asn Val Gln Phe Ser Gly Val Val Phe
    1025                1030                1035

Asn Tyr Pro Thr Arg Pro Ser Ile Pro Val Leu Gln Gly Leu Ser
    1040                1045                1050

Leu Glu Val Lys Lys Gly Gln Thr Leu Ala Leu Val Gly Ser Ser
    1055                1060                1065

Gly Cys Gly Lys Ser Thr Val Val Gln Leu Leu Glu Arg Phe Tyr
    1070                1075                1080

Asp Pro Met Ala Gly Ser Val Phe Leu Asp Gly Lys Glu Ile Lys
    1085                1090                1095

Gln Leu Asn Val Gln Trp Leu Arg Ala Gln Leu Gly Ile Val Ser
    1100                1105                1110

Gln Glu Pro Ile Leu Phe Asp Cys Ser Ile Ala Glu Asn Ile Ala
    1115                1120                1125

Tyr Gly Asp Asn Ser Arg Val Val Ser Tyr Glu Glu Ile Val Arg
    1130                1135                1140

Ala Ala Lys Glu Ala Asn Ile His Gln Phe Ile Asp Ser Leu Pro
    1145                1150                1155

Asp Lys Tyr Asn Thr Arg Val Gly Asp Lys Gly Thr Gln Leu Ser
    1160                1165                1170

Gly Gly Gln Lys Gln Arg Ile Ala Ile Ala Arg Ala Leu Val Arg
    1175                1180                1185

Gln Pro His Ile Leu Leu Leu Asp Glu Ala Thr Ser Ala Leu Asp
    1190                1195                1200

Thr Glu Ser Glu Lys Val Val Gln Glu Ala Leu Asp Lys Ala Arg
    1205                1210                1215

Glu Gly Arg Thr Cys Ile Val Ile Ala His Arg Leu Ser Thr Ile
    1220                1225                1230

Gln Asn Ala Asp Leu Ile Val Val Ile Gln Asn Gly Lys Val Lys
    1235                1240                1245

Glu His Gly Thr His Gln Gln Leu Leu Ala Gln Lys Gly Ile Tyr
    1250                1255                1260

Phe Ser Met Val Ser Val Gln Ala Gly Ala Lys Arg Ser
    1265                1270                1275
```

-continued

```
<210> SEQ ID NO 332
<211> LENGTH: 1276
<212> TYPE: PRT
<213> ORGANISM: Mus musculus

<400> SEQUENCE: 332

Met Glu Phe Glu Glu Asn Leu Lys Gly Arg Ala Asp Lys Asn Phe Ser
1               5                   10                  15

Lys Met Gly Lys Lys Ser Lys Lys Glu Lys Lys Glu Lys Lys Pro Ala
                20                  25                  30

Val Gly Val Phe Gly Met Phe Arg Tyr Ala Asp Trp Leu Asp Lys Leu
                35                  40                  45

Cys Met Ile Leu Gly Thr Leu Ala Ala Ile Ile His Gly Thr Leu Leu
            50                  55                  60

Pro Leu Leu Met Leu Val Phe Gly Asn Met Thr Asp Ser Phe Thr Lys
65                  70                  75                  80

Ala Glu Ala Ser Ile Leu Pro Ser Ile Thr Asn Gln Ser Gly Pro Asn
                85                  90                  95

Ser Thr Leu Ile Ile Ser Asn Ser Ser Leu Glu Glu Glu Met Ala Ile
                100                 105                 110

Tyr Ala Tyr Tyr Tyr Thr Gly Ile Gly Ala Gly Val Leu Ile Val Ala
                115                 120                 125

Tyr Ile Gln Val Ser Leu Trp Cys Leu Ala Ala Gly Arg Gln Ile His
            130                 135                 140

Lys Ile Arg Gln Lys Phe Phe His Ala Ile Met Asn Gln Glu Ile Gly
145                 150                 155                 160

Trp Phe Asp Val His Asp Val Gly Glu Leu Asn Thr Arg Leu Thr Asp
                165                 170                 175

Asp Val Ser Lys Ile Asn Asp Gly Ile Gly Asp Lys Ile Gly Met Phe
                180                 185                 190

Phe Gln Ser Ile Thr Thr Phe Leu Ala Gly Phe Ile Ile Gly Phe Ile
                195                 200                 205

Ser Gly Trp Lys Leu Thr Leu Val Ile Leu Ala Val Ser Pro Leu Ile
            210                 215                 220

Gly Leu Ser Ser Ala Leu Trp Ala Lys Val Leu Thr Ser Phe Thr Asn
225                 230                 235                 240

Lys Glu Leu Gln Ala Tyr Ala Lys Ala Gly Ala Val Ala Glu Glu Val
                245                 250                 255

Leu Ala Ala Ile Arg Thr Val Ile Ala Phe Gly Gly Gln Gln Lys Glu
                260                 265                 270

Leu Glu Arg Tyr Asn Lys Asn Leu Glu Glu Ala Lys Asn Val Gly Ile
            275                 280                 285

Lys Lys Ala Ile Thr Ala Ser Ile Ser Ile Gly Ile Ala Tyr Leu Leu
            290                 295                 300

Val Tyr Ala Ser Tyr Ala Leu Ala Phe Trp Tyr Gly Thr Ser Leu Val
305                 310                 315                 320

Leu Ser Asn Glu Tyr Ser Ile Gly Glu Val Leu Thr Val Phe Phe Ser
                325                 330                 335

Ile Leu Leu Gly Thr Phe Ser Ile Gly His Leu Ala Pro Asn Ile Glu
                340                 345                 350

Ala Phe Ala Asn Ala Arg Gly Ala Ala Phe Glu Ile Phe Lys Ile Ile
            355                 360                 365

Asp Asn Glu Pro Ser Ile Asp Ser Phe Ser Thr Lys Gly Tyr Lys Pro
            370                 375                 380
```

-continued

```
Asp Ser Ile Met Gly Asn Leu Glu Phe Lys Asn Val His Phe Asn Tyr
385                 390                 395                 400

Pro Ser Arg Ser Glu Val Gln Ile Leu Lys Gly Leu Asn Leu Lys Val
                405                 410                 415

Lys Ser Gly Gln Thr Val Ala Leu Val Gly Asn Ser Gly Cys Gly Lys
                420                 425                 430

Ser Thr Thr Val Gln Leu Met Gln Arg Leu Tyr Asp Pro Leu Glu Gly
            435                 440                 445

Val Val Ser Ile Asp Gly Gln Asp Ile Arg Thr Ile Asn Val Arg Tyr
            450                 455                 460

Leu Arg Glu Ile Ile Gly Val Val Ser Gln Glu Pro Val Leu Phe Ala
465                 470                 475                 480

Thr Thr Ile Ala Glu Asn Ile Arg Tyr Gly Arg Glu Asp Val Thr Met
                485                 490                 495

Asp Glu Ile Glu Lys Ala Val Lys Glu Ala Asn Ala Tyr Asp Phe Ile
                500                 505                 510

Met Lys Leu Pro His Gln Phe Asp Thr Leu Val Gly Glu Arg Gly Ala
            515                 520                 525

Gln Leu Ser Gly Gly Gln Lys Gln Arg Ile Ala Ile Ala Arg Ala Leu
            530                 535                 540

Val Arg Asn Pro Lys Ile Leu Leu Leu Asp Glu Ala Thr Ser Ala Leu
545                 550                 555                 560

Asp Thr Glu Ser Glu Ala Val Val Gln Ala Ala Leu Asp Lys Ala Arg
                565                 570                 575

Glu Gly Arg Thr Thr Ile Val Ile Ala His Arg Leu Ser Thr Val Arg
                580                 585                 590

Asn Ala Asp Val Ile Ala Gly Phe Asp Gly Gly Val Ile Val Glu Gln
            595                 600                 605

Gly Asn His Asp Glu Leu Met Arg Glu Lys Gly Ile Tyr Phe Lys Leu
            610                 615                 620

Val Met Thr Gln Thr Arg Gly Asn Glu Ile Glu Pro Gly Asn Asn Ala
625                 630                 635                 640

Tyr Gly Ser Gln Ser Asp Thr Asp Ala Ser Glu Leu Thr Ser Glu Glu
                645                 650                 655

Ser Lys Ser Pro Leu Ile Arg Arg Ser Ile Tyr Arg Ser Val His Arg
                660                 665                 670

Lys Gln Asp Gln Glu Arg Arg Leu Ser Met Lys Glu Ala Val Asp Glu
            675                 680                 685

Asp Val Pro Leu Val Ser Phe Trp Arg Ile Leu Asn Leu Asn Leu Ser
            690                 695                 700

Glu Trp Pro Tyr Leu Leu Val Gly Val Leu Cys Ala Val Ile Asn Gly
705                 710                 715                 720

Cys Ile Gln Pro Val Phe Ala Ile Val Phe Ser Arg Ile Val Gly Val
                725                 730                 735

Phe Ser Arg Asp Asp Asp His Glu Thr Lys Arg Gln Asn Cys Asn Leu
                740                 745                 750

Phe Ser Leu Phe Phe Leu Val Met Gly Leu Ile Ser Phe Val Thr Tyr
            755                 760                 765

Phe Phe Gln Gly Phe Thr Phe Gly Lys Ala Gly Glu Ile Leu Thr Lys
            770                 775                 780

Arg Val Arg Tyr Met Val Phe Lys Ser Met Leu Arg Gln Asp Ile Ser
785                 790                 795                 800

Trp Phe Asp Asp His Lys Asn Ser Thr Gly Ser Leu Thr Thr Arg Leu
```

-continued

```
                805                 810                 815

Ala Ser Asp Ala Ser Ser Val Lys Gly Ala Met Gly Ala Arg Leu Ala
            820                 825                 830

Val Val Thr Gln Asn Val Ala Asn Leu Gly Thr Gly Val Ile Leu Ser
        835                 840                 845

Leu Val Tyr Gly Trp Gln Leu Thr Leu Leu Leu Val Val Ile Ile Pro
    850                 855                 860

Leu Ile Val Leu Gly Gly Ile Ile Glu Met Lys Leu Leu Ser Gly Gln
865                 870                 875                 880

Ala Leu Lys Asp Lys Lys Gln Leu Glu Ile Ser Gly Lys Ile Ala Thr
            885                 890                 895

Glu Ala Ile Glu Asn Phe Arg Thr Ile Val Ser Leu Thr Arg Glu Gln
        900                 905                 910

Lys Phe Glu Thr Met Tyr Ala Gln Ser Leu Gln Val Pro Tyr Arg Asn
        915                 920                 925

Ala Met Lys Lys Ala His Val Phe Gly Ile Thr Phe Ser Phe Thr Gln
    930                 935                 940

Ala Met Met Tyr Phe Ser Tyr Ala Ala Cys Phe Arg Phe Gly Ala Tyr
945                 950                 955                 960

Leu Val Ala Gln Gln Leu Met Thr Phe Glu Asn Val Met Leu Val Phe
                965                 970                 975

Ser Ala Val Val Phe Gly Ala Met Ala Ala Gly Asn Thr Ser Ser Phe
            980                 985                 990

Ala Pro Asp Tyr Ala Lys Ala Lys  Val Ser Ala Ser His  Ile Ile Arg
        995                 1000                1005

Ile Ile  Glu Lys Thr Pro Glu  Ile Asp Ser Tyr Ser  Thr Glu Gly
    1010                1015                1020

Leu Lys  Pro Thr Leu Leu Glu  Gly Asn Val Lys Phe  Asn Gly Val
    1025                1030                1035

Gln Phe  Asn Tyr Pro Thr Arg  Pro Asn Ile Pro Val  Leu Gln Gly
    1040                1045                1050

Leu Ser  Leu Glu Val Lys Lys  Gly Gln Thr Leu Ala  Leu Val Gly
    1055                1060                1065

Ser Ser  Gly Cys Gly Lys Ser  Thr Val Val Gln Leu  Leu Glu Arg
    1070                1075                1080

Phe Tyr  Asp Pro Met Ala Gly  Ser Val Phe Leu Asp  Gly Lys Glu
    1085                1090                1095

Ile Lys  Gln Leu Asn Val Gln  Trp Leu Arg Ala His  Leu Gly Ile
    1100                1105                1110

Val Ser  Gln Glu Pro Ile Leu  Phe Asp Cys Ser Ile  Ala Glu Asn
    1115                1120                1125

Ile Ala  Tyr Gly Asp Asn Ser  Arg Ala Val Ser His  Glu Glu Ile
    1130                1135                1140

Val Arg  Ala Ala Lys Glu Ala  Asn Ile His Gln Phe  Ile Asp Ser
    1145                1150                1155

Leu Pro  Asp Lys Tyr Asn Thr  Arg Val Gly Asp Lys  Gly Thr Gln
    1160                1165                1170

Leu Ser  Gly Gly Gln Lys Gln  Arg Ile Ala Ile Ala  Arg Ala Leu
    1175                1180                1185

Val Arg  Gln Pro His Ile Leu  Leu Leu Asp Glu Ala  Thr Ser Ala
    1190                1195                1200

Leu Asp  Thr Glu Ser Glu Lys  Val Val Gln Glu Ala  Leu Asp Lys
    1205                1210                1215
```

-continued

```
Ala Arg  Glu Gly Arg Thr Cys  Ile Val Ile Ala His  Arg Leu Ser
    1220                1225                1230

Thr Ile  Gln Asn Ala Asp Leu  Ile Val Val Ile Glu  Asn Gly Lys
    1235                1240                1245

Val Lys  Glu His Gly Thr His  Gln Gln Leu Leu Ala  Gln Lys Gly
    1250                1255                1260

Ile Tyr  Phe Ser Met Val Gln  Ala Gly Ala Lys Arg  Ser
    1265                1270                1275

<210> SEQ ID NO 333
<211> LENGTH: 1280
<212> TYPE: PRT
<213> ORGANISM: Pan troglodytes

<400> SEQUENCE: 333

Met Asp Leu Glu Gly Asp Arg Asn Gly Gly Ala Lys Lys Lys Asn Phe
1               5                   10                  15

Phe Lys Leu Asn Asn Lys Ser Glu Lys Asp Lys Lys Glu Lys Lys Pro
            20                  25                  30

Thr Val Ser Val Phe Ser Met Phe Arg Tyr Ser Asn Trp Leu Asp Lys
        35                  40                  45

Leu Tyr Met Val Val Gly Thr Leu Ala Ala Ile Ile His Gly Ala Gly
    50                  55                  60

Leu Pro Leu Met Met Leu Val Phe Gly Glu Met Thr Asp Ile Phe Ala
65                  70                  75                  80

Asn Ala Gly Asn Leu Glu Asp Leu Met Ser Asn Ile Thr Asn Arg Ser
            85                  90                  95

Asp Ile Asn Asp Thr Gly Phe Phe Met Asn Leu Glu Glu Asp Met Thr
            100                 105                 110

Arg Tyr Ala Tyr Tyr Tyr Ser Gly Ile Gly Ala Gly Val Leu Val Ala
        115                 120                 125

Ala Tyr Ile Gln Val Ser Phe Trp Cys Leu Ala Ala Gly Arg Gln Ile
    130                 135                 140

His Lys Ile Arg Lys Gln Phe Phe His Ala Ile Met Arg Gln Glu Ile
145                 150                 155                 160

Gly Trp Phe Asp Val His Asp Val Gly Glu Leu Asn Thr Arg Leu Thr
                165                 170                 175

Asp Asp Val Ser Lys Ile Asn Glu Gly Ile Gly Asp Lys Ile Gly Met
            180                 185                 190

Phe Phe Gln Ser Met Ala Thr Phe Phe Thr Gly Phe Ile Val Gly Phe
            195                 200                 205

Thr Arg Gly Trp Lys Leu Thr Leu Val Ile Leu Ala Ile Ser Pro Val
    210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
                245                 250                 255

Val Leu Ala Ala Ile Arg Thr Val Ile Ala Phe Gly Gly Gln Lys Lys
            260                 265                 270

Glu Leu Glu Arg Tyr Asn Lys Asn Leu Glu Glu Ala Lys Arg Ile Gly
            275                 280                 285

Ile Lys Lys Ala Ile Thr Ala Asn Ile Ser Ile Gly Ala Ala Phe Leu
    290                 295                 300

Leu Ile Tyr Ala Ser Tyr Ala Leu Ala Phe Trp Tyr Gly Thr Thr Leu
```

-continued

```
305                  310                  315                  320
Val Leu Ser Gly Glu Tyr Ser Ile Gly Gln Val Leu Thr Val Phe Phe
                 325                  330                  335

Ser Val Leu Ile Gly Ala Phe Ser Val Gly Gln Ala Ser Pro Ser Ile
                 340                  345                  350

Glu Ala Phe Ala Asn Ala Arg Gly Ala Ala Tyr Glu Ile Phe Lys Ile
                 355                  360                  365

Ile Asp Asn Lys Pro Ser Ile Asp Ser Tyr Ser Lys Ser Gly His Lys
        370                  375                  380

Pro Asp Asn Ile Lys Gly Asn Leu Glu Phe Arg Asn Val His Phe Ser
385                  390                  395                  400

Tyr Pro Ser Arg Lys Gln Val Lys Ile Leu Lys Gly Leu Asn Leu Lys
                 405                  410                  415

Val Gln Ser Gly Gln Thr Val Ala Leu Val Gly Asn Ser Gly Cys Gly
                 420                  425                  430

Lys Ser Thr Thr Val Gln Leu Met Gln Arg Leu Tyr Asp Pro Thr Glu
                 435                  440                  445

Gly Met Val Ser Val Asp Gly Gln Asp Ile Arg Thr Ile Asn Val Arg
        450                  455                  460

Phe Leu Arg Glu Ile Ile Gly Val Val Ser Gln Glu Pro Val Leu Phe
465                  470                  475                  480

Ala Thr Thr Ile Ala Glu Asn Ile Arg Tyr Gly Arg Glu Asn Val Thr
                 485                  490                  495

Met Asp Glu Ile Glu Lys Ala Val Lys Glu Ala Asn Ala Tyr Asp Phe
                 500                  505                  510

Ile Met Lys Leu Pro His Lys Phe Asp Thr Leu Val Gly Glu Arg Gly
                 515                  520                  525

Ala Gln Leu Ser Gly Gly Gln Lys Gln Arg Ile Ala Ile Ala Arg Ala
        530                  535                  540

Leu Val Arg Asn Pro Lys Ile Leu Leu Leu Asp Glu Ala Thr Ser Ala
545                  550                  555                  560

Leu Asp Thr Glu Ser Glu Ala Val Val Gln Val Ala Leu Asp Lys Ala
                 565                  570                  575

Arg Lys Gly Arg Thr Thr Ile Val Ile Ala His Arg Leu Ser Thr Val
                 580                  585                  590

Arg Asn Ala Asp Val Ile Ala Gly Phe Asp Asp Gly Val Ile Val Glu
                 595                  600                  605

Lys Gly Asn His Asp Glu Leu Met Lys Glu Lys Gly Ile Tyr Phe Lys
        610                  615                  620

Leu Val Thr Met Gln Thr Ala Gly Asn Glu Val Glu Leu Glu Asn Ala
625                  630                  635                  640

Ala Asp Glu Ser Lys Ser Glu Ile Asp Ala Leu Glu Met Ser Ser Asn
                 645                  650                  655

Asp Ser Arg Ser Ser Leu Ile Arg Lys Arg Ser Thr Arg Arg Ser Val
                 660                  665                  670

Arg Gly Ser Gln Ala Gln Asp Arg Lys Leu Ser Thr Lys Glu Ala Leu
                 675                  680                  685

Asp Glu Ser Ile Pro Pro Val Ser Phe Trp Arg Ile Met Lys Leu Asn
        690                  695                  700

Leu Thr Glu Trp Pro Tyr Phe Val Val Gly Val Phe Cys Ala Ile Ile
705                  710                  715                  720

Asn Gly Gly Leu Gln Pro Ala Phe Ala Ile Ile Phe Ser Lys Ile Ile
                 725                  730                  735
```

-continued

```
Gly Val Phe Thr Arg Ile Asp Asp Pro Glu Thr Lys Arg Gln Asn Ser
            740                 745                 750

Asn Leu Phe Ser Leu Leu Phe Leu Val Leu Gly Ile Ile Ser Phe Ile
            755                 760                 765

Thr Phe Phe Leu Gln Gly Phe Thr Phe Gly Lys Ala Gly Glu Ile Leu
            770                 775                 780

Thr Lys Arg Leu Arg Tyr Met Val Phe Arg Ser Met Leu Arg Gln Asp
785                 790                 795                 800

Val Ser Trp Phe Asp Asp Pro Lys Asn Thr Thr Gly Ala Leu Thr Thr
                805                 810                 815

Arg Leu Ala Asn Asp Ala Ala Gln Val Lys Gly Ala Ile Gly Ser Arg
            820                 825                 830

Leu Ala Val Ile Thr Gln Asn Ile Ala Asn Leu Gly Thr Gly Ile Ile
            835                 840                 845

Ile Ser Phe Ile Tyr Gly Trp Gln Leu Thr Leu Leu Leu Leu Ala Ile
            850                 855                 860

Val Pro Ile Ile Ala Ile Ala Gly Val Val Glu Met Lys Met Leu Ser
865                 870                 875                 880

Gly Gln Ala Leu Lys Asp Lys Lys Glu Leu Glu Gly Ala Gly Lys Ile
                885                 890                 895

Ala Ser Glu Ala Ile Glu Asn Phe Arg Thr Val Val Ser Leu Thr Gln
                900                 905                 910

Glu Gln Lys Phe Glu His Met Tyr Ala Gln Ser Leu Gln Val Pro Tyr
            915                 920                 925

Arg Asn Ser Leu Arg Lys Ala His Ile Phe Gly Ile Thr Phe Ser Phe
            930                 935                 940

Thr Gln Ala Met Met Tyr Phe Ser Tyr Ala Gly Cys Phe Arg Phe Gly
945                 950                 955                 960

Ala Tyr Leu Val Ala His Lys Leu Met Ser Phe Glu Asp Val Leu Leu
                965                 970                 975

Val Phe Ser Ala Val Val Phe Gly Ala Met Ala Val Gly Gln Val Ser
                980                 985                 990

Ser Phe Ala Pro Asp Tyr Ala Lys  Ala Lys Ile Ser Ala  Ala His Ile
            995                1000                1005

Ile Met  Ile Ile Glu Lys Thr  Pro Leu Ile Asp Ser  Tyr Ser Thr
    1010                1015                1020

Glu Gly  Leu Thr Pro Asn Thr  Leu Glu Gly Asn Val  Thr Phe Gly
    1025                1030                1035

Glu Val  Val Phe Asn Tyr Pro  Thr Arg Pro Asp Ile  Pro Val Leu
    1040                1045                1050

Gln Gly  Leu Ser Leu Glu Val  Lys Lys Gly Gln Thr  Leu Ala Leu
    1055                1060                1065

Val Gly  Ser Ser Gly Cys Gly  Lys Ser Thr Val Val  Gln Leu Leu
    1070                1075                1080

Glu Arg  Phe Tyr Asp Pro Leu  Ala Gly Lys Val Leu  Leu Asp Gly
    1085                1090                1095

Lys Glu  Ile Lys Arg Leu Asn  Val Gln Trp Leu Arg  Ala His Leu
    1100                1105                1110

Gly Ile  Val Ser Gln Glu Pro  Ile Leu Phe Asp Cys  Ser Ile Ala
    1115                1120                1125

Glu Asn  Ile Ala Tyr Gly Asp  Asn Ser Arg Val Val  Ser Gln Glu
    1130                1135                1140
```

-continued

```
Glu Ile  Val Arg Ala Ala Lys  Glu Ala Asn Ile His  Ala Phe Ile
    1145             1150               1155

Glu Ser  Leu Pro Asn Lys Tyr  Ser Thr Arg Val Gly  Asp Lys Gly
    1160             1165               1170

Thr Gln  Leu Ser Gly Gly Gln  Lys Gln Arg Ile Ala  Ile Ala Arg
    1175             1180               1185

Ala Leu  Val Arg Gln Pro His  Ile Leu Leu Leu Asp  Glu Ala Thr
    1190             1195               1200

Ser Ala  Leu Asp Thr Glu Ser  Glu Lys Val Val Gln  Glu Ala Leu
    1205             1210               1215

Asp Lys  Ala Arg Glu Gly Arg  Thr Cys Ile Val Ile  Ala His Arg
    1220             1225               1230

Leu Ser  Thr Ile Gln Asn Ala  Asp Leu Ile Val Val  Phe Gln Asn
    1235             1240               1245

Gly Arg  Val Lys Glu His Gly  Thr His Gln Gln Leu  Leu Ala Gln
    1250             1255               1260

Lys Gly  Ile Tyr Phe Ser Met  Val Ser Val Gln Ala  Gly Thr Lys
    1265             1270               1275

Arg Gln
    1280

<210> SEQ ID NO 334
<211> LENGTH: 1283
<212> TYPE: PRT
<213> ORGANISM: Macaca fascicularis

<400> SEQUENCE: 334

Met Asp Leu Glu Gly Asp Arg Asn Gly Gly Ala Glu Lys Lys Asn Phe
1               5                   10                  15

Phe Lys Leu Asn Asn Lys Ser Lys Lys Asp Lys Lys Glu Arg Lys Pro
            20                  25                  30

Thr Val Ser Val Phe Ser Met Phe Arg Tyr Ser Asn Trp Leu Asp Lys
        35                  40                  45

Leu Tyr Met Val Val Gly Thr Leu Ala Ala Ile Ile His Gly Ala Gly
    50                  55                  60

Leu Pro Leu Met Met Leu Val Phe Gly Asp Met Thr Asp Thr Phe Ala
65                  70                  75                  80

Asn Ala Gly Asn Leu Gly Asp Leu Gly Ala Leu Leu Phe Asn Asn Thr
                85                  90                  95

Asn Ser Ser Asn Ile Thr Asp Thr Val Pro Val Met Asn Leu Glu Glu
            100                 105                 110

Asp Met Thr Arg Tyr Ala Tyr Tyr Ser Gly Ile Gly Ala Gly Val
        115                 120                 125

Leu Val Ala Ala Tyr Ile Gln Val Ser Phe Trp Cys Leu Ala Ala Gly
    130                 135                 140

Arg Gln Ile His Lys Ile Arg Lys Gln Phe Phe His Ala Ile Met Arg
145                 150                 155                 160

Gln Glu Ile Gly Trp Phe Asp Val His Asp Val Gly Glu Leu Asn Thr
                165                 170                 175

Arg Leu Thr Asp Asp Val Ser Lys Ile Asn Glu Gly Ile Gly Asp Lys
            180                 185                 190

Ile Gly Met Phe Phe Gln Ser Met Ala Thr Phe Phe Thr Gly Phe Ile
        195                 200                 205

Val Gly Phe Thr Arg Gly Trp Lys Leu Thr Leu Val Ile Leu Ala Ile
    210                 215                 220
```

-continued

Ser Pro Val Leu Gly Leu Ser Ala Ala Val Trp Ala Lys Ile Leu Ser
225                 230                 235                 240

Ser Phe Thr Asp Lys Glu Leu Leu Ala Tyr Ala Lys Ala Gly Ala Val
                245                 250                 255

Ala Glu Glu Val Leu Ala Ala Ile Arg Thr Val Ile Ala Phe Gly Gly
                260                 265                 270

Gln Lys Lys Glu Leu Glu Arg Tyr Asn Lys Asn Leu Glu Glu Ala Lys
                275                 280                 285

Arg Ile Gly Ile Lys Lys Ala Ile Thr Ala Asn Ile Ser Ile Gly Ala
    290                 295                 300

Ala Phe Leu Leu Ile Tyr Ala Ser Tyr Ala Leu Ala Phe Trp Tyr Gly
305                 310                 315                 320

Thr Thr Leu Val Leu Ser Lys Glu Tyr Ser Ile Gly Gln Val Leu Thr
                325                 330                 335

Val Phe Phe Ser Val Leu Ile Gly Ala Phe Ser Val Gly Gln Ala Ser
                340                 345                 350

Pro Ser Ile Glu Ala Phe Ala Asn Ala Arg Gly Ala Ala Phe Glu Ile
                355                 360                 365

Phe Lys Ile Ile Asp Asn Lys Pro Ser Ile Asp Ser Tyr Ser Lys Ser
    370                 375                 380

Gly His Lys Pro Asp Asn Ile Lys Gly Asn Leu Glu Phe Arg Asn Val
385                 390                 395                 400

His Phe Ser Tyr Pro Ser Arg Lys Glu Val Lys Ile Leu Lys Gly Leu
                405                 410                 415

Asn Leu Lys Val Gln Ser Gly Gln Thr Val Ala Leu Val Gly Asn Ser
                420                 425                 430

Gly Cys Gly Lys Ser Thr Thr Val Gln Leu Met Gln Arg Leu Tyr Asp
    435                 440                 445

Pro Thr Glu Gly Met Val Ser Val Asp Gly Gln Asp Ile Arg Thr Ile
    450                 455                 460

Asn Val Arg Phe Leu Arg Glu Ile Ile Gly Val Val Ser Gln Glu Pro
465                 470                 475                 480

Val Leu Phe Ala Thr Thr Ile Ala Glu Asn Ile Arg Tyr Gly Arg Glu
                485                 490                 495

Asp Val Thr Met Asp Glu Ile Glu Lys Ala Val Lys Glu Ala Asn Ala
                500                 505                 510

Tyr Asp Phe Ile Met Lys Leu Pro Gln Lys Phe Asp Thr Leu Val Gly
                515                 520                 525

Glu Arg Gly Ala Gln Leu Ser Gly Gly Gln Lys Gln Arg Ile Ala Ile
    530                 535                 540

Ala Arg Ala Leu Val Arg Asn Pro Lys Ile Leu Leu Leu Asp Glu Ala
545                 550                 555                 560

Thr Ser Ala Leu Asp Thr Glu Ser Glu Ala Val Val Gln Val Ala Leu
                565                 570                 575

Asp Lys Ala Arg Lys Gly Arg Thr Thr Ile Val Ile Ala His Arg Leu
                580                 585                 590

Ser Thr Val Arg Asn Ala Asp Val Ile Ala Gly Phe Asp Asp Gly Val
                595                 600                 605

Ile Val Glu Lys Gly Asn His Asp Glu Leu Met Lys Glu Lys Gly Ile
    610                 615                 620

Tyr Phe Lys Leu Val Thr Met Gln Thr Ala Gly Asn Glu Ile Glu Leu
625                 630                 635                 640

-continued

```
Glu Asn Ala Ala Asp Glu Ser Lys Ser Glu Ile Asp Thr Leu Glu Met
            645                 650                 655

Ser Ser His Asp Ser Gly Ser Ser Leu Ile Arg Lys Arg Ser Thr Arg
            660                 665                 670

Arg Ser Val Arg Gly Ser Gln Gly Gln Asp Arg Lys Leu Ser Thr Lys
            675                 680                 685

Glu Ala Leu Asp Glu Ser Ile Pro Pro Val Ser Phe Trp Arg Ile Met
690                 695                 700

Lys Leu Asn Leu Thr Glu Trp Pro Tyr Phe Val Val Gly Val Phe Cys
705                 710                 715                 720

Ala Ile Ile Asn Gly Gly Leu Gln Pro Ala Phe Ala Val Ile Phe Ser
            725                 730                 735

Lys Ile Ile Gly Ile Phe Thr Arg Asn Asp Asp Ala Glu Thr Lys Arg
            740                 745                 750

Gln Asn Ser Asn Leu Phe Ser Leu Leu Phe Leu Val Leu Gly Ile Val
            755                 760                 765

Ser Phe Ile Thr Phe Phe Leu Gln Gly Phe Thr Phe Gly Lys Ala Gly
            770                 775                 780

Glu Ile Leu Thr Lys Arg Leu Arg Tyr Met Val Phe Arg Ser Met Leu
785                 790                 795                 800

Arg Gln Asp Val Ser Trp Phe Asp Asp Pro Lys Asn Thr Thr Gly Ala
                805                 810                 815

Leu Thr Thr Arg Leu Ala Asn Asp Ala Ala Gln Val Lys Gly Ala Ile
            820                 825                 830

Gly Ser Arg Leu Ala Ile Ile Thr Gln Asn Ile Ala Asn Leu Gly Thr
            835                 840                 845

Gly Ile Ile Ile Ser Leu Ile Tyr Gly Trp Gln Leu Thr Leu Leu Leu
            850                 855                 860

Leu Ala Ile Val Pro Ile Ile Ala Ile Ala Gly Val Val Glu Met Lys
865                 870                 875                 880

Met Leu Ser Gly Gln Ala Leu Lys Asp Lys Lys Glu Leu Glu Gly Ala
                885                 890                 895

Gly Lys Ile Ala Thr Glu Ala Ile Glu Asn Phe Arg Thr Val Val Ser
                900                 905                 910

Leu Thr Gln Glu Gln Lys Phe Glu His Met Tyr Asp Gln Ser Leu Gln
            915                 920                 925

Val Pro Tyr Arg Asn Ser Leu Arg Lys Ala His Ile Phe Gly Ile Thr
            930                 935                 940

Phe Ser Phe Thr Gln Ala Met Met Tyr Phe Ser Tyr Ala Gly Cys Phe
945                 950                 955                 960

Arg Phe Gly Ala Tyr Leu Val Ala His Ser Leu Met Ser Phe Glu Asp
                965                 970                 975

Val Leu Leu Val Phe Ser Ala Val Val Phe Gly Ala Met Ala Val Gly
            980                 985                 990

Gln Val Ser Ser Phe Ala Pro Asp  Tyr Ala Lys Ala Lys  Val Ser Ala
            995                 1000                 1005

Ala His  Ile Ile Met Ile Ile  Glu Lys Thr Pro Leu  Ile Asp Ser
        1010                 1015                 1020

Tyr Ser  Thr Glu Gly Leu Lys  Pro Asn Thr Leu Glu  Gly Asn Val
        1025                 1030                 1035

Thr Phe  Asn Glu Val Val Phe  Asn Tyr Pro Thr Arg  Leu Asp Ile
        1040                 1045                 1050

Pro Val  Leu Gln Gly Leu Ser  Leu Glu Val Lys Lys  Gly Gln Thr
```

```
     1055                1060                1065

Leu Ala  Leu Val Gly Ser Ser  Gly Cys Gly Lys Ser  Thr Val Val
     1070                1075                1080

Gln Leu  Leu Glu Arg Phe Tyr  Asp Pro Leu Ala Gly  Lys Val Leu
     1085                1090                1095

Leu Asp  Gly Lys Glu Ile Lys  Gln Leu Asn Val Gln  Trp Leu Arg
     1100                1105                1110

Ala His  Leu Gly Ile Val Ser  Gln Glu Pro Ile Leu  Phe Asp Cys
     1115                1120                1125

Ser Ile  Ser Glu Asn Ile Ala  Tyr Gly Asp Asn Ser  Arg Val Val
     1130                1135                1140

Ser Gln  Glu Glu Ile Val Arg  Ala Ala Lys Glu Ala  Asn Ile His
     1145                1150                1155

Ala Phe  Ile Glu Ser Leu Pro  Asn Lys Tyr Ser Thr  Arg Val Gly
     1160                1165                1170

Asp Lys  Gly Thr Gln Leu Ser  Gly Gly Gln Lys Gln  Arg Ile Ala
     1175                1180                1185

Ile Ala  Arg Ala Leu Val Arg  Gln Pro His Ile Leu  Leu Leu Asp
     1190                1195                1200

Glu Ala  Thr Ser Ala Leu Asp  Thr Glu Ser Glu Lys  Val Val Gln
     1205                1210                1215

Glu Ala  Leu Asp Lys Ala Arg  Glu Gly Arg Thr Cys  Ile Val Ile
     1220                1225                1230

Ala His  Arg Leu Ser Thr Ile  Gln Asn Ala Asp Leu  Ile Val Val
     1235                1240                1245

Phe Gln  Asn Gly Arg Val Lys  Glu His Gly Thr His  Gln Gln Leu
     1250                1255                1260

Leu Ala  Gln Lys Gly Ile Tyr  Phe Ser Met Val Ser  Val Gln Ala
     1265                1270                1275

Gly Ala  Lys Arg Gln
     1280

<210> SEQ ID NO 335
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: REPEAT
<222> LOCATION: (1)..(5)
<223> OTHER INFORMATION: The amino acids at positions 1 to 5 repeat n
      times, where n is an integer of at least one

<400> SEQUENCE: 335

Gly Ser Gly Gly Ser
1               5

<210> SEQ ID NO 336
<211> LENGTH: 4
<212> TYPE: PRT
<213> ORGANISM: Artificial sequence
<220> FEATURE:
<223> OTHER INFORMATION: synthetic sequence
<220> FEATURE:
<221> NAME/KEY: REPEAT
<222> LOCATION: (1)..(4)
<223> OTHER INFORMATION: The amino acids at positions 1 to 4 repeat n
      times, where n is an integer of at least one

<400> SEQUENCE: 336
```

```
Gly Gly Gly Ser
1

<210> SEQ ID NO 337
<211> LENGTH: 4
<212> TYPE: PRT
<213> ORGANISM: Artificial sequence
<220> FEATURE:
<223> OTHER INFORMATION: synthetic sequence

<400> SEQUENCE: 337

Gly Gly Ser Gly
1

<210> SEQ ID NO 338
<211> LENGTH: 5
<212> TYPE: PRT
<213> ORGANISM: Artificial sequence
<220> FEATURE:
<223> OTHER INFORMATION: synthetic sequence

<400> SEQUENCE: 338

Gly Gly Ser Gly Gly
1               5

<210> SEQ ID NO 339
<211> LENGTH: 5
<212> TYPE: PRT
<213> ORGANISM: Artificial sequence
<220> FEATURE:
<223> OTHER INFORMATION: synthetic sequence

<400> SEQUENCE: 339

Gly Ser Gly Ser Gly
1               5

<210> SEQ ID NO 340
<211> LENGTH: 5
<212> TYPE: PRT
<213> ORGANISM: Artificial sequence
<220> FEATURE:
<223> OTHER INFORMATION: synthetic sequence

<400> SEQUENCE: 340

Gly Ser Gly Gly Gly
1               5

<210> SEQ ID NO 341
<211> LENGTH: 5
<212> TYPE: PRT
<213> ORGANISM: Artificial sequence
<220> FEATURE:
<223> OTHER INFORMATION: synthetic sequence

<400> SEQUENCE: 341

Gly Gly Gly Ser Gly
1               5

<210> SEQ ID NO 342
<211> LENGTH: 5
<212> TYPE: PRT
<213> ORGANISM: Artificial sequence
<220> FEATURE:
<223> OTHER INFORMATION: synthetic sequence

<400> SEQUENCE: 342
```

```
Gly Ser Ser Ser Gly
1               5

<210> SEQ ID NO 343
<211> LENGTH: 7
<212> TYPE: PRT
<213> ORGANISM: Artificial sequence
<220> FEATURE:
<223> OTHER INFORMATION: synthetic sequence

<400> SEQUENCE: 343

Gly Phe Thr Phe Ser Arg Tyr
1               5

<210> SEQ ID NO 344
<211> LENGTH: 6
<212> TYPE: PRT
<213> ORGANISM: Artificial sequence
<220> FEATURE:
<223> OTHER INFORMATION: synthetic sequence

<400> SEQUENCE: 344

Ser Ser Gly Gly Gly Asn
1               5

<210> SEQ ID NO 345
<211> LENGTH: 9
<212> TYPE: PRT
<213> ORGANISM: Artificial sequence
<220> FEATURE:
<223> OTHER INFORMATION: synthetic sequence

<400> SEQUENCE: 345

Gly Ala Gly Asp Ala Trp Phe Ala Tyr
1               5

<210> SEQ ID NO 346
<211> LENGTH: 7
<212> TYPE: PRT
<213> ORGANISM: Artificial sequence
<220> FEATURE:
<223> OTHER INFORMATION: synthetic sequence

<400> SEQUENCE: 346

Gly Tyr Thr Phe Thr Asn Tyr
1               5

<210> SEQ ID NO 347
<211> LENGTH: 6
<212> TYPE: PRT
<213> ORGANISM: Artificial sequence
<220> FEATURE:
<223> OTHER INFORMATION: synthetic sequence

<400> SEQUENCE: 347

Tyr Pro Gly Asn Asp Asp
1               5

<210> SEQ ID NO 348
<211> LENGTH: 8
<212> TYPE: PRT
<213> ORGANISM: Artificial sequence
<220> FEATURE:
<223> OTHER INFORMATION: synthetic sequence

<400> SEQUENCE: 348

Gln Gly Ser His Phe Pro Arg Thr
```

-continued

```
1               5

<210> SEQ ID NO 349
<211> LENGTH: 12
<212> TYPE: PRT
<213> ORGANISM: Artificial sequence
<220> FEATURE:
<223> OTHER INFORMATION: synthetic sequence

<400> SEQUENCE: 349

Ala Arg Tyr Gly Ala Gly Asp Ala Trp Phe Ala Tyr
1               5                   10

<210> SEQ ID NO 350
<211> LENGTH: 119
<212> TYPE: PRT
<213> ORGANISM: Artificial sequence
<220> FEATURE:
<223> OTHER INFORMATION: synthetic sequence

<400> SEQUENCE: 350

Glu Val Gln Leu Val Glu Ser Gly Gly Val Val Val Gln Pro Gly Gly
1               5                   10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
        35                  40                  45

Ala Thr Ile Ser Ser Gly Gly Gly Asn Thr Tyr Tyr Pro Asp Ser Val
    50                  55                  60

Lys Gly Arg Phe Thr Val Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Arg Tyr Gly Ala Gly Asp Ala Trp Phe Ala Tyr Trp Gly Gln Gly
                100                 105                 110

Thr Leu Val Thr Val Ser Ser
            115

<210> SEQ ID NO 351
<211> LENGTH: 119
<212> TYPE: PRT
<213> ORGANISM: Artificial sequence
<220> FEATURE:
<223> OTHER INFORMATION: synthetic sequence

<400> SEQUENCE: 351

Glu Val Gln Leu Val Glu Ser Gly Gly Val Val Val Gln Pro Gly Gly
1               5                   10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
        35                  40                  45

Ala Thr Ile Ser Ser Gly Gly Gly Gln Thr Tyr Tyr Pro Asp Ser Val
    50                  55                  60

Lys Gly Arg Phe Thr Val Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Arg Tyr Gly Ala Gly Asp Ala Trp Phe Ala Tyr Trp Gly Gln Gly
                100                 105                 110
```

-continued

```
Thr Leu Val Thr Val Ser Ser
        115

<210> SEQ ID NO 352
<211> LENGTH: 119
<212> TYPE: PRT
<213> ORGANISM: Artificial sequence
<220> FEATURE:
<223> OTHER INFORMATION: synthetic sequence

<400> SEQUENCE: 352

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
            35                  40                  45

Ala Thr Ile Ser Ser Gly Gly Gly Ser Thr Tyr Tyr Pro Asp Ser Val
    50                  55                  60

Lys Gly Arg Phe Thr Val Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Arg Tyr Gly Ala Gly Asp Ala Trp Phe Ala Tyr Trp Gly Gln Gly
            100                 105                 110

Thr Leu Val Thr Val Ser Ser
        115

<210> SEQ ID NO 353
<211> LENGTH: 115
<212> TYPE: PRT
<213> ORGANISM: Artificial sequence
<220> FEATURE:
<223> OTHER INFORMATION: synthetic sequence

<400> SEQUENCE: 353

Asp Val Val Leu Ala Gln Thr Pro Pro Thr Leu Ser Ala Thr Ile Gly
1               5                   10                  15

Gln Ser Val Ser Ile Ser Cys Arg Ser Ser Gln Ser Leu Leu His Ser
            20                  25                  30

Ser Gly Asn Thr Tyr Leu Asn Trp Leu Leu Gln Arg Pro Gly Gln Pro
            35                  40                  45

Pro Gln Leu Leu Ile Tyr Leu Val Ser Arg Leu Glu Ser Arg Val Pro
    50                  55                  60

Asn Arg Phe Ser Gly Ser Gly Ser Gly Thr Asp Phe Thr Leu Lys Ile
65                  70                  75                  80

Ser Gly Val Glu Ala Glu Asp Leu Gly Val Tyr Tyr Cys Val Gln Ser
                85                  90                  95

Thr His Ala Pro Arg Thr Phe Gly Gly Gly Thr Lys Leu Glu Leu Lys
            100                 105                 110

Arg Thr Val
        115

<210> SEQ ID NO 354
<211> LENGTH: 7
<212> TYPE: PRT
<213> ORGANISM: Artificial sequence
<220> FEATURE:
<223> OTHER INFORMATION: synthetic sequence
```

-continued

```
<400> SEQUENCE: 354

Leu Val Ser Arg Leu Glu Ser
1               5

<210> SEQ ID NO 355
<211> LENGTH: 9
<212> TYPE: PRT
<213> ORGANISM: Artificial sequence
<220> FEATURE:
<223> OTHER INFORMATION: synthetic sequence

<400> SEQUENCE: 355

Val Gln Ser Thr His Ala Pro Arg Thr
1               5

<210> SEQ ID NO 356
<211> LENGTH: 112
<212> TYPE: PRT
<213> ORGANISM: Artificial sequence
<220> FEATURE:
<223> OTHER INFORMATION: synthetic sequence

<400> SEQUENCE: 356

Asp Val Val Met Thr Gln Thr Pro Leu Ser Leu Pro Val Ser Leu Gly
1               5                   10                  15

Asp Gln Ala Ser Ile Ser Cys Arg Phe Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Phe Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Ala
                85                  90                  95

Ser His Phe Pro Arg Thr Phe Gly Gly Gly Thr Lys Leu Glu Ile Lys
                100                 105                 110

<210> SEQ ID NO 357
<211> LENGTH: 123
<212> TYPE: PRT
<213> ORGANISM: Artificial sequence
<220> FEATURE:
<223> OTHER INFORMATION: synthetic sequence

<400> SEQUENCE: 357

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Phe Pro Arg Thr Phe Gly Gly Gly Thr Lys Leu Glu Ile Lys
```

-continued

```
              100                 105                 110

Arg Thr Val Ala Ala Pro Ser Val Phe Ile Phe
        115                 120

<210> SEQ ID NO 358
<211> LENGTH: 7
<212> TYPE: PRT
<213> ORGANISM: Artificial sequence
<220> FEATURE:
<223> OTHER INFORMATION: synthetic sequence

<400> SEQUENCE: 358

Gly Phe Ser Leu Thr Ser Tyr
1               5

<210> SEQ ID NO 359
<211> LENGTH: 5
<212> TYPE: PRT
<213> ORGANISM: Artificial sequence
<220> FEATURE:
<223> OTHER INFORMATION: synthetic sequence

<400> SEQUENCE: 359

Trp Ser Asp Gly Ser
1               5

<210> SEQ ID NO 360
<211> LENGTH: 112
<212> TYPE: PRT
<213> ORGANISM: Artificial sequence
<220> FEATURE:
<223> OTHER INFORMATION: synthetic sequence

<400> SEQUENCE: 360

Asp Ile Val Met Thr Gln Thr Pro Leu Ser Ser Pro Val Thr Leu Gly
1               5                  10                  15

Gln Pro Ala Ser Ile Ser Cys Arg Ser Ser Gln Ser Ile Val His Ser
            20                  25                  30

Thr Gly Asn Thr Tyr Leu Glu Trp Tyr Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Ser His Phe Pro Arg Thr Phe Gly Gly Gly Thr Lys Leu Glu Ile Lys
            100                 105                 110

<210> SEQ ID NO 361
<211> LENGTH: 26
<212> TYPE: PRT
<213> ORGANISM: Artificial sequence
<220> FEATURE:
<223> OTHER INFORMATION: synthetic sequence

<400> SEQUENCE: 361

Asp Val Leu Leu Thr Gln Thr Pro Leu Ser Leu Pro Val Ser Leu Gly
1               5                  10                  15

Asp Gln Ala Ser Ile Ser Cys Arg Ser Ser
            20                  25
```

-continued

```
<210> SEQ ID NO 362
<211> LENGTH: 11
<212> TYPE: PRT
<213> ORGANISM: Artificial sequence
<220> FEATURE:
<223> OTHER INFORMATION: synthetic sequence

<400> SEQUENCE: 362

Gln Asn Ile Val His Ser Thr Gly Asn Thr Tyr
1               5                   10

<210> SEQ ID NO 363
<211> LENGTH: 17
<212> TYPE: PRT
<213> ORGANISM: Artificial sequence
<220> FEATURE:
<223> OTHER INFORMATION: synthetic sequence

<400> SEQUENCE: 363

Leu Asp Trp Tyr Leu Gln Lys Pro Gly Gln Ser Pro Lys Leu Leu Ile
1               5                   10                  15

Tyr

<210> SEQ ID NO 364
<211> LENGTH: 8
<212> TYPE: PRT
<213> ORGANISM: Artificial sequence
<220> FEATURE:
<223> OTHER INFORMATION: synthetic sequence

<400> SEQUENCE: 364

Gln Ala Ser His Phe Pro Arg Thr
1               5

<210> SEQ ID NO 365
<211> LENGTH: 117
<212> TYPE: PRT
<213> ORGANISM: Artificial sequence
<220> FEATURE:
<223> OTHER INFORMATION: synthetic sequence

<400> SEQUENCE: 365

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Asn Met His Trp Val Arg Gln Ala Pro Gly Lys Gly Leu Glu Trp Met
        35                  40                  45

Gly Thr Ile Tyr Pro Gly Asn Asp Asp Thr Ser Tyr Asn Gln Lys Phe
    50                  55                  60

Lys Asp Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Arg Ala Met Asp Tyr Trp Gly Gln Gly Thr Leu
            100                 105                 110

Val Thr Val Ser Ser
        115

<210> SEQ ID NO 366
<211> LENGTH: 117
<212> TYPE: PRT
<213> ORGANISM: Artificial sequence
```

```
<220> FEATURE:
<223> OTHER INFORMATION: synthetic sequence

<400> SEQUENCE: 366

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Asn Met His Trp Val Arg Gln Ala Pro Gly Gln Gly Leu Glu Trp Met
            35                  40                  45

Gly Thr Ile Tyr Pro Gly Asn Asp Asp Thr Ser Tyr Asn Gln Lys Phe
        50                  55                  60

Lys Asp Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Gly Gly Tyr Arg Ala Met Asp Tyr Trp Gly Gln Gly Thr Thr
            100                 105                 110

Val Thr Val Ser Ser
        115

<210> SEQ ID NO 367
<211> LENGTH: 112
<212> TYPE: PRT
<213> ORGANISM: Artificial sequence
<220> FEATURE:
<223> OTHER INFORMATION: synthetic sequence

<400> SEQUENCE: 367

Asp Ile Val Met Thr Gln Thr Pro Leu Ser Leu Pro Val Thr Leu Gly
1               5                   10                  15

Asp Pro Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Phe Pro Arg Thr Phe Gly Gly Gly Thr Lys Leu Glu Ile Lys
            100                 105                 110

<210> SEQ ID NO 368
<211> LENGTH: 112
<212> TYPE: PRT
<213> ORGANISM: Artificial sequence
<220> FEATURE:
<223> OTHER INFORMATION: synthetic sequence

<400> SEQUENCE: 368

Asp Ile Val Leu Thr Gln Thr Pro Leu Ser Leu Pro Val Ser Leu Gly
1               5                   10                  15

Asp Pro Ala Ser Ile Ser Cys Arg Ser Ser Gln Ser Leu Val His Ser
                20                  25                  30

Ser Gly Asn Thr Tyr Leu Glu Trp Tyr Leu Gln Lys Pro Gly Gln Ser
            35                  40                  45
```

```
Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Phe Pro Arg Thr Phe Gly Gly Gly Thr Lys Leu Glu Ile Lys
            100                 105                 110

<210> SEQ ID NO 369
<211> LENGTH: 112
<212> TYPE: PRT
<213> ORGANISM: Artificial sequence
<220> FEATURE:
<223> OTHER INFORMATION: synthetic sequence

<400> SEQUENCE: 369

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110

<210> SEQ ID NO 370
<211> LENGTH: 8
<212> TYPE: PRT
<213> ORGANISM: Artificial sequence
<220> FEATURE:
<223> OTHER INFORMATION: synthetic sequence

<400> SEQUENCE: 370

Gln Gly Ser His Val Pro Phe Thr
1               5

<210> SEQ ID NO 371
<211> LENGTH: 476
<212> TYPE: PRT
<213> ORGANISM: Artificial sequence
<220> FEATURE:
<223> OTHER INFORMATION: synthetic sequence

<400> SEQUENCE: 371

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
                20                  25                  30

Asn Met His Trp Val Arg Gln Ala Pro Gly Lys Gly Leu Glu Trp Met
            35                  40                  45

Gly Thr Ile Tyr Pro Gly Asn Asp Asp Thr Ser Tyr Asn Gln Lys Phe
    50                  55                  60

Lys Asp Arg Val Thr Ile Ser Arg Asp Asn Ser Lys Asn Thr Leu Tyr
```

-continued

```
65                70               75                80
Leu Gln Met Asn Ser Leu Arg Ala Glu Asp Thr Ala Val Tyr Tyr Cys
                85                90                95

Ala Arg Gly Gly Tyr Arg Ala Met Asp Tyr Trp Gly Gln Gly Thr Leu
            100               105               110

Val Thr Val Ser Ser Gly Gly Gly Ser Gly Gly Gly Gly Ser Gly
            115               120               125

Gly Gly Gly Ser Asp Ile Gln Met Thr Gln Ser Pro Ser Ser Leu Ser
        130               135               140

Ala Ser Val Gly Asp Arg Val Thr Ile Thr Cys Arg Ser Ser Gln Ser
145               150               155               160

Ile Val Tyr Ser Asn Gly Asn Thr Tyr Leu Gly Trp Tyr Gln Gln Lys
                165               170               175

Pro Gly Lys Ser Pro Lys Leu Leu Ile Tyr Lys Val Ser Asn Arg Phe
            180               185               190

Ser Gly Val Pro Ser Arg Phe Ser Gly Ser Gly Ser Gly Thr Asp Phe
            195               200               205

Thr Leu Thr Ile Ser Ser Leu Gln Pro Glu Asp Val Ala Thr Tyr Tyr
        210               215               220

Cys Phe Gln Gly Ser His Val Pro Tyr Thr Phe Gly Gln Gly Thr Lys
225               230               235               240

Leu Glu Ile Lys Gly Gly Gly Gly Thr Asp Lys Thr His Thr Cys Pro
                245               250               255

Pro Cys Pro Ala Pro Glu Leu Leu Gly Gly Pro Ser Val Phe Leu Phe
            260               265               270

Pro Pro Lys Pro Lys Asp Thr Leu Met Ile Ser Arg Thr Pro Glu Val
            275               280               285

Thr Cys Val Val Val Asp Val Ser His Glu Asp Pro Glu Val Lys Phe
        290               295               300

Asn Trp Tyr Val Asp Gly Val Glu Val His Asn Ala Lys Thr Lys Pro
305               310               315               320

Arg Glu Glu Gln Tyr Asn Ser Thr Tyr Arg Val Val Ser Val Leu Thr
                325               330               335

Val Leu His Gln Asp Trp Leu Asn Gly Lys Glu Tyr Lys Cys Lys Val
            340               345               350

Ser Asn Lys Ala Leu Pro Ala Pro Ile Glu Lys Thr Ile Ser Lys Ala
            355               360               365

Lys Gly Gln Pro Arg Glu Pro Gln Val Tyr Thr Leu Pro Pro Cys Arg
        370               375               380

Glu Glu Met Thr Lys Asn Gln Val Ser Leu Trp Cys Leu Val Lys Gly
385               390               395               400

Phe Tyr Pro Ser Asp Ile Ala Val Glu Trp Glu Ser Asn Gly Gln Pro
            405               410               415

Glu Asn Asn Tyr Lys Thr Thr Pro Pro Val Leu Asp Ser Asp Gly Ser
            420               425               430

Phe Phe Leu Tyr Ser Lys Leu Thr Val Asp Lys Ser Arg Trp Gln Gln
        435               440               445

Gly Asn Val Phe Ser Cys Ser Val Met His Glu Ala Leu His Asn His
        450               455               460

Tyr Thr Gln Lys Ser Leu Ser Leu Ser Pro Gly Lys
465               470               475
```

<210> SEQ ID NO 372

```
<211> LENGTH: 472
<212> TYPE: PRT
<213> ORGANISM: Artificial sequence
<220> FEATURE:
<223> OTHER INFORMATION: synthetic sequence

<400> SEQUENCE: 372

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Gly Tyr
                20                  25                  30

Gly Met Ser Trp Val Arg Gln Ala Pro Gly Gln Arg Leu Glu Trp Val
            35                  40                  45

Ala Thr Ile Thr Ser Gly Gly Thr Tyr Thr Tyr Tyr Pro Asp Ser Val
        50                  55                  60

Lys Gly Arg Phe Thr Ile Thr Arg Asp Asn Ser Ala Ser Thr Leu Tyr
65                  70                  75                  80

Met Glu Leu Ser Ser Leu Arg Ser Glu Asp Thr Ala Val Tyr Tyr Cys
                85                  90                  95

Ala Arg Ser Leu Ala Gly Asn Ala Met Asp Tyr Trp Gly Gln Gly Thr
            100                 105                 110

Met Val Thr Val Ser Ser Gly Gly Gly Gly Ser Gly Gly Gly Gly Ser
            115                 120                 125

Gly Gly Gly Gly Ser Asp Ile Val Met Thr Gln Ser Pro Leu Ser Leu
        130                 135                 140

Pro Val Thr Pro Gly Glu Pro Ala Ser Ile Ser Cys Arg Ala Ser Gln
145                 150                 155                 160

Thr Ile Ser Asp Tyr Leu His Trp Tyr Leu Gln Lys Pro Gly Gln Ser
                165                 170                 175

Pro Gln Leu Leu Ile Lys Phe Ala Ser Gln Ser Ile Ser Gly Ile Pro
            180                 185                 190

Asp Arg Phe Ser Gly Ser Gly Ser Gly Ser Asp Phe Thr Leu Lys Ile
            195                 200                 205

Ser Arg Val Glu Ala Glu Asp Val Gly Val Tyr Tyr Cys Gln Asn Gly
        210                 215                 220

His Gly Phe Pro Arg Thr Phe Gly Gly Gly Thr Lys Leu Glu Ile Lys
225                 230                 235                 240

Gly Gly Gly Gly Thr Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
            275                 280                 285

Val Asp Val Ser His Glu Asp Pro Glu Val Lys Phe Asn Trp Tyr Val
        290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
            355                 360                 365

Arg Glu Pro Gln Val Tyr Thr Leu Pro Pro Cys Arg Glu Glu Met Thr
            370                 375                 380
```

```
Lys Asn Gln Val Ser Leu Trp Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
                420                 425                 430

Ser Lys Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
        450                 455                 460

Ser Leu Ser Leu Ser Pro Gly Lys
465                 470
```

```
<210> SEQ ID NO 373
<211> LENGTH: 449
<212> TYPE: PRT
<213> ORGANISM: Artificial sequence
<220> FEATURE:
<223> OTHER INFORMATION: synthetic sequence

<400> SEQUENCE: 373
```

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Gly Leu Tyr
                20                  25                  30

Thr Met Ser Trp Val Arg Gln Ala Pro Gly Lys Gly Leu Glu Trp Val
            35                  40                  45

Ala Thr Ile Ser Ser Gly Gly Ser Asn Thr Tyr Tyr Pro Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Arg Tyr Asp Ala Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270
```

-continued

```
Pro Glu Val Lys Phe Asn Trp Tyr Val Asp Gly Val Glu Val His Asn
    275             280             285

Ala Lys Thr Lys Pro Arg Glu Glu Gln Tyr Asn Ser Thr Tyr Arg Val
    290             295             300

Val Ser Val Leu Thr Val Leu His Gln Asp Trp Leu Asn Gly Lys Glu
305             310             315             320

Tyr Lys Cys Lys Val Ser Asn Lys Ala Leu Pro Ala Pro Ile Glu Lys
            325             330             335

Thr Ile Ser Lys Ala Lys Gly Gln Pro Arg Glu Pro Gln Val Cys Thr
            340             345             350

Leu Pro Pro Ser Arg Glu Glu Met Thr Lys Asn Gln Val Ser Leu Ser
    355             360             365

Cys Ala Val Lys Gly Phe Tyr Pro Ser Asp Ile Ala Val Glu Trp Glu
    370             375             380

Ser Asn Gly Gln Pro Glu Asn Asn Tyr Lys Thr Thr Pro Pro Val Leu
385             390             395             400

Asp Ser Asp Gly Ser Phe Phe Leu Val Ser Lys Leu Thr Val Asp Lys
            405             410             415

Ser Arg Trp Gln Gln Gly Asn Val Phe Ser Cys Ser Val Met His Glu
            420             425             430

Ala Leu His Asn His Tyr Thr Gln Lys Ser Leu Ser Leu Ser Pro Gly
            435             440             445

Lys
```

<210> SEQ ID NO 374
<211> LENGTH: 219
<212> TYPE: PRT
<213> ORGANISM: Artificial sequence
<220> FEATURE:
<223> OTHER INFORMATION: synthetic sequence

<400> SEQUENCE: 374

```
Glu Val Val Leu Thr Gln Ser Pro Ala Thr Leu Ser Leu Ser Pro Gly
1               5               10              15

Glu Arg Ala Thr Leu Ser Cys Arg Ser Ser Gln Asn Ile Val His Ser
            20              25              30

Thr Gly Asn Thr Tyr Leu Asp Trp Tyr Gln Gln Lys Pro Gly Gln Ser
            35              40              45

Pro Arg Leu Leu Ile Tyr Lys Val Ser Asn Arg Phe Ser Gly Val Pro
    50              55              60

Ala Arg Phe Ser Gly Ser Gly Ser Gly Thr Asp Phe Thr Leu Thr Ile
65              70              75              80

Ser Ser Leu Glu Pro Glu Asp Phe Ala Val Tyr Tyr Cys Phe Gln Gly
            85              90              95

Ser His Ile Pro Arg Thr Phe Gly Gly Gly Thr Lys Leu Glu Ile Lys
            100             105             110

Arg Thr Val Ala Ala Pro Ser Val Phe Ile Phe Pro Pro Ser Asp Glu
            115             120             125

Gln Leu Lys Ser Gly Thr Ala Ser Val Val Cys Leu Leu Asn Asn Phe
    130             135             140

Tyr Pro Arg Glu Ala Lys Val Gln Trp Lys Val Asp Asn Ala Leu Gln
145             150             155             160

Ser Gly Asn Ser Gln Glu Ser Val Thr Glu Gln Asp Ser Lys Asp Ser
            165             170             175
```

-continued

```
Thr Tyr Ser Leu Ser Ser Thr Leu Thr Leu Ser Lys Ala Asp Tyr Glu
            180             185             190

Lys His Lys Val Tyr Ala Cys Glu Val Thr His Gln Gly Leu Ser Ser
        195             200             205

Pro Val Thr Lys Ser Phe Asn Arg Gly Glu Cys
    210             215

<210> SEQ ID NO 375
<211> LENGTH: 452
<212> TYPE: PRT
<213> ORGANISM: Artificial sequence
<220> FEATURE:
<223> OTHER INFORMATION: synthetic sequence

<400> SEQUENCE: 375

Glu Val Gln Leu Gln Glu Ser Gly Pro Gly Leu Val Lys Pro Ser Glu
1               5               10              15

Thr Leu Ser Leu Thr Cys Thr Val Ser Gly Phe Ser Leu Thr Ser Tyr
            20              25              30

Gly Val His Trp Val Arg Gln Pro Pro Gly Lys Gly Leu Glu Trp Leu
        35              40              45

Val Val Ile Trp Ser Asp Gly Ser Thr Thr Tyr Asn Ser Ala Leu Lys
    50              55              60

Ser Arg Leu Thr Ile Ser Lys Asp Asn Ser Lys Asn Gln Val Ser Leu
65              70              75              80

Lys Leu Ser Ser Val Thr Ala Ala Asp Thr Ala Val Tyr Tyr Cys Ala
            85              90              95

Arg His Gly Arg Trp Leu Leu Gln Arg Gly Gly Ala Met Asp Tyr Trp
            100             105             110

Gly Gln Gly Thr Met Val Thr Val Ser Ser Ala Ser Thr Lys Gly Pro
        115             120             125

Ser Val Phe Pro Leu Ala Pro Ser Ser Lys Ser Thr Ser Gly Gly Thr
    130             135             140

Ala Ala Leu Gly Cys Leu Val Lys Asp Tyr Phe Pro Glu Pro Val Thr
145             150             155             160

Val Ser Trp Asn Ser Gly Ala Leu Thr Ser Gly Val His Thr Phe Pro
            165             170             175

Ala Val Leu Gln Ser Ser Gly Leu Tyr Ser Leu Ser Ser Val Val Thr
            180             185             190

Val Pro Ser Ser Ser Leu Gly Thr Gln Thr Tyr Ile Cys Asn Val Asn
        195             200             205

His Lys Pro Ser Asn Thr Lys Val Asp Lys Arg Val Glu Pro Lys Ser
    210             215             220

Cys Asp Lys Thr His Thr Cys Pro Pro Cys Pro Ala Pro Glu Leu Leu
225             230             235             240

Gly Gly Pro Ser Val Phe Leu Phe Pro Pro Lys Pro Lys Asp Thr Leu
            245             250             255

Met Ile Ser Arg Thr Pro Glu Val Thr Cys Val Val Val Asp Val Ser
            260             265             270

His Glu Asp Pro Glu Val Lys Phe Asn Trp Tyr Val Asp Gly Val Glu
        275             280             285

Val His Asn Ala Lys Thr Lys Pro Arg Glu Glu Gln Tyr Asn Ser Thr
    290             295             300

Tyr Arg Val Val Ser Val Leu Thr Val Leu His Gln Asp Trp Leu Asn
305             310             315             320
```

```
Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Cys Thr Leu Pro Pro Ser Arg Glu Glu Met Thr Lys Asn Gln Val
                355                 360                 365

Ser Leu Ser Cys Ala Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Val Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly Lys
            450

<210> SEQ ID NO 376
<211> LENGTH: 214
<212> TYPE: PRT
<213> ORGANISM: Artificial sequence
<220> FEATURE:
<223> OTHER INFORMATION: synthetic sequence

<400> SEQUENCE: 376

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
                35                  40                  45

Tyr Ser Ala Ser Phe Leu Tyr Ser Gly Val Pro Ser Arg Phe Ser Gly
            50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

-continued

<210> SEQ ID NO 377
<211> LENGTH: 214
<212> TYPE: PRT
<213> ORGANISM: Artificial sequence
<220> FEATURE:
<223> OTHER INFORMATION: synthetic sequence

<400> SEQUENCE: 377

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
                20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 378
<211> LENGTH: 214
<212> TYPE: PRT
<213> ORGANISM: Artificial sequence
<220> FEATURE:
<223> OTHER INFORMATION: synthetic sequence

<400> SEQUENCE: 378

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

-continued

```
Thr Phe Gly Gln Gly Thr Lys Val Glu Ile Lys Arg Thr Val Ala Ala
            100             105             110

Pro Ser Val Phe Ile Phe Pro Pro Ser Asp Glu Gln Leu Lys Ser Gly
        115             120             125

Thr Ala Ser Val Val Cys Leu Leu Asn Asn Phe Tyr Pro Arg Glu Ala
        130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
                165             170             175

Ser Thr Leu Thr Leu Ser Lys Ala Asp Tyr Glu Lys His Lys Val Tyr
            180             185             190

Ala Cys Glu Val Thr His Gln Gly Leu Ser Ser Pro Val Thr Lys Ser
        195             200             205

Phe Asn Arg Gly Glu Cys
    210

<210> SEQ ID NO 379
<211> LENGTH: 5
<212> TYPE: PRT
<213> ORGANISM: Artificial sequence
<220> FEATURE:
<223> OTHER INFORMATION: synthetic sequence

<400> SEQUENCE: 379

Gly Tyr Gly Met Ser
1           5

<210> SEQ ID NO 380
<211> LENGTH: 16
<212> TYPE: PRT
<213> ORGANISM: Artificial sequence
<220> FEATURE:
<223> OTHER INFORMATION: synthetic sequence

<400> SEQUENCE: 380

Arg Ser Ser Gln Ser Leu Leu His Ser Ser Gly Asn Thr Tyr Leu Asn
1           5               10              15
```

ANTI-MDR1 ANTIBODIES AND USES THEREOF

CROSS-REFERENCE TO RELATED APPLICATIONS

This application claims the benefit of priority to U.S. Provisional Patent Application No. 62/967,470 filed on Jan. 29, 2020 and to U.S. Provisional Patent Application No. 63/085,818 filed on Sep. 30, 2020, which applications are incorporated herein by reference in their entirety.

INCORPORATION BY REFERENCE OF SEQUENCE LISTING PROVIDED AS TEXT FILE

A Sequence Listing is provided herewith as a text file, "KNJY-003WO SEQ LIST_ST25.txt," created on Jan. 28, 2021 and having a size of 291 KB. The contents of the text file are incorporated by reference herein in their entirety.

Introduction

Drug resistance, a well-known phenomenon that results when diseases become tolerant to pharmaceutical treatments, is a major and increasing challenge in various fields of medicine, including oncology. Although many types of cancers are initially susceptible to chemotherapy, over time they can develop resistance through these and other mechanisms, including DNA mutations and metabolic changes that promote drug inhibition, degradation and enhanced efflux.

Efflux pumps (EP) are proteins expressed by living cells and have evolved to naturally expel various compounds from the cells. Members of the ATP-binding cassette (ABC) transporter family proteins are examples of EPs that enable drug efflux. Though a transporter's structure varies from protein to protein (e.g., there are 49 known members of the ABC family in humans), they are all classified by the presence of two distinct domains—a highly conserved nucleotide binding domain and a more variable transmembrane domain. Multidrug resistance protein 1 (MDR1), encoded by the ATP Binding Cassette Subfamily B Member 1 (ABCB1) gene, was the first of these to be identified and has been studied extensively. MDR1 expression is increased in response to treatment with certain chemotherapeutics.

EPs enable tumors to develop resistance to chemotherapeutic agents. Such resistance is frequently associated with enhanced efflux of the chemotherapeutic agent from the drug resistant cells. This chemotherapy resistance is termed multi drug resistance (MDR) when it applies to more than one chemotherapeutic agent.

As such there is a need to develop reagents that may be used for assaying for expression of EPs and/or inhibiting EPs.

SUMMARY

Provided are antibodies that target the cellular efflux pump MDR1. Also provided are pharmaceutical compositions, nucleic acids, recombinant expression vectors, cells, and kits that include or encode such antibodies. Methods of using the antibodies for detecting presence or absence of MDR1 expression in cells, e.g., tumor cells, level of MDR1 expression, and/or inhibiting MDR1 function are also disclosed. In addition, multi-specific antibodies that bind to MDR1 and a tumor associated antigen (TAA) are provided. Also provided are methods for treating a subject for a cancer that include administering to the subject an anti-MDR1 antibody as disclosed herein or a multi-specific antibody that targets both MDR1 and a TAA are provided.

BRIEF DESCRIPTION OF THE FIGURES

FIG. 8 demonstrates that ABCB1 knock-out in drug resistant tumors induces chemosensitivity to paclitaxel.

FIG. 9 summarizes binding of the listed antibodies to various regions of human MDR1.

FIGS. 10A-10C show binding of B1.129 antibody and humanized versions thereof to human and cynomolgus MDR1.

FIG. 15 shows data for binding of anti-MDR1 and anti-CD47 bispecific antibodies to cynomolgus and human CD47 expressed on the surface of C6 cells.

FIG. 17A shows binding of humanized anti-MDR1 and anti-CD47 bispecific antibodies to C6 cells overexpressing human ABCB1 (hB1) or human CD47 (hKT14) or cynomolgus CD47 (cKT14).

FIG. 17B shows binding of humanized anti-MDR1 and anti-CD47 bispecific antibodies to C6 cells overexpressing human ABCB1 (hB1) or human CD47 (hKT14) or cynomolgus CD47 (cKT14).

FIGS. 18A-18B summarize results from assaying for binding of various bispecific antibodies to CD47 using ELISA or cells expressing CD47 and using cells expressing ABCB1.N.D.=Not Determined.

FIG. 19 illustrates various bispecific antibody formats according to certain embodiments of the present disclosure.

FIG. 22 shows that KT14.5F9hu scFv-B1.261.hu1 and KT14.B6H12hu scFv-B1.261.hu1 antibodies bind to both human CD47 and to human MDR1 expressed on the surface of C6 cells.

FIGS. 23A-23C shows effect of anti-MDR1 and anti-CD47 bispecific antibodies of the present disclosure on tumor volume in an MES-SA-DX5 xenograft model when administered alone or coadministered with paclitaxel.

FIG. 24 lists the various combinations of anti-MDR1 heavy chains, anti-HER2 heavy chains, and anti-MDR1 common light chains tested in a bispecific antibody format to identify a combination that binds to both antigens.

FIG. 25 lists the various combinations of anti-MDR1 heavy chains, anti-PDL1 heavy chains, and anti-MDR1 common light chains tested in a bispecific antibody format to identify a combination that binds to both antigens.

DEFINITIONS

Figure 1:
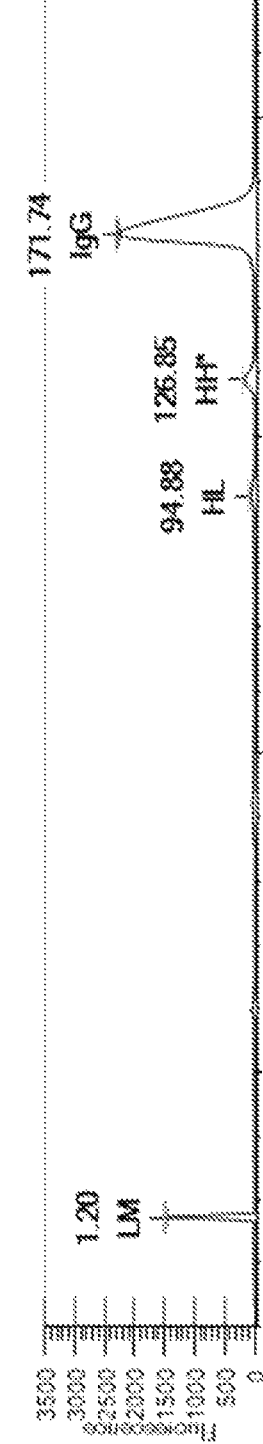
FIG. 1 shows a chromatogram for a purified anti-MDR1 antibody of the present disclosure. IgG antibody (MW 171.74 kDa) at 92.08% purity was obtained. Heavy/Light Dimer "HL" (MW 94.88 kDa), and Heavy/Heavy "HH" (MW 126.85 kDa) were also present in insignificant amounts.
Figure 2A:
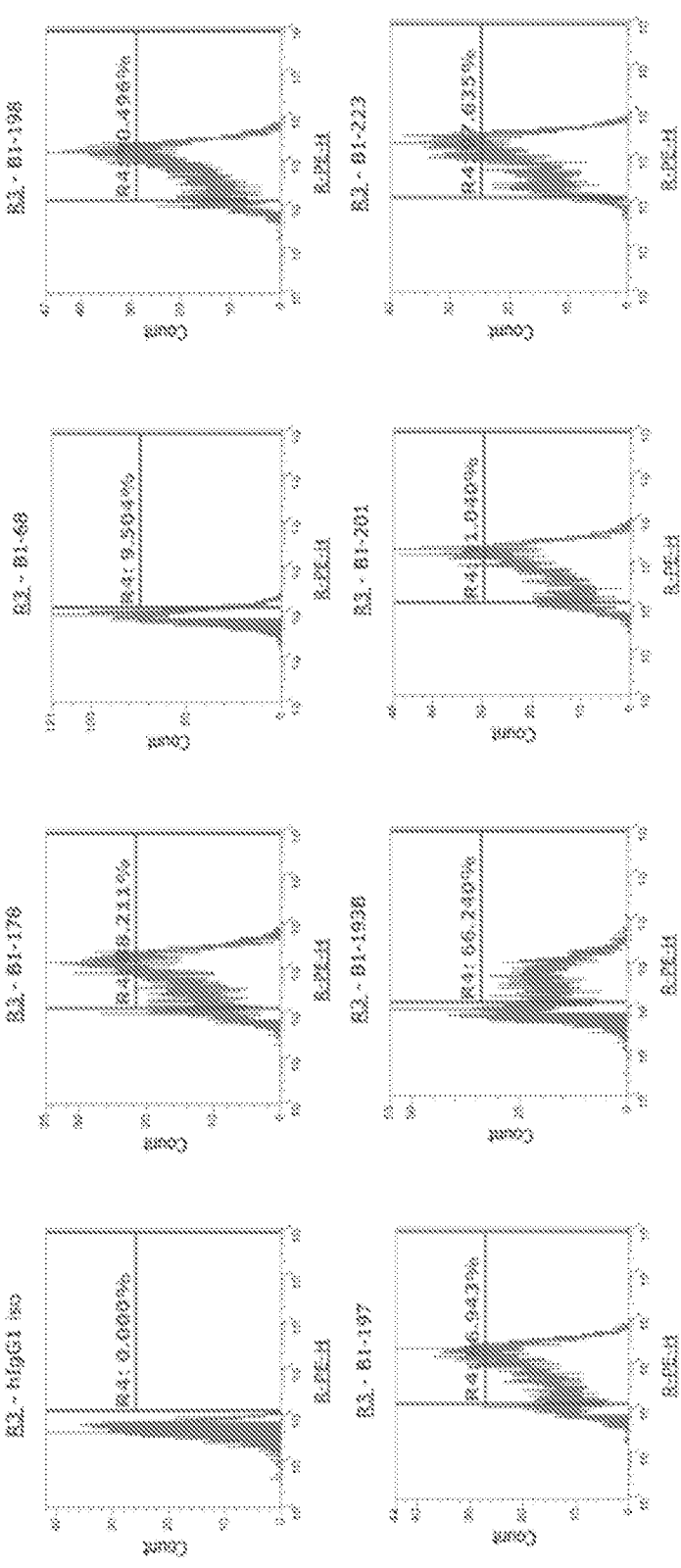
FIGS. 2A-2B depict anti-MDR1 antibody single point binding to 293T cells overexpressing MDR1.
Figure 2B:
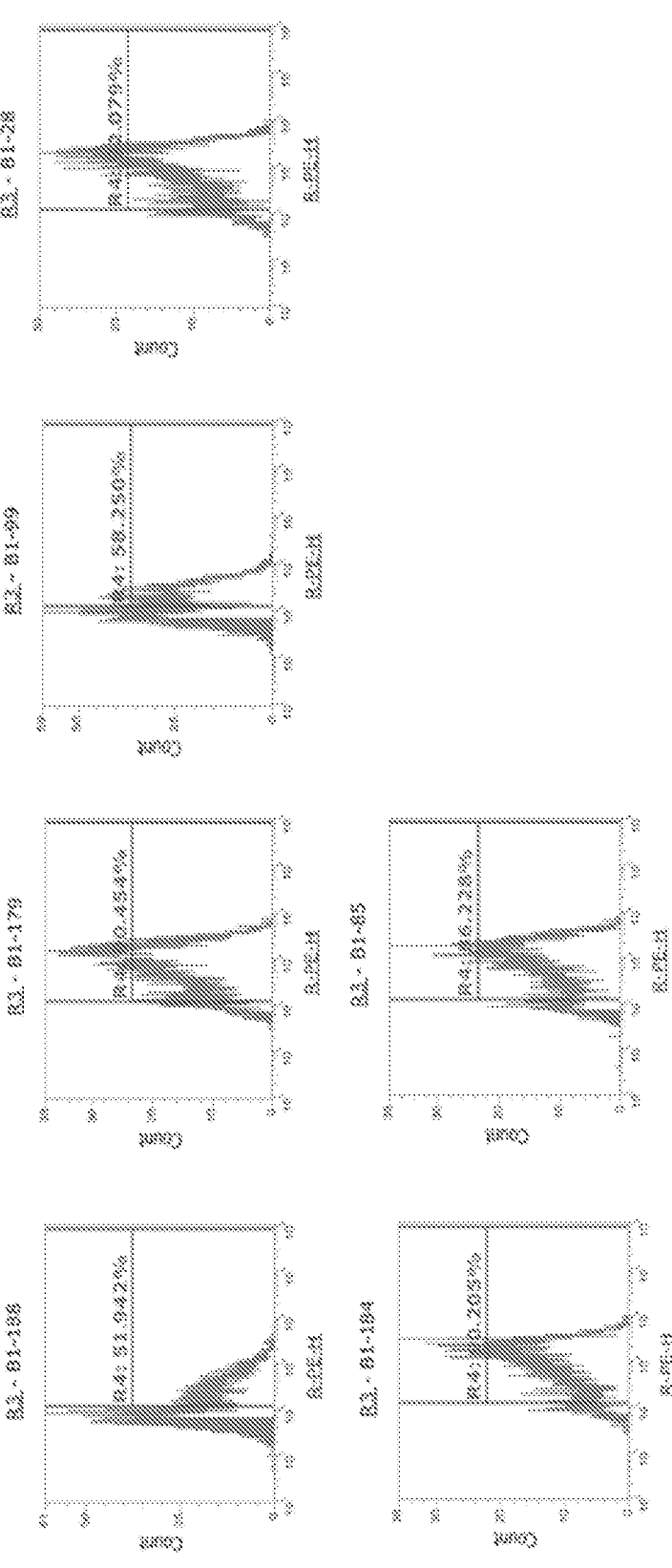

The terms "antibody" and "immunoglobulin" include antibodies or immunoglobulins of any isotype, fragments of antibodies which retain specific binding to antigen, including, but not limited to, Fab, Fv, scFv, Fd, Fab', Fv, F(ab')$_2$, chimeric antibodies, humanized antibodies, monoclonal antibodies, single-chain antibodies, including antibodies comprising only heavy chains (e.g. VHH camelid antibodies), bispecific antibodies, and fusion proteins comprising an antigen-binding portion of an antibody and a non-antibody protein. Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The terms "antibody" and "immunoglobulin" specifically include, without limitation, IgG1, IgG2, IgG3 and IgG4 antibodies. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. An antibody may be monovalent or bivalent. An antibody may be conjugated to a toxic moiety, such as, a chemotherapeutic agent.

"Antibody fragments" comprise a portion of an intact antibody, for example, the antigen binding or variable region of the intact antibody. Examples of antibody fragments include Fab, Fab', F(ab')$_2$, and Fv fragments; diabodies; linear antibodies (Zapata et al., Protein Eng. 8(10): 1057-1062 (1995)); single-chain antibody molecules, including antibodies comprising only heavy chains (e.g. VHH camelid antibodies); and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site comprising the three CDRs of each variable domain.

The "Fab" fragment also contains the constant domain of the light chain and the first constant domain (CH$_1$) of the heavy chain. Fab fragments differ from Fab' fragments by the addition of a few residues at the carboxyl terminus of the heavy chain CH$_1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

"Single-chain Fv", "sFv" or "scFv" antibody fragments comprise the V$_H$ and V$_L$ domains of antibody, wherein these domains are present in a single polypeptide chain. In some embodiments, the Fv polypeptide further comprises a polypeptide linker between the V$_H$ and V$_L$ domains, which enables the sFv to form the desired structure for antigen binding. For a review of sFv, see Pluckthun in *The Pharmacology of Monoclonal Antibodies, vol.* 113, Rosenburg and Moore eds., Springer-Vedag, New York, pp. 269-315 (1994).

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA,* 90:6444-6448 (1993).

Various non-traditional antibody configurations are shown in FIG. 19.

As used herein, the term "affinity" refers to the equilibrium constant for the reversible binding of two agents and is expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "binding" refers to a direct association between two molecules, due to, for example, covalent, electrostatic, hydrophobic, and ionic and/or hydrogen-bond interactions, including interactions such as salt bridges and water bridges. A MDR1-specific antibody binds specifically to an epitope within a MDR1 polypeptide. In certain embodiments, the anti-MDR1 antibodies do not bind to, or bind with significantly less affinity, to cells not expressing MDR1. The epitope may be a linear epitope formed by a contiguous stretch of amino acids or a non-linear or a conformational epitope formed by non-contiguous stretches of amino acids. Non-specific binding would refer to binding with an affinity of less than about $10^{-7}$ M, e.g., binding with an affinity of $10^{-8}$ M, $10^{-5}$ M, $10^{-4}$ M, etc.

As used herein, the term "CDR" or "complementarity determining region" is intended to mean the non-contiguous antigen combining sites found within the variable region of both heavy and light chain polypeptides. CDRs are hypervariable regions and are interspersed with regions that are more conserved, termed "framework regions (FR)". CDRs have been described by Kabat et al., J. Biol. Chem. 252: 6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison.

TABLE 1

| CDR Definitions | | | |
| --- | --- | --- | --- |
| | Kabat[1] | Chothia[2] | MacCallum[3] |
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra As used herein, the term "framework" when used in reference to an antibody variable region is intended to mean all amino acid residues outside the CDR regions within the variable region of an antibody. A variable region framework is generally a discontinuous amino acid sequence between about 100-120 amino acids in length but is intended to reference only those amino acids outside of the CDRs. As used herein, the term "framework region" is intended to mean each domain of the framework that is separated by the CDRs. A VH chain can comprise three CDRs and four FRs arranged from N-terminus to C-terminus in the following order FR1, CDR1, FR2, CDR2, FR3, CDR3, FR4. Similarly, a VL chain can comprise three CDRs and four FRs arranged from N-terminus to C-terminus in the following order: FR1, CDR1, FR2, CDR2, FR3, CDR3, FR4.

As used herein the term antibody encompasses a tetramer of two heavy and two light chains, wherein the heavy and light chains are interconnected by, for example, disulphide bonds. The heavy chain constant region is comprised of three domains, CH1, CH2 and CH3. The light chain constant region is comprised of one domain, CL. The variable regions of the heavy and light chains comprise binding regions that interact with antigen. The constant regions of the antibodies typically mediate the binding of the antibody to host tissues and factors, including various cells of the immune system and the first component of the complement system. The term "antibody" includes immunoglobulins of types IgA, IgG, IgE, IgD, IgM and subtypes thereof. In some embodiments, a subject antibody is an IgG isotype, e.g., IgG1.

As used herein the term "immunoglobulin" refers to a protein including one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes; and numerous immunoglobulin variable region genes. Full-length immunoglobulin light chains (about 25 kD or 214 amino acids) are encoded by a variable region gene at the N-terminus (about 110 amino acids) and a kappa or lambda constant region at the C-terminus. Full-length immunoglobulin heavy chains (about 50 kD or 446 amino acids) are encoded by a variable region gene at the N-terminus (about 116 amino acids) and one of the other aforementioned constant region genes at the C-terminus, e.g. gamma (encoding about 330 amino acids). In some embodiments, a subject antibody comprises full-length immunoglobulin heavy chain and a full-length immunoglobulin light chain.

The term "antigen-binding fragment" refers to one or more fragments of a full-length antibody that are capable of specifically binding to an antigen. Examples of binding fragments include (i) a Fab fragment (a monovalent fragment including, e.g., consisting of, the VL, VH, CL and CH1 domains; (ii) a F(ab')$_2$ fragment (a bivalent fragment comprising two Fab fragments linked by a disulfide bridge at the hinge region; (iii) a Fd fragment (including, e.g., consisting of, the VH and CH1 domains); (iv) a Fv fragment (including, e.g., consisting of, the VH and VL domains of a single arm of an antibody); (v) a dAb fragment (including, e.g., consisting of, the VH domain); (vi) an isolated CDR; (vii) a single chain Fv (scFv) (including, e.g., consisting of, the VH and VL domains of a single arm of an antibody joined by a synthetic linker using recombinant means such that the VH and VL domains pair to form a monovalent molecule); (viii) diabodies (including, e.g., consisting of, two scFvs in which the VH and VL domains are joined such that they do not pair to form a monovalent molecule; the VH of each one of the scFv pairs with the VL domain of the other scFv to form a bivalent molecule).

The term "chimeric" antibody refers to an antibody in which a portion of the heavy and/or light chain is derived from a particular source or species, while the remainder of the heavy and/or light chain is derived from a different source or species.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework (FR) which represents the most commonly occurring amino acid residues in a selection of human immunoglobulin variable light chain (VL) or variable heavy chain (VH) framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup 111 as in Kabat et al., supra.

A "humanized" antibody refers to a chimeric antibody comprising amino acid residues from non-human CDRs and amino acid residues from human frameworks (FRs). At least a portion of a humanized antibody constant region is derived from a human antibody, e.g., a human IgG1 antibody. In preferred embodiments, the antibody molecules disclosed herein include a heavy chain comprising a variable heavy chain region as provided herein and a human IgG1 constant region having the amino acid sequence sequence set forth in UniProt: P01857-1, version 1. In preferred embodiments, the antibody molecules disclosed herein include a light chain comprising a variable light chain region as provided herein and a human light chain constant region. In preferred embodiments, the human light chain constant region is a human kappa light chain constant region having the amino acid set forth in UniProtKB/Swiss-Prot: P01834.2. In certain aspects, the human IgG1 heavy chain constant region present in the subject antibodies may include mutations, e.g., substitutions to modulate Fc function. For example, the LALAPG effector function mutations (L234A, L235A, and P329G) or the N297A mutation may be introduced to reduce antibody dependent cellular cytotoxicity (ADCC). The numbering of the substitutions is based on the EU numbering system. The "EU numbering system" or "EU index" is generally used when referring to a residue in an immunoglobulin heavy chain constant region (e.g., the EU index reported in Kabat et al., Sequences of Proteins of Immunological Interest, 5th Ed. Public Health Service, National Institutes of Health, Bethesda, MD. (1991)). The "EU index as in Kabat" refers to the residue numbering of the human IgG 1 EU antibody.

A "humanized form" of an antibody, e.g., a non-human antibody, refers to an antibody that has undergone humanization.

The term "epitope" refers to a region of an antigen that is recognized by the immune system, for example by antibodies, B cells, or T cells. For example, the epitope is the specific region of the antigen to which an antibody binds. The term specifically includes linear (continuous) epitopes and non-linear (conformational or discontinuous) epitopes.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In some embodiments, the antibody will be purified (1) to greater than 90%, greater than 95%, or greater than 98%, by weight of antibody as determined by the Lowry method, for example, more than 99% by weight, (2) to a degree sufficient to obtain at least 15 residues of N-terminal or internal amino acid sequence by use of a spinning cup sequenator, or (3) to homogeneity by sodium dodecyl sulfate-polyacrylamide gel electrophoresis (SDS-PAGE) under reducing or nonreducing conditions using Coomassie blue or silver stain. Isolated antibody includes the antibody in situ within recombinant cells since at least one component of the antibody's natural environment will not be present. In some instances, isolated antibody will be prepared by at least one purification step.

The terms "MDR1" and "ABCB1" are used herein interchangeably, and refer to a native sequence multi-drug resistant cellular efflux pump protein, including human MDR1 and its naturally occurring variants, such as allelic variants.

The term "cytotoxic agent" as used herein refers to a substance that inhibits or prevents a cellular function and/or causes cell death or destruction. A "chemotherapeutic agent," also referred to an "antineoplastic agent," can be a cytotoxic agent which is used for treating a cancer or other disease or disorder.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, including in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc.

A "therapeutically effective amount" or "efficacious amount" refers to the amount of a target-specific antibody that, when administered to a mammal or other subject for treating a disease, is sufficient to affect such treatment for the disease. The "therapeutically effective amount" will vary depending on the antibody, the disease and its severity and the age, weight, etc., of the subject to be treated.

The term "refractory", used herein, refers to a disease or condition that does not respond to treatment. With regard to cancer, "refractory cancer", as used herein, refers to cancer that does not respond to treatment. A refractory cancer may be resistant at the beginning of treatment or it may become resistant during treatment. Refractory cancer may also be called resistant cancer.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples.

Percent identity between a pair of sequences may be calculated by multiplying the number of matches in the pair by 100 and dividing by the length of the aligned region, including gaps. Identity scoring only counts perfect matches and does not consider the degree of similarity of amino acids to one another. Only internal gaps are included in the length, not gaps at the sequence ends. Percent Identity=(Matches× 100)/Length of aligned region (with gaps)

The phrase "conservative amino acid substitution" refers to substitution of amino acid residues within the following groups: 1) L, I, M, V, F; 2) R, K; 3) F, Y, H, W, R; 4) G, A, T, S; 5) Q, N; and 6) D, E. Conservative amino acid substitutions may preserve the activity of the protein by replacing an amino acid(s) in the protein with an amino acid with a side chain of similar acidity, basicity, charge, polarity, or size of the side chain.

The term "vector" means any molecule or entity (e.g., nucleic acid, plasmid, bacteriophage or virus) used to transfer protein coding information into a host cell.

The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct may include, but is not limited to, sequences that affect or control transcription, translation, and, if introns are present, affect RNA splicing of a coding region operably linked thereto.

The term "stimulation," refers to a primary response induced by binding of a stimulatory molecule (e.g., a TCR/CD3 complex or CAR) with its cognate ligand (or tumor antigen in the case of a CAR) thereby mediating a signal transduction event, such as, but not limited to, signal transduction via the TCR/CD3 complex or signal transduction via the appropriate NK receptor or signaling domains of the CAR. Stimulation can mediate altered expression of certain molecules.

The term "stimulatory molecule," refers to a molecule expressed by an immune cell (e.g., T cell, NK cell, B cell) that provides the cytoplasmic signaling sequence(s) that regulate activation of the immune cell in a stimulatory way for at least some aspect of the immune cell signaling pathway. In one aspect, the signal is a primary signal that is initiated by, for instance, binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or ITAM. Examples of an ITAM containing cytoplasmic signaling sequence that is of particular use in the invention includes, but is not limited to, those derived from CD3 zeta, common FcR gamma (FCER1G), Fc gamma RIIa, FcR beta (Fc Epsilon R1b), CD3 gamma, CD3 delta, CD3 epsilon, CD79a, CD79b, DAP10, and DAP12.

The term a "costimulatory molecule" refers to a cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are contribute to an efficient immune response. Costimulatory molecules include, but are not limited to an MHC class I molecule, BTLA and a Toll ligand receptor, as well as OX40, CD27, CD28, CDS, ICAM-1, LFA-1 (CD11a/CD18), ICOS (CD278), and 4-1BB (CD137).

The term "autologous" refers to any material derived from the same individual to whom it is later to be re-introduced into the individual.

An "intracellular signaling domain," as the term is used herein, refers to an intracellular portion of a molecule. The intracellular signaling domain generates a signal that promotes an immune effector function of the CAR containing cell, e.g., a CAR-T cell. Examples of immune effector function, e.g., in a CAR-T cell, include cytolytic activity and helper activity, including the secretion of cytokines.

"Immune effector cell," as that term is used herein, refers to a cell that is involved in an immune response, e.g., in the promotion of an immune effector response. Examples of immune effector cells include T cells, e.g., alpha/beta T cells and gamma/delta T cells, B cells, natural killer (NK) cells, natural killer T (NKT) cells, mast cells, and myeloid-derived phagocytes.

Guidance for substitutions, insertions, or deletions may be based on alignments of amino acid sequences of proteins from different species or from a consensus sequence based on a plurality of proteins having the same or similar function.

DETAILED DESCRIPTION

Provided are antibodies that target the cellular efflux pump MDR1. Also provided are pharmaceutical compositions, nucleic acids, recombinant expression vectors, cells, and kits that include or encode such antibodies. Methods of using the antibodies for detecting presence or absence of MDR1 expression in cells, e.g., tumor cells, level of MDR1 expression, and/or inhibiting MDR1 function are also disclosed. In addition, multi-specific antibodies that bind to MDR1 and a TAA are provided. Also provided are methods for treating a subject for a cancer that include administering to the subject an anti-MDR1 antibody as disclosed herein or a multi-specific antibody that targets both MDR1 and a tumor-associated antigen.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the methods and compositions have or will be described for the sake of grammatical fluidity with functional explanations, it is to be expressly understood that the claims, unless expressly formulated under 35 U.S.C. § 112(f), are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112(f) are to be accorded full statutory equivalents under 35 U.S.C. § 112(f).

Antibodies

As summarized above, the present disclosure provides antibodies that bind a cellular efflux pump MDR1, also known as P-glycoprotein 1 (Pgp) or ABCB1.

MDR1, also known as P-glycoprotein 1 (Pgp) or ABCB1, is an energy-dependent efflux pump responsible for decreased drug accumulation in multidrug-resistant cells that is expressed from the ATP binding cassette subfamily B member 1 (ABCB1) gene. Anti-MDR1 antibodies are also referred to herein as anti-Pgp, anti-ABCB1, or anti-B1 antibodies.

In some aspects, the antibodies disclosed herein bind to an epitope comprising one or more sites on the extracellular domain of the MDR1. In certain aspects, the anti-MDR1 antibodies of the present disclosure bind to human MDR1. In certain aspects, the anti-MDR1 antibodies of the present disclosure bind to human MDR1 expressed on the cell surface of a human cell. In certain aspects, the antibodies disclosed herein bind to an epitope comprising one or more sites on an extracellular domain (ECD) of the human MDR1, where the ECD may include the sequence: MMLVFGEMTDIFANAGN- LEDLMSNITNRSDINDTGFFMNLEEDMTRYAY (SEQ ID NO:1), which sequence corresponds to amino acid residue 68-116 of the human MDR1 sequence having the Accession No. NP_000918. In certain aspects, the antibodies disclosed herein bind to an epitope comprising one or more sites on an extracellular domain (ECD) of the human MDR1, where the ECD may include the sequence TRGWKL (SEQ ID NO:2), which sequence corresponds to amino acid residue 209-215 of the human MDR1 sequence having the Accession No. NP_000918. In certain aspects, the antibodies disclosed herein bind to an epitope comprising one or more sites on an extracellular domain (ECD) of the human MDR1, where the ECD may include the sequence GTTLVLSGEYSIGQ (SEQ ID NO:3), which sequence corresponds to amino acid residue 317-330 of the human MDR1 sequence having the Accession No. NP_000918. In certain aspects, the antibodies disclosed herein bind to an epitope comprising one or more sites on an extracellular domain (ECD) of the human MDR1, where the ECD may include the sequence SKIIGVFTRIDDPETKRQNSNLFS (SEQ ID NO:4), which sequence corresponds to amino acid residue 733-756 of the human MDR1 sequence having the Accession No. NP_000918. In certain aspects, the antibodies disclosed herein bind to an epitope comprising one or more sites on an extracellular domain (ECD) of the human MDR1, where the ECD may include the sequence RFGAY-LVAHKLMSFED (SEQ ID NO:5), which sequence corresponds to amino acid residue 958-973 of the human MDR1 sequence having the Accession No. NP_000918.

An anti-MDR1 antibody of the present disclosure may have one or more of the following properties:
   i) Inhibits efflux from MDR1;
   ii) increases sensitivity of cancer cell to treatment with a chemotherapeutic agent thereby lowering the IC50 of the chemotherapeutic agent by at least a factor of 5, 10, 50, or 100;
   iii) binds to human and cynomolgus MDR1;
   iv) does not cross-react with CD47;
   v) is effective in in vitro cell killing assays;
   vi) is effective in inhibiting tumor growth even in absence of chemotherapy;
   vii) binds preferentially to an MDR1 mutant constrained in an open configuration;
   viii) binds preferentially to an MDR1 mutant constrained in a closed configuration; and
   ix) binds preferentially to a region outside the extracellular loop 1 of human MDR1 or binds to extracellular loop 1 and extracellular loop 4 of human MDR1.

In certain aspects, in addition to having one or more properties i)-ix) listed above, the antibodies of the present disclosure may have an EC50 of 100 nM or lower, e.g., 100 nM-4 nM, 80 nM-4 nM, 60 nM-4 nM, 40 nM-4 nM, 30 nM-4 nM, 20 nM-4 nM, 15 nM-4 nM, or 10 nM-4 nM. In certain aspects, in addition to having one or more properties i)-ix) listed above, the antibodies of the present disclosure may have an EC50 that is at least half of the EC50 of anti-MDR1 antibodies such as 15D3, MRK16, MM4, and/or UIC2.

The EC50 of a test antibody many be determined by flow cytometry or ELISA. For example, flow cytometry may involve contacting a cell expressing MDR1 (e.g. human wild type MDR1 or a mutant MDR1) with the antibody in a flow cytometry buffer, where the antibody is serially diluted, and incubating at room temperature or 4° C. for a period of time sufficient for the antibody to bind to the cells (e.g. 10 min-1 hr). After incubating, the cells may optionally be washed to remove and non-specifically bound antibody and/or the cells may be contacted with a fluorescently labeled secondary antibody that specifically binds to the test antibody. After incubation, the fluorescently labeled secondary antibody may be removed and the cells washed. The washed cells may be sorted by flow cytometry and the number of cells bound to the fluorescently labeled secondary antibody counted. The concentration that provides half maximal response (e.g., half of the maximum fluorescence intensity) is measured as the EC50. In variations of the flow cytometry assay, the cell may be a 293T cell overexpressing MDR1.

The IC50 of a test antibody may be determined by measuring inhibition of cell growth. IC50 may be measured by using the test antibody alone to determine the concentration of the antibody that produced half maximal response. The IC50 of a chemotherapeutic agent may be measured in the absence and in the presence of the test antibody to determine the effect of the antibody on the IC50 chemotherapeutic agent. The chemotherapeutic agent may be vincristine. The cell may be a cancer cell line. The cancer cell line may be N6/ADR, a doxorubicin-selected, B1-positive variant of the human acute lymphoblastic leukemia (ALL) cell line, NALM6. N6/ADR cells is also referred to as NALM6/ADR cells. Cells may be contacted with antibody alone if determining the IC50 of the antibody, wherein the antibody is tested at serial dilutions. Cells may be contacted with antibody and the chemotherapeutic agent to determine the effect of the antibody on the IC50 of the agent, where the agent is tested at serial dilutions. The cells may be incubated at 37° C. for a period of time (e.g. 24 hr-84 hr) and cell viability assessed using standard reagents and methods. The antibodies disclosed herein may increase sensitivity of cancer cell to treatment with a chemotherapeutic agent thereby lowering the IC50 of the chemotherapeutic agent by at least a factor of 5. The cancer cell may be N6/ADR. The chemotherapeutic agent may be vincristine. In certain aspects, the antibodies of the present disclosure may lower the IC50 of vincristine for inhibiting growth of N6/ADR cancer cells by factor of 5 or more, e.g., factor of 6 or more, factor of 7 or more, factor of 8 or more, factor of 9 or more, or factor of 10 or more, e.g., by a factor of 5 to 50 or more, e.g., by a factor of at least 60, 70, 80, 90, or 100. The anti-MDR1 antibodies B1-207, B1-223, KB1-225, KB1.116, KB1.80, KB1.261, and KB1.263 lower the IC50 for vincristine for inhibiting growth of N6/ADR cancer cells by a factor of at least 400, i.e., from 4118 pM to 10.3 pM or lower. See FIG. 4A-4D and Table 7.

In certain aspects, the anti-MDR1 antibodies bind to both human and cynomolgus MDR-1. This property may be utilized in determining safety of the antibody in an animal model.

In certain aspects, the anti-MDR1 antibodies disclosed herein are specific for MDR1 and do not show significant binding to other antigens. For example, the antibodies disclosed herein do not cross-react with the tumor-associated antigen, CD47, in contrast to the anti-MDR1 antibody, 15D3.

In certain aspects, the anti-MDR1 in vitro cell killing activity of the presently disclosed antibodies may be superior to that observed for 15D3, MRK16, MM4, and/or UIC2. For example, the presently disclosed antibodies may have in vitro cell killing activity that is twice or more than that of 15D3, MRK16, MM4, and/or UIC2.

In certain aspects, the antibodies provided herein bind preferentially to an MDR1 mutant constrained in an open configuration. The MDR1 mutant may be a human or a cynomolgus MDR1 comprising the substitutions E556Q and E1201Q, where the numbering of the amino acid positions is with reference to human MDR1. Such antibodies may bind to an MDR1 mutant constrained in an open configuration with an affinity that is at least two times (e.g. 2×, 3×, 4×, 5×, 6×, 7×, 8×, 9×, 10×, or more) as compared to the wild-type MDR1 or an MDR1 mutant constrained in a closed configuration.

In certain aspects, the antibodies provided herein bind preferentially to an MDR1 mutant constrained in a closed configuration. The MDR1 mutant may be a human or a cynomolgus MDR1 comprising the substitutions: (i) K433M, S434A, K1076M, S1077A; (ii) K433M, S434A, Q475A, K1076M, S1077A, Q1118A; and/or (iii) K433M, S434A, Q475A, R588E, K1076M, S1077A, Q1118A, R1233E, where the numbering of the amino acid positions is with reference to human MDR1. Such antibodies may bind to an MDR1 mutant constrained in a closed configuration with an affinity that is at least two times (e.g. 3×, 4×, 5×, 6×, 7×, 8×, 9×, 10×, or more) as compared to the wild-type MDR1 or an MDR1 mutant constrained in an open configuration.

In certain aspects, the antibodies provided herein bind preferentially to an MDR1 mutant comprising a deletion in loop 1 in the ECD. The deletion may include deletion of amino acid residues 82-99 or 79-102, where the numbering of the amino acid positions is with reference to human MDR1. Such antibodies may bind to an MDR1 mutant comprising a deletion in loop 1 with an affinity that is at least two times (e.g. 3×, 4×, 5×, 6×, 7×, 8×, 9×, 10×, or more) as compared to the wild-type MDR1 or an MDR1 mutant constrained in an open or a closed configuration.

In certain aspects, the antibodies provided herein bind to an epitope comprising extracellular loop 1 and extracellular loop 4 of human MDR1. Examples of such antibodies include antibodies comprising a VH chain comprising HCDRs1-3 and a VL chain comprising LCDRs1-3, of the anti-MDR1 antibody B1.228B, B1.198, B1.223, B1.219, B1.184, B1.207, B1.201, B1.129, B1.273, or B1.236 as listed in Table 2.

In certain aspects, the antibodies provided herein are monospecific bivalent anti-MDR1 antibodies. In certain aspects, the monospecific bivalent anti-MDR1 antibodies of the present disclosure do not include at least one, two, three, four, five, six, seven, eight, nine, ten, eleven, or all twelve of HCDR1-3 and LCDR1-3 present in the anti-MDR1 antibodies, 15D3, MRK16, MM4, and UIC2.

In certain aspects, the antibody of the present disclosure competes for binding to MDR1 with an antibody comprising heavy chain complementarity determining regions (HCDRs) and light chain CDRs (LCDRs) of the variable heavy chain (VH) region and the variable light chain (VL) region pair, respectively, of an antibody listed in Table 2. For example, in one aspect, an anti-MDR1 antibody of the present disclosure competes for binding to MDR1 with the B1.201 antibody listed in Table 2.

In certain aspects, the antibody comprises the HCDR1, HCDR2, and HCDR3 of the VH region of the antibody listed in Table 2. In certain aspects, the HCDR1, HCDR2, and HCDR3 are defined as per Kabat nomenclature. For example, in one aspect, the anti-MDR1 antibody of the present disclosure that competes for binding to MDR1 with the B1.27 antibody listed in Table 2 comprises the HCDR1, HCDR2, and HCDR3 of the VH region of the B1.27 antibody.

Any suitable approach for determining whether a first antibody competes with a second antibody for binding to MDR1 may be employed. Whether a first antibody "competes with" a second antibody for binding to a compound may be readily determined using competitive binding assays known in the art. Competing antibodies may be identified, for example, via an antibody competition assay. For example, a sample of a first antibody can be bound to a solid support. Then, a sample of a second antibody suspected of being able to compete with such first antibody is added. One of the two antibodies is labelled. If the labeled antibody and the unlabeled antibody bind to separate and discrete sites on the compound, the labeled antibody will bind to the same level whether or not the suspected competing antibody is present. However, if the sites of interaction are identical or overlapping, the unlabeled antibody will compete, and the amount of labeled antibody bound to the antigen will be lowered. If the unlabeled antibody is present in excess, very little, if any, labeled antibody will bind.

For purposes of the present disclosure, competing antibodies are those that decrease the binding of an antibody to the compound by about 30% or more, about 40% or more, about 50% or more, about 60% or more, about 70% or more, about 80% or more, about 85% or more, about 90% or more, about 95% or more, or about 99% or more. Details of procedures for carrying out such competition assays are well known in the art and can be found, for example, in Harlow and Lane, Antibodies, A Laboratory Manual, Cold Spring Harbor Laboratory Press, Cold Spring Harbor, New York, 1988, 567-569, 1988, ISBN 0-87969-314-2. Such assays can be made quantitative by using purified antibodies. A standard curve may be established by titrating one antibody against itself, i.e., the same antibody is used for both the label and the competitor. The capacity of an unlabeled competing antibody to inhibit the binding of the labeled antibody to the target epitope may be titrated. The results may be plotted, and the concentrations necessary to achieve the desired degree of binding inhibition may be compared.

In certain aspects, an antibody molecule that binds multidrug resistance protein 1 (MDR1), comprises (i) HCDRs 1-3 and light chain CDRs (LCDRs 1-3) of a pair of variable heavy chain (VH) region and variable light chain (VL) region of an antibody listed in Table 2; (ii) HCDRs 1-3 of a VH region of an antibody listed in Table 2; or (iii) LCDRs 1-3 of a VH region of an antibody listed in Table 2. The HCDRs and the LCDRs may be defined based on the Kabat nomenclature.

The term "antibody molecule" encompasses antibodies as defined herein and includes antigen-binding fragments thereof. In certain aspects, the antibody molecule includes two variable light (VL) and two variable heavy (VH) chains. In certain aspects, the antibody molecule includes heavy chain and light chain constant regions as well. The heavy and light chain constant regions may be from a human antibody, e.g., human IgG1 antibody. The human IgG1 heavy chain (HC) constant region may be modified to include mutations that reduce antibody dependent cellular cytotoxicity (ADCC). In addition, or alternatively, the two VH chains may each be conjugated to a different human IgG1 HC constant region where the individual human IgG1 HC constant region has substitutions that favour formation of dimers between the different human IgG1 HC constant regions. Such HC regions are described in further detail herein. In certain aspects, where the antibody molecule is a bispecific antibody molecule, one of the human IgG1 HC constant regions may include substitutions to introduce one or more amino acids having a positively-charged side chain and the other human IgG1 HC constant region may include substitutions to introduce one or more amino acids having a negatively-charged side chain to favour formation of dimers between the two different HCs.

In certain aspects, the antibody molecule comprises HCDRs 1-3 and/or LCDRs 1-3 of a pair of VH region and VL region of an antibody listed in Table 2. In one aspect, the antibody molecule comprises the HCDRs 1-3 and/or LCDRs 1-3 of the B1-27 antibody listed in Table 2. In one aspect, the antibody molecule comprises the HCDRs 1-3 and/or LCDRs 1-3 of the B1-28 antibody listed in Table 2. In one aspect, the antibody molecule comprises the HCDRs 1-3 and/or LCDRs 1-3 of the B1-30 antibody listed in Table 2. In one aspect, the antibody molecule comprises the HCDRs 1-3 and/or LCDRs 1-3 of the B1-39 antibody listed in Table 2. In one aspect, the antibody molecule comprises the HCDRs 1-3 and/or LCDRs 1-3 of the B1-85 antibody listed in Table 2. In one aspect, the antibody molecule comprises the HCDRs 1-3 and/or LCDRs 1-3 of the B1-99 antibody listed in Table 2. In one aspect, the antibody molecule comprises the HCDRs 1-3 and/or LCDRs 1-3 of the B1-178 antibody listed in Table 2. In one aspect, the antibody molecule comprises the HCDRs 1-3 and/or LCDRs 1-3 of the B1-179 antibody listed in Table 2. In one aspect, the antibody molecule comprises the HCDRs 1-3 and/or LCDRs 1-3 of the B1-184 antibody listed in Table 2. In one aspect, the antibody molecule comprises the HCDRs 1-3 and/or LCDRs 1-3 of the B1-188 antibody listed in Table 2. In one aspect, the antibody molecule comprises the HCDRs 1-3 and/or LCDRs 1-3 of the B1-193b antibody listed in Table 2. In one aspect, the antibody molecule comprises the HCDRs 1-3 and/or LCDRs 1-3 of the B1-197 antibody listed in Table 2. In one aspect, the antibody molecule comprises the HCDRs 1-3 and/or LCDRs 1-3 of the B1-198 antibody listed in Table 2. In one aspect, the antibody molecule comprises the HCDRs 1-3 and/or LCDRs 1-3 of the B1-201 antibody listed in Table 2. In one aspect, the antibody molecule comprises the HCDRs 1-3 and/or LCDRs 1-3 of the B1-207 antibody listed in Table 2. In one aspect, the antibody molecule comprises the HCDRs 1-3 and/or LCDRs 1-3 of the B1-223 antibody listed in Table 2.

In certain aspects, the antibody comprises HCDRs 1-3 and/or LCDRs 1-3 of a pair of VH region and VL region of an antibody listed in Table 2 and lowers IC50 of a chemotherapeutic agent by a factor of 5 or more, factor of 6 or more, factor of 7 or more, factor of 8 or more, factor of 9 or more, ore factor of 10 or more, e.g., by a factor of 5 to 50 or more, e.g., by a factor of at least 60, 70, 80, 90, or 100. The anti-MDR1 antibodies B1-207, B1-223, KB1-225, KB1.116, KB1.80, KB1.261, and KB1.263 lower the IC50 for vincristine for inhibiting growth of N6/ADR cancer cells by a factor of at least 400, i.e., from 4118 pM to 10.3 pM or lower. See FIG. 4A-4D and Table 7.

Figure 3A:
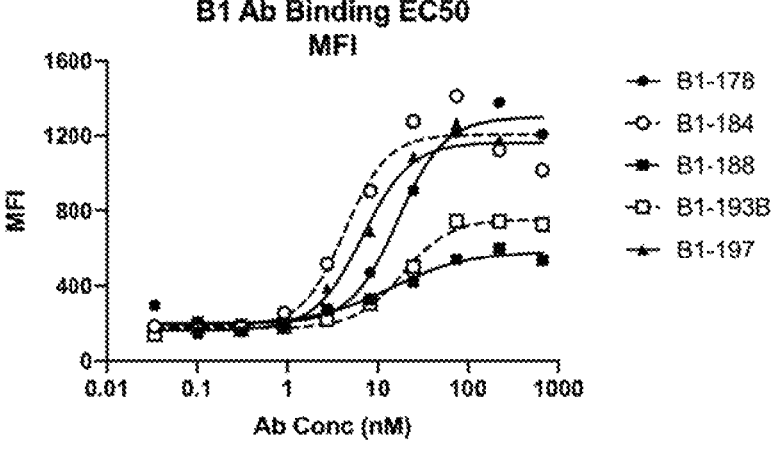
FIGS. 3A-3D depict anti-MDR1 monoclonal antibody titration binding to MDR1.
Figure 3B:
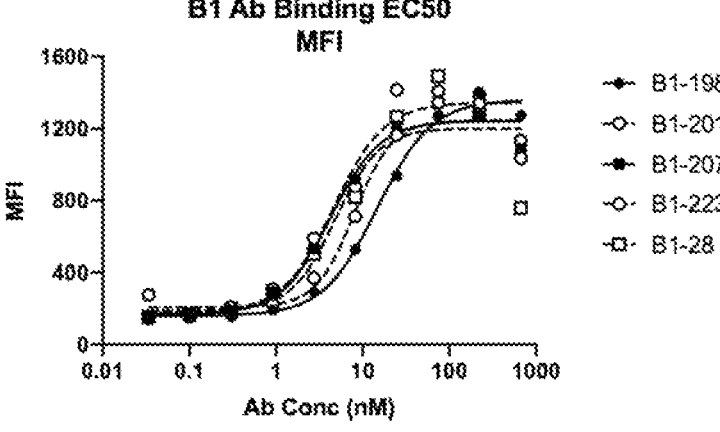
Figures 3C, 3D:
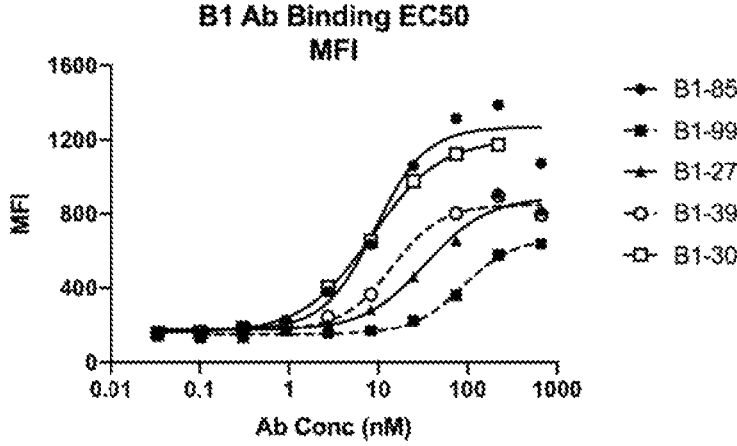
Figures 4A, 4B, 4C, 4D:
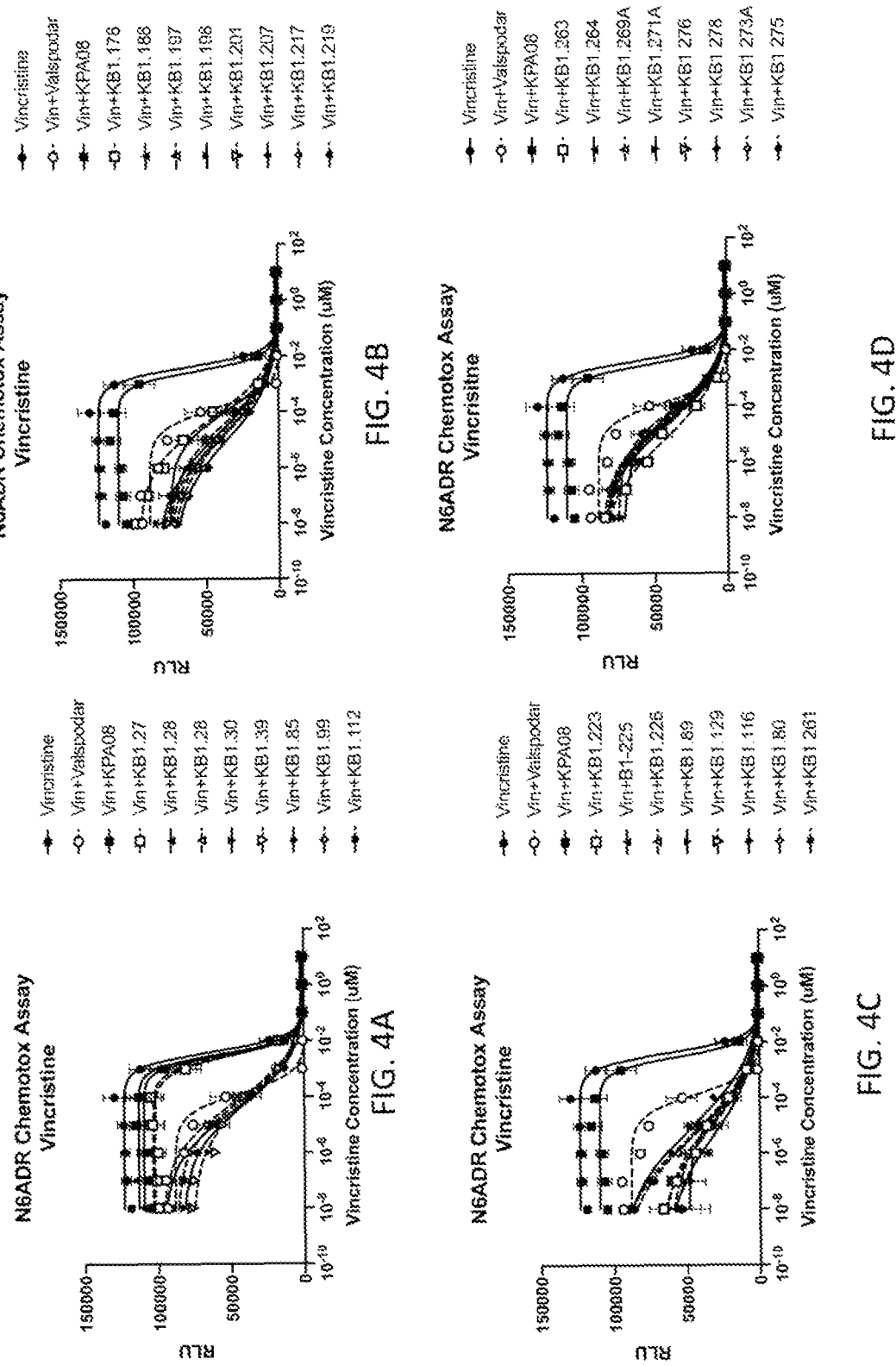
FIGS. 4A-4D illustrate effect of the listed anti-MDR1 antibodies on vincristine cytotoxicity.

EC50 may be the antibody concentration that produces 50% maximal response (e.g., the response is the binding of the antibody to its antigen). In one aspect, the antibody has an EC50 of 100 nM or lower and/or EC50 that is at least half of the EC50 of an anti-MDR1 antibody such as 15D3, MRK16, MM4, and/or UIC2 and comprises the HCDRs 1-3 and/or LCDRs 1-3 of the B1-27 antibody listed in Table 2. In one aspect, the antibody has an EC50 of 100 nM or lower and/or EC50 that is at least half of the EC50 of an anti-MDR1 antibody such as 15D3, MRK16, MM4, and/or UIC2 and comprises the HCDRs 1-3 and/or LCDRs 1-3 of the B1-28 antibody listed in Table 2. In one aspect, the antibody has an EC50 of 100 nM or lower and/or EC50 that is at least half of the EC50 of an anti-MDR1 antibody such as 15D3, MRK16, MM4, and/or UIC2 and comprises the HCDRs 1-3 and/or LCDRs 1-3 of the B1-30 antibody listed in Table 2. In one aspect, the antibody has an EC50 of 100 nM or lower and/or EC50 that is at least half of the EC50 of an anti-MDR1 antibody such as 15D3, MRK16, MM4, and/or UIC2 and comprises the HCDRs 1-3 and/or LCDRs 1-3 of the B1-39 antibody listed in Table 2. In one aspect, the antibody has an EC50 of 100 nM or lower and/or EC50 that is at least half of the EC50 of an anti-MDR1 antibody such as 15D3, MRK16, MM4, and/or UIC2 and comprises the HCDRs 1-3 and/or LCDRs 1-3 of the B1-85 antibody listed in Table 2. In one aspect, the antibody has an EC50 of 100 nM or lower and/or EC50 that is at least half of the EC50 of an anti-MDR1 antibody such as 15D3, MRK16, MM4, and/or UIC2 and comprises the HCDRs 1-3 and/or LCDRs 1-3 of the B1-99 antibody listed in Table 2. In one aspect, the antibody has an EC50 of 100 nM or lower and/or EC50 that is at least half of the EC50 of an anti-MDR1 antibody such as 15D3, MRK16, MM4, and/or UIC2 and comprises the HCDRs 1-3 and/or LCDRs 1-3 of the B1-178 antibody listed in Table 2. In one aspect, the antibody has an EC50 of 100 nM or lower and/or EC50 that is at least half of the EC50 of an anti-MDR1 antibody such as 15D3, MRK16, MM4, and/or UIC2 and comprises the HCDRs 1-3 and/or LCDRs 1-3 of the B1-179 antibody listed in Table 2. In one aspect, the antibody has an EC50 of 100 nM or lower and/or EC50 that is at least half of the EC50 of an anti-MDR1 antibody such as 15D3, MRK16, MM4, and/or UIC2 and comprises the HCDRs 1-3 and/or LCDRs 1-3 of the B1-184 antibody listed in Table 2. In one aspect, the antibody has an EC50 of 100 nM or lower and/or EC50 that is at least half of the EC50 of an anti-MDR1 antibody such as 15D3, MRK16, MM4, and/or UIC2 and comprises the HCDRs 1-3 and/or LCDRs 1-3 of the B1-188 antibody listed in Table 2. In one aspect, the antibody has an EC50 of 100 nM or lower and/or EC50 that is at least half of the EC50 of an anti-MDR1 antibody such as 15D3, MRK16, MM4, and/or UIC2 and comprises the HCDRs 1-3 and/or LCDRs 1-3 of the B1-193b antibody listed in Table 2. In one aspect, the antibody has an EC50 of 100 nM or lower and/or EC50 that is at least half of the EC50 of an anti-MDR1 antibody such as 15D3, MRK16, MM4, and/or UIC2 and comprises the HCDRs 1-3 and/or LCDRs 1-3 of the B1-197 antibody listed in Table 2. In one aspect, the antibody has an EC50 of 100 nM or lower and/or EC50 that is at least half of the EC50 of an anti-MDR1 antibody such as 15D3, MRK16, MM4, and/or UIC2 and comprises the HCDRs 1-3 and/or LCDRs 1-3 of the B1-198 antibody listed in Table 2. In one aspect, the antibody has an EC50 of 100 nM or lower and/or EC50 that is at least half of the EC50 of an anti-MDR1 antibody such as 15D3, MRK16, MM4, and/or UIC2 and comprises the HCDRs 1-3 and/or LCDRs 1-3 of the B1-201 antibody listed in Table 2. In one aspect, the antibody has an EC50 of 100 nM or lower and/or EC50 that is at least half of the EC50 of an anti-MDR1 antibody such as 15D3, MRK16, MM4, and/or UIC2 and comprises the HCDRs 1-3 and/or LCDRs 1-3 of the B1-207 antibody listed in Table 2. In one aspect, the antibody has an EC50 of 100 nM or lower and/or EC50 that is at least half of the EC50 of an anti-MDR1 antibody such as 15D3, MRK16, MM4, and/or UIC2 and comprises the HCDRs 1-3 and/or LCDRs 1-3 of the B1-223 antibody listed in Table 2. In certain aspects, the antibody of the present disclosure has an EC50 of 4-10 nM as measured using FACS of 293T cell line expressing human MDR1. In certain aspects, the antibody of the present disclosure having an EC50 of 4-10 nM as measured using FACS of 293T cell line expressing human MDR1 comprises the HCDRs 1-3 and LCDRs 1-3 of the B1-28 antibody, B1-184 antibody, B1-197 antibody, B1-201 antibody, B1-207 antibody, B1-223 antibody, B1-85 antibody, or B1-30 antibody listed in Table 2. See for example, FIG. 3D.

In some embodiments, the subject antibodies may, when bound to a cell expressing MDR1, prevent the functioning of the cellular MDR1 protein. Accordingly, antibodies of the present disclosure may inhibit efflux by the MDR1 protein, including e.g., where efflux is reduced by 5% or more, including e.g., 10% or more, 15% or more, 20% or more, 25% or more, 30% or more, 40% or more, 50% or more, 60% or more, 70% or more, 80% or more, or 90% or more, as compared to efflux by MDR1 in the absence of the subject antibody. In some embodiments, the subject antibodies may, when bound to a cell expressing MDR1 may otherwise impede the action of MDR1 by other mechanisms, e.g., rendering MDR1 leaky which in turn may enhance uptake of a chemotherapeutic agent and/or decrease viability of the cell.

In certain embodiments, an antibody of the present disclosure comprises a VH chain comprising HCDRs 1-3 of the B1-28 antibody and a VL chain comprising LCDRs 1-3 of the B1-28 antibody.

In certain embodiments, an antibody of the present disclosure comprises a VH chain comprising HCDRs 1-3 of the B1-261 antibody and a VL chain comprising LCDRs 1-3 of the B1-261 antibody.

In certain embodiments, an antibody of the present disclosure binds to both human ABCB1 and to cynomolgus ABCB1. Such an antibody may comprise a VH chain comprising HCDRs 1-3 of the B1-28 antibody and a VL chain comprising LCDRs 1-3 of the B1-28 antibody or a VH chain comprising HCDRs 1-3 of the B1-261 antibody and a VL chain comprising LCDRs 1-3 of the B1-261 antibody. In certain embodiments, the antibody may comprise the VH chain of the B1-28 antibody and the VL chain of the B1-28 antibody or the VH chain of the B1-261 antibody and the VL chain of the B1-261 antibody.

In certain embodiments, an antibody of the present disclosure comprises a VH chain comprising HCDRs 1-3 of the B1-129 antibody and a VL chain comprising LCDRs 1-3 of the B1-129 antibody.

In certain embodiments, an antibody of the present disclosure binds to the loop1 in the ECD of ABCB1. In certain embodiments, the antibody may comprise a VH chain comprising HCDRs 1-3 of the B1-129 antibody and a VL chain comprising LCDRs 1-3 of the B1-129 antibody. In certain embodiments, the antibody may comprise the VH chain of the B1-129 antibody and the VL chain of the B1-129 antibody.

In certain embodiments, an antibody of the present disclosure comprises a VH chain comprising HCDRs 1-3 of the B1-225 antibody and a VL chain comprising LCDRs 1-3 of the B1-225 antibody.

In certain embodiments, an antibody of the present disclosure comprises a VH chain comprising HCDRs 1-3 of the B1-223 antibody and a VL chain comprising LCDRs 1-3 of the B1-223 antibody.

In certain aspects, an antibody of the present disclosure that binds specifically to human MDR1 comprises the HCDR1, HCDR2, and HCDR3 sequences and the LCDR1, LCDR2, and LCDR3 sequences of an antibody listed in Table 2. In addition to binding to human MDR1, the antibodies provided herein may bind to MDR1 from other mammalian species, such as, mouse, monkey, chimpanzee, etc.

TABLE 2

From left to right, 1st column: Anti-MDR1 antibody name, 2nd column: VH region,
3rd column: HCDR1, 4th column: HCDR2, 5th column: HCDR3, 6th column: VL region, 7th column:
LCDR1, 8th column: LCDR2, 9th column: LCDR3.

| Antibody | Heavy Chain Variable Region | CDRH1 | CDRH2 | CDRH3 | Light Chain Variable Region |
|---|---|---|---|---|---|
| B1.27 | EVKLVESGGGLVKPGGSLKLSCAASGF TFSSYTMSWVRQTPEKRLEWVATVS SGGGGNTYYPDSVKGRFTISRDNAKNN LYLQMSSPRSEDTALYYCARYGNYG WFTYWGQGTLVTVSS (SEQ ID NO: 6) | SYTMS (SEQ ID NO: 7) | TVSSGGG NTYYPDSV KG (SEQ ID NO: 8) | YGNYGW FTY (SEQ ID NO: 9) | DVVMTQTPLSLPVSLGDQASISCR SSQNIVHSTGNTYLDWYLQKPGQ SPKLLIYKVSNRFSGVPDRFSGSGS GTDFTLKISRVEAEDLGVYFCFQG SHIPRTFGGGTKLEIK (SEQ ID NO: 10) |
| B1.28 | EVKLVESGGGLVKPGGSLKLSCAASGF TFGLYTMSWVRQTPERRLEWVATISS GGSNTYYPDSVKGRFTISRDNAKNNL FLQMNSLRSEDTALYYCARYYRYDA WFAYWGQGTLVTVSS (SEQ ID NO: 14) | LYTMS (SEQ ID NO: 15) | TISSGGSN TYYPDSVK G (SEQ ID NO: 16) | YYRYDA WFAY (SEQ ID NO: 17) | DVLLTQTPLSLPVSLGDQASISCRS SQNIVHSTGNTYLDWYLQKPGQS PKLLIYKVSNRFSGVPDRFSGSGS GTDFTLKISRVEAEDLGVYFCFQG SHIPRTFGGGTKLEIK (SEQ ID NO: 18) |
| B1.28 human1 | EVQLVESGGGLVKPGGSLRLSCAASG FTFGLYTMSWVRQAPGKGLEWVATI SSGGGSNTYYPDSVKGRFTISRDNAKN SLYLQMNSLRAEDTAVYYCARYYRYD AWFAYWGQGTLVTVSS (SEQ ID NO: 19) | LYTMS (SEQ ID NO: 15) | TISSGGSN TYYPDSVK G (SEQ ID NO: 16) | YYRYDA WFAY (SEQ ID NO: 17) | DVVLTQSPLSLPVTLGQPASISCRS SQNIVHSTGNTYLDWYQRPGQ SPRLLIYKVSNRFSGVPDRFSGSGS GTDFTLKISRVEAEDVGVYFCFQG SHIPRTFGQGTKLEIK (SEQ ID NO: 20) |
| B1.28.hu11 | EVQLVESGGGLVKPGGSLRLSCAASG FTFGLYTMSWVRQAPGKGLEWVATI SSGGGSNTYYPDSVKGRFTISRDNAKN SLYLQMNSLRAEDTAVYYCARYYRYD AWFAYWGQGTLVTVSS (SEQ ID NO: 19 | LYTMS (SEQ ID NO: 15) | TISSGGSN TYYPDSVK G (SEQ ID NO: 16) | YYRYDA WFAY (SEQ ID NO: 17) | DVVLTQSPLSLPVTLGQPASISCRS SQNIVHSTGNTYLDWYQRPGQ SPRLLIYKVSNRFSGVPDRFSGSGS GTDFTLKISRVEAEDVGVYFCFQG SHIPRTFGQGTKLEIK (SEQ ID NO: 20) |
| B1.28.hu12 | EVQLVESGGGLVKPGGSLRLSCAASG FTFGLYTMSWVRQAPGKGLEWVATI SSGGGSNTYYPDSVKGRFTISRDNAKN SLYLQMNSLRAEDTAVYYCARYYRYD AWFAYWGQGTLVTVSS (SEQ ID NO: 19) | LYTMS (SEQ ID NO: 15) | TISSGGSN TYYPDSVK G (SEQ ID NO: 16) | YYRYDA WFAY (SEQ ID NO: 17) | DVVLTQSPLSLPVTPGEPASISCRS SQNIVHSTGNTYLDWYLQKPGQS PQLLIYKVSNRFSGVPDRFSGSGS GTDFTLKISRVEAEDVGVYYCFQG SHIPRTFGQGTKLEIK (SEQ ID NO: 21) |
| B1.28.hu13 | EVQLVESGGGLVKPGGSLRLSCAASG FTFGLYTMSWVRQAPGKGLEWVATI SSGGGSNTYYPDSVKGRFTISRDNAKN SLYLQMNSLRAEDTAVYYCARYYRYD AWFAYWGQGTLVTVSS (SEQ ID NO: 19 | LYTMS (SEQ ID NO: 15) | TISSGGSN TYYPDSVK G (SEQ ID NO: 16) | YYRYDA WFAY (SEQ ID NO: 17) | EVVLTQSPATLSLSPGERATLSCRS SQNIVHSTGNTYLDWYQQKPGQ SPRLLIYKVSNRFSGVPARFSGSGS GTDFTLTISSLEPEDFAVYYCFQGS HIPRTFGGGTKLEIK (SEQ ID NO: 22) |
| B1.30 | EVMLVESGGGLVKPGGSLKLSCAASG FTFSSYTMSWVRQTPEKRLEWVATIS SGGGGNTYYPDSVKGRFTISRDNAKNN LYLQMSSLRSEDTALYYCARYYRYDA WFAYWGQGTLVTVSA (SEQ ID NO: 23) | SYTMS (SEQ ID NO: 7) | TISSGGGN TYYPDSVK G (SEQ ID NO: 16) | YYRYDA WFAY (SEQ ID NO: 17) | DVLMTQTPLSLPVSLGDQASISCR SSQSIVHSTGNTYLEWYLQKPGQS PKLLIYKVSNRFSGVPDRFSGSGS GTDFTLKISRVETEDLGVYYCFQG SHVPRTFGGGTKLEIK (SEQ ID NO: 24) |
| B1.39 | EVMLVESGGGLVKPGGSLKLSCAASG FTFSSYTMSWVRQTPEKRLEWVATV SSGGGGNTYYPDSVKGRFTISRDNAKN NLYLQMSSLRSEDTALYYCARYGNYG WFTYWGQGTLVTVSA (SEQ ID NO: 26) | SYTMS (SEQ ID NO: 7) | TVSSGGG NTYYPDSV KG (SEQ ID NO: 8) | YGNYGW FTY (SEQ ID NO: 9) | DVLMTQTPLSLPVSLGDQASISCR SSQSILHSNGNTYLEWYLQKPGQ SPKLLIYKVSNRFSGVPDRFSASGS GTDFTLKISRVEAEDLGIYYCFQGS HVPRTFGGGTKLEIK (SEQ ID NO: 27) |
| B1.85 | EVQLVESGGALVKPGGSLKLSCAASG FTFSNYGVSWVRQTPEKRLEWVATIS SSGSYTYYPDIVRGRFTISRDNAKNTL YLQMSSLRSEDTAFYYCARGYGNFA WFAYWGQGTLVTVSA (SEQ ID NO: 29) | NYGVS (SEQ ID NO: 30) | TISSSGSYT YYPDIVRG (SEQ ID NO: 31) | GYGNFA WFAY (SEQ ID NO: 32) | DIQMTQSPLSLPVSLGDQASISCR SSQSIVHSTGNTYLEWYLQKPGQS PKLLIYKVSNRFSGVPDRFSGSGS GTDFTLKINRVEAEDLGVYYCFQG SHVPYTFGGGTKLEIK (SEQ ID NO: 33) |
| B1.89 | KVQLVESGGALVKPGGSLKLSCAASG FTFSNYAMSWVRQTPEKRLEWVATI SSSGSYTYYPDSVKGRFTISRDNAKNT LYLQMSSLRSEDTALYYCARYGYDEA WFASWGQGTLVTVSA (SEQ ID NO: 34) | NYAMS (SEQ ID NO: 35) | TISSSGSYT YFPDSVKG (SEQ ID NO: 36) | YGYDEA WFAS (SEQ ID NO: 37) | DVLMTQTPLSLPVSLGDQASISCR SSQTIVHSNGNTYLEWYLQKPGQ SPKLLIYKVSKRFSGVPDRFSGSGS GTDFTLKISRVEAEDLGVYYCFQG SHFPRTFGGGTKLEIK (SEQ ID NO: 38) |
| B1.92 | EVILVESGEGLVKPGGSLKVSCAASGF TFSNYYMSWVRQTPEKRLELVAAINS NGGNTYYPDTVKGRFTISRDNARNIL | NYYMS (SEQ ID | AINSNGG NTYYPDTV KG (SEQ | HYYGYEG WYFDV (SEQ ID | QIVLSQSPAILSASPGEKVTMTCR ASSSVSYMHWYQQKPGSSPKPW IYATSNLASGVPSRFSGSGSGTSYS |

TABLE 2-continued

From left to right, 1st column: Anti-MDR1 antibody name, 2nd column: VH region, 3rd column: HCDR1, 4th column: HCDR2, 5th column: HCDR3, 6th column: VL region, 7th column: LCDR1, 8th column: LCDR2, 9th column: LCDR3.

| Antibody name | VH region | HCDR1 | HCDR2 | HCDR3 | VL region |
|---|---|---|---|---|---|
| | YLQMSSLKSEDTALYYCARHYYGYEG WYFDVWGAGTTVTVSS (SEQ ID NO: 43) | NO: 44) | ID NO: 45) | NO: 46) | LTISRVEAEDAATYYCQQWSSNP PTFGGGTKLEIK (SEQ ID NO: 47) |
| B1.99 | EVQLVESGGALVKPGGSLKLSCAASG FTFSNYAMSWVRQTPERRLEWVATI SSGGGSYTYYPDSVKGRFTISRDNAKNT LYLQMSSLISEDTALYYCTRGYGNFA WFAYWGHGTLVTVSA (SEQ ID NO: 51) | NYAMS (SEQ ID NO: 35) | TISSGGSYT YYPDSVKG (SEQ ID NO: 52) | GYGNFA WFAY (SEQ ID NO: 32) | DVVMTQTPLSLPVSLGDQVSISCR SSQSIVHSYGSTYLEWYLQKPGQS PKLLIYKVSNRFSGVPDRFSGSGS GTDFTLKISRVEAEDLGVYFCFQG SHIPYTFGGGTKLELK (SEQ ID NO: 53) |
| B1.129 | EVQLQQSGPELVKPGASVKMSCKAS GYTFSTYVIHWVKQKPGQGLEWIGYI YPYNDYTKYNEKFKDKATLTSDKSSST AYMEIRSLTSEDSAVYYCSRAYYGNLV GYGVDYWGQGTSVTVSS (SEQ ID NO: 56) | TYVIH (SEQ ID NO: 57) | YIYPYNDY TKYNEKFK D (SEQ ID NO: 58) | AYYGNLV GYGVDY (SEQ ID NO: 59) | QIVLTQSPAILPASPGEKVTMTCR ASSSVSFIYWYQQRPGSSPKPWIF ATSNLASGVPARFSGSGSGTSYSL TISRVEAEDAATYYCHQWGSNLP TFGGGTKLEIK (SEQ ID NO: 60) |
| B1.129.huH1-huL1(KV3) | EVQLVQSGAEVKKPGASVKVSCKASG YTFSTYVIHWVRQAPGQGLEWIGYIY PYNDYTKYNEKFKDRATLTSDKSTSTA YMELRSLRSDDTAVYYCSRAYYGNLV GYGVDYWGQGTTVTVSS (SEQ ID NO: 63) | TYVIH (SEQ ID NO: 57) | YIYPYNDY TKYNEKFK D (SEQ ID NO: 58) | AYYGNLV GYGVDY (SEQ ID NO: 59) | EIVLTQSPATLSLSPGERATLSCRAS SSVSFIYWYQQKPGQSPRPWIFA TSNLASGVPARFSGSGSGTDYTLTI SSLEPEDFAVYYCHQWGSNLPTF GGGTKLEIK~~ (SEQ ID NO: 64) |
| B1.129.huH1-huL1(KV1) | EVQLVQSGAEVKKPGASVKVSCKASG YTFSTYVIHWVRQAPGQGLEWIGYIY PYNDYTKYNEKFKDRATLTSDKSTSTA YMELRSLRSDDTAVYYCSRAYYGNLV GYGVDYWGQGTTVTVSS (SEQ ID NO: 63) | TYVIH (SEQ ID NO: 57) | YIYPYNDY TKYNEKFK D (SEQ ID NO: 58) | AYYGNLV GYGVDY (SEQ ID NO: 59) | DIQLTQSPSSLSASVGDRVTITCRA SSSVSFIYWYQQKPGKSPKPWIFA TSNLASGVPSRFSGSGSGTDYTLTI SSLQPEDFATYYCHQWGSNLPTF GGGTKLEIK (SEQ ID NO: 65) |
| B1.177 | EVMLVESGGALVKPGGSLKLSCAASG FTFSNYAMSWVRQTPEKRLEWVATI SSGGGSYTYYPDSVKGRFTISRDNARNT LYLQMSSLRSEDTAMYYCARGYGNF AWFAYWGQGTLVTVSA (SEQ ID NO: 66) | NYAMS (SEQ ID NO: 35) | TISSGGSYT YYPDSVKG (SEQ ID NO: 52) | GYGNFA WFAY (SEQ ID NO: 32) | DVVMTQTPLSLPVSLGDQASISCR SSQSIVHSNGNTYLEWYLQKPGQ SPKLMIYKVSNRFSGVPDRFSGSG SGTDFTLKISRVEAEDVGVYYCFQ GSHVPYTFGGGTKLEIK (SEQ ID NO: 67) |
| B1.178 | EAQLVESGGALVKPGGSLKLSCSASGF TFSNYAMSWVRQTPEKRLEWVATIS SGGTNTYYPGSVKGRFTIARDNAKNT LYLLMSSLRSEDTALYFCARYSNLAWF ASWGQGTLVTVSA (SEQ ID NO: 70) | NYAMS (SEQ ID NO: 35) | TISSGGTN TYYPGSVK G (SEQ ID NO: 71) | YSNLAW FAS (SEQ ID NO: 72) | DVVMTQTPLSLPVSLGDQASISCR SSQSIVHSNGNTYLEWYLQKPGQ SPKFLISKVSNRFSGVPDRFSGSGS GTDFTLKISRVEAEDLGIYYCFQGS HVPYTFGGGTKLEIK (SEQ ID NO: 73) |
| B1.179 | EAQLVESGGALVKPGGSLKLSCSASGF TFSNYAMSWVRQTPEKRLEWVATIS SGGTNTYYPGSVKGRFTIARDNAKNT LYLLMSSLRSEDTALYFCARYSNLAWF ASWGQGTLVTVSA (SEQ ID NO: 70) | NYAMS (SEQ ID NO: 35) | TISSGGTN TYYPGSVK G (SEQ ID NO: 71) | YSNLAW FAS (SEQ ID NO: 72) | DVVMTQTPLSLPVSLGDQASISCR SSQSIVHSNGNTYLEWYLQKPGQ SPKFLISKVSNRFSGVPDRFSGSGS GTDFTLKISRVEAEDLGIYYCFQGS HVPYTFGGGTKLEIK (SEQ ID NO: 73) |
| B1.184 | GVQLVESGGALVKPGGSLKLSCAASG FTFSNYAMSWVRQTPEKRLEWVATI SSGGGSYTYYPDSVKGRFTISRDNAKTT LYLQMSGLRSEDTALYYCAKYSNYGR FASWGQGTLVTVST (SEQ ID NO: 74) | NYAMS (SEQ ID NO: 35) | TISSGGSYT YYPDSVKG (SEQ ID NO: 52) | YSNYGRF AS (SEQ ID NO: 75) | DVLMTQTPLSLPVSLGDQASISCR SSQSIVHSSGNTYLEWYLQKPGQS PRLLIYKVSNRFFGVPDRISGSGSG TDFTLRISRVEAEDLGVYYCFQGS HVPYTFGGGTKLEIK (SEQ ID NO: 76) |
| B1.188 | EVMLVESGGALVKPGGSLKLSCAASG FTFSNYAMSWVRQTPEKRLEWVATI SSGGGSYTYYPDSVKGRFTISRDNARNT LYLQMSSLRSEDTAMYYCARGYGNF AWFAYWGQGTLVTVSA (SEQ ID NO: 66) | NYAMS (SEQ ID NO: 35) | TISSGGSYT YYPDSVKG (SEQ ID NO: 52) | GYGNFA WFAY (SEQ ID NO: 32) | DIQMTQSPLSLPVSLGDQASISCR SSQSIVHSTGNTYLEWYLQKPGQS PKLLIYKVSNRFSGVPDRFSGSGS GTDFTLKISRVEAEDLGVYYCFQG SHVPFTFGSGTKLEIK (SEQ ID NO: 79) |
| B1.193b | EVQLVESGGALVKPGGSLKLSCAASG FTFSNYAMSWVRQTPEKRLEWVATL SSGGTNTYYSDSVKGRFTISRDNVKN TLYLQMSSLRSEDTALYYCARYSNLA WFAYWGQGTLVTVSA (SEQ ID NO: 81) | NYAMS (SEQ ID NO: 35) | TLSSGGTN TYYSDSVK G (SEQ ID NO: 82) | YSNLAW FAY (SEQ ID NO: 83) | DIVMTQSPLSLPVSLGDQASISCRS SQSIVHSTGNTYLEWYLQKPGQS PKFLISKVSNRFSGVPERFSGSGSG TDFTLKISRVEAEDLGVYYCFQGS HVPYTFGGGTKLEIK (SEQ ID NO: 84) |
| B1.197a | EVMLVESGGGLVKPGGSLKLSCAASG FTFSNYAMSWVRQTPEKRLEWVATI | NYAMS (SEQ | TISSGGGY TYYPDSVK | GYGNFA WFAY | EVKLVESGGGLVKPGGSLKLSCAA SGFTFSNYAMSWVRQTPEKRLE |

TABLE 2-continued

From left to right, 1st column: Anti-MDR1 antibody name, 2nd column: VH region, 3rd column: HCDR1, 4th column: HCDR2, 5th column: HCDR3, 6th column: VL region, 7th column: LCDR1, 8th column: LCDR2, 9th column: LCDR3.

| Antibody name | VH region | HCDR1 | HCDR2 | HCDR3 | VL region |
|---|---|---|---|---|---|
| | SSGGGGYTYYPDSVKGRFTISRDNARN TLYLQMSSLRSEDTAMYYCARGYGNF AWFAYWGQGTLVTVSA (SEQ ID NO: 85) | ID NO: 35) | G (SEQ ID NO: 86) | (SEQ ID NO: 32) | WVATISSGGGYTYYPDSVKGRFTI SRDNARNTLYLQMSSLRSEDTAM YYCARGYGNFAWFAYWGQGTLV TVSS (SEQ ID NO: 87) |
| B1.198 | EVQLVESGGALVKPGGSLKLSCAASG FTFSNYAMSWVRQTPEKRLEWVATI SSGGSYTYYPDSVKGRFTISRDNAKNT LYLQMSSLRSEDTALYYCAKYSNYGRF AYWGQGTLVTVSA (SEQ ID NO: 88) | NYAMS (SEQ ID NO: 35) | TISSGGSYT YYPDSVKG (SEQ ID NO: 52) | YSNYGRF AY (SEQ ID NO: 89) | DVVMTQTPLSLPVSLGDQASISCR SSQSIVDSNGNTYLEWYLQKPGQ SPKLLIYKVSNRFFGVPDRFSGSGS GTDFTLKISRVEAEDLGVYYCFQG SHVPYTFGGGTKLEIK (SEQ ID NO: 90) |
| B1.201 | EVQLVESGGALMKPGGSLKFSCAASG FTFTNYAMSWVRQTPEKRLEWVATI SSGGSNTYYSDSVKGRFTISRDNAKTT LYLQMSGLRSEDTALYYCAKFSNFGR FASWGQGTLVTVSA (SEQ ID NO: 92) | NYAMS (SEC ID NO: 35) | TISSGGSN TYYSDSVK G (SEQ ID NO: 93) | FSNFGRF AS (SEQ ID NO: 94) | DVLMTQTPLSLPVSLGDQASISCR FSQSIVHSSGNTYLEWYLQKPGQS PRLLIYKVSNRFFGVPDRISGSGSG TDFTLRISRVEAEDLGVYYCFQGS HVPYTFGGGTKLEIK (SEQ ID NO: 95) |
| B1.207 | GVQLVESGGALVKPGGSLKLSCAASG FTFSNYAMSWVRQTPEKRLEWVATI SSGGSYTYYPDSVKGRFTISRDNAKTT LYLQMSGLRSEDTALYYCAKYSNYGR FASWGQGTLVTVST (SEQ ID NO: 74) | NYAMS (SEQ ID NO: 35) | TISSGGSYT YYPDSVKG (SEQ ID NO: 52) | YSNYGRF AS (SEQ ID NO: 75) | DVLMTQTPLSLPVSLGDQASISCR SSQSIVHSSGNTYLEWYLQKPGQS PRLLIYKVSNRFFGVPDRISGSGSG TDFTLRISRVEAEDLGVYYCFQGS HVPYTFGGGTKLEIK (SEQ ID NO: 76) |
| B1.217 | EVQLVESGGALVKPGGSLKLSCAASG FTFSNYAMSWVRQTPEKRLEWVATI SSGGSYTYYPDSVKGRFTISRDNAKNT LYLQMSSLRSEDTALYYCTKYSNYGRF AYWGQGTLVTVST (SEQ ID NO: 97) | NYAMS (SEQ ID NO: 35) | TISSGGSYT YYPDSVKG (SEQ ID NO: 52) | YSNYGRF AY (SEQ ID NO: 89) | DVLMTQTPLSLPVSLGDQASISCR SSQSIVHSTGNTYLEWYLQKPGQS PKLLIYKVSNRFSGVPDRFSGSGS GTDFTLKISRVEAEDLGVYYCFQG SHIPYTFGGGTKLEIK (SEQ ID NO: 98) |
| B1.219 | EVQLVESGGALVKPGGSLKLSCAASG FTFSNYAMSWVRQTPEKRLEWVATI SSVGSYTYYPDSVKGRFTISRDNAKTT LYLQMSGLRSEDTALYYCAKYSNYGR FASWGQGTLVTVST (SEQ ID NO: 99) | NYAMS (SEQ ID NO: 35) | TISSVGSYT YYPDSVKG (SEQ ID NO: 100) | YSNYGRF AS (SEQ ID NO: 75) | DVLMTQTPLSLPASLGDQASISCR SSQSIVHSSGNTYLEWYLQKPGQS PRLLIYKVSNRFFGVPDRISGSGSG TDFTLRISRVEAEDLGVYYCFQGS HVPYTFGGGTKLEIE (SEQ ID NO: 101) |
| B1.223 | EVKLVESGGALVKPGGSLKLSCAASGF TFSNYAMSWVRQTPEKRLEWVATIS SGGSYTYYPDSVKGRFTISRDNAKTTL YLQMSGLRSEDTALYYCAKFSNYGRF ASWGQGTLVTVSS (SEQ ID NO: 102) | NYAMS (SEQ ID NO: 35) | TISSGGSYT YYPDSVKG (SEQ ID NO: 52) | FSNYGRF AS (SEQ ID NO: 103) | DIQMIQSPLSLPVSLGDQASISCRS SQSIVHSSGNTYLEWYLQKPGQS PRLLIYKVSNRFFGVPDRISGSGSG TDFTLRISRVEAEDLGVYYCFQGS HVPYTFGGGTKLELK (SEQ ID NO: 104) |
| B1.225 | EVQLVESGGALVKPGGSLKLSCAASG FTFSNYGMSWVRQTPEKRLEWVATI SSGGSYTYYPDTVKGRFTISRDNAKNT LHLQMSSLRSEDTALYYCARRGTNDA WFGYWGQGTLVTVSA (SEQ ID NO: 105) | NYGM S (SEQ ID NO: 106) | TISSGGSYT YYPDTVKG (SEQ ID NO: 107) | RGTNDA WFGY (SEQ ID NO: 108) | DVVMTQTPLSLPVSLGDQASISCR FSQSIVHSNGNTYLEWYLQKPGQ SPKLLIYKVSNRFFGVPDRFSGSGS GTDFTLKISRVEAEDLGVYFCFQG SHVPQYTFGGGTKLEIK (SEQ ID NO: 109) |
| B1.226 | EVQLVESGGALVKPGGSLKLSCAASG FTFSNYAMSWVRQTPETRLEWVATI SSGGSYTYYPDSVKGRFTISRDNAKNT LYLQMSSLRSEDTALYYCARYSNLAW FAYWGQGTLVTVSA (SEQ ID NO: 112) | NYAMS (SEQ ID NO: 35) | TISSGGSYT YYPDSVKG (SEQ ID NO: 52) | YSNLAW FAY (SEQ ID NO: 83) | DVVMTQTPLSLPVSLGDQASISCR SSQSIVHSNGNTYLDWYLQKPGQ SPKFMIYKVSNRFSGVPDRFSGSG SGTDFTLKISRVEAEDLGVYYCFQ GSHVPYTFGGGTKLEIK (SEQ ID NO: 113) |
| B1.228A | EVQLVESGGALVKPGGSLKLSCAASG FTFSNYAMSWVRQTPEKRLEWVATI SSVGSYTYYPDSVKGRFTISRDNAKTT LYLQMSGLRSEDTALYYCAKYSNYGR FASWGQGTLVTVST (SEQ ID NO: 99) | NYAMS (SEQ ID NO: 35) | TISSVGSYT YYPDSVKG (SEQ ID NO: 100) | YSNYGRF AS (SEQ ID NO: 75) | DVLMTQTPLSLPASLGDQASISCR FSQSIVHSSGNTYLEWYLQKPGQS PRLLIYKVSNRFFGVPDRISGSGSG TDFTLRISRVEAEDLGVYYCFQGS HVPYTFGGGTKLEIE (SEQ ID NO: 114) |
| B1.236 | EAQLVESGGALVKPGGSLKLSCSASGF TFSNYAMSWVRQTPEKRLEWVATIS SGGTNTYYPGSVKGRFTIARDNAKNT LYLLMSSLRSEDTALYFCAKYSNLAWF ASWGQGTLVTVSA (SEQ ID NO: 115) | NYAMS (SEQ ID NO: 35) | TISSGGTN TYYPGSVK G (SEQ ID NO: 71) | YSNLAW FAS (SEQ ID NO: 72) | QIVLTQSPLSLPVSLGDQASISCRS SQSLVHSIGNTYLEWYLQKPGQSP KFLISKVSNRFGVPDRFSGSGSGT DFTLKISRVEAEDLGIYYCFQGSHV PYTFGGGTKLEIK (SEQ ID NO: 116) |

TABLE 2-continued

From left to right, 1st column: Anti-MDR1 antibody name, 2nd column: VH region,
3rd column: HCDR1, 4th column: HCDR2, 5th column: HCDR3, 6th column: VL region, 7th column:
LCDR1, 8th column: LCDR2, 9th column: LCDR3.

| | | | | | |
|---|---|---|---|---|---|
| B1.261 | QVQLKESGPGLVAPSQSLSITCTVSGF SLTSYGVHWVRQPPGKGLEWLVVIW SDGSTTYNSALKSRLSISKDNSKSQVFL KMNSLQIDDTAMYYCARHGRWLLQ RGGAMDYWGQGTSVTVSS (SEQ ID NO: 118) | SYGVH (SEQ ID NO: 119) | VIWSDGST TYNSALKS (SEQ ID NO: 120) | HGRWLL QRGGA MDY (SEQ ID NO: 121) | DVVMTQAPKFMSTSVGDRVSVT CRASQNVGSYIAWYQQKLGQSP KALIYSASYRCSGVPDRFTGSGAG TDFTLTIRNVQSEDLAEYFCQQYN SYPLTFGGGTKLEIK (SEQ ID NO: 122) |
| B1.261.huH1 (VH4)-huL1 | EVQLQESGPGLVKPSETLSLTCTVSGF SLTSYGVHWVRQPPGKGLEWLVVIW SDGSTTYNSALKSRLTISKDNSKNOVS LKLSSVTAADTAVYYCARHGRWLLQR GGAMDYWGQGTMVTVSS (SEQ ID NO: 126) | SYGVH (SEC ID NO: 119) | VIWSDGST TYNSALKS (SEQ ID NO: 120) | HGRWLL QRGGA MDY (SEQ ID NO: 121) | DVQMTQSPSSLSASVGDRVTITCR ASQNVGSYIAWYQQKPGKSPKAL IYSASYRSSGVPSRFSGSGAGTDFT LTISSLQPEDFATYFCQQYNSYPLT FGGGTKLEIK (SEQ ID NO: 127) |
| B1.261.huH2 (VH3)-huL1 | EVQLVESGGGLIQPGGSLRLSCAVSGF SLTSYGVHWVRQPPGKGLEWLVVIW SDGSTTYNSALKSRLTISKDNSKNTVY LQMNSLRAEDTAVYYCARHGRWLLQ RGGAMDYWGQGTMVTVSS (SEQ ID NO: 129) | SYGVH (SEQ ID NO: 119) | VIWSDGST TYNSALKS (SEQ ID NO: 120) | HGRWLL QRGGA MDY (SEQ ID NO: 121) | DVQMTQSPSSLSASVGDRVTITCR ASQNVGSYIAWYQQKPGKSPKAL IYSASYRSSGVPSRFSGSGAGTDFT LTISSLQPEDFATYFCQQYNSYPLT FGGGTKLEIK (SEQ ID NO: 127) |
| B1.262-sub1 | QVQMKESGPGLVAPSQSLSITCTVSG FSLTSYGVHWVRQPPGKGLEWLVVI WSDGSTTYNSALKSRLSISKDNSKSQV FLKMNSLQIDDTAMYYCARHGRWLL QRGGAMDYWGQGTSVTVSS (SEQ ID NO: 130) | SYGVH (SEQ ID NO: 119) | VIWSDGST TYNSALKS (SEQ ID NO: 120) | HGRWLL QRGGA MDY (SEQ ID NO: 121) | DVVMTQTPSFMSTSVGDRVSVTC RASQNVGSYVAWYQQKLGQSPK ALIYSASYRCSGVPDRFTGSGAGT DFTLTIRNVQSEDLAEYFCQQYNS YPLTFGGGTKLEIK (SEQ ID NO: 131) |
| B1.263 | EVKLVESGGGLVKPGGSLKLSCAASGF TFSNYGMSWVRQTPEKRLEWVAAIS SNGAYTYFPDTVKGRFTISRDNAKNT LYLQMNSLRSEDTALYYCTRRGWDT WFAYWGQGTLVTVSS (SEQ ID NO: 133) | NYGM S (SEQ ID NO: 106) | AISSNGAY TYFPDTVK G (SEQ ID NO: 134) | RGWDT WFAY (SEQ ID NO: 135) | DVVMTQTPLSLPVSLGDQASISCR SSQNIVHSTGNTYLEWYLQKPGQ SPKLLIYKVSNRFSGVPDRFSGSGS GTDFTLKISRVEAEDLGVYYCFQG SHVPWTFGGGTKLEIK (SEQ ID NO: 136) |
| B1.264 | EVKLVESGGALVKPGGSLKLSCAASGF TFSNYAMSWVRQTPEKRLEWVATIS SGGSNTYYPDSVMGRFTISRDNAKNT LYLQMSSLRSEDTALYYCARYSNYGW FAYWGQGTLVTVSS (SEQ ID NO: 139) | NYAMS (SEQ ID NO: 35) | TISSGGSN TYYPDSV MG (SEQ ID NO: 140) | YSNYGW FAY (SEQ ID NO: 141) | DVVMTQTPLSLPVSLGDQASISCR SSQSIVHSNGNTYLEWYLQKPGQ SPKLLIYKVSNRFSGVPDRFSGSGS GTDFTLKISRVEAEDLGVYYCFQG SLVPRTFGGGTKLEIK (SEQ ID NO: 142) |
| B1.269 | EVQLVESGGASVKPGGSLKLSCAASG FTFSNYAMSWVRQTPEKRLEWVATI SSGGSYTYYLDSVKGRFTISRDNAKNT LYLQMSSLRSEDTALYYCARYYVYDA WFAYWGQGTLVTVSA (SEQ ID NO: 144) | NYAMS (SEQ ID NO: 35) | TISSGGSYT YYLDSVKG (SEQ ID NO: 145) | YYVYDA WFAY (SEQ ID NO: 146) | DVVMTQTPLSLPVSLGDQASISCR SSQSIVHSTGNTYLEWYLQKPGQS PKLLIYKVSNRFSGVPDRFSGSGS GTDFTLKISRVEAEDLGVFYCFQG SHVPRTFGGGTKLEIK (SEQ ID NO: 147) |
| B1-open.272 | EVMLVESGGALVKPGGSLKLSCVVSG FTFSNYAMSWVRRTPEKRLEWVATIS SDGTYTYYPFSVKGRFTISRDNARNIL YLQMSSLRSEDTAMYYCGRQGHWG RTWFAYWGQGTTLTVSS (SEQ ID NO: 148) | NYAMS (SEQ ID NO: 35) | TISSDGTYT YYPFSVKG (SEQ ID NO: 149) | QGHWG RTWFAY (SEQ ID NO: 150) | ENVLTQSPAIMSASPGEKVTMTC RASSSVSSSYLHWFQQKSGASPKL WIYSTSSLASGVPSRFSGSGWGTS YSLTISSVEGEDGATYYCQQYSGY PLTFGAGTKLELK (SEQ ID NO: 151) |
| B1-open.273 (A) | QVQLQQSGPELVKTGASVKISCKASG YSFSNYYIHWKQSHGKSLEWIGFISC YNGATFYNOKFKGKATFTVDTSSSTA YMKFNSLTFEDSAVYYCARLPIQFGNF YPMDYWGQGTSVTVSS (SEQ ID NO: 155) | NYYIH (SEQ ID NO: 156) | FISCYNGA TFYNOKFK G (SEQ ID NO: 157) | LPIQFGN FYPMDY (SEQ ID NO: 158) | QIVLTQSPAIMSASLGERVTMTCT ASSSVSSSYLHWYQQKPGSSPKL WIYSTSNLASGVPARFSGSGSGTS YSLTISSMEAEDAATYYCHQYHRS PPTFGAGTKLELK (SEQ ID NO: 159) |
| B1.275 | EVMLVESGGALVKPGGSLKVSCAASG FTFSNYAMSWVRQSPEMRLEWVATI SSGGTNTYYPDSVKGRFTISRDNARN TLYLQMSSLRSKDTAMYYCARYSNYG WFPYWGQGTTLTVSS (SEQ ID NO: 163) | NYAMS (SEQ ID NO: 35) | TISSGGTN TYYPDSV G (SEQ ID NO: 164) | YSNYGW FPY (SEQ ID NO: 165) | DVVMTQTPLSLPVSLGDQASISCR SSQTIVHSDGYTYLEWYLQKPGQS PKLLIYKVSNRFSGVPDRFSGSGS GTDFTLRISRVEAEDLGVYYCFQG SHVPYTFGGGTKLEIK (SEQ ID NO: 166) |
| B1.276 | EVKLVESGGALVKPGGSLKLSCAASGF TFRNYAMSWVRQTPEKRLEWVATIS SDGSYTYHPDSVKGRFTISRDNARNT LYLQMSSLRSEDTAMYSCTRQGNWG | NYAMS (SEQ ID NO: 35) | TISSDGSYT YHPDSVK G (SEQ ID NO: 169) | QGNWG RTWFTY (SEQ ID NO: 170) | QIVLTQSPAIMSASPGEKVTMTCR ASSSVSSSYLHWYQQKSGASPKL WIYSTSSLASGVPARFSGSGSGTS YSLTISSVEAEDAATYYCQQYSGYP |

TABLE 2-continued

From left to right, 1st column: Anti-MDR1 antibody name, 2nd column: VH region, 3rd column: HCDR1, 4th column: HCDR2, 5th column: HCDR3, 6th column: VL region, 7th column: LCDR1, 8th column: LCDR2, 9th column: LCDR3.

| Name | VH region | HCDR1 | HCDR2 | HCDR3 | VL region |
|---|---|---|---|---|---|
| | RTWFTYWGQGTLVTVSS (SEQ ID NO: 168) | | | | LTFGAGTKLELK (SEQ ID NO: 171) |
| B1-open.277B | EVILVESGGALVKPGGSLKVSCAASGF TFSNYGMSWVRQSPEKRLEWVATIS SGGTNTYYPDSVKGRFTISRDNARNT LYLQMSSLRSKDTAMYYCGRYSNYG WFAYWGQGTLVTVSA (SEQ ID NO: 172) | NYGM S (SEQ ID NO: 106) | TISSGGTN TYYPDSVK G (SEQ ID NO: 164) | YSNYGW FAY (SEQ ID NO: 141) | DILMTQTPLSLPVSLGDQASISCRS SQSIVHTNGNTYLEWYLQKPGQS PKLLIYKVSNRFSGVPDRFSGSGS GTDFTLRISRVEAEDLGVYYCFQG SHVPYTFGGGTKLEIK (SEQ ID NO: 173) |
| B1.278 | QVQLQQSGPELVKPGASVKISCKASG YSFTGYFMNWVMQSHGKSLEWIGRI NPYNGDTFYNQKFKGKATLTVDKSSG TAHMELRSLASEDSAVYYCARCYYYG SSSYGMDYWGQGTSVTVSS (SEQ ID NO: 175) | GYFM N (SEQ ID NO: 176) | RINPYNGD TFYNQKFK G (SEQ ID NO: 177) | CYYYGSS SYGMDY (SEQ ID NO: 178) | QIVLTQSPASLAVSLGQRATISCRA SESVHNYGVSFMNWFQQRPGQ PPKLLIHAASHQGSGVPARFTGSG SGTDFSLNIHPMEEDDIAMYFCQ QSKEVPLTFGAGTKLKLK (SEQ ID NO: 179) |
| 799A | VQLKESGPGLVKPSQSLSLTCSVTGFSI TSGYGWNWIRKFPGNKLEWMGFIN SAGSTNYNPPLKSQISITRDTSKNOFF LHLTSVTPEDTATYYCARWGHTLGVT RDFWYFDFWGPGTMVTVSSASTKG PSVFPLAPSSKSTSGGTAALGCLVKDY FPEPVTVSWNSGALTSGVHTFPAVLQ SSGLYSLSSVVTVPSSSLGTQTYICNVN HKPSNTKVDKRVEPKSCDKTHTCPPC PAPELLGGPSVFLFPPPKPKDTLMIS (SEQ ID NO: 183) | SGYG WN (SEQ ID NO: 184) | FINSAGST NYNPPLKS (SEQ ID NO: 185) | WGHTLG VTRDFW YFDF (SEQ ID NO: 186) | MTQSPSSLPASLGESVTIICRASQG ISNNLNWYRQKPDGTIKPLIYYTSI LQSGVPSSFSGSRSGTDYSLTISSLE PEDFAMYYCQQDASFPWTFGGG TKLELKRTVAAPSVFIFPPPSDEQLK SGTASVVCLLNNFYPREAKVQWK VDNALQSGNSQESVTEQDSKDST YSLSSTLTLSKADYEKHKVYACEVT HQGLSSPVTKSFNRGEC (SEQ ID NO: 187) |
| 801 | EVQLVESGGGLVQPGRSLKLSCVASG FTFNNYWMTWIRQAPGKGLEWVAS ITNIGGSTFYPDSVKGRFTISRDNAKST LYLQMNSLRSEDTATYYCTRHYYSSYI YPTGGFAYWGQGTLVTVSSASTKGPS VFPLAPSSKSTSGGTAALGCLVKDYFP EPVTVSWNSGALTSGVHTFPAVLQSS GLYSLSSVVTVPSSSLGTQTYICNVNH KPSNTKVDKRVEPKSCDKTHTCPPCP APELLGGPSVFLFPPPKPKDTLMISRTP EVTCVVVDVSHEDPEVKFNWYVDGV EVHNAQTKPREEQYNS (SEQ ID NO: 191) | NYWM T (SEQ ID NO: 192) | SITNIGGST FYPDSVKG (SEQ ID NO: 193) | HYYSSYIY PTGGFAY (SEQ ID NO: 194) | IVMTQSPTTIAASPGEKVTITCRAS SSVSYMWYQQKSGASPKLWLY DTSKLASGVPNRFSGSGSGTSYSL TINTMETEDAATYYCQQWSSTPP TFGGGTKLELKRTVAAPSVFIFPPS DEQLKSGTASVVCLLNNFYPREAK VQWKVDNALQSGNSQESVTEQD SKDSTYSLSSTLTLSKADYEKHKVY ACEVTHQGLSSPVTKSFNRGEC (SEQ ID NO195) |
| 802B | EVQLVESGGGLVQPGRSLKLSCVASG FTFNNYWMTWIRQAPGKGLEWVAS ITNIGGSTFYPDSVKGRFTISRDNAKST LYLQMNSLRSEDTATYYCTRHYYSSYI YPTGGFAYWGQGTLVTVSSASTKGPS VFPLAPSSKSTSGGTAALGCLVKDYFP EPVTVSWNSGALTSGVHTFPAVLQSS GLYSLSSVVTVPSSSLGTQTYICNVNH KPSNTKVDKRVEPKSCDKTHTCPPCP APELLGGPSVFLFPPPKPKDTLMISRTP EVTCVVVDVSHEDPEVKFNWYVDGV EVHNAQTKPREEQYNS (SEQ ID NO: 191) | NYWM T (SEQ ID NO: 192) | SITNIGGST FYPDSVKG (SEQ ID NO: 193) | HYYSSYIY PTGGFAY (SEQ ID NO: 194) | MTQSPSLLSASVGDRVTLTCKGSQ NINNFLAWYQQKRGEAPKLLIYKT NSLHTGIPSRFSGSGSGTEYTLTISS LHSEDLATYYCYQYNNGYTFGAG TKLELKRTVAAPSVFIFPPPSDEQLK SGTASVVCLLNNFYPREAKVQWK VDNALQSGNSQESVTEQDSKDST YSLSSTLTLSKADYEKHKVYACEVT HQGLSSPVTKSFNRGEC (SEQ ID NO: 199) |
| 803A | EVQLLESGPGLVKPSQSLSLTCSVTGY SITSGYGWNWIRKFPGNKLEWMGYI NSAGSTNYNPPLKSQISITRDTSKNOF FLQLTSVTTEDTATYYCARWGHTMG TIRDFWYFDFWGPGTMVTVSSASTK GPSVFPLAPSSKSTSGGTAALGCLVKD YFPEPVTVSWNSGALTSGVHTFPAVL QSSGLYSLSSVVTVPSSSLGTQTYICNV NHKPSNTKVDKRVEPKSCDKTHTCPP CPAPELLGGPSVFLFPPPKPKDTLMISR TPEVTCVVVDVSHxDPEVKFNWYVD GV (SEQ ID NO: 203) | SGYG WN (SEQ ID NO: 184) | YINSAGST NYNPPLKS (SEQ ID NO: 204) | WGHTM GTIRDF WYFDF (SEQ ID NO: 205) | MTQSPSLLSASVGDRVTLTCKGSQ NINNFLAWYQQKRGEAPKLLIYKT NSLHTGIPSRFSGSGSGTEYTLTISS LHSEDLATYYCYQYNNGYTFGAG TKLELKRTVAAPSVFIFPPPSDEQLK SGTASVVCLLNNFYPREAKVQWK VDNALQSGNSQESVTEQDSKDST YSLSSTLTLSKADYEKHKVYACEVT HQGLSSPVTKSFNRGEC (SEQ ID NO: 199) |
| B1.807 | EVQLQESGPGLVKTSQSLSLTCSVTGF SITSGFGWNWIRKFPGNKLEWMGYI NSAGSTNYNPPLKSQISITRDTSKNOF FLQLTSVTTEDTGTYYCARWGHSMG | SGFG WN (SEQ ID NO: | YINSAGST NYNPPLKS (SEQ ID NO: 204) | WGHSM GTTRDY WYFDF (SEQ ID | DIQMTQSPSSLPASLGERVTIICRA SQGISNNLNWYQQKPDGTIKPLIY YTSILQSGVPSSFSGSRSGTDYSLTI SSLEPEDFTMYFCQQDASFPWTF |

TABLE 2-continued

From left to right, 1st column: Anti-MDR1 antibody name, 2nd column: VH region, 3rd column: HCDR1, 4th column: HCDR2, 5th column: HCDR3, 6th column: VL region, 7th column: LCDR1, 8th column: LCDR2, 9th column: LCDR3.

| | | | | | |
|---|---|---|---|---|---|
| | TTRDYWYFDFWGPGTMVTVSS (SEQ ID NO: 206) | 207) | | NO: 208) | GGGTKLELK (SEQ ID NO: 209) |
| B1.809 | EVKLVESGGGLVQPGRSLKLSCLASGF TFTNYWMTWVRQAPGKGLEWVASI TNTGAATFYPDSVKGRFTLSRDNAKS TLYLQMNSLRSEDTATYYCTRHYYSSY VYPTGGFAYWGQGTLVTVSS (SEQ ID NO: 210) | NYWM T (SEQ ID NO: 192) | SITNTGAA TFYPDSVK G (SEQ ID NO: 211) | HYYSSYV YPTGGFA Y (SEQ ID NO: 212) | EIVLTQSPTTIAASPGEKVTITCRAR SSVSYMYWYQQKSGATPKLCIYD TSKLASGVPNRFSGSGSGTSYSLTI NTMETEDAATYYCQQWTTNPPT FGGGTKLELK (SEQ ID NO: 213) |
| B1.811A | EVQLVESGGGLVQPGRSLKLSCVASG FTFNNYWMTWIRQAPGKGLEWVAS ITHTGGNTFYPDSVKGRFTISRDNAKS TLYLQMNSLRSEDTATYYCTRHYYSSY VYPTGGFAYWGQGTLVTVSS (SEQ ID NO: 216) | NYWM T (SEQ ID NO: 192) | SITHTGGN TFYPDSVK G (SEQ ID NO: 217) | HYYSSYV YPTGGFA Y (SEQ ID NO: 212) | DIVLTQSPTTIAASPGEKVTITCRAS SSVSYMYWYQQKSGASPKLWIYD TSKLASGVPNRFSGSGSGTSYSLTI NTMETEDAATYYCQQWTSTPPTF GGGTKLELK (SEQ ID NO: 218) |
| B1.813 | EVQILESGPGLVKPSQSLSLTCSVTGFS ITSGYGWNWIRKFPGNKLEWMGYIN SAGSTNYNPPLKGQISITRDTSKNOFF LQLTSVTTEDTATYYCARWGHTMGV TRDFWHFDFWGPGVMVTVSS (SEQ ID NO: 220) | SGYG WN (SEQ ID NO: 184) | YINSAGST NYNPPLK G (SEQ ID NO: 220) | WGHTM GVTRDF WHFDF (SEQ ID NO: 221) | DIHMTQSPSSLPASLGERVTIICRA SQGISNNLNWYQQKPDGAIKPLIY YTSILQSGVPSTFSGSRSGTDYSLTI SSLGPEDFAMYYCQQDASFPWTF GGGTKLELK (SEQ ID NO: 222) |
| B1.815 | EVQLQESGPGLVKPSQSLSLTCSVTGY SITSAYGWNWIRKFPGNKLEWMGYI NSAGSTNYNPPLKSQISITRDTSKNOF FLQLTSVTTEDTATYYCARWGHTMG VTRDYWYFDFWGPGTMVTVSS (SEQ ID NO: 223) | SAYG WN (SEC ID NO: 224) | YINSAGST NYNPPLKS (SEQ ID NO: 204) | WGHTM GVTRDY WYFDF (SEQ ID NO: 225) | DIQLTQSPSSLPASLGERVTIICRAS QGISNNLNWYQQKPDGTIKPLIYY TSILHSGVPSSFSGSRSGTDYSLTIS SLEPEDFAMYYCQQDASFPWTFG GGTKLELK (SEQ ID NO: 226) |
| B1.880 | EVKLLESGGGLVQPGGSMRLSCAASG FTFTDFYMNWIRQPSGKAPEWLGFIR DKVNGYTTVYNPSVQGRFTSRDNSK NILYLQMNTLRGEDTATYYCVRNWA LDYWGQGVMVTVSS (SEQ ID NO: 228) | DFYM N (SEQ ID NO: 229) | FIRDKVNG YTTVYNPS VQG (SEQ ID NO: 230) | NWALDY (SEQ ID NO: 231) | DIQMTQFPSFLFASVGDRVTIKCK ASQNINKYLNWYQQKLGEAPKRL IYDTNSLLTGIPSRFSGSGFGTHYT LTISSLQPEDVATYFCQQYNNWP YTFGAGTKLELK (SEQ ID NO: 232) |
| B1.882 | EVKLEESGGGLVQPGRSLQLSCLASGF TFRNYGMTWIRQAPGRGLEWVASIS STGSYIYYADTMRGRFTISREDAKNAL YLRMTSLRSEDTALYYCTRQEGAAYW GQGVMVTVSS (SEQ ID NO: 236) | NYGM T (SEQ ID NO: 237) | SISSTGSYI YYADTMR G (SEQ ID NO: 282) | QEGAAY (SEQ ID NO: 238) | EIVMIQSPSSLSVSLGDSVTITCRAS QDVGIYVNWFQQKPGKSPRRMI YRATNLADGVPSRFSGSRSGSDYS LTISSLESEDVAAYHCLQYNKYPYT FGAGTKLELK (SEQ ID NO: 239) |
| B1.892 | EVKLLESGGGLVQPGGSMRLSCAASG FTFTDFYMNWIRQPAGKAPEWLGLI RSKANGYTTEYNTSVKGRFTISRDNT QNMLYLQMNTLRAEDTATYYCARNY YFDYWGQGTLVTVSS (SEQ ID NO: 243) | DFYM N (SEQ ID NO: 229) | LIRSKANG YTTEYNTS VKG ID NO: 244) | NYYFDY (SEQ ID NO: 245) | DVQMTQSPSNLAASPGESVSINC KASKSIYKYLAWYQQKPGKANKLL IYSGGTLQSGTPSRFSGSGSGTDFT LTIRNLEPEDFGLYYCQQHNEYPY TFGAGTKLELK (SEQ ID NO: 246) |
| B1.896 | EVKLLESGGGLVQPGRSLKLSCVASGF TFNNYYMSWTRQAPGKGLEWVASIT NSGGTTYYPGSVKGRFTISRDNAQNT LYLQMNSLRSEDTATYYCTRAWGGS YLHWYFDFWGPGTMVTVSS (SEQ ID NO: 250) | NYYMS (SEQ ID NO: 44) | SITNSGGT TYYPGSVK G (SEQ ID NO: 251) | AWGGSY LHWYFD F (SEQ ID NO: 252) | DIVMTQSPSSLAVSAGETVTIKCKS SQSLLYSRNOKNYLAWYQQKPG QSPTLLIYWASTRQSGVPDRFIGS GSGTDFTLTISSVQAEDLAIYYCQ QYYDTPYTFGAGTKLELK (SEQ ID NO: 253) |
| B1.898A | EVQILETGGGLVQPGRSLKLSCVGSGF TFKNSWMSWTRQAPGKGLEWVASI TNSGGTTYYPDSVKGRFTISRDNAQN TLYLQMNSLRSEDTATYYCTRAWGG VYLHWYFDFWGPGTMVTVSS (SEQ ID NO: 257) | NSWM S (SEQ ID NO: 258) | SITNSGGT TYYPDSVK G (SEQ ID NO: 259) | AWGGVY LHWYFD F (SEQ ID NO: 260) | DIVMTQSPSSLAVSAGETVTIKCKS SQSLLYSRNOKNYLAWYQQKPG QSPTLLIYWASTRQSGVPDRFIGS GSGTDFTLTISSVQAEDLAIYYCQ QYYDTPYTFGAGTKLELK (SEQ ID NO: 253) |
| B1.900 | EVQILETGGGLVQPGRSLKLSCVGSGF TFKNSWMSWTRQAPGKGLEWVASI TNSGGTTYYPDSVKGRFTISRDNAQN TLYLQMNSLRSEDTATYYCTRAWGG VYLHWYFDFWGPGTMVTVSS (SEQ ID NO: 257) | NSWM S (SEQ ID NO: 258) | SITNSGGT TYYPDSVK G (SEQ ID NO: 259) | AWGGVY LHWYFD F (SEQ ID NO: 260) | DIVMTQSPSSLAVSAGETVTINCK SSQSLLYSGNOKNYLAWYQQKPG QSPKLLIYWASARQSGVPDRFIGS GSGTDFTLTISSVQAEDLAIYYCQ QYYDTPYTFGAGTKLEIK (SEQ ID NO: 261) |
| B1.908 | EVQLVESGGGLVQPGRSLKLSCVASG FTFNNYWMTWIRQAPGKGLEWVAS IINTGGSTYYPDSVKGRFTISRDNAKST | NYWM T (SEQ ID NO: | SIINTGGST YYPDSVKG (SEQ ID | EWTTVG DY (SEQ ID | DIVLTQSPALAVSLGQRATISCKTN QNVDYYGNSYMHWYQQKPGQ QPKLLIYLASNLASGIPARFSGRGS |

TABLE 2-continued

From left to right, 1ˢᵗ column: Anti-MDR1 antibody name, 2ⁿᵈ column: VH region, 3ʳᵈ column: HCDR1, 4ᵗʰ column: HCDR2, 5ᵗʰ column: HCDR3, 6ᵗʰ column: VL region, 7ᵗʰ column: LCDR1, 8ᵗʰ column: LCDR2, 9ᵗʰ column: LCDR3.

| | | | | | |
|---|---|---|---|---|---|
| | LYLQMNSLRSEDTATYYCTREWTTVG DYWGQGVMVTVSS (SEQ ID NO: 264) | 192) | NO: 265) | NO: 266) | GTDFTLTIDPVEADDTATYYCQQS RNLRTFGGGTKLELK (SEQ ID NO: 267) |
| B1.909A | EVQLVESGGGLVQPGRSLKLSCVASG FTFNNYWMTWIRQAPGKGLEWVAS IINTGGSTYYPDSVKGRFTISRDNAKST LYLQMNSLRSEDTATYYCTREWTTVG DYWGQGVMVTVSS (SEQ ID NO: 264) | NYWM T (SEQ ID NO: 192) | SIINTGGST YYPDSVKG (SEQ ID NO: 265) | EWTTVG DY (SEQ ID NO: 266) | DIWMTQSPALAVSLGQRATISCK TNONVDYGNSYMHWYQQKPG QQPKLLIYLASNLASGIPARFSGRG SGTDFTLTIDPVEADDTATYYCQQ SRNLRTFGGGTKLELK (SEQ ID NO: 271) |
| B1.912 | EVQLVETGGGLVQPGRSLKLSCVASG FTFNNYWMSWTRQAPGKGLEWVA SITNSGGTTYYPDSVKGRFTISRDNAQ NTLSLQMNSLRSEDTATYYCTRAWG AVYLHWFFDFWGPGTMVTVSS (SEQ ID NO: 272) | NYWM S (SEQ ID NO: 273) | SITNSGGT TYYPDSVK G (SEQ ID NO: 259) | AWGAVY LHWFFD F (SEQ ID NO: 274) | DIVMTQSPSSLAVSAGETVTIKCKS SQSLLYSRNOKNYLAWYQQKPG QSPTLLIYWASTRQSGVPDRFIGS GSGTDFTLTISSVQAEDLAIYYCQ QYYDTPYTFGAGTKLELK (SEQ ID NO: 253) |
| B1.915 | EVKLLESGGGLVQPGGSMRLSCAASG FTFTDFYMNWIRQPAGKAPEWLGFI RNKHNGYTTEYNSSLKGRFTISRDNT QNMVYLQMNILRAEDTATYYCARGG TTGTDYWGQGVMVTVSS (SEQ ID NO: 275) | DFYM N (SEQ ID NO: 229) | FIRNKHNG YTTEYNSS LKG (SEQ ID NO: 276) | GGTTGT DY (SEQ ID NO: 277) | DIQMTQSPSFLSASVGDRVTINCK ASQNIYKYLNWYQQKLGEAPKRLI YNTKSLQTGIPSRFSGSGSGTDYTL TISSLQPEDVATYFCQQYNSWPYT FGAGTKLELK (SEQ ID NO: 278) |

| Antibody | CDRL1 | CDRL2 | CDRL3 | Species |
|---|---|---|---|---|
| B1.27 | RSSQNIVHST GNTYLD (SEQ ID NO: 11) | KVSNRFS (SEQ ID NO: 12) | FQGSHIP RT (SEQ ID NO: 13) | Mouse |
| B1.28 | RSSQNIVHST GNTYLD (SEQ ID NO: 11) | KVSNRFS (SEQ ID NO: 12) | FQGSHIP RT (SEQ ID NO: 13) | Mouse |
| B1.28 human1 | RSSQNIVHST GNTYLD (SEQ ID NO: 11) | KVSNRFS (SEQ ID NO: 12) | FQGSHIP RT (SEQ ID NO: 13) | humanized |
| B1.28.hu11 | RSSQNIVHST GNTYLD (SEQ ID NO: 11) | KVSNRFS (SEQ ID NO: 12) | FQGSHIP RT (SEQ ID NO: 13) | humanized |
| B1.28.hu12 | RSSQNIVHST GNTYLD (SEQ ID NO: 11) | KVSNRFS (SEQ ID NO: 12) | FQGSHIP RT (SEQ ID NO: 13) | humanized |
| B1.28.hu13 | RSSQNIVHST GNTYLD (SEQ ID NO: 11) | KVSNRFS (SEQ ID NO: 12) | FQGSHIP RT (SEQ ID NO: 13) | humanized |
| B1.30 | RSSQSIVHSTG NTYLE (SEQ ID NO: 25) | KVSNRFS (SEQ ID NO: 12) | FQGSHVP RT (SEQ ID NO: 41) | Mouse |
| B1.39 | RSSQSILHSNG NTYLE (SEQ ID NO: 28) | KVSNRFS (SEQ ID NO: 12) | FQGSHVP RT (SEQ ID NO: 41) | Mouse |
| B1.85 | RSSQSIVHSTG NTYLE (SEQ ID NO: 25) | KVSNRFS (SEQ ID NO: 12) | FQGSHVP YT (SEQ ID NO: 69) | Mouse |

TABLE 2-continued

From left to right, 1$^{st}$ column: Anti-MDR1 antibody name, 2$^{nd}$ column: VH region,
3$^{rd}$ column: HCDR1, 4$^{th}$ column: HCDR2, 5$^{th}$ column: HCDR3, 6$^{th}$ column: VL region, 7$^{th}$ column:
LCDR1, 8$^{th}$ column: LCDR2, 9$^{th}$ column: LCDR3.

| | | | | |
|---|---|---|---|---|
| B1.89 | RSSQTIVHSN GNTYLE (SEQ ID NO: 39) | KVSKRFS (SEQ ID NO: 40) | FQGSHFP RT (SEQ ID NO: 42) | Mouse |
| B1.92 | RASSSVSYMH (SEQ ID NO: 48) | ATSNLAS (SEQ ID NO: 49) | QQWSSN PPT (SEQ ID NO: 50) | Mouse |
| B1.99 | RSSQSIVHSYG STYLE (SEQ ID NO: 54) | KVSNRFS (SEQ ID NO: 12) | FQGSHIP YT (SEQ ID NO: 55) | Mouse |
| B1.129 | RASSSVSFIY (SEQ ID NO: 61) | ATSNLAS (SEQ ID NO: 49) | HQWGSN LPT (SEQ ID NO: 62) | Mouse |
| B1.129.huH1-huL1(KV3) | RASSSVSFIY (SEQ ID NO: 61) | ATSNLAS (SEQ ID NO: 49) | HQWGSN LPT (SEQ ID NO: 62) | humanized |
| B1.129.huH1-huL1(KV1) | RASSSVSFIY (SEQ ID NO: 61) | ATSNLAS (SEQ ID NO: 49) | HQWGSN LPT (SEQ ID NO: 62) | humanized |
| B1.177 | RSSQSIVHSN GNTYLE (SEQ ID NO: 68) | KVSNRFS (SEQ ID NO: 12) | FQGSHVP YT (SEQ ID NO: 69) | Mouse |
| B1.178 | RSSQSIVHSN GNTYLE (SEQ ID NO: 68) | KVSNRFS (SEQ ID NO: 12) | FQGSHVP YT (SEQ ID NO: 69) | Mouse |
| B1.179 | RSSQSIVHSN GNTYLE (SEQ ID NO: 68) | KVSNRFS (SEQ ID NO: 12) | FQGSHVP YT (SEQ ID NO: 69) | Mouse |
| B1.184 | RSSQSIVHSSG NTYLE (SEQ ID NO: 77) | KVSNRFF (SEQ ID NO: 78) | FQGSHVP YT (SEQ ID NO: 69) | Mouse |
| B1.188 | RSSQSIVHSTG NTYLE (SEQ ID NO: 25) | KVSNRFS (SEQ ID NO: 12) | FQGSHVP FT (SEQ ID NO: 80) | Mouse |
| B1.193b | RSSQSIVHSTG NTYLE (SEQ ID NO: 25) | KVSNRFS (SEQ ID NO: 12) | FQGSHVP YT (SEQ ID NO: 69) | Mouse |
| B1.197a | NYAMS (SEQ ID NO: 35) | TISSGGG YTYYPDS VKG (SEQ ID NO: 86) | GYGNFA WFAY (SEQ ID NO: 32) | Mouse |
| B1.198 | RSSQSIVDSN GNTYLE (SEQ ID NO: 91) | KVSNRFF (SEQ ID NO: 78) | FQGSHVP YT (SEQ ID NO: 69) | Mouse |
| B1.201 | RFSQSIVHSSG NTYLE (SEQ ID NO: 96) | KVSNRFF (SEQ ID NO: 78) | FQGSHVP YT (SEQ ID NO: 69) | Mouse |

TABLE 2-continued

From left to right, 1$^{st}$ column: Anti-MDR1 antibody name, 2$^{nd}$ column: VH region,
3$^{rd}$ column: HCDR1, 4$^{th}$ column: HCDR2, 5$^{th}$ column: HCDR3, 6$^{th}$ column: VL region, 7$^{th}$ column:
LCDR1, 8$^{th}$ column: LCDR2, 9$^{th}$ column: LCDR3.

| | | | | |
|---|---|---|---|---|
| B1.207 | RSSQSIVHSSG NTYLE (SEQ ID NO: 77) | KVSNRFF (SEQ ID NO: 78) | FQGSHVP YT (SEQ ID NO: 69) | Mouse |
| B1.217 | RSSQSIVHSTG NTYLE (SEQ ID NO: 25) | KVSNRFS (SEQ ID NO: 12) | FQGSHIP YT (SEQ ID NO: 55) | Mouse |
| B1.219 | RSSQSIVHSSG NTYLE (SEQ ID NO: 77) | KVSNRFF (SEQ ID NO: 78) | FQGSHVP YT (SEQ ID NO: 69) | Mouse |
| B1.223 | RSSQSIVHSSG NTYLE (SEQ ID NO: 77) | KVSNRFF (SEQ ID NO: 78) | FQGSHVP YT (SEQ ID NO: 69) | Mouse |
| B1.225 | RFSQSIVHSN GNTYLE (SEQ ID NO: 110) | KVSNRFF (SEQ ID NO: 78) | FQGSHVP QYT (SEQ ID NO: 111) | Mouse |
| B1.226 | NYAMS (SEQ ID NO: 35) | TISSGGSY TYYPDSV KG (SEQ ID NO: 52) | YSNLAW FAY (SEQ ID NO: 83) | Mouse |
| B1.228A | RFSQSIVHSSG NTYLE (SEQ ID NO: 96) | KVSNRFF (SEQ ID NO: 78) | FQGSHVP YT (SEQ ID NO: 69) | Mouse |
| B1.236 | RSSQSLVHSIG NTYLE (SEQ ID NO: 117) | KVSNRFS (SEQ ID NO: 12) | FQGSHVP YT (SEQ ID NO: 69) | Mouse |
| B1.261 | RASQNVGSYI A (SEQ ID NO: 123) | SASYRCS (SEQ ID NO: 124) | QQYNSY PLT (SEQ ID NO: 125) | Mouse |
| B1.261.huH1 (VH4)-huL1 | RASQNVGSYI A (SEQ ID NO: 123) | SASYRSS (SEQ ID NO: 128) | QQYNSY PLT (SEQ ID NO: 125) | Mouse |
| B1.261.huH2 (VH3)-huL1 | RASQNVGSYI A (SEQ ID NO: 123) | SASYRSS (SEQ ID NO: 128) | QQYNSY PLT (SEQ ID NO: 125) | Mouse |
| B1.262-sub1 | RASQNVGSYV A (SEQ ID NO: 132) | SASYRCS (SEQ ID NO: 124) | QQYNSY PLT (SEQ ID NO: 125) | Mouse |
| B1.263 | RSSQNIVHST GNTYLE (SEQ ID NO: 137) | KVSNRFS (SEQ ID NO: 12) | FQGSHVP WT (SEQ ID NO: 138) | Mouse |
| B1.264 | RSSQSIVHSN GNTYLE (SEQ ID NO: 68) | KVSNRFS (SEQ ID NO: 12) | FQGSLVP RT (SEQ ID NO: 143) | Mouse |
| B1.269 | RSSQSIVHSTG NTYLE (SEQ ID NO: 25) | KVSNRFS (SEQ ID NO: 12) | FQGSHVP RT (SEQ ID NO: 41) | Mouse |

TABLE 2-continued

From left to right, 1$^{st}$ column: Anti-MDR1 antibody name, 2$^{nd}$ column: VH region, 3$^{rd}$ column: HCDR1, 4$^{th}$ column: HCDR2, 5$^{th}$ column: HCDR3, 6$^{th}$ column: VL region, 7$^{th}$ column: LCDR1, 8$^{th}$ column: LCDR2, 9$^{th}$ column: LCDR3.

| | | | | |
|---|---|---|---|---|
| B1-open.272 | RASSSVSSSYL H (SEQ ID NO: 152) | STSSLAS (SEQ ID NO: 153) | QQYSGYP LT (SEQ ID NO: 154) | Mouse |
| B1-open.273 (A) | TASSSVSSSYL H (SEQ ID NO: 160) | STSNLAS (SEQ ID NO: 161) | HQYHRSP PT (SEQ ID NO: 162) | Mouse |
| B1.275 | RSSQTIVHSD GYTYLE (SEQ ID NO: 167) | KVSNRFS (SEQ ID NO: 12) | FQGSHVP YT (SEQ ID NO: 69) | Mouse |
| B1.276 | RASSSVSSSYL H (SEQ ID NO: 152) | STSSLAS (SEQ ID NO: 153) | QQYSGYP LT (SEQ ID NO: 154) | Mouse |
| B1-open.277B | RSSQSIVHTN GNTYLE (SEQ ID NO: 174) | KVSNRFS (SEQ ID NO: 12) | FQGSHVP YT (SEQ ID NO: 69) | Mouse |
| B1.278 | RASESVHNYG VSFMN (SEQ ID NO: 180) | AASHQG S (SEQ ID NO: 181) | QQSKEVP LT (SEQ ID NO: 182) | Mouse |
| 799A | RASQGISNNL N (SEQ ID NO: 188) | YTSILQS (SEQ ID NO: 189) | QQDASF PWT (SEQ ID NO: 190) | rat |
| 801 | RASSSVSYMY (SEQ ID NO: 196) | DTSKLAS (SEQ ID NO: 197) | QQWSST PPT (SEQ ID NO: 198) | rat |
| 802B | KGSQNINNFL A (SEQ ID NO: 200) | KTNSLHT (SEQ ID NO: 201) | YQYNNG YT (SEQ ID NO: 202) | rat |
| 803A | KGSQNINNFL A (SEQ ID NO: 200) | KTNSLHT (SEQ ID NO: 201) | YQYNNG YT (SEQ ID NO: 202) | rat |
| B1.807 | RASQGISNNL N (SEQ ID NO: 188) | YTSILQS (SEQ ID NO: 189) | QQDASF PWT (SEQ ID NO: 190) | mouse |
| B1.809 | RARSSVSYMY (SEQ ID NO: 214) | DTSKLAS (SEQ ID NO: 197) | QQWTTN PPT (SEQ ID NO: 215) | mouse |
| B1.811A | RASSSVSYMY (SEQ ID NO: 196) | DTSKLAS (SEQ ID NO: 197) | QQWTST PPT (SEQ ID NO: 219) | mouse |
| B1.813 | RASQGISNNL N (SEQ ID NO: 188) | YTSILQS (SEQ ID NO: 189) | QQDASF PWT (SEQ ID NO: 190) | mouse |
| B1.815 | RASQGISNNL N (SEQ ID NO: 188) | YTSILHS (SEQ ID NO: 227) | QQDASF PWT (SEQ ID NO: 190) | mouse |

TABLE 2-continued

From left to right, 1$^{st}$ column: Anti-MDR1 antibody name, 2$^{nd}$ column: VH region,
3$^{rd}$ column: HCDR1, 4$^{th}$ column: HCDR2, 5$^{th}$ column: HCDR3, 6$^{th}$ column: VL region, 7$^{th}$ column:
LCDR1, 8$^{th}$ column: LCDR2, 9$^{th}$ column: LCDR3.

| | | | | |
|---|---|---|---|---|
| B1.880 | KASQNINKYL N (SEQ ID NO: 233) | DTNSLLT (SEQ ID NO: 234) | QHYNN WPYT (SEQ ID NO: 235) | mouse |
| B1.882 | RASQDVGIYV N (SEQ ID NO: 240) | RATNLAD (SEQ ID NO: 241) | LQYNKYP YT (SEQ ID NO: 242) | mouse |
| B1.892 | KASKSIYKYLA (SEQ ID NO: 247) | SGSTLQS (SEQ ID NO: 248) | QQHNEY PYT (SEQ ID NO: 249) | mouse |
| B1.896 | KSSQSLLYSRN QKNYLA (SEQ ID NO: 254) | WASTRQ S (SEQ ID NO: 255) | QQYYDT PYT (SEQ ID NO: 256) | mouse |
| B1.898A | KSSQSLLYSRN QKNYLA (SEQ ID NO: 254) | WASTRQ S (SEQ ID NO: 255) | QQYYDT PYT (SEQ ID NO: 256) | mouse |
| B1.900 | KSSQSLLYSGN QKNYLA (SEQ ID NO: 262) | WASARQ S (SEQ ID NO: 263) | QQYYDT PYT (SEQ ID NO: 256) | mouse |
| B1.908 | KTNONVDYY GNSYMH (SEQ ID NO: 268) | LASNLAS (SEQ ID NO: 269) | QQSRNL RT (SEQ ID NO: 270) | mouse |
| B1.909A | KTNONVDYY GNSYMH (SEQ ID NO: 268) | LASNLAS (SEQ ID NO: 269) | QQSRNL RT (SEQ ID NO: 270) | mouse |
| B1.912 | KSSQSLLYSRN QKNYLA (SEQ ID NO: 254) | WASTRQ S (SEQ ID NO: 255) | QQYYDT PYT (SEQ ID NO: 256) | mouse |
| B1.915 | KASQNIYKYLN (SEQ ID NO: 279) | NTKSLQT (SEQ ID NO: 280) | QQYNSW PYT (SEQ ID NO: 281) | mouse |

The antibodies listed in table 2 were raised in either mouse or rat.

The anti-MDR1 antibodies listed in Table 2 are also referred to herein as anti-KPB1 or B1 antibodies and can be referred to by the antibody number listed in Table 2 which number may additionally include the suffix B1 (e.g., B1-28 or B1.28 or KNJY-B1.28) to indicate that the antibody binds to KPB1 or "B1."

In some embodiments, the antibody comprises a VL region and a VH region that are present in separate polypeptides; in other embodiments, the VL region and a VH region are contained within a single polypeptide.

The antibody of the present disclosure may include a humanized light chain, a humanized heavy chain, or both.

The antibody of the present disclosure may be selected from the group consisting of an Ig monomer, a Fab fragment, a F(ab')$_2$ fragment, a Fd fragment, a scFv, a scAb, a dAb, and a Fv.

In certain aspects, a subject antibody may include a VH chain comprising HCDRs of a VH chain listed in Table 2 and a VL chain comprising LCDRs of the MRK16 antibody, 15D3 antibody, or UIC2 antibody. The VL chain sequences of the MRK16 antibody, 15D3 antibody, and UIC2 antibody are as follows:

MRK16 VL Chain:

(SEQ ID NO: 283)
DVLMTQTPVSLSVSLGDQASISCRSSQSIVHSTGNTYLEWYLQKPGQSP

KLLIYKISNRFSGVPDRFSGSGSGTDFTLKISRVEAEDLGVYYCFQASH

FPRTFGGGTKLEIK

15D3 VL Chain:

(SEQ ID NO: 284)
DVLMTQTPLSLPVSLGDQASISCRSSQSIVHSTGNTYLEWYLQKPGQSP

KLLIYKVSNRFSGVPDRFSGSGSGTDFTLKISRLEAEDLGVYYCFQGSH

FPRTFGGGTRLEIK

UIC2 VL Chain:

```
(SEQ ID NO: 285)
DVVMTQTPRSLPVSLGDQASISCRSSQSLLHSNGNTYLHWYLQKPGQSP

KLLIYKVSNRFSGVPDRFSGSGSGTDFTLKISRVEAEDLGVYFCSQSTH

IPPWTFGGGTKLDIK
```

In certain aspects, a subject antibody may include a VL chain comprising LCDRs of a VL chain listed in Table 2 and a VH chain comprising HCDRs of the MRK16 antibody, 15D3 antibody, or UIC2 antibody. The VH chain sequences of the MRK16 antibody, 15D3 antibody, and UIC2 antibody are as follows:

MRK16 VH Chain:

```
(SEQ ID NO: 286)
EVILVESGGGLVKPGGSLKLSCAASGFTFSSYTMSWVRQTPEKRLEWVA

TISSGGGNTYYPDSVKGRFTISRDNAKNNLYLQMSSLRSEDTALYYCAR

YYRYEAWFASWGQGTLVTVSA
```

15D3 VH Chain:

```
(SEQ ID NO: 287)
EVKVVESGGVLVRPGGSLKLSCAASGFTFSRYTMSWVRQTPEKRLEWVA

TISSGGGNTYYPDSVKGRFTVSRDNAMSSLYLQMSSLRSEDTALYYCAR

YGAGDAWFAYWGQGTLVTVSS
```

UIC2 VH Chain:

```
(SEQ ID NO: 288)
AVQLQQSGPELVKTGASVKISCKASGYSFSNYYIHWVKQSHGKSLEWIG

FISCYNGATFYNQKFKGKATFTVDTSSSTAYMKFNSLTFEDSAVYYCAR

LPIQFGNFYPMDYWGQGTSVTVSS
```

In certain antibodies, the foregoing antibodies are mono-specific bivalent antibodies.

In certain aspects, the antibody of the present disclosure is a multi-specific capable of binding at least two different epitopes present on two different target proteins. The number of different target proteins, and thus different epitopes, bound by a multi-specific antibody may vary and may be two (i.e., bispecific), three (tri-specific), four, or greater.

In certain aspects, the antibody of the present disclosure is a multi-specific capable of binding at least two different epitopes, where one of the epitopes is on MDR1 (e.g., human MDR1) and the other epitope is a tumor-associated antigen (TAA). The TAA may be any antigen that is known to be overexpressed in cancer cells. For example, the TAA may be an antigen that is not expressed at detectable levels in a normal cell and is expressed in cancer cells, where the normal and cancer cells are the same cell type, e.g., epithelial cells. For example, TAAs may be neoantigens that are a class of tumor antigens that arise from a tumor-specific mutation(s) which alters the amino acid sequence of encoded proteins as compared to the amino acid sequence of the unmutated protein. In other aspects, a TAA is an antigen that is expressed in normal cells but is expressed at higher levels in cancer cells. The TAA may be expressed on the cell surface of a mammalian cancer cell. In certain aspects, the TAA may be CD47, Her2, or PDL1.

In certain aspects, the multi-specific antibody increases sensitivity of cancer cell to treatment with a chemotherapeutic agent thereby lowering the IC50 of the chemotherapeutic agent by at least a factor of 2 when co-administered with the multi-specific antibody as compared to the IC50 of the chemotherapeutic agent when co-administered with an anti-MDR1 monospecific bivalent antibody. The IC50 may be measured by a method as provided herein. The chemotherapeutic agent may be vincristine. The cancer cell may be a drug-resistant cancer cell, N6/ADR. In certain aspects, the multi-specific antibodies of the present disclosure may lower the IC50 of the chemotherapeutic agent by factor of 5 or more, e.g., factor of 6 or more, factor of 7 or more, factor of 8 or more, factor of 9 or more, ore factor of 10 or more, e.g., by a factor of 5 to 10.

In certain aspects, the multi-specific antibody may have in vivo cell killing activity, e.g., reduction of tumor volume even in absence of administration of a chemotherapeutic agent, such as, vincristine.

In certain aspects, the multi-specific antibody may a bispecific antibody molecule that binds multidrug resistance protein 1 (MDR1) and a tumor associated antigen (TAA), the antibody molecule comprising two identical variable light (VL) chains, a first variable heavy (VH) chain, and a second VH chain, wherein the VL chains each comprise an antigen-binding site for MDR1, the first VH chain comprises an antigen-binding site for MDR1, and the second VH chain comprises an antigen-binding site for the TAA, and wherein the second VH chain binds the TAA when paired with one of the light chains.

In certain aspects, the antigen-binding site of the two VL chains comprises light chain CDRs 1-3 (LCDRs 1-3) of an antibody listed in Table 2. In certain aspects, the antigen-binding site of the two VL chains comprises light chain CDRs 1-3 (LCDRs 1-3) of an anti-MDR1 antibody, V6, comprising a VL chain having the amino acid sequence:

```
(SEQ ID NO: 289)
LWVPGSTGDVLMTQTPLSLPVSLGDQASISCRSSQSLVHSNGNTYLEWY

LQKPGQSPKLLIYKVSNRFSGVPDRFSGSGSGTDFTLKISRVEAEDLGV

YYCFQGSHFPRTFGGGTKLEIK.
```

In certain aspects, the LCDR1 comprises the amino acid sequence: RSSQSLVHSNGNTYLE (SEQ ID NO:290): the LCDR2 comprises the amino acid sequence: KVSNRFS (SEQ ID NO:12); and the LCDR3 comprises the amino acid sequence: FQGSHFPRT (SEQ ID NO:42).

In certain aspects, the antigen-binding site of the first VH chain comprises heavy chain CDRs 1-3 (HCDRs 1-3) of an antibody listed in Table 2.

In certain aspects, the first VH chain comprises HCDRs 1-3 of an anti-MDR1 antibody other than an antibody listed in Table 2, optionally wherein the first VH chain comprises the amino acid sequence of the VH chain of an anti-MDR1 antibody other than an antibody listed in Table 2.

In certain aspects, the anti-MDR1 antibody comprises a VH chain having the amino acid sequence:

```
(SEQ ID NO: 291)
EVKVVESGGVLVRPGGSLKLSCAASGFTFSRYTMSWVRQTPEKRLEWVA

TISSGGGX²TYYPDSVKGRFTVSRDNAMSSLYLQMSSLRSEDTALYYCA

RYGAGDAWFAYWGQGTLVTVSS,
``` wherein $X^2$ is N, Q or S;

```
                                        (SEQ ID NO: 288)
AVQLQQSGPELVKTGASVKISCKASGYSFSNYYIHWVKQSHGKSLEWIG

FISCYNGATFYNQKFKGKATFTVDTSSSTAYMKFNSLTFEDSAVYYCAR

LPIQFGNFYPMDYWGQGTSVTVSS; or
```

```
                                        (SEQ ID NO: 286)
EVILVESGGGLVKPGGSLKLSCAASGFTFSSYTMSWVRQTPEKRLEWVA

TISSGGGNTYYPDSVKGRFTISRDNAKNNLYLQMSSLRSEDTALYYCAR

YYRYEAWFASWGQGTLVTVSA.
```

In certain aspects, the anti-MDR1 antibody comprises a VH chain having the amino acid sequence:

```
                                        (SEQ ID NO: 292)
EVKVVESGGVLVRPGGSLKLSCAASGFTFSRYTMSWVRQTPEKRLEWVA

TISSGGGX²TYYPDSVKGRFTVSRDNAMSSLYLQMSSLRSEDTALYYCA

RYGAGDAWFAYWGQGTLVTVSS,
``` wherein $X^2$ is N, Q or S, optionally wherein $X^2$ is Q or S.

The VL chain(s) may comprise LCDRs 1-3 of the B1-28 antibody listed in Table 2, optionally wherein the VL chains comprise the amino acid sequence of the VL chain of the B1-28 antibody listed in Table 2.

In certain aspects, the VL chains may comprise LCDRs 1-3 of an anti-MDR1 antibody other than an antibody listed in Table 2, optionally wherein the variable light chains comprise the amino acid sequence of the VL chain of the antibody other than an antibody listed in Table 2.

In certain aspects, the anti-MDR1 antibody comprises the light chain amino acid sequence:

```
                                        (SEQ ID NO: 283)
DVLMTQTPVSLSVSLGDQASISCRSSQSIVHSTGNTYLEWYLQKPGQSP

KLLIYKISNRFSGVPDRFSGSGSGTDFTLKISRVEAEDLGVYYCFQASH

FPRTFGGGTKLEIK;
```

```
                                        (SEQ ID NO: 284)
DVLMTQTPLSLPVSLGDQASISCRSSQSIVHSTGNTYLEWYLQKPGQSP

KLLIYKVSNRFSGVPDRFSGSGSGTDFTLKISRLEAEDLGVYYCFQGSH

FPRTFGGGTRLEIK; or
```

```
                                        (SEQ ID NO: 285)
DVVMTQTPRSLPVSLGDQASISCRSSQSLLHSNGNTYLHWYLQKPGQSP

KLLIYKVSNRFSGVPDRFSGSGSGTDFTLKISRVEAEDLGVYFCSQSTH

IPPWTFGGGTKLDIK.
```

In certain aspect, the bispecific antibody binds to MDR1 and a TAA and lowers the IC50 of the chemotherapeutic agent by factor of 5 or more and comprises a common light chain, a VH chain comprising HCDRs from a VH chain listed in Table 2 and a VH chain comprising HCDRs from an anti-TAA antibody. The common light chain may include LCDRs from a VL chain listed in Table 2 (e.g., the VL of an antibody in Table 2 from which the VH HCDRs are derived) or from another anti-MDR1 antibody, such as, MRK16, 15D3, or UIC2.

In certain aspect, the bispecific antibody is capable of increasing sensitivity of a cancer cell to treatment with a chemotherapeutic agent, wherein the half maximal inhibitory concentration (IC50) of the chemotherapeutic agent when co-administered with the antibody is at least 5 times lower (e.g., 6 times lower, 10 times lower, 15 times lower, or 20 times lower) than the IC50 of the chemotherapeutic agent when co-administered with an anti-MDR1 antibody comprising a VH chain having the sequence:

```
                                        (SEQ ID NO: 293)
EVKVVESGGVLVRPGGSLKLSCAASGFTFSRYTMSWVRQTPEKRLEWVA

TISSGGGNTYYPDSVKGRFTVSRDNAMSSLYLQMSSLRSEDTALYYCAR

YGAGDAWFAYWGQGTLVTVSA; and
```

A VL Chain Having the Sequence:

```
                                        (SEQ ID NO: 284)
DVLMTQTPLSLPVSLGDQASISCRSSQSIVHSTGNTYLEWYLQKPGQSP

KLLIYKVSNRFSGVPDRFSGSGSGTDFTLKISRLEAEDLGVYYCFQGSH

FPRTFGGGTRLEIK.
```

In certain aspects, the second VH chain comprises HCDRs 1-3 of a VH chain of an anti-CD47 antibody, 5F9, comprising the amino acid sequence:

```
                                        (SEQ ID NO: 294)
QVQLVQSGAEVKKPGASVKVSCKASGYTFTNYNMHWVRQAPGQRLEWMG

TIYPGNDDTSYNQKFKDRVTITADTSASTAYMELSSLRSEDTAVYYCAR

GGYRAMDYWGQGTLVTVSS.
```

In certain aspects, the second VH chain comprises HCDRs 1-3 of a VH chain of an anti-CD47 antibody, B6H12, comprising the amino acid sequence:

```
                                        (SEQ ID NO: 295)
EVQLVESGGDLVKPGGSLKLSCAASGFTFSGYGMSWVRQTPDKRLEWVA

TITSGGTYTYYPDSVKGRFTISRDNAKNTLYLQIDSLKSEDTAIYFCAR

SLAGNAMDYWGQGTSVTVSS
```

B6H12 antibody is a murine antibody that binds to human CD47 and comprises a VL region comprising the amino acid sequence:

```
                                        (SEQ ID NO: 296)
DIVMTQSPATLSVTPGDRVSLSCRASQTISDYLHWYQQKSHESPRLLIK

FASQSISGIPSRFSGSGSGSDFTLSINSVEPEDVGVYYCQNGHGFPRTF

GGGTKLEIK.
```

A humanized version of the B6H12 antibody has a VH region and a VL region as set forth below:
B6H12 Humanized VH Sequence:

```
                                        (SEQ ID NO: 297)
EVQLVESGGGLVQPGGSLRLSCAASGFTFSGYGMSWVRQAPGKGLEWVA

TITSGGTYTYYPDSVKGRFTISRDNAKNSLYLQMNSLRAEDTAVYYCAR

SLAGNAMDYWGQGTMVTVSS
```

The HCDRs1-3 are underlined and bolded.

B6H12 Humanized VL Sequence:

(SEQ ID NO: 298)
EIVLTQSPATLSLSPGERATLSCRASQTISDYLHWYQQKPGQAPRLLIK

FASQSISGIPARFSGSGSGTDFTLTISSLEPEDFAVYYCQNGHGFPRTF

GQGTKLEIK.

The LCDRs1-3 are underlined and bolded.

In certain aspect, the bispecific antibody binds to MDR1 and a TAA and lowers the IC50 of the chemotherapeutic agent by factor of 5 or more and comprises a common light chain comprising LCDRs from a VL chain listed in Table 2, a VH chain comprising HCDRs from another anti-MDR1 antibody, such as, MRK16, 15D3, or UIC2 or from a VH chain listed in Table 2 (e.g., the VH of an antibody in Table 2 from which the VL LCDRs are derived) and a VH chain comprising HCDRs from an anti-TAA antibody. The anti-TAA antibody may be an anti-CD47 antibody, such as, murine antibody 5F9 or murine antibody B6H13, or humanized versions thereof. For example, the bispecific antibody comprises:

HCDRs1-3 of a VH region of an anti-CD47 antibody, 5F9, wherein the VH region comprises the amino acid sequence:

(SEQ ID NO: 294)
QVQLVQSGAEVKKPGASVKVSCKASGYTFTNYNMHWVRQAPGQRLEWMG

TIYPGNDDTSYNQKFKDRVTITADTSASTAYMELSSLRSEDTAVYYCAR

GGYRAMDYWGQGTLVTVSS; or

HCDRs1-3 of a VH region of an anti-CD47 antibody, B6H12, wherein the VH region comprises the amino acid sequence:

(SEQ ID NO: 295)
EVQLVESGGDLVKPGGSLKLSCAASGFTFSGYGMSWVRQTPDKRLEWVA

TITSGGTYTYYPDSVKGRFTISRDNAKNTLYLQIDSLKSEDTAIYFCAR

SLAGNAMDYWGQGTSVTVSS.

In certain embodiments, the VH region of the B6H12 antibody comprises HCDR1 comprising the sequence: GYGMS (SEQ ID NO:379); HCDR2 comprising the sequence: TITSGGTYTYYPDSVKG (SEQ ID NO:299); and HCDR3 comprising the sequence: SLAGNAMDY (SEQ ID NO:300).

In certain embodiments, the bispecific antibody comprises a VH region of the anti-CD47 mouse antibody B6H12 or a humanized version thereof, wherein the VH region of the B6H12 antibody comp rises the amino acid sequence:

(SEQ ID NO: 295)
EVQLVESGGDLVKPGGSLKLSCAASGFTFSGYGMSWVRQTPDKRLEWVA

TITSGGTYTYYPDSVKGRFTISRDNAKNTLYLQIDSLKSEDTAIYFCAR

SLAGNAMDYWGQGTSVTVSS.

In certain embodiments, the bispecific antibody comprises a VH region of a humanized version of the anti-CD47 mouse antibody B6H12, wherein the VH region comprises the amino acid sequence:

(SEQ ID NO: 297)
EVQLVESGGGLVQPGGSLRLSCAASGFTFSGYGMSWVRQAPGKGLEWVA

TITSGGTYTYYPDSVKGRFTISRDNAKNSLYLQMNSLRAEDTAVYYCAR

SLAGNAMDYWGQGTMVTVSS.

In certain aspects, the bispecific antibody comprises an MDR1 binding domain comprising HCDRs of a VH region from an anti-MDR1 antibody having VH region:

(SEQ ID NO: 293)
EVKVVESGGVLVRPGGSLKLSCAASGFTFSRYTMSWVRQTPEKRLEWVA

TISSGGGNTYYPDSVKGRFTVSRDNAMSSLYLQMSSLRSEDTALYYCAR

YGAGDAWFAYWGQGTLVTVSA;

and a TAA-binding domain, where optionally the TAA-binding domain is a CD47-binding domain comprising HCDRs of a VH region from an anti-CD47 antibody having VH region:

(SEQ ID NO: 294)
QVQLVQSGAEVKKPGASVKVSCKASGYTFTNYNMHWVRQAPGQRLEWMG

TIYPGNDDTSYNQKFKDRVTITADTSASTAYMELSSLRSEDTAVYYCAR

GGYRAMDYWGQGTLVTVSS;

and a common light chain comprising LCDRs from a VL chain listed in Table 2, e.g., comprising LCDRs from a VL chain of the antibody B1-28, B1-178, B1-28, B1-184, B1-188, B1-193B, B1-197, B1-198, B1-201, B1-207, B1-223, B1-85, B1-99, B1-27, B1-39, or B1-30.

In certain aspects, the bispecific antibody may include HCDRs 1-3 of a VH region from an anti-MDR1 antibody having the following HCDR sequences: HCDR1: RYTMS (SEQ ID NO:301), HCDR2: TISSGGGNTYYPDSVKG (SEQ ID NO:302), TISSGGGQTYYPDSVKG (SEQ ID NO:303), or TISSGGGSTYYPDSVKG (SEQ ID NO:304), and HCDR3: YGAGDAWFAY (SEQ ID NO:305); HCDRs of a VH region from an anti-CD47 antibody having the following HCDR sequences: HCDR1: NYNMH (SEQ ID NO:306), HCDR2: TIYPGNDDTSYNQKFKD (SEQ ID NO:307), and HCDR3: GGYRAMDY (SEQ ID NO:308); and a common light chain comprising LCDRs of a VL region of the anti-MDR1 antibody B1-28. In certain aspects, the LCDR sequences are: LCDR1: RSSQNIVHSTGN-TYLD (SEQ ID NO:11), LCDR2: KVSNRFS (SEQ ID NO:12), and LCDR3: FQGSHIPRT (SEQ ID NO:13).

Unless specified otherwise, the CDRs are defined as per Kabat nomenclature.

In certain aspects, the first VH chain of the bispecific antibody molecule comprises an amino acid sequence comprising (SEQ ID NO: 291)
EVKVVESGGVLVRPGGSLKLSCAASGFTFSRYTMSWVRQTPEKRLEWVA

TISSGGGX$^2$TYYPDSVKGRFTVSRDNAMSSLYLQMSSLRSEDTALYYCA

RYGAGDAWFAYWGQGTLVTVSS, wherein X$^2$ is N, Q or S; the second VH chain comprises an amino acid sequence comprising (SEQ ID NO: 294)

QVQLVQSGAEVKKPGASVKVSCKASGYTFTNYNMHWVRQAPGQRLEWMG

TIYPGNDDTSYNQKFKDRVTITADTSASTAYMELSSLRSEDTAVYYCAR

GGYRAMDYWGQGTLVTVSS;

and/or the two VL chains comprise an amino acid sequence comprising the VL chain of the B1-28 antibody listed in Table 2.

In certain embodiments, the bispecific antibody comprises a VH chain comprising HCDRs1-3 from VH chain of B1.188, a common VL chain comprising LCDRs1-3 from VL chain of an anti-MDR1 antibody, MRK16, and a VH chain comprising HCDRs1-3 from VH chain of an anti-CD47 antibody, 5F9. The HCDRs1-3 from VH chain of B1.188, the LCDRs1-3 from VL chain of MRK16, and the HCDRs1-3 from VH chain of 5F9 are listed in Table 5. In certain embodiments, the bispecific antibody comprises the VH chain of B1.188, the VL chain of MRK16 as a common light chain, and the VH chain of 5F9.

In certain embodiments, the bispecific antibody comprises a VH chain comprising HCDRs1-3 from VH chain of B1.261, a common VL chain comprising LCDRs1-3 from VL chain of an anti-MDR1 antibody, MRK16, and a VH chain comprising HCDRs1-3 from VH chain of an anti-CD47 antibody, 5F9. The HCDRs1-3 from VH chain of B1.261, the LCDRs1-3 from VL chain of MRK16, and the HCDRs1-3 from VH chain of 5F9 are listed in Table 5. In certain embodiments, the bispecific antibody comprises the VH chain of B1.261, the VL chain of MRK16 as a common light chain, and the VH chain of 5F9.

In certain embodiments, the bispecific antibody comprises a VH chain comprising HCDRs1-3 from VH chain of B1.129, a common VL chain comprising LCDRs1-3 from VL chain of an anti-MDR1 antibody, MRK16, and a VH chain comprising HCDRs1-3 from VH chain of an anti-CD47 antibody, 5F9. The HCDRs1-3 from VH chain of B1.129, the LCDRs1-3 from VL chain of MRK16, and the HCDRs1-3 from VH chain of 5F9 are listed in Table 5. In certain embodiments, the bispecific antibody comprises the VH chain of B1.129, the VL chain of MRK16 as a common light chain, and the VH chain of 5F9.

In certain embodiments, the bispecific antibody comprises a VH chain comprising HCDRs1-3 from VH chain of B1.225, a common VL chain comprising LCDRs1-3 from VL chain of an anti-MDR1 antibody, MRK16, and a VH chain comprising HCDRs1-3 from VH chain of an anti-CD47 antibody, 5F9. The HCDRs1-3 from VH chain of B1.225, the LCDRs1-3 from VL chain of MRK16, and the HCDRs1-3 from VH chain of 5F9 are listed in Table 5. In certain embodiments, the bispecific antibody comprises the VH chain of B1.225, the VL chain of MRK16 as a common light chain, and the VH chain of 5F9.

In certain embodiments, the bispecific antibody comprises a VH chain comprising HCDRs1-3 from VH chain of B1.223, a common VL chain comprising LCDRs1-3 from VL chain of an anti-MDR1 antibody, MRK16, and a VH chain comprising HCDRs1-3 from VH chain of an anti-CD47 antibody, 5F9. The HCDRs1-3 from VH chain of B1.223, the LCDRs1-3 from VL chain of MRK16, and the HCDRs1-3 from VH chain of 5F9 are listed in Table 5. In certain embodiments, the bispecific antibody comprises the VH chain of B1.223, the VL chain of MRK16 as a common light chain, and the VH chain of 5F9.

In certain embodiments, the bispecific antibody comprises a VH chain comprising HCDRs1-3 from VH chain of B1.28, a common VL chain comprising LCDRs1-3 from VL chain of B1.28, and a VH chain comprising HCDRs1-3 from VH chain of an anti-CD47 antibody, 5F9. The HCDRs1-3 from VH chain of B1.28, the LCDRs1-3 from VL chain of B1.28, and the HCDRs1-3 from VH chain of 5F9 are listed in Table 5. In certain embodiments, the bispecific antibody comprises the VH chain of B1.28, the VL chain of B1.28 as a common light chain, and the VH chain of 5F9. In certain embodiments, the VH chain of B1.28, the VL chain of B1.28, and the VH chain of 5F9 may be humanized and have sequences as set forth in Table 5.

In certain instances, a first anti-MDR1 and anti-CD47 bispecific antibody of the present disclosure comprises the following sequences:

a first VH chain comprising HCDRs 1-3 of the VH chain of the 15D3 antibody;

a second VH chain comprising HCDRs 1-3 of the VH chain of the 5F9 antibody; and a common VL chain comprising LCDRs 1-3 of the VL chain of the B1.27 antibody, B1.VL6.CDR3mod antibody, B1.225v1 antibody, or the B1.89v antibody. Sequences of LCDRs 1-3 as well as VL chains of B1.VL6.CDR3mod antibody, B1.225v1 antibody, and the B1.89v antibody are set forth in Table 5.

In certain instances, a second anti-MDR1 and anti-CD47 bispecific antibody of the present disclosure comprises the following sequences:

a first VH chain comprising HCDRs 1-3 of the VH chain of the B1.188 antibody;

a second VH chain comprising HCDRs 1-3 of the VH chain of the 5F9 antibody; and a common VL chain comprising LCDRs 1-3 of the VL chain of the MRK16 antibody.

In certain instances, a third anti-MDR1 and anti-CD47 bispecific antibody of the present disclosure comprises the following sequences:

a first VH chain comprising HCDRs 1-3 of the VH chain of the B1.225 antibody;

a second VH chain comprising HCDRs 1-3 of the VH chain of the 5F9 antibody; and a common VL chain comprising LCDRs 1-3 of the VL chain of the MRK16 antibody.

In certain instances, a fourth anti-MDR1 and anti-CD47 bispecific antibody of the present disclosure comprises the following sequences:

a first VH chain comprising HCDRs 1-3 of the VH chain of the B1.28 antibody;

a second VH chain comprising HCDRs 1-3 of the VH chain of the 5F9 antibody; and a common VL chain comprising LCDRs 1-3 of the VL chain of the B1.28 antibody.

In certain instances, the first VH chain may comprise the amino acid sequence for a humanized VH chain of the B1.28.

In certain instances, a fifth anti-MDR1 and anti-CD47 bispecific antibody of the present disclosure comprises the following sequences:

a first VH chain comprising HCDRs 1-3 of the VH chain of the B1.261 antibody;

a second VH chain comprising HCDRs 1-3 of the VH chain of the 5F9 antibody; and a common VL chain comprising LCDRs 1-3 of the VL chain of the MRK16 antibody.

In certain instances, the first VH chain may be a humanized VH chain of the B1.261 antibody. In certain instances, the humanized version may comprise the amino acid sequence the VH of the B1.261 VH4 antibody. In certain instances, the common VL chain may be a humanized VL chain of the MRK16 antibody.

In certain instances, a sixth anti-MDR1 and anti-CD47 bispecific antibody of the present disclosure comprises the following sequences:

a first VH chain comprising HCDRs 1-3 of the VH chain of the B1.261 antibody;

a second VH chain comprising HCDRs 1-3 of the VH chain of the 5F9 antibody; and a common VL chain comprising LCDRs 1-3 of the VL chain of the B1.261 antibody.

In certain instances, the first VH chain may be a humanized VH chain of the B1.261 antibody. In certain instances, the humanized version may comprise the amino acid sequence the VH of the B1.261 VH4 antibody. In certain instances, the common VL chain may be a humanized VL chain of the B1.261 antibody. In certain instances, the humanized version may comprise the amino acid sequence the VL of the B1.261 VH4 antibody.

The following bispecific antibodies may be especially useful for binding to human and cynomolgus CD47 and to human ABCB1 on cell surface 15D3DD KT14KK B1.28.huL2 LC; 15D3DD KT14KK B1VL6/CDR3v2 LC; 15D3DD KT14KK MRK16v5 LC; and 15D3DD KT14KK B1.89v1 LC (See FIGS. 17A-17B). The amino acid sequences of the heavy and light chains of these antibodies are as follows:

15D3DD Heavy Chain:

```
                                    (SEQ ID NO: 309)
EVQLVESGGVVVQPGGSLRLSCAASGFTFSRYTMSWVRQAPGKGLEWVA

TISSGGGNTYYPDSVKGRFTVSRDNSKNSLYLQMNSLRTEDTALYYCAR

YGAGDAWFAYWGQGTLVTVSSASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YDTTPPVLDSDGSFFLYSDLTVDKSRWQQGNVFSCSVMHEALHNHYTQK

SLSLSPG
```

KT14KK Heavy Chain:

```
                                    (SEQ ID NO: 310)
QVQLVQSGAEVKKPGASVKVSCKASGYTFTNYNMHWVRQAPGQRLEWMG

TIIYPGNDDTSYNQKFKDRVTITADTSASTAYMELSSLRSEDTAVYYCAR

GGYRAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQP

REPQVYTLPPSRKELTKNQVSLTCLVKGFYPSDIAVEWESNGQPENNYK

TTPPVLKSDGSFFLYSKLTVDKSRWQQGNVFSCSVMHEALHNHYTQKSL

SLSPG
```

The VH region is indicated in bold in the heavy chain sequences set forth above. The HCDRs are italicized and underlined. The bispecific antibodies encompassed by the invention can include these heavy chains or only the HCDRs or only the VH chains present in these heavy chains.

B1.28.huL2 Common Light Chain:

```
                                    (SEQ ID NO: 21)
DVVLTQSPLSLPVTPGEPASISCRSSQNIVHSTGNTYLDWYLQKPGQSP

QLLIYKVSNRFSGVPDRFSGSGSGTDFTLKISRVEAEDVGVYYCFQGSH

IPRTFGQGTKLEIK
```

B1VL6/CDR3v2 Common Light Chain:

```
                                    (SEQ ID NO: 311)
DIVMTQSPLSLPVSLGDPASISCRSSQSLVHSNGNTYLEYYLQKPGQSP

KLLIYKVSNRFSGVPDRFSGSGSGTDFTLKISRVEAEDLGVYYCFQGSH

FPRTFGGGTKLEIK
```

MRK16v5 LC Common Light Chain:

```
                                    (SEQ ID NO: 312)
DIVMTQTPLSSPVTLGQPASISCRSSQSIVYSNGNTYLEWYQQKPGQPP

RLLIYKISNRFSGVPDRFSGSGAGTDFTLKISRVEAEDVGVYYCFQASH

FPRTFGGGTKLEIK
```

B1.89v1 Common Light Chain:

```
                                    (SEQ ID NO: 313)
DVLMTQTPLSLPVSLGDQASISCRSSQTIVHSNGNTYLEWYLQKPGQSP

KLLIYKVSKRFSGVPDRFSGSGSGTDFTLKISRVEAEDLGVYYCFQASH

FPRTFGGGTKLEIK
```

The LCDRs are in bold font. The bispecific antibodies encompassed by the invention can include one of these common light chains in combination with the 15D3DD Heavy Chain and the KT14 heavy chain as set forth above or the HCDRs or the VH chains thereof.

In certain instances, the TAA is Her2 or PD-1.

Anti-MDR1 and Anti-PD-L1 Bispecific Antibody

In certain aspects, the TAA may be Programmed death-ligand 1 (PD-L1). PD-L1 is also known as cluster of differentiation 274 (CD274) or B7 homolog 1 (B7-H1). In certain aspects, the bispecific antibody molecule that binds to MDR1 and PD-L1 includes the common light chain and the first VH chain as described in the preceding sections and the second VH chain comprises the HCDRs 1-3 of a VH chain comprising the amino acid sequence:

```
                                    (SEQ ID NO: 314)
EVQLVESGGGLVQPGGSLRLSCAASGFTFSDSWIHWVRQAPGKGLEWVA

WISPYGGSTYYADSVKGRFTISADTSKNTAYLQMNSLRAEDTAVYYCAR

RHWPGGFDYWGQGTLVTVSS
```

The HCDRs 1-3 defined as per Kabat nomenclature are:

HCDR1: DSWIH (SEQ ID NO:315)

HCDR2: WISPYGGSTYYADSVKG (SEQ ID NO:316)

HCDR3: RHWPGGFDY (SEQ ID NO:317)

The second VH chain of the bispecific antibody that binds to MDR1 and PD-L1 may have an amino acid sequence at least 80%, at least 90%, at least 95%, or a 100% identical to the amino acid sequence:

(SEQ ID NO: 314)
EVQLVESGGGLVQPGGSLRLSCAASGFTFSDSWIHWVRQAPGKGLEWVA

WISPYGGSTYYADSVKGRFTISADTSKNTAYLQMNSLRAEDTAVYYCAR

RHWPGGFDYWGQGTLVTVSS

The second VH chain of the bispecific antibody that binds to MDR1 and PD-L1 may be present in heavy chain having an amino acid sequence at least 80%, at least 90%, at least 95%, or a 100% identical to the amino acid sequence:

(SEQ ID NO: 318)
EVQLVESGGGLVQPGGSLRLSCAASGFTFSDSWIHWVRQAPGKGLEWVA

WISPYGGSTYYADSVKGRFTISADTSKNTAYLQMNSLRAEDTAVYYCAR

RHWPGGFDYWGQGTLVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPRE

EQYASTYRVVSVLTVLHQDWLNGKEYKCKVSNKALPAPIEKTISKAKGQ

PREPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQKS

LSLSPGK

In certain instances, an anti-MDR1 and anti-PDL1 bispecific antibody of the present disclosure comprises the following sequences:
  a first VH chain comprising HCDRs 1-3 of the VH chain of the B1.261 antibody;
  a second VH chain comprising HCDRs 1-3 of the VH chain of the Atezolizumab antibody; and
  a common VL chain comprising LCDRs 1-3 of the VL chain of the B1.261 antibody or the MRK16 antibody.
  In certain instances, the first VH chain of the anti-MDR1 and anti-PD-L1 bispecific antibody is humanized and comprises the amino acid sequence:
B1.261.huH1(VH4):

(SEQ ID NO: 126)
EVQLQESGPGLVKPSETLSLTCTVSGFSLTSYGVHWVRQPPGKGLEWLV

VIWSDGSTTYNSALKSRLTISKDNSKNQVSLKLSSVTAADTAVYYCARH

GRWLLQRGGAMDYWGQGTMVTVSS

B1.261.huH2(VH3):

(SEQ ID NO: 129)
EVQLVESGGGLIQPGGSLRLSCAVSGFSLTSYGVHWRQPPGKGLEWLVV

IWSDGSTTYNSALKSRLTISKDNSKNTVYLQMNSLRAEDTAVYYCARHG

RWLLQRGGAMDYWGQGTMVTVSS

In certain instances, the common VL chain of the anti-MDR1 and anti-PDL1 bispecific antibody is humanized and comprises the amino acid sequence:

(SEQ ID NO: 319)
DVQMTQSPSSLSASVGDRVTITCRASQNVGSYIAWYQQKPGKSPKALIY

-continued
SASYRSSGVPSRFSGSGAGTDFTLTISSLQPEDFATYFCQQYNSYPLTF

GGGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

Anti-MDR1 and Anti-HER2 Bispecific Antibody

In certain aspects, the TAA may be HER2. Erb-B2 Receptor Tyrosine Kinase 2 or HER2 is a member of the epidermal growth factor (EGF) receptor family of receptor tyrosine kinases. HER2 protein has no ligand binding domain of its own and therefore cannot bind growth factors. However, it does bind tightly to other ligand-bound EGF receptor family members to form a heterodimer, stabilizing ligand binding and enhancing kinase-mediated activation of downstream signaling pathways. Amplification and/or overexpression of the gene encoding HER2 has been reported in numerous cancers, including breast and ovarian tumors.

In certain aspects, the bispecific antibody molecule that binds to MDR1 and HER2 includes the common light chain and the first VH chain as described in the preceding sections and the second VH chain comprises the HCDRs 1-3 of a VH chain of an anti-Her2 antibody such as Trastuzumab or Pertuzumab.

Trastuzumab Heavy Chain Sequence:

(SEQ ID NO: 320)
EVQLVESGGGLVQPGGSLRLSCAASGFNIKDTYIHWVRQAPGKGLEWVA

RIYPTNGYTRYADSVKGRFTISADTSKNTAYLQMNSLRAEDTAVYYCSR

WGGDGFYAMDYWGQGTLVTVSSASTKGPSVFPLAPSSKSTSGGTAALGC

LVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFL

FPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAK

GQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQ

KSLSLSPGK

The VH region is underlined.
The HCDRs 1-3 defined as per Kabat nomenclature are:
HCDR1: GFNIKDT (SEQ ID NO:321)
HCDR2: YPTNGY (SEQ ID NO:322)
HCDR3: WGGDGFYAMDY (SEQ ID NO:323)
The second VH chain of the bispecific antibody that binds to MDR1 and HER2 may have an amino acid sequence at least 80%, at least 90%, at least 95%, or a 100% identical to the amino acid sequence of the VH chain of Trastuzumab or the heavy chain of Trastuzumab.

Pertuzumab Heavy Chain Sequence:

(SEQ ID NO: 324)
EVQLVESGGGLVQPGGSLRLSCAASGFTFTDYTMDWVRQAPGKGLEWVA

DVNPNSGGSIYNQRFKGRFTLSVDRSKNTLYLQMNSLRAEDTAVYYCAR

NLGPSFYFDYWGQGTLVTVSSASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

-continued

```
PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSREEMTKNQVSLTCLVKGFYPSDIAVEWESNGQPENN

YKTTPPVLDSDGSFFLYSKLTVDKSRWQQGNVFSCSVMHEALHNHYTQK

SLSLSPG
```

The VH region is underlined.
The HCDRs 1-3 defined as per Kabat nomenclature are:

```
HCDR1:
                                    (SEQ ID NO: 325)
GFTFTDY

HCDR2:
                                    (SEQ ID NO: 326)
NPNSGG

HCDR3:
                                    (SEQ ID NO:327)
NLGPSFYFDY
```

The second VH chain of the bispecific antibody that binds to MDR1 and HER2 may have an amino acid sequence at least 80%, at least 90%, at least 95%, or a 100% identical to the amino acid sequence of the VH chain of Pertuzumab or the heavy chain of Pertuzumab.

In certain instances, a first anti-MDR1 and anti-HER2 bispecific antibody of the present disclosure comprises the following sequences:
  a first VH chain comprising HCDRs 1-3 of the VH chain of the B1.129 antibody;
  a second VH chain comprising HCDRs 1-3 of the VH chain of the Pertuzumab or the Pertuzumab antibody; and
  a common VL chain comprising LCDRs 1-3 of the VL chain of the B1.129 antibody.

In certain instances, a second anti-MDR1 and anti-HER2 bispecific antibody of the present disclosure comprises the following sequences:
  a first VH chain comprising HCDRs 1-3 of the VH chain of the B1.188 antibody;
  a second VH chain comprising HCDRs 1-3 of the VH chain of the Pertuzumab or the Pertuzumab antibody; and
  a common VL chain comprising LCDRs 1-3 of the VL chain of the B1.188 antibody or the MRK16 antibody.

In certain instances, a third anti-MDR1 and anti-HER2 bispecific antibody of the present disclosure comprises the following sequences:
  a first VH chain comprising HCDRs 1-3 of the VH chain of the B1.261 antibody;
  a second VH chain comprising HCDRs 1-3 of the VH chain of the Pertuzumab or the Pertuzumab antibody; and
  a common VL chain comprising LCDRs 1-3 of the VL chain of the B1.261 antibody or the MRK16 antibody.

In certain instances, the first VH chain of the anti-MDR1 and anti-PDL1 bispecific antibody is humanized and comprises the amino acid sequence:
B1.261.huH1(VH4):

```
                                    (SEQ ID NO: 126)
EVQLQESGPGLVKPSETLSLTCTVSGFSLTSYGVHWVRQPPGKGLEWLV
```

-continued

```
VIWSDGSTTYNSALKSRLTISKDNSKNQVSLKLSSVTAADTAVYYCARH

GRWLLQRGGAMDYWGQGTMVTVSS
```

B1.261.huH2(VH3):

```
                                    (SEQ ID NO: 129)
EVQLVESGGGLIQPGGSLRLSCAVSGFSLTSYGVHWVRQPPGKGLEWLV

VIWSDGSTTYNSALKSRLTISKDNSKNTVYLQMNSLRAEDTAVYYCARH

GRWLLQRGGAMDYWGQGTMVTVSS
```

In certain instances, the common VL chain of the anti-MDR1 and anti-PDL1 bispecific antibody is humanized and comprises the amino acid sequence:

```
                                    (SEQ ID NO: 319)
DVQMTQSPSSLSASVGDRVTITCRASQNVGSYIAWYQQKPGKSPKALIY

SASYRSSGVPSRFSGSGAGTDFTLTISSLQPEDFATYFCQQYNSYPLTF

GGGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC
```

As described elsewhere herein, at least one, two, or all of the VL chain, the first VH chain, and the second VH may be humanized. In addition, the Fc regions of the VH chains may include substitutions to increase heterodimerization between the first and second VH chain. In certain aspects, the first heavy chain may be humanized and include the charged pair substitutions K392D and K409D and the second heavy chain and include the charged pair substitutions E356K and D399K.

In certain embodiments, one or more of the VH and VL chains may be humanized by, e.g., replacing at least one, two, three or four framework regions with framework regions from a human antibody.

In certain aspects, the bispecific antibody specifically binds to a cancer cell that expresses both MDR1 and a tumor-associated antigen. In certain aspects, the bispecific antibody preferentially binds to a cancer cell that expresses both MDR1 and a tumor-associated antigen as compared to its binding to a cell that expresses either MDR1 or a tumor-associated antigen.

In certain aspects, the bispecific antibody binds to a cancer cell that expresses both MDR1 and a tumor-associated antigen but not to (or with significantly less affinity to) normal cells that display low or undetectable expression of MDR1 or the relevant tumor-associated antigen. In other words, the bispecific antibody of the present disclosure does not bind to a cell that does not express both MDR1 and a TAA.

In some embodiments, multi-specific antibodies of the present disclosure may include a common light chain. As used herein, the term "common light chain" will generally refer to the use, and incorporation, of two copies of the same light chain into the multi-specific antibody. Put another way, a light chain, in the assembled multi-specific antibody, will associate with the MDR1-specific heavy chain and a second copy of the same light chain will associate with the cancer-associated antigen-specific heavy chain. In certain aspects, the common light chain may include the LCDRs of a VL chain listed in Table 2. The VH chain may include the HCDRs of a VH chain listed in Table 2.

The bispecific antibodies encompassed by the present disclosure do not include bispecific antibodies that bind to MDR-1 and CD47 and include HCDRs from the VH chain of the 15D3 antibody; HCDRs from the VH chain of the 5F9 antibody; and the LCDRs from the VL chain of the MRK16 antibody. Specifically, the bispecific antibodies of the present disclosure do not include the combination of:

a VH chain having the HCDRs present in the VH sequence:

(SEQ ID NO: 293)

EVKVVESGGVLVRPGGSLKLSCAASGFTFSRYTMSWVRQTPEKRLEWVA

TISSGGGNTYYPDSVKGRFTVSRDNAMSSLYLQMSSLRSEDTALYYCAR

YGAGDAWFAYWGQGTLVTVSA;

a VH chain having the HCDRs present in the VH sequence:

(SEQ ID NO: 294)

QVQLVQSGAEVKKPGASVKVSCKASGYTFTNYNMHWVRQAPGQRLEWMG

TIYPGNDDTSYNQKFKDRVTITADTSASTAYMELSSLRSEDTAVYYCAR

GGYRAMDYWGQGTLVTVSS;

and a common variable light chain having LCDRs present in the VL sequence:

(SEQ ID NO: 283)

DVLMTQTPVSLSVSLGDQASISCRSSQSIVHSTGNTYLEWYLQKPGQSP

KLLIYKISNRFSGVPDRFSGSGSGTDFTLKISRVEAEDLGVYYCFQASH

FPRTFGGGTKLEIK.

Specifically, the bispecific antibodies of the present disclosure do not include the combination of:

HCDRs of a VH region from an anti-MDR1 antibody having the following HCDR sequences: HCDR1: RYTMS (SEQ ID NO:301), HCDR2: TISSGGGN-TYYPDSVKG (SEQ ID NO:302), and HCDR3: YGAGDAWFAY (SEQ ID NO:305);

HCDRs of a VH region from an anti-CD47 antibody having the following HCDR sequences: HCDR1: NYNMH (SEQ ID NO:306), HCDR2: TIYPGNDDT-SYNQKFKD (SEQ ID NO:307), and HCDR3: GGY-RAMDY (SEQ ID NO:308);

and a common light chain having LCDRs of anti-MDR1 antibody having the following LCDR sequences: LCDR1: RSSQSIVHSTGNTYLE (SEQ ID NO:25), LCDR2: KISNRFS (SEQ ID NO:328), and LCDR3: FQASHFPRT (SEQ ID NO:329).

Certain bispecific antibodies that bind to MDR1 and CD47 on cell surface may include the LCDRs1-3 of a VL chain of an anti-MDR1 antibody, V6, as the common light chain and may include the HCDRs1-3 of a VH chain of the anti-MDR1 antibody B1.28, B1.30, B1.89, B1.129, B1.225, B1.261, 15D3, or MRK16 and the HCDRs1-3 of the VH chain of the 5F9 antibody or the B6H12 antibody. Certain bispecific antibodies that bind to MDR1 and CD47 on cell surface may include the VL chain of an anti-MDR1 antibody, V6, as the common light chain or a humanized version thereof and may include the VH chain of the anti-MDR1 antibody the anti-MDR1 antibody B1.28, B1.30, B1.89, B1.129, B1.225, B1.261, 15D3, or MRK16 or a humanized version thereof and the VH chain of the 5F9 antibody or the VH chain of the B6H12 antibody or the VH chain of a humanized version of the B6H12 antibody or the 5F9 antibody.

In some embodiments, a subject antibody is a recombinant or modified antibody, e.g., a chimeric, humanized, deimmunized or an in vitro generated antibody. The term "recombinant" or "modified" antibody as used herein is intended to include all antibodies that are prepared, expressed, created, or isolated by recombinant means, such as (i) antibodies expressed using a recombinant expression vector transfected into a host cell; (ii) antibodies isolated from a recombinant, combinatorial antibody library; (iii) antibodies isolated from an animal (e.g. a mouse) that is transgenic for human immunoglobulin genes; or (iv) antibodies prepared, expressed, created, or isolated by any other means that involves splicing of human immunoglobulin gene sequences to other DNA sequences. Such recombinant antibodies include humanized, CDR grafted, chimeric, deimmunized, and in vitro generated antibodies; and can optionally include constant regions derived from human germline immunoglobulin sequences.

Modified antibodies may include modified domains, including where any antibody domain may be modified from a naturally occurring form. In some embodiments, a modified antibody may include a modified heavy chain, including a modified Fc domain, including a modified CH2 and/or modified CH3 domain. In some instances, modified Fc domains may employ electrostatic steering effects, including but not limited to e.g., through the use of the procedures described in Gunasekeran et al, (2010) Journal of Biological Chemistry 285, 19637-19646; the disclosure of which is incorporated herein by reference in its entirety. In some instances, a bispecific antibody is assembled through charge pair substitutions at the CH3 domain, including but not limited to e.g., where one heavy chain is modified to contain K392D and K409D substitutions and the other heavy chain is modified to contained E356K and D399K substitutions. Charge pair substituted chains may preferentially form a heterodimer with one another. The numbering of the amino acid substitutions is per EU numbering system for Ig HCs.

In some instances, an antibody of the present disclosure includes charge pair substitutions. In some instances, an antibody of the present disclosure does not include charge pair substitutions. In some instances, an alternative means of promoting preferential heterodimer formation of desired chains may be employed.

In some instances, a modified heavy chain may include a knob-into-hole modification. "Knobs-into-holes" amino acid modification is a rational design strategy in antibody engineering, used for heterodimerization of the heavy chains, in the production of multi-specific antibodies, including bispecific IgG antibodies. For example, in incorporating the knobs-into-holes strategy into a bispecific antibody made from two monoclonal antibodies of different specificities, amino acid changes are engineered in order to create a "knob" on the CH3 of the heavy chain of monoclonal antibody 1 (mAb1) and a "hole" on the CH3 of the heavy chain of monoclonal antibody 2 (mAb2). The knob may be represented by a large amino acid, such as e.g., a tyrosine (Y), whereas the hole may be represented by small amino acid, such as a threonine (T). For example, a knobs-into-holes pair modification may be created a T22Y substitution in a first CH3 domain and Y86T substitution in the partner CH3 domain. Examples of knobs-into-holes modifications are described in Carter, J. Immunol. Methods, 248(1-2):7-15 (2001); Ridgway, J. B. et al. Protein Eng. 9(7):617-2 (1996); and Merchant, A. M. et al. Nat. Biotechnol. 16(7):677-81 (1998); the disclosures of which are incorporated herein in their entirety. In antibodies generated from paired knob-into-hole modified domains the bispecific heterodimer will generally represent the major fraction.

As noted above, the subject anti-MDR1 antibody specifically binds one or more epitopes of MDR1. Thus, the epitope is a MDR1 epitope. The size of a MDR1 epitope bound by anti-MDR1 antibody may vary, including where the MDR1 epitope is formed by a polypeptide having a contiguous stretch of a MDR1 sequence that may range from 3 aa or less to 12 aa or more, including but not limited to e.g., 4 aa, 5 aa, 6 aa, 7 aa, 8 aa, 9 aa, 10 aa, 11 aa, 12 aa, 4 aa to 10 aa, 5 aa to 10 aa, 6 aa to 10 aa, 4 aa to 8 aa, 5 aa to 8 aa, 6 aa to 8 aa, etc.

In some embodiments, the MDR1 epitope can be formed by a polypeptide having at least about 75%, at least about 80%, at least about 85%, at least about 90%, at least about 95%, at least about 98%, at least about 99%, or 100%, amino acid sequence identity to a contiguous stretch of a MDR1 sequence, including but not limited to e.g., the human MDR1 sequence:

```
                                    (SEQ ID NO: 330)
MDLEGDRNGGAKKKNFFKLNNKSEKDKKEKKPTVSVFSMFRYSNWLDKL

YMVVGTLAAIIHGAGLPLMMLVFGEMTDIFANAGNLEDLMSNITNRSDI

NDTGFFMNLEEDMTRYAYYYSGIGAGVLVAAYIQVSFWCLAAGRQIHKI

RKQFFHAIMRQEIGWFDVHDVGELNTRLTDDVSKINEGIGDKIGMFFQS

MATFFTGFIVGFTRGWKLTLVILAISPVLGLSAAVWAKILSSFTDKELL

AYAKAGAVAEEVLAAIRTVIAFGGQKKELERYNKNLEEAKRIGIKKAIT

ANISIGAAFLLIYASYALAFWYGTTLVLSGEYSIGQVLTVFFSVLIGAF

SVGQASPSIEAFANARGAAYEIFKIIDNKPSIDSYSKSGHKPDNIKGNL

EFRNVHFSYPSRKEVKILKGLNLKVQSGQTVALVGNSGCGKSTTVQLMQ

RLYDPTEGMVSVDGQDIRTINVRFLREIIGVVSQEPVLFATTIAENIRY

GRENVTMDEIEKAVKEANAYDFIMKLPHKFDTLVGERGAQLSGGQKQRI

AIARALVRNPKILLLDEATSALDTESEAVVQVALDKARKGRTTIVIAHR

LSTVRNADVIAGFDDGVIVEKGNHDELMKEKGIYFKLVTMQTAGNEVEL

ENAADESKSEIDALEMSSNDSRSSLIRKRSTRRSVRGSQAQDRKLSTKE

ALDESIPPVSFWRIMKLNLTEWPYFVVVGVFCAIINGGLQPAFAIIFSKI

IGVFTRIDDPETKRQNSNLFSLLFLALGIISFITFFLQGFTFGKAGEIL

TKRLRYMVFRSMLRQDVSWFDDPKNTTGALTTRLANDAAQVKGAIGSRL

AVITQNIANLGTGIIISFIYGWQLTLLLLAIVPIIAIAGVVEMKMLSGQ

ALKDKKELEGSGKIATEAIENFRTVVSLTQEQKFEHMYAQSLQVPYRNS

LRKAHIFGITFSFTQAMMYFSYAGCFRFGAYLVAHKLMSFEDVLLVFSA

VVFGAMAVGQVSSFAPDYAKAKISAAHIIMIIEKTPLIDSYSTEGLMPN

TLEGNVTFGEVVFNYPTRPDIPVLQGLSLEVKKGQTLALVGSSGCGKST

VVQLLERFYDPLAGKVLLDGKEIKRLNVQWLRAHLGIVSQEPILFDCSI

AENIAYGDNSRVVSQEEIVRAAKEANIHAFIESLPNKYSTKVGDKGTQL

SGGQKQRIAIARALVRQPHILLLDEATSALDTESEKVVQEALDKAREGR

TCIVIAHRLSTIQNADLIVVFQNGRVKEHGTHQQLLAQKGIYFSMVSVQ

AGTKRQ;
``` or a rodent MDR1 sequence, such as e.g., the mouse MDR1a sequence or mouse MDR1b sequence:
Mouse MDR1a Sequence:

```
                                    (SEQ ID NO: 331)
MELEEDLKGRADKNFSKMGKKSKKEKKEKKPAVSVLTMFRYAGWLDRLY

MLVGTLAAIIHGVALPLMMLIFGDMTDSFASVGNVSKNSTNMSEADKRA

MFAKLEEEMTTYAYYYTGIGAGVLIVAYIQVSFWCLAAGRQIHKIRQKF

FHAIMNQEIGWFDVHDVGELNTRLTDDVSKINEGIGDKIGMFFQAMATF

FGGFIIGFTRGWKLTLVILAISPVLGLSAGIWAKILSSFTDKELHAYAK

AGAVAEEVLAAIRTVIAFGGQKKELERYNNNLEEAKRLGIKKAITANIS

MGAAFLLIYASYALAFWYGTSLVISKEYSIGQVLTVFFSVLIGAFSVGQ

ASPNIEAFANARGAAYEVFKIIDNKPSIDSFSKSGHKPDNIQGNLEFKN

IHFSYPSRKEVQILKGLNLKVKSGQTVALVGNSGCGKSTTVQLMQRLYD

PLDGMVSIDGQDIRTINVRYLREIIGVVSQEPVLFATTIAENIRYGRED

VTMDEIEKAVKEANAYDFIMKLPHQFDTLVGERGAQLSGGQKQRIAIAR

ALVRNPKILLLDEATSALDTESEAVVQAALDKAREGRTTIVIAHRLSTV

RNADVIAGFDGGVIVEQGNHDELMREKGIYFKLVMTQTAGNEIELGNEA

CKSKDEIDNLDMSSKDSGSSLIRRRSTRKSICGPHDQDRKLSTKEALDE

DVPPASFWRILKLNSTEWPYFVVGIFCAIINGGLQPAFSVIFSKVVGVF

TNGGPPETQRQNSNLFSLLFLILGIISFITFFLQGFTFGKAGEILTKRL

RYMVFKSMLRQDVSWFDDPKNTTGALTTRLANDAAQVKGATGSRLAVIF

QNIANLGTGIIISLIYGWQLTLLLLAIVPIIAIAGVVEMKMLSGQALKD

KKELEGSGKIATEAIENFRTVVSLTREQKFETMYAQSLQIPYRNAMKKA

HVFGITFSFTQAMMYFSYAACFRFGAYLVTQQLMTFENVLLVFSAIVFG

AMAVGQVSSFAPDYAKATVSASHIIRIIEKTPEIDSYSTQGLKPNMLEG

NVQFSGVVFNYPTRPSIPVLQGLSLEVKKGQTLALVGSSGCGKSTVVQL

LERFYDPMAGSVFLDGKEIKQLNVQWLRAQLGIVSQEPILFDCSIAENI

AYGDNSRVVSYEEIVRAAKEANIHQFIDSLPDKYNTRVGDKGTQLSGGQ

KQRIAIARALVRQPHILLLDEATSALDTESEKVVQEALDKAREGRTCIV

IAHRLSTIQNADLIVVIQNGKVKEHGTHQQLLAQKGIYFSMVSVQAGAK

RS
```

```
                                    (SEQ ID NO: 332)
MEFEENLKGRADKNFSKMGKKSKKEKKEKKPAVGVFGMFRYADWLDKLC

MILGTLAAIIHGTLLPLLMLVFGNMTDSFTKAEASILPSITNQSGPNST

LIISNSSLEEEMAIYAYYYTGIGAGVLIVAYIQVSLWCLAAGRQIHKIR

QKFFHAIMNQEIGWFDVHDVGELNTRLTDDVSKINDGIGDKIGMFFQSI

TTFLAGFIIGFISGWKLTLVILAVSPLIGLSSALWAKVLTSFTNKELQA

YAKAGAVAEEVLAAIRTVIAFGGQQKELERYNKNLEEAKNVGIKKAITA

SISIGIAYLLVYASYALAFWYGTSLVLSNEYSIGEVLTVFFSILLGTFS

IGHLAPNIEAFANARGAAFEIFKIIDNEPSIDSFSTKGYKPDSIMGNLE

FKNVHFNYPSRSEVQILKGLNLKVKSGQTVALVGNSGCGKSTTVQLMQR
```

-continued

```
LYDPLEGVVSIDGQDIRTINVRYLREIIGVVSQEPVLFATTIAENIRYG

REDVTMDEIEKAVKEANAYDFIMKLPHQFDTLVGERGAQLSGGQKQRIA

IARALVRNPKILLLDEATSALDTESEAVVQAALDKAREGRTTIVIAHRL

STVRNADVIAGFDGGVIVEQGNHDELMREKGIYFKLVMTQTRGNEIEPG

NNAYGSQSDTDASELTSEESKSPLIRRSIYRSVHRKQDQERRLSMKEAV

DEDVPLVSFWRILNLNLSEWPYLLVGVLCAVINGCIQPVFAIVFSRIVG

VFSRDDDHETKRQNCNLFSLFFLVMGLISFVTYFFQGFTFGKAGEILTK

RVRYMVFKSMLRQDISWFDDHKNSTGSLTTRLASDASSVKGAMGARLAV

VTQNVANLGTGVILSLVYGWQLTLLLVVIIPLIVLGGIIEMKLLSGQAL

KDKKQLEISGKIATEAIENFRTIVSLTREQKFETMYAQSLQVPYRNAMK

KAHVFGITFSFTQAMMYFSYAACFRFGAYLVAQQLMTFENVMLVFSAVV

FGAMAAGNTSSFAPDYAKAKVSASHIIRIIEKTPEIDSYSTEGLKPTLL

EGNVKFNGVQFNYPTRPNIPVLQGLSLEVKKGQTLALVGSSGCGKSTVV

QLLERFYDPMAGSVFLDGKEIKQLNVQWLRAHLGIVSQEPILFDCSIAE

NIAYGDNSRAVSHEEIVRAAKEANIHQFIDSLPDKYNTRVGDKGTQLSG

GQKQRIAIARALVRQPHILLLDEATSALDTESEKVVQEALDKAREGRTC

IVIAHRLSTIQNADLIVVIENGKVKEHGTHQQLLAQKGIYFSMVQAGAK

RS,
``` or a non-human primate sequence, such as e.g., the *Pan troglodytes* (Chimpanzee) sequence:

```
                                        (SEQ ID NO: 333)
MDLEGDRNGGAKKKNFFKLNNKSEKDKKEKKPTVSVFSMFRYSNWLDKL

YMVVGTLAAIIHGAGLPLMMLVFGEMTDIFANAGNLEDLMSNITNRSDI

NDTGFFMNLEEDMTRYAYYYSGIGAGVLVAAYIQVSFWCLAAGRQIHKI

RKQFFHAIMRQEIGWFDVHDVGELNTRLTDDVSKINEGIGDKIGMFFQS

MATFFTGFIVGFTRGWKLTLVILAISPVLGLSAAVWAKILSSFTDKELL

AYAKAGAVAEEVLAAIRTVIAFGGQKKELERYNKNLEEAKRIGIKKAIT

ANISIGAAFLLIYASYALAFWYGTTLVLSGEYSIGQVLTVFFSVLIGAF

SVGQASPSIEAFANARGAAYEIFKIIDNKPSIDSYSKSGHKPDNIKGNL

EFRNVHFSYPSRKQVKILKGLNLKVQSGQTVALVGNSGCGKSTTVQLMQ

RLYDPTEGMVSVDGQDIRTINVRFLREIIGVVSQEPVLFATTIAENIRY

GRENVTMDEIEKAVKEANAYDFIMKLPHKFDTLVGERGAQLSGGQKQRI

AIARALVRNPKILLLDEATSALDTESEAVVQVALDKARKGRTTIVIAHR

LSTVRNADVIAGFDDGVIVEKGNHDELMKEKGIYFKLVTMQTAGNEVEL

ENAADESKSEIDALEMSSNDSRSSLIRKRSTRRSVRGSQAQDRKLSTKE

ALDESIPPVSFWRIMKLNLTEWPYFVVGVFCAIINGGLQPAFAIIFSKI

IGVFTRIDDPETKRQNSNLFSLLFLVLGIISFITFFLQGFTFGKAGEIL

TKRLRYMVFRSMLRQDVSWFDDPKNTTGALTTRLANDAAQVKGAIGSRL

AVITQNIANLGTGIIISFIYGWQLTLLLLAIVPIIAIAGVVEMKMLSGQ

ALKDKKELEGAGKIASEAIENFRTVVSLTQEQKFEHMYAQSLQVPYRNS

LRKAHIFGITFSFTQAMMYFSYAGCFRFGAYLVAHKLMSFEDVLLVFSA
```

-continued

```
VVFGAMAVGQVSSFAPDYAKAKISAAHIIMIIEKTPLIDSYSTEGLTPN

TLEGNVTFGEVVFNYPTRPDIPVLQGLSLEVKKGQTLALVGSSGCGKST

VVQLLERFYDPLAGKVLLDGKEIKRLNVQWLRAHLGIVSQEPILFDCSI

AENIAYGDNSRVVSQEEIVRAAKEANIHAFIESLPNKYSTRVGDKGTQL

SGGQKQRIAIARALVRQPHILLLDEATSALDTESEKVVQEALDKAREGR

TCIVIAHRLSTIQNADLIVVFQNGRVKEHGTHQQLLAQKGIYFSMVSVQ

AGTKRQ,
``` or the *Macaca fascicularis* (Crab-eating macaque) sequence:

```
                                        (SEQ ID NO: 334)
MDLEGDRNGGAEKKNFFKLNNKSKKDKKERKPTVSVFSMFRYSNWLDKL

YMVVGTLAAIIHGAGLPLMMLVFGDMTDTFANAGNLGDLGALLFNNTNS

SNITDTVPVMNLEEDMTRYAYYYSGIGAGVLVAAYIQVSFWCLAAGRQI

HKIRKQFFHAIMRQEIGWFDVHDVGELNTRLTDDVSKINEGIGDKIGMF

FQSMATFFTGFIVGFTRGWKLTLVILAISPVLGLSAAVWAKILSSFTDK

ELLAYAKAGAVAEEVLAAIRTVIAFGGQKKELERYNKNLEEAKRIGIKK

AITANISIGAAFLLIYASYALAFWYGTTLVLSKEYSIGQVLTVFFSVLI

GAFSVGQASPSIEAFANARGAAFEIFKIIDNKPSIDSYSKSGHKPDNIK

GNLEFRNVHFSYPSRKEVKILKGLNLKVQSGQTVALVGNSGCGKSTTVQ

LMQRLYDPTEGMVSVDGQDIRTINVRFLREIIGVVSQEPVLFATTIAEN

IRYGREDVTMDEIEKAVKEANAYDFIMKLPQKFDTLVGERGAQLSGGQK

QRIAIARALVRNPKILLLDEATSALDTESEAVVQVALDKARKGRTTIVI

AHRLSTVRNADVIAGFDDGVIVEKGNHDELMKEKGIYFKLVTMQTAGNE

IELENAADESKSEIDTLEMSSHDSGSSLIRKRSTRRSVRGSQGQDRKLS

TKEALDESIPPVSFWRIMKLNLTEWPYFVVGVFCAIINGGLQPAFAVIF

SKIIGIFTRNDDAETKRQNSNLFSLLFLVLGIVSFITFFLQGFTFGKAG

EILTKRLRYMVFRSMLRQDVSWFDDPKNTTGALTTRLANDAAQVKGAIG

SRLAIITQNIANLGTGIIISLIYGWQLTLLLLAIVPIIAIAGVVEMKML

SGQALKDKKELEGAGKIATEAIENFRTVVSLTQEQKFEHMYDQSLQVPY

RNSLRKAHIFGITFSFTQAMMYFSYAGCFRFGAYLVAHSLMSFEDVLLV

FSAVVFGAMAVGQVSSFAPDYAKAKVSAAHIIMIIEKTPLIDSYSTEGL

KPNTLEGNVTFNEVVFNYPTRLDIPVLQGLSLEVKKGQTLALVGSSGCG

KSTVVQLLERFYDPLAGKVLLDGKEIKQLNVQWLRAHLGIVSQEPILFD

CSISENIAYGDNSRVVSQEEIVRAAKEANIHAFIESLPNKYSTRVGDKG

TQLSGGQKQRIAIARALVRQPHILLLDEATSALDTESEKVVQEALDKAR

EGRTCIVIAHRLSTIQNADLIVVFQNGRVKEHGTHQQLLAQKGIYFSMV

SVQAGAKRQ,
``` or the like.

A subject anti-MDR1 antibody exhibits high affinity binding to MDR1. For example, a subject anti-MDR1 antibody binds to a human MDR1 with an affinity of at least about $10^{-7}$ M, at least about $10^{-8}$ M, at least about $10^{-9}$ M, or at least about $10^{-10}$ M. A subject anti-MDR1 antibody binds to an epitope present on MDR1 with an affinity of from about $10^{-7}$ M to about $10^{-8}$ M, from about $10^{-8}$ M to about $10^{-9}$M, or from about $10^{-9}$ M to about $10^{-10}$ M.

A subject anti-MDR1 antibody exhibits substantially no binding to any epitopes formed by amino acids within other related, but sequence dissimilar, proteins such as related but sequence dissimilar EPs. Any binding of a subject anti-MDR1 antibody to an epitope formed by amino acids within a related, but sequence dissimilar, protein is generally non-specific binding of a substantially lower affinity than the specific binding of the anti-MDR1 antibody to the epitope on MDR1. A substantially lower affinity is generally at least a 2 fold, 3 fold, 5 fold, 10 fold, 50 fold, 100 fold, 500 fold, or 1000 fold lower affinity.

A subject anti-MDR1 antibody can reduce transport of molecules through a MDR1 transporter, e.g., a human MDR1. For example, a subject anti-MDR1 antibody can reduce transport by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the degree of transport in the absence of the anti-MDR1 antibody.

In some embodiments, a subject antibody comprises FR regions that are mammalian sequences, including e.g., rodent, non-human primate, and human sequences (e.g., encoded by the respective heavy chain FR-encoding sequences).

A subject antibody can comprise a heavy chain variable (VH) region comprising an amino acid sequence that is 85%, 86%, 87%, 88%, 89%, 90%, 91%, 92%, 93%, 94%, 95%, 96%, 97%, 98%, 99%, or more, including 100%, identical to a sequence for a VH region of a VH-VL pair of an antibody set forth in Table 2. The subject antibody can comprise a light chain variable (VL) region comprising an amino acid sequence that is 85%, 86%, 87%, 88%, 89%, 90%, 91%, 92%, 93%, 94%, 95%, 96%, 97%, 98%, 99%, or more, including 100%, identical to a sequence for a VL of the VH-VL region pair of the antibody set forth in Table 2.

Regions and/or chains of the subject antibodies may or may not be joined by one or more linker regions. Where present, the linker region can be from about 5 amino acids to about 50 amino acids in length, e.g., from about 5 aa to about 10 aa, from about 10 aa to about 15 aa, from about 15 aa to about 20 aa, from about 20 aa to about 25 aa, from about 25 aa to about 30 aa, from about 30 aa to about 35 aa, from about 35 aa to about 40 aa, from about 40 aa to about 45 aa, or from about 45 aa to about 50 aa in length.

Linkers suitable for use a subject antibody include "flexible linkers". If present, the linker molecules are generally of sufficient length to permit some flexible movement between linked regions. The linker molecules are generally about 6-50 atoms long. The linker molecules may also be, for example, aryl acetylene, ethylene glycol oligomers containing 2-10 monomer units, diamines, diacids, amino acids, or combinations thereof. Other linker molecules which can bind to polypeptides may be used in light of this disclosure.

Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers $(G)_n$, glycine-serine polymers (including, for example, $(GS)_n$, GSGGS$_n$ (SEQ ID NO:335) and GGGS$_n$ (SEQ ID NO:336), where n is an integer of at least one), glycine-alanine polymers, alanine-serine polymers, and other flexible linkers known in the art. Glycine and glycine-serine polymers are of interest since both of these amino acids are relatively unstructured, and therefore may serve as a neutral tether between components. Glycine polymers are of particular interest since glycine accesses significantly more phi-psi space than even alanine, and is much less restricted than residues with longer side chains (see Scheraga, *Rev. Computational Chem.* 11173-142 (1992)). Exemplary flexible linkers include, but are not limited to GGSG (SEQ ID NO:337), GGSGG (SEQ ID NO:338), GSGSG (SEQ ID NO:339), GSGGG (SEQ ID NO:340), GGGSG (SEQ ID NO:341), GSSSG (SEQ ID NO:342), and the like. The ordinarily skilled artisan will recognize that design of a peptide conjugated to any elements described above can include linkers that are all or partially flexible, such that the linker can include a flexible linker as well as one or more portions that confer less flexible structure.

In other instances, the flexibility of the hinge region of an antibody of the present disclosure may be reduced by either mutating amino acid C220 to serine or any other natural amino acid, by removing C220, by removing the complete hinge, or by replacing the IgG1 hinge with an IgG3 hinge, an antibody is formed in which the light chains are connected via their C-terminal cysteines, analogous to the situation found in the human isotype IgA2m. This results in a reduced flexibility of the Fabs relative to the Fc and consequently reduced cross-linking capacity. Another strategy to reduce the flexibility of an IgG1 molecule is to replace the IgG1 hinge with the IgG2 hinge or IgG2-like hinge. Alternatively, a variant of the IgG1 hinge that resembles the IgG2 hinge can be introduced. This mutant (TH7Δ6-9) contains mutation T223C and two deletions (K222 and T225) in order to create a shorter hinge with an additional cysteine.

The substitution of mouse CDRs into a human variable domain framework can result in retention of their correct spatial orientation where, e.g., the human variable domain framework adopts the same or similar conformation to the mouse variable framework from which the CDRs originated. This can be achieved by obtaining the human variable domains from human antibodies whose framework sequences exhibit a high degree of sequence identity with the murine variable framework domains from which the CDRs were derived. The heavy and light chain variable framework regions can be derived from the same or different human antibody sequences. The human antibody sequences can be the sequences of naturally occurring human antibodies or can be consensus sequences of several human antibodies. See Kettleborough et al., Protein Engineering 4:773 (1991); Kolbinger et al., Protein Engineering 6:971 (1993).

Having identified the complementarity determining regions of the murine donor immunoglobulin and appropriate human acceptor immunoglobulins, the next step is to determine which, if any, residues from these components should be substituted to optimize the properties of the resulting humanized antibody. In general, substitution of human amino acid residues with murine should be minimized, because introduction of murine residues increases the risk of the antibody eliciting a human-anti-mouse-antibody (HAMA) response in humans. Art-recognized methods of determining immune response can be performed to monitor a HAMA response in a particular patient or during clinical trials. Patients administered humanized antibodies can be given an immunogenicity assessment at the beginning and throughout the administration of said therapy. The HAMA response is measured, for example, by detecting antibodies to the humanized therapeutic reagent, in serum samples from the patient using a method known to one in the art, including surface plasmon resonance technology (BIA-CORE) and/or solid-phase ELISA analysis. In many embodiments, a subject humanized antibody does not substantially elicit a HAMA response in a human subject.

Certain amino acids from the human variable region framework residues are selected for substitution based on their possible influence on CDR conformation and/or binding to antigen. The unnatural juxtaposition of murine CDR regions with human variable framework region can result in conformational restraints, which, unless corrected by substitution of certain amino acid residues, lead to loss of binding affinity.

The selection of amino acid residues for substitution can be determined, in part, by computer modeling. Computer hardware and software for producing three-dimensional images of immunoglobulin molecules are known in the art. In general, molecular models are produced starting from solved structures for immunoglobulin chains or domains thereof. The chains to be modeled are compared for amino acid sequence similarity with chains or domains of solved three-dimensional structures, and the chains or domains showing the greatest sequence similarity is/are selected as starting points for construction of the molecular model. Chains or domains sharing at least 50% sequence identity are selected for modeling, and preferably those sharing at least 60%, 70%, 80%, 90% sequence identity or more are selected for modeling. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

In some embodiments, a subject antibody comprises scFv multimers. For example, in some embodiments, a subject antibody is an scFv dimer (e.g., comprises two tandem scFv (scFv$_2$)), an scFv trimer (e.g., comprises three tandem scFv (scFv$_3$)), an scFv tetramer (e.g., comprises four tandem scFv (scFv$_4$)), or is a multimer of more than four scFv (e.g., in tandem). The scFv monomers can be linked in tandem via linkers of from about 2 amino acids to about 15 amino acids in length, e.g., 2 aa, 3 aa, 4 aa, 5 aa, 6 aa, 7 aa, 8 aa, 9 aa, 10 aa, 11 aa, 12 aa, 13 aa, 14 aa, or 15 aa in length. Suitable linkers include, e.g., (Gly)$_x$, where x is an integer from 2 to 15. Other suitable linkers are those discussed above. In some embodiments, each of the scFv monomers in a subject scFV multimer is humanized, as described above. In certain aspects, a bispecific antibody may be in any molecular format known in the literature. For a comprehensive overview of different bispecific antibody formats and method of making see, e.g. Brinkmann and Kontermann, *MAbs.* 2017, 9(2):182-212. For example, a bispecific antibody of the present disclosure may have a molecular format described in Spiess C. et al., Mol Immunol. 2015 October; 67(2 Pt A):95-106.

In some embodiments, a subject antibody comprises a constant region of an immunoglobulin (e.g., an Fc region). The Fc region, if present, can be a human Fc region. If constant regions are present, the antibody can contain both light chain and heavy chain constant regions. Suitable heavy chain constant region include CH1, hinge, CH2, CH3, and CH4 regions. The antibodies described herein include antibodies having all types of constant regions, including IgM, IgG, IgD, IgA and IgE, and any isotype, including IgG1, IgG2, IgG3 and IgG4. An example of a suitable heavy chain Fc region is a human isotype IgG1 Fc. Light chain constant regions can be lambda or kappa. A subject antibody (e.g., a subject humanized antibody) can comprise sequences from more than one class or isotype. Antibodies can be expressed as tetramers containing two light and two heavy chains, as separate heavy chains, light chains, as Fab, Fab' F(ab')2, and Fv, or as single chain antibodies in which heavy and light chain variable domains are linked through a spacer.

In some embodiments, a subject antibody comprises a free thiol (—SH) group at the carboxyl terminus, where the free thiol group can be used to attach the antibody to a second polypeptide (e.g., another antibody, including a subject antibody), a scaffold, a carrier, etc.

A subject antibody can be covalently linked to a second moiety (e.g., a lipid, a polypeptide other than a subject antibody, a synthetic polymer, a carbohydrate, a toxin and the like) using for example, glutaraldehyde, a homobifunctional cross-linker, or a heterobifunctional cross-linker. Glutaraldehyde cross-links polypeptides via their amino moieties. Homobifunctional cross-linkers (e.g., a homobifunctional imidoester, a homobifunctional N-hydroxysuccinimidyl (NHS) ester, or a homobifunctional sulfhydryl reactive cross-linker) contain two or more identical reactive moieties and can be used in a one-step reaction procedure in which the cross-linker is added to a solution containing a mixture of the polypeptides to be linked. Homobifunctional NHS ester and imido esters cross-link amine containing polypeptides. In a mild alkaline pH, imido esters react only with primary amines to form imidoamides, and overall charge of the cross-linked polypeptides is not affected. Homobifunctional sulfhydryl reactive cross-linkers includes bismaleimidohexane (BMH), 1,5-difluoro-2,4-dinitrobenzene (DFDNB), and 1,4-Bis[3-(2-pyridyldithio)propionamido]butane (DPDPB).

Compositions and Formulations

The present disclosure provides a composition comprising a subject antibody. A subject antibody composition can comprise, in addition to a subject antibody, one or more of: a salt, e.g., NaCl, MgCl$_2$, KCl, MgSO$_4$, etc.; a buffering agent, e.g., a Tris buffer, a histidine buffer, N-(2-Hydroxyethyl)piperazine-N'-(2-ethanesulfonic acid) (HEPES), 2-(N-Morpholino)ethanesulfonic acid (MES), 2-(N-Morpholino) ethanesulfonic acid sodium salt (MES), 3-(N-Morpholino) propanesulfonic acid (MOPS), N-tris[Hydroxymethyl] methyl-3-aminopropanesulfonic acid (TAPS), etc.; a solubilizing agent; a detergent, e.g., a non-ionic detergent such as Tween-20, etc.; a protease inhibitor; glycerol; and the like.

Compositions of the present disclosure also include pharmaceutical compositions that include an antibody described herein. In general, a formulation comprises an effective amount of the subject antibody. An "effective amount" means a dosage sufficient to produce a desired result, e.g., reduction in a cancer of a subject, reduction in the growth rate of a cancer in a subject, amelioration of a symptom of cancer, and the like. Generally, the desired result is at least a reduction in a symptom of a cancer, reduction in the growth of a cancer, reduction in the size of a cancer, etc., as compared to a control. A subject antibody can be delivered, or be formulated, in such a manner as to avoid the blood-brain barrier.

In some instances, an antibody may include a delivery enhancer, including where such enhancers may facilitate crossing of the blood-brain barrier, increased permeability, e.g., allowing for efficient transdermal delivery, and the like.

In some instances, the antibodies of the present disclosure may not be administered in a formulation with a delivery enhancer. In some instances, the antibodies of the present disclosure may themselves enhance permeability across the blood-brain barrier. In some instances, the antibodies of the present disclosure may be used as a delivery enhancer to facilitate crossing of the blood-brain barrier by an anti-neoplastic agent, e.g., an immunotherapeutic agent or a chemotherapeutic agent. In some instances, the antibodies of the present disclosure may be used as a delivery enhancer to facilitate crossing of the blood-brain barrier, blood-cerebro-spinal fluid (CSF) barrier, blood-testis barrier, or blood-placenta barrier by an active agent, such as, another antibody or a chemotherapeutic agent.

In the subject methods, a subject antibody can be administered to the host using any convenient means capable of resulting in the desired therapeutic effect or diagnostic effect. Thus, the agent can be incorporated into a variety of formulations for therapeutic administration. More particularly, a subject antibody can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, a subject antibody can be administered in conjunction with a pharmaceutically acceptable excipient, or they may also be used alone or in appropriate association, as well as in combination, with other pharmaceutically active compounds. The following methods and excipients are merely exemplary and are in no way limiting.

A subject antibody can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Pharmaceutical compositions comprising a subject antibody are prepared by mixing the antibody having the desired degree of purity with optional physiologically acceptable carriers, excipients, stabilizers, surfactants, buffers and/or tonicity agents. Acceptable carriers, excipients and/or stabilizers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as Tween, Brij Pluronics, Triton-X, or polyethylene glycol (PEG).

The pharmaceutical composition may be in a liquid form, a lyophilized form or a liquid form reconstituted from a lyophilized form, wherein the lyophilized preparation is to be reconstituted with a sterile solution prior to administration.

Exemplary antibody concentrations in a subject pharmaceutical composition may range from about 1 mg/mL to about 200 mg/ml or from about 50 mg/mL to about 200 mg/mL, or from about 150 mg/mL to about 200 mg/mL.

An aqueous formulation of the antibody may be prepared in a pH-buffered solution, e.g., at pH ranging from about 4.0 to about 7.5 or from about 5.0 to about 6.0, or alternatively about 5.5. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

In some embodiments, the aqueous formulation is isotonic, although hypertonic or hypotonic solutions may be suitable. The term "isotonic" denotes a solution having the same tonicity as some other solution with which it is compared, such as physiological salt solution or serum. Tonicity agents may be used in an amount of about 5 mM to about 350 mM, e.g., in an amount of 100 mM to 350 nM.

A surfactant may also be added to the antibody formulation to reduce aggregation of the formulated antibody and/or minimize the formation of particulates in the formulation and/or reduce adsorption. Exemplary surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulfate (SDS). Exemplary concentrations of surfactant may range from about 0.001% to about 1% w/v.

A lyoprotectant may also be added in order to protect the labile active ingredient (e.g. a protein) against destabilizing conditions during the lyophilization process. For example, known lyoprotectants include sugars (including glucose and sucrose); polyols (including mannitol, sorbitol and glycerol); and amino acids (including alanine, glycine and glutamic acid). Lyoprotectants can be included in an amount of about 10 mM to 500 nM.

In some embodiments, a subject formulation includes a subject antibody, and one or more of the above-identified agents (e.g., a surfactant, a buffer, a stabilizer, a tonicity agent) and is essentially free of one or more preservatives, such as ethanol, benzyl alcohol, phenol, m-cresol, p-chlor-m-cresol, methyl or propyl parabens, benzalkonium chloride, and combinations thereof. In other embodiments, a preservative is included in the formulation, e.g., at concentrations ranging from about 0.001 to about 2% (w/v).

For example, a subject formulation can be a liquid or lyophilized formulation suitable for parenteral administration, and can comprise: about 1 mg/mL to about 200 mg/mL of a subject antibody; about 0.001% to about 1% of at least one surfactant; about 1 mM to about 100 mM of a buffer; optionally about 10 mM to about 500 mM of a stabilizer; and about 5 mM to about 305 mM of a tonicity agent; and has a pH of about 4.0 to about 7.0.

A subject antibody can be utilized in aerosol formulation to be administered via inhalation. A subject antibody can be formulated into pressurized acceptable propellants such as dichlorodifluoromethane, propane, nitrogen and the like.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for a subject antibody may depend on the particular antibody employed and the effect to be achieved, and the pharmacodynamics associated with each antibody in the host.

A subject antibody can be administered as an injectable formulation. Typically, injectable compositions are prepared as liquid solutions or suspensions; solid forms suitable for solution in, or suspension in, liquid vehicles prior to injection may also be prepared. The preparation may also be emulsified or the antibody encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, a subject antibody is formulated in a controlled release formulation. Sustained-release preparations may be prepared using methods well known in the art.

Dosages

A suitable dosage can be determined by an attending physician or by other qualified medical personnel, based on various clinical factors. As is well known in the medical arts, dosages for any one patient depend upon many factors, including the patient's size, body surface area, age, the particular compound to be administered, sex of the patient, time, and route of administration, general health, and other drugs being administered concurrently. A subject antibody may be administered in amounts between 1 ng/kg body weight and 20 mg/kg body weight per dose, e.g. between 0.1 mg/kg body weight to 10 mg/kg body weight, e.g. between 0.5 mg/kg body weight to 5 mg/kg body weight; however, doses below or above this exemplary range are envisioned, especially considering the aforementioned factors. If the regimen is a continuous infusion, it can also be in the range of 1 μg to 10 mg per kilogram of body weight per minute.

Those of skill will readily appreciate that dose levels can vary as a function of the specific antibody, the severity of the symptoms and the susceptibility of the subject to side effects. Preferred dosages for a given compound are readily determinable by those of skill in the art by a variety of means.

In addition to body size-based dosing schedules, in view of the relatively minor effects of body size on distribution and elimination of monoclonal antibodies, fixed-dose administration of the subject antibodies is also contemplated. See, e.g. Hendrikx et al, *Oncologist* 2017, 22(10): 1212-1221.

Routes of Administration

A subject antibody is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, subcutaneous, intradermal, topical application, intravenous, intraarterial, rectal, nasal, oral, and other enteral and parenteral routes of administration. Routes of administration may be combined, if desired, or adjusted depending upon the antibody and/or the desired effect. A subject antibody composition can be administered in a single dose or in multiple doses. In some embodiments, a subject antibody composition is administered orally. In some embodiments, a subject antibody composition is administered via an inhalational route. In some embodiments, a subject antibody composition is administered intranasally. In some embodiments, a subject antibody composition is administered locally. In some embodiments, a subject antibody composition is administered intracranially. In some embodiments, a subject antibody composition is administered intravenously.

The agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of a subject antibody. Where systemic delivery is desired, administration typically involves invasive or systemically absorbed topical or mucosal administration of pharmaceutical preparations.

A subject antibody can also be delivered to the subject by enteral administration. Enteral routes of administration include, but are not necessarily limited to, oral and rectal (e.g., using a suppository) delivery.

The subject antibodies are normally administered by intravenous infusion of by parenteral (intravenous, subcutaneous, intramuscular, or intradermal) injection, preferably by intravenous infusion or injection, or by subcutaneous injection. Especially for patients receiving treatment over prolonged periods, subcutaneous administration offers significant benefits. Such benefits include patient convenience, shorter delivery times, and lack of need for dedicated infusion facilities. Thus, subcutaneous formulations and delivery can improve convenience and quality of life for patients and provide cost savings to healthcare systems. Subcutaneous administration can be particularly beneficial in combination therapy, for example using subcutaneous fixed-dose combinations that contain two or more active molecules co-formulated within the same formulation. Alternatively, multi-chamber devices can either inject the products sequentially or premix them directly before subcutaneous injection. For further details see, for example, Bittner et al, *BioDrugs* 2018, 32:425-440; and Viola et al, *J Control Release* 2018, 286:301-314.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as cancer and/or the growth of a cancer and pain associated therewith. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of subjects (wherein the term "subject" is used interchangeably herein with the terms "individual" and "patient") are treatable according to the presently disclosed methods. Generally, such subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, the hosts will be humans.

Kits with unit doses of a subject antibody, e.g. in oral or injectable doses, are provided. In some embodiments, in addition to the containers containing the unit doses will be an informational package insert describing the use and attendant benefits of the antibody in treating pathological condition of interest.

Nucleic Acids

The present disclosure provides nucleic acids comprising nucleotide sequences encoding a subject antibody. A nucleotide sequence encoding a subject antibody can be operably linked to one or more regulatory elements, such as a promoter and enhancer, that allow expression of the nucleotide sequence in the intended target cells (e.g., a cell that is genetically modified to synthesize and/or secrete the encoded antibody).

Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

A nucleotide sequence encoding a subject antibody can be present in an expression vector and/or a cloning vector. Where a subject antibody comprises two or more separate polypeptides, nucleotide sequences encoding the two polypeptides can be cloned in the same or separate vectors. Separate polypeptides may be expressed from a single nucleic acid or single vector using various strategies, such as separate promoters, one or more internal ribosomal entry sites (IRES), one or more self-cleaving sequences (e.g., 2A cleavage sequences, e.g., P2A, T2A, E2A, and F2A), combinations thereof, and the like. An expression vector can include a selectable marker, an origin of replication, and other features that provide for replication and/or maintenance of the vector.

Large numbers of suitable vectors and promoters are known to those of skill in the art; many are commercially available for generating a subject recombinant construct. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus; adeno-associated virus; SV40; herpes simplex virus; human immunodeficiency virus; a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

Nucleic acids, e.g., as described herein, may, in some instances, be introduced into a cell, e.g., by contacting the cell with the nucleic acid. Cells with introduced nucleic acids will generally be referred to herein as genetically modified cells. Various methods of nucleic acid delivery may be employed including but not limited to e.g., naked nucleic acid delivery, viral delivery, chemical transfection, biolistics, and the like.

Cells

The present disclosure provides isolated genetically modified cells (e.g., in vitro cells, ex vivo cells, cultured cells, etc.) that are genetically modified with a subject nucleic acid. In some embodiments, a subject isolated genetically modified cell can produce a subject antibody. In some instances, a genetically modified cell can deliver an antibody, e.g., to a subject in need thereof. In some instances, a genetically modified cell may be used in the production, screening, and/or discovery of multi-specific antibodies.

Suitable cells include eukaryotic cells, such as a mammalian cell, an insect cell, a yeast cell; and prokaryotic cells, such as a bacterial cell. Introduction of a subject nucleic acid into the host cell can be effected, for example by calcium phosphate precipitation, DEAE dextran mediated transfection, liposome-mediated transfection, electroporation, or other known method.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells, CHO cells, 293 cells, 3T3 cells, Vero cells, Huh-7 cells, BHK cells, PC12 cells, COS cells, COS-7 cells, RAT1 cells, mouse L cells, human embryonic kidney (HEK) cells, HLHepG2 cells, and the like.

In some instances, useful mammalian cells may include cells derived from a mammalian tissue or organ. In some instances, cells employed are kidney cells, including e.g., kidney cells of an established kidney cell line, such as HEK 293T cells.

In some instances, cells of the present disclosure may be immune cells. As used herein, the term "immune cells" generally includes white blood cells (leukocytes) which are derived from hematopoietic stem cells (HSC) produced in the bone marrow. "Immune cells" includes, e.g., lymphocytes (T cells, B cells, natural killer (NK) cells) and myeloid-derived cells (neutrophil, eosinophil, basophil, monocyte, macrophage, dendritic cells). "T cell" includes all types of immune cells expressing CD3 including T-helper cells (CD4+ cells), cytotoxic T-cells (CD8+ cells), T-regulatory cells (Treg) and gamma-delta T cells. A "cytotoxic cell" includes CD8+ T cells, natural-killer (NK) cells, and neutrophils, which cells are capable of mediating cytotoxicity responses.

In some instances, useful cells expressing an antibody such as a multi-specific antibody of the present disclosure may include producer T cells. Producer T cells engineered to include nucleic acid sequence encoding an antibody of the present disclosure may, in some instances, be employed to deliver the antibody to a subject in need thereof.

In some instances, immune cells of the present disclosure include immune effector cell comprising a chimeric antigen receptor (CAR) comprising a MDR1 binding domain, a transmembrane domain, and an intracellular signaling domain, and wherein the MDR1 binding domain comprises heavy chain complementarity determining regions (HCDRs) and light chain CDRs (LCDRs) of a pair of variable heavy chain (VH) region and variable light chain (VL) region of an antibody listed in Table 2. In one aspect, the intracellular signaling domain may include one or more functional signaling domains derived from at least one costimulatory molecule, e.g., 4-1BB (i.e., CD137), CD27 and/or CD28. The intracellular signaling domain may include a functional signaling domain derived from a costimulatory molecule and a functional signaling domain derived from a stimulatory molecule.

The immune effector cell may be a T-cell. The immune effector cell may be an autologous cell.

Methods

As summarized above, methods of the present disclosure include methods of contacting a cell with an antibody of the present disclosure, methods of treating a subject according to a method that involves administering to the subject an antibody of the present disclosure, methods of making elements described in the instant application, including e.g., antibodies, multi-specific antibodies, bispecific antibody molecules, compositions and formulations, nucleic acids, expression vectors, cells, and the like.

As summarized above, methods of the present disclosure include contacting a cancer cell with an antibody of the present disclosure, e.g., to detect presence of expression of MDR1 on the cancer cell, measure level of expression of MDR1 on the cancer cell, or to facilitate and/or enhance killing of the cancer cell. In some instances, killing of the cancer cell is mediated by an immune response or immune cell acting upon the cancer cell bound by the antibody. In some instances, killing of the cancer cell is mediated by inhibition of cellular efflux of the cancer cell, e.g., as a result of MDR1 inhibition by the antibody. In some instances, killing of the cancer cell is mediated by a combination of inhibition of cellular efflux of the cancer cell plus an immune mediated response (e.g., via Fc region of the antibody). In some instances, the cell contacted with the multi-specific antibody may be a multidrug resistant cancer cell. Methods that involve contacting a cancer cell with an antibody of the present disclosure may or may not include contacting the cancer cell with an additional therapy or active agent, including e.g., a chemotherapeutic, an immunotherapy, radiation therapy, or the like.

Contacting a cancer cell with a multi-specific antibody of the present disclosure will generally enhance the killing of the cancer cell, e.g., as compared to the level of killing of the cancer cell in the absence of the multi-specific antibody. In some instances, where an additional active agent is employed, enhanced killing of the cancer cell may be seen as compared to the level of killing observed using the additional active agent alone. The amount of enhancement of cancer cell killing attributable to the multi-specific antibody will vary and may range from at least a 5% increase in cancer cell killing to at least 90% or more, including but not limited to e.g., at least 10%, at least 20%, at least 30%, at least 40%, at least 50%, at least 60%, at least 70%, at least 80%, etc. Such increases may be compared to contacting with one or more additional active agents alone.

Enhanced killing of a cancer cell may be assessed by a variety of means including but not limited to e.g., observational studies, in vitro cell-based cytotoxicity assays, flow cytometry, cell viability labeling (e.g., using one or more cell viability stains), and the like.

Treatment Methods

The present disclosure provides methods of treating a cancer, in particular MDR1-expressing or MRD1-overexpressing cancer, the methods generally involving administering to an individual in need thereof (e.g., an individual having such cancer) an effective amount of an antibody as provided herein, alone (e.g., in monotherapy) or in combination (e.g., in combination therapy) with one or more additional therapeutic agents. Administration of an antibody of the present disclosure may be performed by any convenient and appropriate route of delivery.

Accordingly, administration includes but is not limited to e.g., delivery of the antibody by injection, delivery of the antibody by infusion, delivery of a nucleic acid or expression vector encoding the antibody, delivery of the antibody by administering to the subject a cell that expresses and secretes the antibody, delivery of an immune effector cell (e.g., a CAR-T cell) that expresses on the cell surface a chimeric antigen receptor (CAR) comprising a MDR1 binding domain, a transmembrane domain, and an intracellular signaling domain, and wherein the MDR1 binding domain comprises HCDRs and LCDRs of a pair of VH region and VL region of an antibody listed in Table 2, and the like. Administration of an agent, a nucleic acid encoding an agent, a cell expressing an agent, etc. may include contacting with the agent, contacting with the nucleic acid, contacting with the cell, and the like.

In some embodiments, an effective amount of a subject antibody is an amount that, when administered alone (e.g., in monotherapy) or in combination (e.g., in combination therapy) with one or more additional therapeutic agents, in one or more doses, is effective to reduce an adverse symptom of cancer by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the severity of the adverse symptom in the absence of treatment with the antibody.

In some embodiments, an effective amount of a subject antibody is an amount that, when administered alone (e.g., in monotherapy) or in combination (e.g., in combination therapy) with one or more additional therapeutic agents, in one or more doses, is effective to improve the cancer (i.e., slow the growth of the cancer, stop the growth of the cancer, reverse the growth of the cancer, kill cancer cells (including tumor cells, or the like) in the individual being treated. For example, an effective amount of a subject antibody can reduce a cancer growth rate or reduce a cancer size in an individual by at least about 5%, at least about 10%, at least about 15%, at least about 20%, at least about 25%, at least about 30%, at least about 40%, at least about 50%, or more, compared to in the absence of treatment with an antibody.

In some instances, a subject may be treated systemically, including with the subject antibody, with or without one or more additional reagents. By "systemic treatment", as used herein, is meant a treatment that is not directed solely to target a specific tumor (such as e.g., a primary tumor or a defined secondary tumor) or a specific cancer containing tissue (such as e.g., the liver in the case of liver cancer, the blood in the case of a blood cancer, etc.). Systemic treatments will generally be directed to the subject's body as a whole and may include but are not limited to e.g., systemic radiation therapy, systemic chemotherapy, systemic immunotherapy, combinations thereof and the like.

In some instances, a subject may be treated locally, including with the subject antibody, with or without one or more additional reagents. By "local treatment", as used herein, is meant a treatment that is specifically directed to the location of a tumor (such as e.g., a primary tumor or a defined secondary tumor) or specifically directed to a cancer containing tissue (such as e.g., the liver in the case of liver cancer, the blood in the case of a blood cancer, etc.). In some instances, local treatment may also be administered in such a way as to affect the environment surrounding a tumor, such as tissue surrounding the tumor, such as tissue immediately adjacent to the tumor. Local treatment will generally not affect or not be targeted to tissues distant from the site of cancer including the site of a tumor, such as a primary tumor. Useful local treatments that may be administered in addition to or in combination with a subject antibody, e.g., include but are not limited to surgery, local radiation therapy, local cryotherapy, local laser therapy, local topical therapy, combinations thereof, and the like.

In some embodiments, a subject treatment method involves administering a subject antibody and one or more additional therapeutic agents. Suitable additional therapeutic agents include, but are not limited to, chemotherapeutic agents, radiation therapy reagents, immunotherapy reagents, other antibody or multi-specific antibody agents, and the like. Additional therapies that may be administered to a subject before, during or after a subject administering a multi-specific antibody of the present disclosure will vary depending on numerous factors including e.g., the type of cancer, the subject's medical history, general state of health and/or any co-morbidities, and the like. Useful cancer therapies include but are not limited to e.g., radiation therapy, chemotherapy, immunotherapy, and the like.

Radiation therapy includes, but is not limited to, x-rays or gamma rays that are delivered from either an externally applied source such as a beam, or by implantation of small radioactive sources.

Suitable antibodies for use in cancer treatment include, but are not limited to, naked antibodies, e.g., trastuzumab (Herceptin), bevacizumab (Avastinm™), cetuximab (Erbitux™), panitumumab (Vectibix™), Ipilimumab (Yervoy™), rituximab (Rituxan), alemtuzumab (Lemtrada™), Ofatumumab (Arzerra™), Oregovomab (OvaRex™), Lambrolizumab (MK-3475), pertuzumab (Perjeta™), ranibizumab (Lucentis™) etc., and conjugated antibodies, e.g., gemtuzumab ozogamicin (Mylortarg™), Brentuximab vedotin (Adcetris™), 90Y-labelled ibritumomab tiuxetan (Zevalin™), 131I-labelled tositumoma (Bexxar™), etc.

Suitable antibodies for use in cancer treatment also include, but are not limited to, antibodies raised against tumor-associated antigens. Such antigens include, but are not limited to, CD20, CD30, CD33, CD52, EpCAM, CEA, gpA33, Mucins, TAG-72, CAIX, PSMA, Folate-binding protein, Gangliosides (e.g., GD2, GD3, GM2, etc.), Ley, VEGF, VEGFR, Integrin alpha-V-beta-3, Integrin alpha-5-beta-1, EGFR, ERBB2, ERBB3, MET, IGF1R, EPHA3, TRAILR1, TRAILR2, RANKL, FAP, Tenascin, Programmed Death-Ligand 1 (PD-L1), androgen receptor (AR), Bruton's Tyrosine Kinase (BTK), BCR-Abl, c-kit, PIK3CA, EML4-ALK, KRAS, ALK, ROS1, AKT1, BRAF, MEKJ, MEK2, NRAS, RAC1, ESR1, CTLA-4, LAG-3 and TIM-3, etc. These antibodies may be administered as a combination therapy with an anti-MDR1 antibody provided herein or as a multi-specific antibody comprising at least the antigen binding portion of one of these antibodies and the antigen-binding portion of an anti-MDR1 antibody provided herein.

Conventional cancer therapies also include targeted therapies for cancer including but not limited to e.g., Adotrastuzumab emtansine (Kadcyla) targeting HER2 (ERBB2/neu) (approved for use in Breast cancer); Afatinib (Gilotrif) targeting EGFR (HER1/ERBB1), HER2 (ERBB2/neu) (approved for use in Non-small cell lung cancer); Aldesleukin (Proleukin) targeting (approved for use in Renal cell carcinoma, Melanoma); Alectinib (Alecensa) targeting ALK (approved for use in Non-small cell lung cancer); Alemtuzumab (Campath) targeting CD52 (approved for use in B-cell chronic lymphocytic leukemia); Atezolizumab (Tecentriq) targeting PD-L1 (approved for use in Urothelial carcinoma, Non-small cell lung cancer); Avelumab (Bavencio) targeting PD-L1 (approved for use in Merkel cell carcinoma); Axitinib (Inlyta) targeting KIT, PDGFRβ, VEGFR1/2/3 (approved for use in Renal cell carcinoma); Belimumab (Benlysta) targeting BAFF (approved for use in Lupus erythematosus); Belinostat (Beleodaq) targeting HDAC (approved for use in Peripheral T-cell lymphoma); Bevacizumab (Avastin) targeting VEGF ligand (approved for use in Cervical cancer, Colorectal cancer, Fallopian tube cancer, Glioblastoma, Non-small cell lung cancer, Ovarian cancer, Peritoneal cancer, Renal cell carcinoma); Blinatumomab (Blincyto) targeting CD19/CD3 (approved for use in Acute lymphoblastic leukemia (precursor B-cell)); Bortezomib (Velcade) targeting Proteasome (approved for use in Multiple myeloma, Mantle cell lymphoma); Bosutinib (Bosulif) targeting ABL (approved for use in Chronic myelogenous leukemia); Brentuximab vedotin (Adcetris) targeting CD30 (approved for use in Hodgkin lymphoma, Anaplastic large cell lymphoma); Brigatinib (Alunbrig) targeting ALK (approved for use in Non-small cell lung cancer (ALK+)); Cabozantinib (Cabometyx, Cometriq) targeting FLT3, KIT, MET, RET, VEGFR2 (approved for use in Medullary thyroid cancer, Renal cell carcinoma); Carfilzomib (Kyprolis) targeting Proteasome (approved for use in Multiple myeloma); Ceritinib (Zykadia) targeting ALK (approved for use in Non-small cell lung cancer); Cetuximab (Erbitux) targeting EGFR (HER1/ERBB1) (approved for use in Colorectal cancer, Squamous cell cancer of the head and neck); Cobimetinib (Cotellic) targeting MEK (approved for use in Melanoma); Crizotinib (Xalkori) targeting ALK, MET, ROS1 (approved for use in Non-small cell lung cancer); Dabrafenib (Tafinlar) targeting BRAF (approved for use in Melanoma, Non-small cell lung cancer); Daratumumab (Darzalex) targeting CD38 (approved for use in Multiple myeloma); Dasatinib (Sprycel) targeting ABL (approved for use in Chronic myelogenous leukemia, Acute lymphoblastic leukemia); Denosumab (Xgeva) targeting RANKL (approved for use in Giant cell tumor of the bone); Dinutuximab (Unituxin) targeting B4GALNT1 (GD2) (approved for use in Pediatric neuroblastoma); Durvalumab (Imfinzi) targeting PD-L1 (approved for use in Urothelial carcinoma); Elotuzumab (Empliciti) targeting SLAMF7 (CS1/CD319/CRACC) (approved for use in Multiple myeloma); Enasidenib (Idhifa) targeting IDH2 (approved for use in Acute myeloid leukemia); Erlotinib (Tarceva) targeting EGFR (HER1/ERBB1) (approved for use in Non-small cell lung cancer, Pancreatic cancer); Everolimus (Afinitor) targeting mTOR (approved for use in Pancreatic, gastrointestinal, or lung origin neuroendocrine tumor, Renal cell carcinoma, Nonresectable subependymal giant cell astrocytoma, Breast cancer); Gefitinib (Iressa) targeting EGFR (HER1/ERBB1) (approved for use in Non-small cell lung cancer); Ibritumomab tiuxetan (Zevalin) targeting CD20 (approved for use in Non-Hodgkin's lymphoma); Ibrutinib (Imbruvica) targeting BTK (approved for use in Mantle cell lymphoma, Chronic lymphocytic leukemia, Waldenstrom's macroglobulinemia); Idelalisib (Zydelig) targeting PI3Kδ (approved for use in Chronic lymphocytic leukemia, Follicular B-cell non-Hodgkin lymphoma, Small lymphocytic lymphoma); Imatinib (Gleevec) targeting KIT, PDGFR, ABL (approved for use in GI stromal tumor (KIT+), Dermatofibrosarcoma protuberans, Multiple hematologic malignancies); Ipilimumab (Yervoy) targeting CTLA-4 (approved for use in Melanoma); Ixazomib (Ninlaro) targeting Proteasome (approved for use in Multiple Myeloma); Lapatinib (Tykerb) targeting HER2 (ERBB2/neu), EGFR (HER1/ERBB1) (approved for use in Breast cancer (HER2+)); Lenvatinib (Lenvima) targeting VEGFR2 (approved for use in Renal cell carcinoma, Thyroid cancer); Midostaurin (Rydapt) targeting FLT3 (approved for use in acute myeloid leukemia (FLT3+)); Necitumumab (Portrazza) targeting EGFR (HER1/ERBB1) (approved for use in Squamous non-small cell lung cancer); Neratinib (Nerlynx) targeting HER2 (ERBB2/neu) (approved for use in Breast cancer); Nilotinib (Tasigna) targeting ABL (approved for use in Chronic myelogenous leukemia); Niraparib (Zejula) targeting PARP (approved for use in Ovarian cancer, Fallopian tube cancer, Peritoneal cancer); Nivolumab (Opdivo) targeting PD-1 (approved for use in Colorectal cancer, Head and neck squamous cell carcinoma, Hodgkin lymphoma, Melanoma, Non-small cell lung cancer, Renal cell carcinoma, Urothelial carcinoma); Obinutuzumab (Gazyva) targeting CD20 (approved for use in Chronic lymphocytic leukemia, Follicular lymphoma); Ofatumumab (Arzerra, HuMax-CD20) targeting CD20 (approved for use in Chronic lymphocytic leukemia); Olaparib (Lynparza) targeting PARP (approved for use in Ovarian cancer); Olaratumab (Lartruvo) targeting PDGFRα (approved for use in Soft tissue sarcoma); Osimertinib (Tagrisso) targeting EGFR (approved for use in Non-small cell lung cancer); Palbociclib (Ibrance) targeting CDK4, CDK6 (approved for use in Breast cancer); Panitumumab (Vectibix) targeting EGFR (HER1/ERBB1) (approved for use in Colorectal cancer); Panobinostat (Farydak) targeting HDAC (approved for use in Multiple myeloma); Pazopanib (Votrient) targeting VEGFR, PDGFR, KIT (approved for use in Renal cell carcinoma); Pembrolizumab (Keytruda) targeting PD-1 (approved for use in Classical Hodgkin lymphoma, Melanoma, Non-small cell lung cancer (PD-L1+), Head and neck squamous cell carcinoma, Solid tumors (MSI-H)); Pertuzumab (Perjeta) targeting HER2 (ERBB2/neu) (approved for use in Breast cancer (HER2+)); Ponatinib (Iclusig) targeting ABL, FGFR1-3, FLT3, VEGFR2 (approved for use in Chronic myelogenous leukemia, Acute lymphoblastic leukemia); Ramucirumab (Cyramza) targeting VEGFR2 (approved for use in Colorectal cancer, Gastric cancer or Gastroesophageal junction (GEJ) adenocarcinoma, Non-small cell lung cancer); Regorafenib (Stivarga) targeting KIT, PDGFRβ, RAF, RET, VEGFR1/2/3 (approved for use in Colorectal cancer, Gastrointestinal stromal tumors, Hepatocellular carcinoma); Ribociclib (Kisqali) targeting CDK4, CDK6 (approved for use in Breast cancer (HR+, HER2−)); Rituximab (Rituxan, Mabthera) targeting CD20 (approved for use in Non-Hodgkin's lymphoma, Chronic lymphocytic leukemia, Rheumatoid arthritis, Granulomatosis with polyangiitis); Rituximab/hyaluronidase human (Rituxan Hycela) targeting CD20 (approved for use in Chronic lymphocytic leukemia, Diffuse large B-cell lymphoma, Follicular lymphoma); Romidepsin (Istodax) targeting HDAC (approved for use in Cutaneous T-cell lymphoma, Peripheral T-cell lymphoma); Rucaparib (Rubraca) targeting PARP (approved for use in Ovarian cancer); Ruxolitinib (Jakafi) targeting JAK1/2 (approved for use in Myelofibrosis); Siltuximab (Sylvant) targeting IL-6 (approved for use in Multicentric Castleman's disease); Sipuleucel-T (Provenge) targeting (approved for use in Prostate cancer); Sonidegib (Odomzo) targeting Smoothened (approved for use in Basal cell carcinoma); Sorafenib (Nexavar) targeting VEGFR, PDGFR, KIT, RAF (approved for use in Hepatocellular carcinoma, Renal cell carcinoma, Thyroid carcinoma); Temsirolimus (Torisel) targeting mTOR (approved for use in Renal cell carcinoma); Tositumomab (Bexxar) targeting CD20 (approved for use in Non-Hodgkin's lymphoma); Trametinib (Mekinist) targeting MEK (approved for use in Melanoma, Non-small cell lung cancer); Trastuzumab (Herceptin) targeting HER2 (ERBB2/neu) (approved for use in Breast cancer (HER2+), Gastric cancer (HER2+)); Vandetanib (Caprelsa) targeting EGFR (HER1/ERBB1), RET, VEGFR2 (approved for use in Medullary thyroid cancer); Vemurafenib (Zelboraf) targeting BRAF (approved for use in Melanoma); Venetoclax (Venclexta) targeting BCL2 (approved for use in Chronic lymphocytic leukemia); Vismodegib (Erivedge) targeting PTCH, Smoothened (approved for use in Basal cell carcinoma); Vorinostat (Zolinza) targeting HDAC (approved for use in Cutaneous T-cell lymphoma); Ziv-aflibercept (Zaltrap) targeting PIGF, VEGFA/B (approved for use in Colorectal cancer); and the like. These antibodies may be administered as a combination therapy with an anti-MDR1 antibody provided herein.

Biological response modifiers suitable for use in connection with the methods of the present disclosure include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) interferon-α; (7) interferon-γ; (8) colony-stimulating factors; (9) inhibitors of angiogenesis; and (10) antagonists of tumor necrosis factor.

Chemotherapeutic agents or antineoplastic agents are non-peptidic (i.e., non-proteinaceous) compounds that reduce proliferation of cancer cells, and encompass cytotoxic agents and cytostatic agents. Non-limiting examples of chemotherapeutic agents include alkylating agents (e.g., nitrosoureas), antimetabolites (e.g., methotrexate), antitumor antibiotics (e.g., anthracyclins), plant alkaloids (e.g., vinca alkaloids, taxanes, etc.), toposiomerase inhibitors, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., *vinca* alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex. Estrogens stimulate proliferation and differentiation, therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., Abraxane (albumin bound), paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but are not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Useful immunotherapies include: anti-PD-1/PD-L1 immunotherapies, and/or other immunotherapy targets, such as e.g., immune check point markers, such as CTLA-4, LAG-3 and TIM-3, that may be targeted in treatment methods. Anti-PD-1/PD-L1 immunotherapies which include but are not limited to e.g., those therapies that include administering to a subject an effective amount of one or more anti-PD-1/PD-L1 therapeutic antagonists where such antagonists include but are not limited to e.g., OPDIVO® (nivolumab), KEYTRUDA® (pembrolizumab), Tecentriq™ (atezolizumab), durvalumab (MEDI4736), avelumab (MSB0010718C), BMS-936559 (MDX-1105), CA-170, BMS-202, BMS-8, BMS-37, BMS-242 and the like. These antibodies may be administered as a combination therapy with an anti-MDR1 antibody provided herein.

CTLA-4, also known as CD152, binds to CD80 and CD86. Antibodies against CTLA-4 have been approved for treating some cancer types. The co-inhibitory effect of CTLA-4 with other immunotherapies make CTLA-4 a good candidate for use in combination with other immunotherapies to treat certain cancers. TIM-3 may also be targeted for immunotherapy for several cancer types.

LAG-3 is in clinical trials for treating cancers. Anti-LAG-3 immunotherapies include those that employ antagonist LAG-3 antibodies that can both activate T effector cells (by downregulating the LAG-3 inhibiting signal into pre-activated LAG-3+ cells) and inhibit induced (i.e. antigen-specific) Treg suppressive activity. Useful LAG-3 antagonistic antibodies include relatlimab (BMS-986016; developed by Bristol-Myers Squibb), IMP701 (developed by Immutep), TSR-033 (anti-LAG-3 mAb; developed by TESARO, Inc.), and the like.

Immunotherapies also include T cell-based immunotherapies such as e.g., adoptive cell therapy (ACT) and chimeric antigen receptor (CAR) T cell therapies. For example, a subject may be administered a population of CAR T cells engineered to target an antigen expressed by the subject's cancer. A T cell-based therapy may involve, in some instances, obtaining a cellular sample from a subject, such as a blood sample or a tumor biopsy, and culturing immune cells from the sample ex vivo, with or without genetic modification of the cultured immune cells. As an example, immune cells may be obtained from a subject, cultured ex vivo and modified with a CAR specific for an antigen expressed by the cancer to produce a population of CAR T cells. Then, the CAR T cells may be reintroduced into the subject to target the cancer. T cell-based immunotherapies may be configured in various ways, e.g., by targeting various antigens, by collecting/culturing various cell types, etc., depending on a particular cancer to be treated. In addition, T cell-based immunotherapies may be administered systemically, e.g., by intravenous injection, or locally, e.g., by infusion (e.g., intraperitoneal infusion, pleural catheter infusion, etc.), direct injection, and the like.

In some instances, a method of treatment described herein may include administering to a subject one or more inhibitors of a multidrug resistance transporter, including but not limited to e.g., a multidrug resistance transporter other than MDR1. Useful inhibitors of multidrug resistance transporters include e.g., tyrosine kinase inhibitors, natural products, microRNAs, and small molecule inhibitors. Inhibitors of multidrug resistance transporters include ABC transporter inhibitors.

Individuals suitable for treatment using a method of the present disclosure include an individual having a cancer; an individual diagnosed as having a cancer; an individual being treated for a cancer with chemotherapy, radiation therapy, antibody therapy, surgery, etc.); an individual who has been treated for a cancer (e.g., with one or more of chemotherapy, radiation therapy, antibody therapy, surgery, etc.), and who has failed to respond to the treatment; an individual who has been treated for a cancer (e.g., with one or more of chemotherapy, radiation therapy, antibody therapy, surgery, etc.), and who initially responded to the treatment but who subsequently relapsed, i.e., the cancer recurred.

The methods of the present disclosure may be employed to target and treat a variety of cancers, including e.g., primary cancer, secondary cancers, re-growing cancers, recurrent cancers, refractory cancers and the like. For example, in some instances, the methods of the present disclosure may be employed as an initial treatment of a primary cancer identified in a subject. In some instances, the methods of the present disclosure may be employed as a non-primary (e.g., secondary or later) treatment, e.g., in a subject with a cancer that is refractory to a prior treatment, in a subject with a cancer that is re-growing following a prior treatment, in a subject with a mixed response to a prior treatment (e.g., a positive response to at least one tumor in the subject and a negative or neutral response to at least a second tumor in the subject), and the like.

In some instances, the methods of the present disclosure may be employed to treat a subject with a drug resistant cancer, such as a multi-drug resistant cancer. Multidrug resistance (MDR) is the mechanism by which many cancers develop resistance to chemotherapy drugs, resulting in minimal cell death and the expansion of drug-resistant tumors. MDR cancers may involve one or more resistance mechanisms including but not limited to e.g., increased expression of efflux pumps, decreased absorption of drug, inhibition of cell death or apoptosis, modulating drug metabolism, and the like. In some instances, the methods of the present disclosure may prevent, reverse or circumvent MDR.

In some instances, methods of the present disclosure may include treating a subject having a cancer that is resistant to a first agent with an effective amount of a subject antibody described herein in combination with a second agent that is different from the first agent. For example, in some instances, cancer of a subject may be resistant to a first chemotherapeutic and the subject may be treated by administering an effective amount of a subject antibody as described herein in combination with a second chemotherapeutic that is different from the first. Various combinations of first and second chemotherapeutics may be employed depending on e.g., the type of cancer to be treated, the likelihood of developing resistance, etc.

Numerous cancers are known to develop drug resistance. For this and other reasons the methods of the present disclosure may find use in treating various cancers including but not limited to, e.g., Acute Lymphoblastic Leukemia (ALL), Acute Myeloid Leukemia (AML), Adrenocortical Carcinoma, AIDS-Related Cancers (e.g., Kaposi Sarcoma, Lymphoma, etc.), Anal Cancer, Appendix Cancer, Astrocytomas, Atypical Teratoid/Rhabdoid Tumor, Basal Cell Carcinoma, Bile Duct Cancer (Extrahepatic), Bladder Cancer, Bone Cancer (e.g., Ewing Sarcoma, Osteosarcoma and Malignant Fibrous Histiocytoma, etc.), Brain Stem Glioma, Brain Tumors (e.g., Astrocytomas, Central Nervous System Embryonal Tumors, Central Nervous System Germ Cell Tumors, Craniopharyngioma, Ependymoma, etc.), Breast Cancer (e.g., female breast cancer, male breast cancer, childhood breast cancer, etc.), Bronchial Tumors, Burkitt Lymphoma, Carcinoid Tumor (e.g., Childhood, Gastrointestinal, etc.), Carcinoma of Unknown Primary, Cardiac (Heart) Tumors, Central Nervous System (e.g., Atypical Teratoid/Rhabdoid Tumor, Embryonal Tumors, Germ Cell Tumor, Lymphoma, etc.), Cervical Cancer, Childhood Cancers, Chordoma, Chronic Lymphocytic Leukemia (CLL), Chronic Myelogenous Leukemia (CML), Chronic Myeloproliferative Neoplasms, Colon Cancer, Colorectal Cancer, Craniopharyngioma, Cutaneous T-Cell Lymphoma, Duct (e.g., Bile Duct, Extrahepatic, etc.), Ductal Carcinoma In Situ (DCIS), Embryonal Tumors, Endometrial Cancer, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer (e.g., Intraocular Melanoma, Retinoblastoma, etc.), Fibrous Histiocytoma of Bone (e.g., Malignant, Osteosarcoma, etc.), Gallbladder Cancer, Gastric (Stomach) Cancer, Gastrointestinal Carcinoid Tumor, Gastrointestinal Stromal Tumors (GIST), Germ Cell Tumor (e.g., Extracranial, Extragonadal, Ovarian, Testicular, etc.), Gestational Trophoblastic Disease, Glioma, Hairy Cell Leukemia, Head and Neck Cancer, Heart Cancer, Hepatocellular (Liver) Cancer, Histiocytosis (e.g., Langerhans Cell, etc.), Hodgkin Lymphoma, Hypopharyngeal Cancer, Intraocular Melanoma, Islet Cell Tumors (e.g., Pancreatic Neuroendocrine Tumors, etc.), Kaposi Sarcoma, Kidney Cancer (e.g., Renal Cell, Wilms Tumor, Childhood Kidney Tumors, etc.), Langerhans Cell Histiocytosis, Laryngeal Cancer, Leukemia (e.g., Acute Lymphoblastic (ALL), Acute Myeloid (AML), Chronic Lymphocytic (CLL), Chronic Myelogenous (CML), Hairy Cell, etc.), Up and Oral Cavity Cancer, Liver Cancer (Primary), Lobular Carcinoma In Situ (LCIS), Lung Cancer (e.g., Non-Small Cell, Small Cell, etc.), Lymphoma (e.g., AIDS-Related, Burkitt, Cutaneous T-Cell, Hodgkin, Non-Hodgkin, Primary Central Nervous System (CNS), etc.), Macroglobulinemia (e.g., Waldenström, etc.), Male Breast Cancer, Malignant Fibrous Histiocytoma of Bone and Osteosarcoma, Melanoma, Merkel Cell Carcinoma, Mesothelioma, Metastatic Squamous Neck Cancer with Occult Primary, Midline Tract Carcinoma Involving NUT Gene, Mouth Cancer, Multiple Endocrine Neoplasia Syndromes, Multiple Myeloma/ Plasma Cell Neoplasm, Mycosis Fungoides, Myelodysplastic Syndromes, Myelodysplastic/Myeloproliferative Neoplasms, Myelogenous Leukemia (e.g., Chronic (CML), etc.), Myeloid Leukemia (e.g., Acute (AML), etc.), Myeloprolif-
erative Neoplasms (e.g., Chronic, etc.), Nasal Cavity and
Paranasal Sinus Cancer, Nasopharyngeal Cancer, Neuro-
blastoma, Non-Hodgkin Lymphoma, Non-Small Cell Lung
Cancer, Oral Cancer, Oral Cavity Cancer (e.g., Up, etc.),
Oropharyngeal Cancer, Osteosarcoma and Malignant
Fibrous Histiocytoma of Bone, Ovarian Cancer (e.g., Epi-
thelial, Germ Cell Tumor, Low Malignant Potential Tumor,
etc.), Pancreatic Cancer, Pancreatic Neuroendocrine Tumors
(Islet Cell Tumors), Papillomatosis, Paraganglioma, Para-
nasal Sinus and Nasal Cavity Cancer, Parathyroid Cancer,
Penile Cancer, Pharyngeal Cancer, Pheochromocytoma,
Pituitary Tumor, Pleuropulmonary Blastoma, Primary Cen-
tral Nervous System (CNS) Lymphoma, Prostate Cancer,
Rectal Cancer, Renal Cell (Kidney) Cancer, Renal Pelvis
and Ureter, Transitional Cell Cancer, Retinoblastoma, Rhab-
domyosarcoma, Salivary Gland Cancer, Sarcoma (e.g.,
Ewing, Kaposi, Osteosarcoma, Rhabdomyosarcoma, Soft
Tissue, Uterine, etc.), Sézary Syndrome, Skin Cancer (e.g.,
Childhood, Melanoma, Merkel Cell Carcinoma, Nonmela-
noma, etc.), Small Cell Lung Cancer, Small Intestine Can-
cer, Soft Tissue Sarcoma, Squamous Cell Carcinoma, Squa-
mous Neck Cancer (e.g., with Occult Primary, Metastatic,
etc.), Stomach (Gastric) Cancer, T-Cell Lymphoma, Testicu-
lar Cancer, Throat Cancer, Thymoma and Thymic Carci-
noma, Thyroid Cancer, Transitional Cell Cancer of the Renal
Pelvis and Ureter, Ureter and Renal Pelvis Cancer, Urethral
Cancer, Uterine Cancer (e.g., Endometrial, etc.), Uterine
Sarcoma, Vaginal Cancer, Vulvar Cancer, Waldenström
Macroglobulinemia, Wilms Tumor, and the like.

The methods of treating described herein may, in some
instances, be performed in a subject that has previously
undergone one or more conventional treatments. For
example, in the case of oncology, the methods described
herein may, in some instances, be performed following a
conventional cancer therapy including but not limited to
e.g., conventional chemotherapy, conventional radiation
therapy, conventional immunotherapy, surgery, etc. In some
instances, the methods described herein may be used when
a subject has not responded to or is refractory to a conven-
tional therapy. In some instances, the methods described
herein may be used when a subject has responded to a
conventional therapy.

In some instances, the method of the present disclosure
may be employed to target, treat or clear a subject for
minimal residual disease (MRD) remaining after a prior
cancer therapy. Targeting, treating and/or clearance of MRD
may be pursued using the instant methods whether the MRD
is or has been determined to be refractory to the prior
treatment or not. In some instances, a method of the present
disclosure may be employed to target, treat and/or clear a
subject of MRD following a determination that the MRD is
refractory to a prior treatment or one or more available
treatment options other than those employing the herein
described multi-specific antibodies.

In certain embodiments, the antibodies herein may be
used in the treatment of MDR1-expressing or -overexpress-
ing blood cancers and solid tumors, including, without
limitation, cancers that do not respond or show poor
response to, or are resistant or refractory to one or more
chemotherapeutic and/or biologic agents, including multi-
drug resistant cancers. In certain embodiments, the cancers
treated by the present antibodies additionally express or
overexpress another co-stimulatory molecule, such as
4-1BB (i.e., CD137), CD27 and/or CD28.

Preferably, the cancers that may be treated by the anti-
MDR1 antibodies of the present invention additionally overexpress CD47, a cell surface molecule known to play an
immunoregulatory role in human malignancies and for its
involvement in tumor invasion and metastasis. The anti-
MDR1 antibodies used in the treatment of cancers express-
ing both MDR1 and CD47 preferably are multi-specific (e.g.
bispecific), having binding affinity for both MDR1 and
CD47.

The antibodies disclosed herein may be used to treat such
cancers, either as single agents (monotherapy) or in combi-
nation with other treatment modalities. The other treatment
modalities include, for example, administration of at least
one additional active agent, such as a chemotherapeutic
agent, an inhibitor of a multidrug resistance transporter, an
immunotherapy agent, or a combination thereof. The treat-
ment may improve tumor response to other treatment
options, including the reduction of the effective amounts of
chemotherapeutic and/or biologic agents, reduction or
avoidance of side-effects, and/or improvement of treatment
response of patients with refractory or drug-resistant (in-
cluding multidrug resistant) cancers. Targeted tumors
include, without limitation, leukemias, such as Acute
Myeloid Leukemia (AML) and Acute Lymphoblastic Leu-
kemia (ALL), ovarian, colorectal, gastric, breast, urothelial,
kidney, and lung cancers. In one embodiment, the adminis-
tration of an anti-MDR1 antibody herein improves patient
response to treatment with a taxane, such as paclitaxel
and/or docetaxel, an anthracycline, such as doxorubicin,
daunorubicin, epirubicin, or idarubicin, especially doxoru-
bicin, and/or a *vinca* alkaloid, such as vinblastine, vincris-
tine, vindesine, or vinorelbine, especially vinblastine or
vincristine.

In some instances, the instant methods may be employed
prophylactically for surveillance. For example, a subject in
need thereof may be administered a treatment involving one
or more of the herein described mono or multi-specific
antibodies when the subject does not have detectable disease
but is at risk of developing a recurrent cancer, including e.g.,
a drug resistant cancer. In some instances, a prophylactic
approach may be employed when a subject is at particularly
high risk of developing a primary cancer that would be
predicted to be drug resistant or expected to become drug
resistant. In some instances, a prophylactic approach may be
employed when a subject has been previously treated for a
cancer and is at risk of reoccurrence or development of drug
resistance.

In some instances, methods of the present disclosure may
involve analyzing a cancer for expression of one or more
markers or therapeutic targets. For example, in some
instances, methods may involve analyzing a sample of a
cancer from a subject to determine whether the cancer
expresses MDR1 above a predetermined threshold, a cancer-
associated antigen above a predetermined threshold, or both.

In some instances, whether a subject is treated with an
antibody of the present disclosure may depend on the results
of MDR1 expression assessment, cancer-associated antigen
expression or both. For example, in some instances, if a
cancer expresses MDR1 at or above a predetermined thresh-
old then the subject may be treated with an anti-MDR1
antibody of the present disclosure or a multi-specific anti-
body of the present disclosure, and if the cancer expresses
MDR1 below the predetermined threshold then the subject
may not be treated with an anti-MDR1 antibody but treated
with a multi-specific antibody of the present disclosure.

Any convenient assay may be employed for analyzing
MDR1 and/or cancer-associated antigen levels, including
but not limited to e.g., flow cytometry, nucleic acid-based
assays (e.g., amplification, sequencing, etc.), cell cytometry, immunohistochemistry, and the like. Any convenient biological sample may be employed, including but not limited to e.g., cancer biopsy samples. Useful predetermined thresholds for assessing expression of one or more markers and/or targets may be determined by any convenient and appropriate method, including comparison of the measured level of expression to a corresponding control. For example, in some instances, a useful predetermined threshold for the level of MDR1 and/or a cancer-associated antigen assayed in a sample may correspond to a level of MDR1 and/or cancer-associated antigen as measured in a reference cell, such as a healthy/normal cell.

Methods of Making

As summarized above, methods of the present disclosure also include methods or making and/or identifying antibodies as described herein. A subject antibody can be produced by any known method, e.g., conventional synthetic methods for protein synthesis; recombinant DNA methods; etc.

Where a subject antibody is a single chain polypeptide, it can be synthesized using standard chemical peptide synthesis techniques. Where a polypeptide is chemically synthesized, the synthesis may proceed via liquid-phase or solid-phase. Solid phase polypeptide synthesis (SPPS), in which the C-terminal amino acid of the sequence is attached to an insoluble support followed by sequential addition of the remaining amino acids in the sequence, is an example of a suitable method for the chemical synthesis of a subject antibody. Various forms of SPPS, such as Fmoc and Boc, are available for synthesizing a subject antibody.

Standard recombinant methods can be used for production of a subject antibody. For example, nucleic acids encoding light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences. The expression control sequences can be eukaryotic promoter systems in vectors capable of transforming or transfecting eukaryotic host cells (e.g., COS or CHO cells). Once the vector has been incorporated into the appropriate host, the host is maintained under conditions suitable for high level expression of the nucleotide sequences, and the collection and purification of the antibodies.

Because of the degeneracy of the genetic code, a variety of nucleic acid sequences can encode each immunoglobulin amino acid sequence. The desired nucleic acid sequences can be produced by de novo solid-phase DNA synthesis or by polymerase chain reaction (PCR) mutagenesis of an earlier prepared variant of the desired polynucleotide. Oligonucleotide-mediated mutagenesis is an example of a suitable method for preparing substitution, deletion and insertion variants of target polypeptide DNA. See Adelman et al., DNA 2:183 (1983). Briefly, the target polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer, and encodes the selected alteration in the target polypeptide DNA.

Suitable expression vectors are typically replicable in the host organisms either as episomes or as an integral part of the host chromosomal DNA. Commonly, expression vectors contain selection markers (e.g., ampicillin-resistance, hygromycin-resistance, tetracycline resistance, kanamycin resistance or neomycin resistance) to permit detection of those cells transformed with the desired DNA sequences.

*Escherichia coli* is an example of a prokaryotic host cell that can be used for cloning a subject antibody-encoding polynucleotide. Other microbial hosts suitable for use include bacilli, such as *Bacillus subtilis*, and other enterobacteriaceae, such as *Salmonella, Serratia*, and various *Pseudomonas* species.

Other microbes, such as yeast, are also useful for expression. *Saccharomyces* (e.g., *S. cerevisiae*) and *Pichia* are examples of suitable yeast host cells, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian cells (e.g., mammalian cells grown in in vitro cell culture) can also be used to express and produce the polypeptides of the present invention (e.g., polynucleotides encoding immunoglobulins or fragments thereof). See Winnacker, From Genes to Clones, VCH Publishers, N.Y., N.Y. (1987). Suitable mammalian host cells include CHO cell lines, various Cos cell lines, HeLa cells, HEK cells, myeloma cell lines, and transformed B-cells or hybridomas. Expression vectors for these cells can include expression control sequences, such as an origin of replication, a promoter, and an enhancer (Queen et al., Immunol. Rev. 89:49 (1986)), and necessary processing information sites, such as ribosome binding sites, RNA splice sites, polyadenylation sites, and transcriptional terminator sequences. Examples of suitable expression control sequences are promoters derived from immunoglobulin genes, SV40, adenovirus, bovine papilloma virus, cytomegalovirus and the like. See Co et al., J. Immunol. 148: 1149 (1992).

Once synthesized (either chemically or recombinantly), the whole antibodies, their dimers, individual light and heavy chains, or other forms of a subject antibody (e.g., scFv, etc.) can be purified according to standard procedures of the art, including ammonium sulfate precipitation, affinity columns, column chromatography, high performance liquid chromatography (HPLC) purification, gel electrophoresis, and the like (see generally Scopes, Protein Purification (Springer-Verlag, N.Y., (1982)). A subject antibody can be substantially pure, e.g., at least about 80% to 85% pure, at least about 85% to 90% pure, at least about 90% to 95% pure, or 98% to 99%, or more, pure, e.g., free from contaminants such as cell debris, macromolecules other than a subject antibody, etc.

In some embodiments, methods of generating a multi-specific antibody of the present disclosure may include producing candidate antibodies and screening for activity. Such methods may generate a multi-specific antibody that specifically binds a cell expressing both MDR1 and a cancer-associated antigen through the use of a series of steps. Steps of such methods may include: producing a multi-specific antibody or a plurality of antibodies that each include or are expected to include a MDR1-binding domain and a cancer-associated antigen-binding domain; contacting a first test cell expressing MDR1 and cancer-associated antigen with the multi-specific antibody or plurality of antibodies; contacting a second cell expressing either MDR1 or the cancer-associated antigen with the multi-specific antibody or plurality of antibodies; comparing the binding of the multi-specific antibody to the first cell with the binding of the multi-specific antibody to the second cell to determine a binding-specificity ratio; and identifying the multi-specific antibody, or one or more of the antibodies of the plurality, as specific for the cell expressing both MDR1 and the cancer-associated antigen when the ratio is above a predetermined threshold. Where such a threshold for comparative binding is employed, the threshold may vary and may range from 1.5:1 or more, including but not limited to e.g., 2:1, 3:1, 4:1, 5:1, 6:1, 7:1, 8:1, 9:1, 10:1, 20:1, 50:1, 100:1, etc.

Various cells may be used in such methods, including but not limited to e.g., the cells described herein. In some instances, the binding of the antibody to both MDR1-only expressing cells and the cancer-associated antigen-only expressing cells may be performed. For example, in some instances, the method may include, relative to the steps describe above, where the second cell expresses MDR1 and not the cancer-associated antigen and the method further comprises contacting a third cell expressing the cancer-associated antigen but not MDR1 with the multi-specific antibody.

In some instances, such methods may employ one or more controls, including but not limited to e.g., control cells, control reagents, and the like. Useful control cells include those that have a known expression or known lack of expression of one or more relevant genes or proteins. Useful control reagents may include but are not limited to e.g., control antibodies such as but not limited to e.g., monospecific antibodies to known targets. For example, in some instances, such methods of the present disclosure may further include contacting the first cell, the second cell, and/or the third cell with a control antibody selected from: a monospecific anti-MDR1 antibody and a monospecific anti-cancer-associated antigen antibody. Depending on the particular method used, various other or additional controls, as appropriate, may be employed.

Kits

Aspects of the present disclosure also include kits. The kits may include, e.g., any combination of the antibodies, multi-specific antibodies, reagents, compositions, formulations, cells, nucleic acids, expression vectors, or the like, described herein. A subject kit can include one or more of: a subject antibody, a nucleic acid encoding the same, or a cell comprising a subject nucleic acid. Kits may be configured for various purposes, including e.g., treatment kits (e.g., where a kit may include an anti-MDR1 antibody or a multi-specific antibody and e.g., one or more additional active agents, such as a chemotherapeutic), kits for producing antibodies, kits for screening antibodies, and the like.

Optional components of the kit will vary and may, e.g., include: a buffer; a protease inhibitor; etc. Where a subject kit comprises a subject nucleic acid, the nucleic acid may also have restrictions sites, multiple cloning sites, primer sites, etc. The various components of the kit may be present in separate containers or certain compatible components may be pre-combined into a single container, as desired.

In addition to above-mentioned components, a subject kit can include instructions for using the components of the kit to practice a subject method. The instructions for practicing a subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. compact disc-read only memory (CD-ROM), digital versatile disk (DVD), diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Exemplary Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure are provided below. As will be apparent to those of ordinary skill in the art upon reading this disclosure, each of the individually numbered aspects may be used or combined with any of the preceding or following individually numbered aspects. This is intended to provide support for all such combinations of aspects and is not limited to combinations of aspects explicitly provided below. It will be apparent to one of ordinary skill in the art that various changes and modifications can be made without departing from the spirit or scope of the invention.

1. An antibody that specifically binds to a multidrug resistance protein 1 (MDR1) wherein the antibody competes for binding to MDR1 with an antibody comprising: heavy chain complementarity determining regions 1-3 (HCDRs 1-3) and light chain CDRs 1-3 (LCDRs 1-3) of a pair of variable heavy chain (VH) region and variable light chain (VL) region of an antibody listed in Table 2.

2. The antibody of aspect 1, wherein the antibody competes for binding to MDR1 with an antibody comprising a pair of variable heavy chain (VH) and variable light chain (VL) region of an antibody listed in Table 2.

3. The antibody of aspect 1, wherein the antibody competes for binding to MDR1 with an antibody selected from the group consisting of antibodies B1.28, B1.261, B1.129, B1.225, and B1.223 listed in Table 2.

4. The antibody of aspect 1, wherein the antibody comprises HCDRs of a VH region of an antibody listed in Table 2.

5. The antibody of aspect 1 or 2, wherein the antibody comprises LCDRs of a VL region of an antibody listed in Table 2.

6. The antibody of aspect 1, antibody comprising:
heavy chain complementarity determining regions (HCDRs) and light chain CDRs (LCDRs) of a pair of variable heavy chain (VH) region and variable light chain (VL) region of an antibody listed in Table 2.

7. An antibody molecule that specifically binds to a multidrug resistance protein 1 (MDR1), wherein the antigen-binding site of the antibody molecule comprises:
heavy chain complementarity determining regions 1-3 (HCDRs 1-3) and light chain CDRs 1-3 (LCDRs 1-3) of a pair of variable heavy chain (VH) region and variable light chain (VL) region of an antibody listed in Table 2;
HCDRs 1-3 of a VH region of an antibody listed in Table 2; or
LCDRs 1-3 of a VL region of an antibody listed in Table 2.

8. The antibody molecule according to aspect 7, wherein the antibody comprises HCDRs 1-3 and LCDRs 1-3 of a pair of VH region and VL region of an antibody listed in Table 2.

9. The antibody according to aspect 7, wherein the antibody comprises the HCDRs 1-3 of the VH region of a first antibody listed in Table 2.

10. The antibody molecule according to aspect 7, wherein the antibody comprises the LCDRS 1-3 of the VL region of a second antibody in Table 2.

11. The antibody molecule according to aspect 7, wherein the antibody molecule comprises the variable light (VL) chain and/or the variable heavy (VH) chain of an antibody listed in Table 2.

12. The antibody molecule according to aspect 8, wherein the antibody comprises (i) HCDRs 1-3 of VH region of B1.28 antibody and LCDRs 1-3 of VL region of the B1.28 antibody;

(ii) HCDRs 1-3 of VH region of B1.261 antibody and LCDRs 1-3 of VL region of the B1.261 antibody;

(iii) HCDRs 1-3 of VH region of B1.129 antibody and LCDRs 1-3 of VL region of the B1.129 antibody;

(iv) HCDRs 1-3 of VH region of B1.225 antibody and LCDRs 1-3 of VL region of the B1.225 antibody;

(v) HCDRs 1-3 of VH region of B1.188 antibody and LCDRs 1-3 of VL region of the B1.188 antibody;

(vi) HCDRs 1-3 of VH region of B1.27 antibody and LCDRs 1-3 of VL region of the B1.27 antibody; or (vii) HCDRs 1-3 of VH region of B1.223 antibody and LCDRs 1-3 of VL region of the B1.223 antibody, wherein the VH and VL regions are listed in Table 2.

13. The antibody molecule according to any one of aspects 7-12, wherein the antibody molecule binds to human MDR1 and to cynomolgus MDR1.

14. The antibody molecule according to aspect 13, wherein the antibody molecule comprises HCDRs 1-3 of VH region of B1.129 antibody and LCDRs 1-3 of VL region of the B1.129 antibody, HCDRs 1-3 of VH region of B1.28 antibody and LCDRs 1-3 of VL region of the B1.28 antibody, or wherein the antibody molecule comprises HCDRs 1-3 of VH region of B1.261 antibody and LCDRs 1-3 of VL region of the B1.261 antibody.

15. The antibody molecule according to any one of aspects 7-14, wherein the antibody molecule binds to loop 1 in the extracellular domain of MDR1.

16. The antibody molecule according to aspect 15, wherein the antibody molecule comprises: HCDRs 1-3 of VH region and LCDRs 1-3 of VL region of the B1.129 antibody or HCDRs 1-3 of VH region and LCDRs 1-3 of VL region of the B1.223 antibody.

17. The antibody molecule according to any one of aspects 7-16, wherein the antibody molecule inhibits efflux of one or more of calcein, Daunorubcin (Dioc2), and rhodamine by a cancer cell.

18. The antibody molecule according to aspect 17, wherein the cancer cell is a 293T cell overexpressing MDR1.

19. The antibody molecule according to aspect 17, wherein the cancer cell is a MES-SA-DX5 cancer cell.

20. The antibody molecule according to any one of aspects 17-20, wherein the comprises antibody comprises HCDRs 1-3 of VH region and LCDRs 1-3 of VL region of the B1.129 antibody.

21. An antibody molecule that specifically binds to MDR1 expressed on a cell surface, the antibody comprising:

(i) a variable heavy (VH) chain comprising heavy chain complementarity determining region (HCDR) 1 comprising the amino acid sequence: GFTFSRY (SEQ ID NO:343); HCDR2 comprising the amino acid sequence: SSGGGN (SEQ ID NO:344); and HCDR3 comprising the amino acid sequence: GAGDAWFAY (SEQ ID NO:345); and (ii) a variable light (VL) chain comprising light chain complementarity determining region (LCDR) 1 comprising the amino acid sequence: RSSQNIVHSTGN-TYLD (SEQ ID NO:11); LCDR2 comprising the amino acid sequence: KVSNRFS (SEQ ID NO:12); and LCDR3 comprising the amino acid sequence: FQGSHIPRT (SEQ ID NO:13); a VH chain comprising the amino acid sequence:

```
                                    (SEQ ID NO: 287)
EVKVVESGGVLVRPGGSLKLSCAASGFTFSRYTMSWVRQTPEKRLEWVA

TISSGGGNTYYPDSVKGRFTVSRDNAMSSLYLQMSSLRSEDTALYYCAR

YGAGDAWFAYWGQGTLVTVSS;
``` and a VL chain comprising the amino acid sequence:

```
                                    (SEQ ID NO: 20)
DVVLTQSPLSLPVTLGQPASISCRSSQNIVHSTGNTYLDWYQQRPGQSP

RLLIYKVSNRFSGVPDRFSGSGSGTDFTLKISRVEAEDVGVYFCFQGSH

IPRTFGQGTKLEIK;
```

(iii) a heavy chain comprising the amino acid sequence:

```
                                    (SEQ ID NO: 309)
EVQLVESGGVVVQPGGSLRLSCAASGFTFSRYTMSWVRQAPGKGLEWVA

TISSGGGNTYYPDSVKGRFTVSRDNSKNSLYLQMNSLRTEDTALYYCAR

YGAGDAWFAYWGQGTLVTVSSASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YDTTPPVLDSDGSFFLYSDLTVDKSRWQQGNVFSCSVMHEALHNHYTQK

SLSLSPG
``` and a light chain comprising the amino acid sequence:

```
                                    (SEQ ID NO: 21)
DVVLTQSPLSLPVTPGEPASISCRSSQNIVHSTGNTYLDWYLQKPGQSP

QLLIYKVSNRFSGVPDRFSGSGSGTDFTLKISRVEAEDVGVYYCFQGSH

IPRTFGQGTKLEIK;
```

(iv) a VH chain comprising HCDR1 comprising the amino acid sequence: GYTFTNY (SEQ ID NO:346); HCDR2 comprising the amino acid sequence: YPGNDD (SEQ ID NO:347); and HCDR3 comprising the amino acid sequence: GGYRAMDY (SEQ ID NO:308); and a VL chain comprising LCDR1 comprising the amino acid sequence: RSSQNIVHSTGNTYLD (SEQ ID NO:11); LCDR2 comprising the amino acid sequence: KVSNRFS (SEQ ID NO:12); and LCDR3 comprising the amino acid sequence: FQGSHIPRT (SEQ ID NO:13);

(v) a VH chain comprising the amino acid sequence:

```
                                  (SEQ ID NO: 294)
QVQLVQSGAEVKKPGASVKVSCKASGYTFTNYNMHWVRQAPGQRLEWMG

TIYPGNDDTSYNQKFKDRVTITADTSASTAYMELSSLRSEDTAVYYCAR

GGYRAMDYWGQGTLVTVSS
``` and a light chain comprising the amino acid sequence:

```
                                  (SEQ ID NO: 21)
DVVLTQSPLSLPVTPGEPASISCRSSQNIVHSTGNTYLDWYLQKPGQSP

QLLIYKVSNRFSGVPDRFSGSGSGTDFTLKISRVEAEDVGVYYCFQGSH

IPRTFGQGTKLEIK;
```

(vi) a heavy chain comprising the amino acid sequence:

```
                                  (SEQ ID NO: 310)
QVQLVQSGAEVKKPGASVKVSCKASGYTFTNYNMHWVRQAPGQRLEWMG

TIYPGNDDTSYNQKFKDRVTITADTSASTAYMELSSLRSEDTAVYYCAR

GGYRAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQP

REPQVYTLPPSRKELTKNQVSLTCLVKGFYPSDIAVEWESNGQPENNYK

TTPPVLKSDGSFFLYSKLTVDKSRWQQGNVFSCSVMHEALHNHYTQKSL

SLSPG
``` and a light chain comprising the amino acid sequence:

```
                                  (SEQ ID NO: 21)
DVVLTQSPLSLPVTPGEPASISCRSSQNIVHSTGNTYLDWYLQKPGQSP

QLLIYKVSNRFSGVPDRFSGSGSGTDFTLKISRVEAEDVGVYYCFQGSH

IPRTFGQGTKLEIK;
```

(vii) a VH chain comprising HCDR1 comprising the amino acid sequence GFTFSRY (SEQ ID NO:343); HCDR2 comprising the amino acid sequence: SSGGGN (SEQ ID NO:344); and HCDR3 comprising the amino acid sequence: GAGDAWFAY (SEQ ID NO:345); and a VL chain comprising LCDR1 comprising the amino acid sequence: RSSQSLVHSNGNTYLE (SEQ ID NO:290); LCDR2 comprising the amino acid sequence: KVSNRFS (SEQ ID NO:12); and LCDR3 comprising the amino acid sequence: QGSHFPRT (SEQ ID NO:348);

(viii) a VH chain comprising the amino acid sequence: evkvvesggvlvrpggslklscaasgftfsrytmswvrgtpekriewva-tissgggntyypdsvkgrftvsrdna msslylqmsslrsedtalyy-carygagdawfaywgqgtlvtvss (SEQ ID NO:287); and a VL chain comprising the amino acid sequence:

```
                                  (SEQ ID NO: 311)
DIVMTQSPLSLPVSLGDPASISCRSSQSLVHSNGNTYLEYYLQKPGQSP

KLLIYKVSNRFSGVPDRFSGSGSGTDFTLKISRVEAEDLGVYYCFQGSH

FPRTFGGGTKLEIK;
```

(ix) a heavy chain comprising the amino acid sequence:

```
                                  (SEQ ID NO: 309)
EVQLVESGGVVVQPGGSLRLSCAASGFTFSRYTMSWVRQAPGKGLEWVA

TISSGGGNTYYPDSVKGRFTVSRDNSKNSLYLQMNSLRTEDTALYYCAR

YGAGDAWFAYWGQGTLVTVSSASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YDTTPPVLDSDGSFFLYSDLTVDKSRWQQGNVFSCSVMHEALHNHYTQK

SLSLSPG
``` and a light chain comprising the amino acid sequence:

```
                                  (SEQ ID NO: 311)
DIVMTQSPLSLPVSLGDPASISCRSSQSLVHSNGNTYLEYYLQKPGQSP

KLLIYKVSNRFSGVPDRFSGSGSGTDFTLKISRVEAEDLGVYYCFQGSH

FPRTFGGGTKLEIK;
```

(x) a VH chain comprising HCDR1 comprising the amino acid sequence: GYTFTNY (SEQ ID NO:346); HCDR2 comprising the amino acid sequence: YPGNDD (SEQ ID NO:347); and HCDR3 comprising the amino acid sequence: GGYRAMDY (SEQ ID NO:308); and a VL chain comprising LCDR comprising the amino acid sequence: RSSQSLVHSNGNTYLE (SEQ ID NO:290); LCDR2 comprising the amino acid sequence: KVSNRFS (SEQ ID NO:12); and LCDR3 comprising the amino acid sequence: QGSHFPRT (SEQ ID NO:348);

(xi) a VH chain comprising the amino acid sequence:

```
                                  (SEQ ID NO: 294)
QVQLVQSGAEVKKPGASVKVSCKASGYTFTNYNMHWVRQAPGQRLEWMG

TIYPGNDDTSYNQKFKDRVTITADTSASTAYMELSSLRSEDTAVYYCAR

GGYRAMDYWGQGTLVTVSS
``` and a light chain comprising the amino acid sequence:

```
                                  (SEQ ID NO: 311)
DIVMTQSPLSLPVSLGDPASISCRSSQSLVHSNGNTYLEYYLQKPGQSP

KLLIYKVSNRFSGVPDRFSGSGSGTDFTLKISRVEAEDLGVYYCFQGSH

FPRTFGGGTKLEIK;
```

(xii) a heavy chain comprising the amino acid sequence:

(SEQ ID NO: 310)
QVQLVQSGAEVKKPGASVKVSCKASGYTFTNYNMHWVRQAPGQRLEWMG

TIYPGNDDTSYNQKFKDRVTITADTSASTAYMELSSLRSEDTAVYYCAR

GGYRAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQP

REPQVYTLPPSRKELTKNQVSLTCLVKGFYPSDIAVEWESNGQPENNYK

TTPPVLKSDGSFFLYSKLTVDKSRWQQGNVFSCSVMHEALHNHYTQKSL

SLSPG and a light chain comprising the amino acid sequence:

(SEQ ID NO: 311)
DIVMTQSPLSLPVSLGDPASISCRSSQSLVHSNGNTYLEYYLQKPGQSP

KLLIYKVSNRFSGVPDRFSGSGSGTDFTLKISRVEAEDLGVYYCFQGSH

FPRTFGGGTKLEIK;

(xiii) a VH chain comprising HCDR1 comprising the amino acid sequence GFTFSRY (SEQ ID NO:343); HCDR2 comprising the amino acid sequence: SSGGGN (SEQ ID NO:344); and HCDR3 comprising the amino acid sequence: GAGDAWFAY (SEQ ID NO:345); and a VL chain comprising LCDR1 comprising the amino acid sequence: RSSQTIVHSNGNTYLE (SEQ ID NO:39); LCDR2 comprising the amino acid sequence: KVSKRFS (SEQ ID NO: 40); and LCDR3 comprising the amino acid sequence: FQASHFPRT (SEQ ID NO:329);

(xiv) a VH chain comprising the amino acid sequence:

(SEQ ID NO: 287)
EVKVVESGGGVLVRPGGSLKLSCAASGFTFSRYTMSWVRQTPEKRLEWVA

TISSGGGNTYYPDSVKGRFTVSRDNAMSSLYLQMSSLRSEDTALYYCAR

YGAGDAWFAYWGQGTLVTVSS;

and a VL chain comprising the amino acid sequence:

(SEQ ID NO: 313)
DVLMTQTPLSLPVSLGDQASISCRSSQTIVHSNGNTYLEWYLQKPGQSP

KLLIYKVSKRFSGVPDRFSGSGSGTDFTLKISRVEAEDLGVYYCFQASH

FPRTFGGGTKLEIK;

(xv) a heavy chain comprising the amino acid sequence:

(SEQ ID NO: 309)
EVQLVESGGGVVVQPGGSLRLSCAASGFTFSRYTMSWVRQAPGKGLEWVA

TISSGGGNTYYPDSVKGRFTVSRDNSKNSLYLQMNSLRTEDTALYYCAR

YGAGDAWFAYWGQGTLVTVSSASTKGPSVFPLAPSSKSTSGGTAALGCL

VKDYFPEPVTVSWNSGALTSGVHTFPAVLQSSGLYSLSSVVTVPSSSLG

-continued
TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YDTTPPVLDSDGSFFLYSDLTVDKSRWQQGNVFSCSVMHEALHNHYTQK

SLSLSPG and a VL chain comprising the amino acid sequence:

(SEQ ID NO: 313)
DVLMTQTPLSLPVSLGDQASISCRSSQTIVHSNGNTYLEWYLQKPGQSP

KLLIYKVSKRFSGVPDRFSGSGSGTDFTLKISRVEAEDLGVYYCFQASH

FPRTFGGGTKLEIK;

(xvi) a VH chain comprising HCDR1 comprising the amino acid sequence: GYTFTNY (SEQ ID NO:346); HCDR2 comprising the amino acid sequence: YPGNDD (SEQ ID NO:347); and HCDR3 comprising the amino acid sequence: GGYRAMDY (SEQ ID NO:308); and a VL chain comprising LCDR1 comprising the amino acid sequence: RSSQTIVHSNGNTYLE (SEQ ID NO:39); LCDR2 comprising the amino acid sequence: KVSKRFS (SEQ ID NO:40); and LCDR3 comprising the amino acid sequence: FQASHFPRT (SEQ ID NO:329); CDRs 5F9/VL B1-89v1

(xvii) a VH chain comprising the amino acid sequence: qvqlvqsgaevkkpgasvkvsckasgytftnynmhwvrqapgqrlewmgtiypgnddtsynqkfkdrvtitad tsastaymelsslrsedtavyycarggyramdywgqgtivtvss (SEQ ID NO:294) and a light chain comprising the amino acid sequence:

(SEQ ID NO: 313)
DVLMTQTPLSLPVSLGDQASISCRSSQTIVHSNGNTYLEWYLQKPGQSP

KLLIYKVSKRFSGVPDRFSGSGSGTDFTLKISRVEAEDLGVYYCFQASH

FPRTFGGGTKLEIK;

or (xviii) a heavy chain comprising the amino acid sequence:

(SEQ ID NO: 310)
QVQLVQSGAEVKKPGASVKVSCKASGYTFTNYNMHWVRQAPGQRLEWMG

TIYPGNDDTSYNQKFKDRVTITADTSASTAYMELSSLRSEDTAVYYCAR

GGYRAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQP

REPQVYTLPPSRKELTKNQVSLTCLVKGFYPSDIAVEWESNGQPENNYK

TTPPVLKSDGSFFLYSKLTVDKSRWQQGNVFSCSVMHEALHNHYTQKSL

SLSPG and a light chain comprising the amino acid sequence:

(SEQ ID NO: 313)
DVLMTQTPLSLPVSLGDQASISCRSSQTIVHSNGNTYLEWYLQKPGQSP

KLLIYKVSKRFSGVPDRFSGSGSGTDFTLKISRVEAEDLGVYYCFQASH

FPRTFGGGTKLEIK.

22. A bispecific antibody molecule that binds multidrug resistance protein 1 (MDR1) and a tumor associated antigen (TAA), the antibody molecule comprising two identical variable light (VL) chains, a first variable heavy (VH) chain, and a second VH chain, wherein the VL chains each comprise an antigen-binding site for MDR1, the first VH chain comprises an antigen-binding site for MDR1, and the second VH chain comprises an antigen-binding site for the TAA, and wherein the second VH chain binds the TAA when paired with one of the light chains.

23. The bispecific antibody molecule according to aspect 22, wherein the antigen-binding site of the two VL chains comprises light chain CDRs 1-3 (LCDRs 1-3) of an antibody listed in Table 2.

24. The bispecific antibody molecule according to aspect 22 or 23, wherein the antigen-binding site of the first VH chain comprises heavy chain CDRs 1-3 (HCDRs 1-3) of an antibody listed in Table 2.

25. The bispecific antibody molecule according to aspect 22 or 23 wherein the first VH chain comprises HCDRs 1-3 of an anti-MDR1 antibody other than an antibody listed in Table 2, optionally wherein the first VH chain comprises the amino acid sequence of the VH chain of an anti-MDR1 antibody other than an antibody listed in Table 2.

26. The bispecific antibody molecule according to aspect 25, wherein the anti-MDR1 antibody comprises:

a VH chain of the 15D3 antibody having the amino acid sequence:

(SEQ ID NO: 293)
EVKVVESGGVLVRPGGSLKLSCAASGFTFSRYTMSWVRQTPEKRLEWVA

TISSGGGNTYYPDSVKGRFTVSRDNAMSSLYLQMSSLRSEDTALYYCAR

YGAGDAWFAYWGQGTLVTVSA;

a VH chain of the UIC2 antibody having the amino acid sequence:

LPIQFGNFYPMDYWGQGTSVTVSS;

or a VH chain of the MRK16 antibody having the amino acid sequence:

(SEQ ID NO: 286)
EVILVESGGGLVKPGGSLKLSCAASGFTFSSYTMSWVRQTPEKRLEWVA

TISSGGGNTYYPDSVKGRFTISRDNAKNNLYLQMSSLRSEDTALYYCAR

YYRYEAWFASWGQGTLVTVSA.

27. The bispecific antibody molecule according to aspect 26, wherein the anti-MDR1 antibody comprises a VH chain having the amino acid sequence:

(SEQ ID NO: 292)
EVKVVESGGVLVRPGGSLKLSCAASGFTFSRYTMSWVRQTPEKRLEWVA

TISSGGGX$^2$TYYPDSVKGRFTVSRDNAMSSLYLQMSSLRSEDTALYYCA

RYGAGDAWFAYWGQGTLVTVSS, wherein X$^2$ is N, Q or S,
optionally wherein X$^2$ is Q or S.

28. The bispecific antibody molecule according to any one of aspects 22 to 27, wherein the VL chain(s) comprise LCDRs 1-3 of the B1-28 antibody listed in Table 2, optionally wherein the VL chains comprise the amino acid sequence of the VL chain of the B1-28 antibody listed in Table 2; or wherein the VL chain(s) comprise LCDRs 1-3 of an anti-MDR1 V6 antibody having a VL chain comprising the amino acid sequence:

(SEQ ID NO: 289)
LWVPGSTGDVLMTQTPLSLPVSLGDQASISCRSSQSLVHSNGNTYLEWY

LQKPGQSPKLLIYKVSNRFSGVPDRFSGSGSGTDFTLKISRVEAEDLGV

YYCFQGSHFPRTFGGGTKLEIK, optionally wherein the VL chains comprise the amino acid sequence of the VL chain of the V6 antibody.

29. The bispecific antibody molecule according to aspects 22 or 24, wherein the VL chains comprise LCDRs 1-3 of an anti-MDR1 antibody other than an antibody listed in Table 2, optionally wherein the light chains comprise the amino acid sequence of the VL chain of the antibody other than an antibody listed in Table 2.

30. The bispecific antibody molecule according to aspect 29, wherein the anti-MDR1 antibody comprises the LCDRs1-3 of:
the variable light chain of the MRK16 antibody comprising the amino acid sequence:

(SEQ ID NO: 283)
DVLMTQTPVSLSVSLGDQASISCRSSQSIVHSTGNTYLEWYLQKPGQSP

KLLIYKISNRFSGVPDRFSGSGSGTDFTLKISRVEAEDLGVYYCFQASH

FPRTFGGGTKLEIK;

the variable light chain of the 15D3 antibody comprising the amino acid sequence:

(SEQ ID NO: 284)
DVLMTQTPLSLPVSLGDQASISCRSSQSIVHSTGNTYLEWYLQKPGQSP
(SEQ ID NO: 288)AVQLQQSGPELVKTGASVKISCKASGYSFSNYYIHWVKQSHGKSLEWIGFISCYNGATFY
KLLIYKVSNRFSGVPDRFSGSGSGTDFTLKISRLEAEDLGVYYCFQGSH

FPRTFGGGTRLEIK;

or the variable light chain of the UIC2 antibody comprising the amino acid sequence:

(SEQ ID NO: 285)
DVVMTQTPRSLPVSLGDQASISCRSSQSLLHSNGNTYLHWYLQKPGQSP

KLLIYKVSNRFSGVPDRFSGSGSGTDFTLKISRVEAEDLGVYFCSQSTH

IPPWTFGGGTKLDIK.

31. The antibody molecule, or bispecific antibody molecule according to any of the preceding aspects, wherein the antibody, when bound to a cell expressing MDR1, inhibits efflux by the MDR1.

32. The bispecific antibody molecule according to any one of aspects 22 to 31, wherein the antibody is capable of increasing sensitivity of a cancer cell to treatment with a chemotherapeutic agent, wherein the half maximal inhibitory concentration (IC50) of the chemotherapeutic agent when co-administered with the antibody is at least 5 times lower than the IC50 of the chemotherapeutic agent when co-administered with an anti-MDR1 antibody comprising a VH chain having the sequence:

```
                                      (SEQ ID NO: 293)
EVKVVESGGVLVRPGGSLKLSCAASGFTFSRYTMSWVRQTPEKRLEWVA

TISSGGGNTYYPDSVKGRFTVSRDNAMSSLYLQMSSLRSEDTALYYCAR

YGAGDAWFAYWGQGTLVTVSA;
``` and
a VL chain having the sequence:

```
                                      (SEQ ID NO: 284)
DVLMTQTPLSLPVSLGDQASISCRSSQSIVHSTGNTYLEWYLQKPGQSP

KLLIYKVSNRFSGVPDRFSGSGSGTDFTLKISRLEAEDLGVYYCFQGSH

FPRTFGGGTRLEIK.
```

33. The bispecific antibody molecule according to any one of aspects 22 to 32, wherein the TAA is CD47.

34. The bispecific antibody molecule according to aspect 33, wherein the bispecific antibody comprises HCDRs1-3 of a VH region of an anti-CD47 antibody, 5F9, wherein the VH region comprises the amino acid sequence:

```
                                      (SEQ ID NO: 294)
QVQLVQSGAEVKKPGASVKVSCKASGYTFTNYNMHWVRQAPGQRLEWMG

TIYPGNDDTSYNQKFKDRVTITADTSASTAYMELSSLRSEDTAVYYCAR

GGYRAMDYWGQGTLVTVSS;
``` or
wherein the bispecific antibody comprises HCDRs1-3 of a VH region of an anti-CD47 antibody, B6H12, wherein the VH region comprises the amino acid sequence:

```
                                      (SEQ ID NO: 295)
EVQLVESGGDLVKPGGSLKLSCAASGFTFSGYGMSWVRQTPDKRLEWVA

TITSGGTYTYYPDSVKGRFTISRDNAKNTLYLQIDSLKSEDTAIYFCAR

SLAGNAMDYWGQGTSVTVSS.
```

35. The bispecific antibody molecule according to aspect 34, wherein:
the first VH chain comprises HCDRs 1-3 of a VH chain from an anti-MDR1 antibody having the following HCDR sequences: HCDR1: RYTMS (SEQ ID NO:301), HCDR2: TISSGGGNTYYPDSVKG (SEQ ID NO:302), TISSGGGQTYYPDSVKG (SEQ ID NO:303), or TISSGGGSTYYPDSVKG (SEQ ID NO:304), and HCDR3: ARYGAGDAWFAY (SEQ ID NO:349); and
the VL chains each comprise LCDRs 1-3 of a VL region of the B1-28 antibody listed in Table 2, wherein the LCDR sequences are: LCDR1: RSSQNIVHSTGN-TYLD (SEQ ID NO:11), LCDR2: KVSNRFS (SEQ ID NO:12), and LCDR3: FQGSHIPRT (SEQ ID NO:13).

36. The bispecific antibody molecule according to aspect 35, wherein:
the first VH chain comprises an amino acid sequence comprising

```
                                      (SEQ ID NO: 291)
EVKVVESGGVLVRPGGSLKLSCAASGFTFSRYTMSWVRQTPEKRLEWVA

TISSGGGX2TYYPDSVKGRFTVSRDNAMSSLYLQMSSLRSEDTALYYCA

RYGAGDAWFAYWGQGTLVTVSS,
``` wherein X2 is N, Q or S;
the second VH chain comprises an amino acid sequence comprising

```
                                      (SEQ ID NO: 294)
QVQLVQSGAEVKKPGASVKVSCKASGYTFTNYNMHWVRQAPGQRLEWMG

TIYPGNDDTSYNQKFKDRVTITADTSASTAYMELSSLRSEDTAVYYCAR

GGYRAMDYWGQGTLVTVSS;
``` and
the two VL chains comprise an amino acid sequence comprising the VL region chain of the B1-28 antibody listed in Table 2.

37. The bispecific antibody molecule according to aspect 22, wherein
the first VH chain comprises HCDRs1-3 of the VH chain of the (i) B1.28 antibody; (ii) B1.30 antibody; (iii) B1.89 antibody; (iv) B1.129 antibody; (v) B1.225; (vi) B1.261 antibody set forth in Table 2; or HCDRs1-3 of the VH chain of the 15D3 or the MRK16 antibody;
the identical VL chains each comprise (i) the LCDRs1-3 of the VL chain of the MRK16 antibody or (ii) the LCDRs1-3 of the VL chain of the V6 antibody; and
the second VH chain comprises HCDRs1-3 of the VH chain of the 5F9 antibody or the B6H12 antibody.

38. The bispecific antibody molecule according to aspect 22, wherein the first VH chain comprises HCDRs1-3 of the VH chain of the (i) B1.188 antibody; (ii) B1.28 antibody; (iii) B1.261 antibody; (iv) B1.129 antibody; or (v) B1.223 antibody set forth in Table 2; the identical VL chains each comprise LCDRs1-3 of the VL chain of the MRK16 antibody; and the second VH chain comprises HCDRs1-3 of the VH chain of the 5F9 antibody or the B6H12 antibody.

39. The bispecific antibody molecule according to aspect 38, wherein the first VH chain comprises the VH chain of the (i) B1.188 antibody; (ii) B1.28 antibody; (iii) B1.261 antibody; (iv) B1.129 antibody; or (v) B1.223 antibody set forth in Table 2; the identical VL chains each comprise the VL chain of the MRK16 antibody; and the second VH chain comprises the VH chain of the 5F9 antibody or the B6H12 antibody.

40. The bispecific antibody molecule according to aspect 27, wherein the first VH chain comprises HCDRs1-3 of the VH chain of the B1.225 antibody set forth in Table 2; the identical VL chains each comprise LCDRs1-3 of the VL chain of the MRK16 antibody; and the second VH chain comprises HCDRs1-3 of the VH chain of the 5F9 antibody or the B6H12 antibody.

41. The bispecific antibody molecule according to aspect 40, wherein the first VH chain comprises the VH chain of the B1.225 antibody set forth in Table 2; the identical VL chains each comprise the VL chain of the MRK16 antibody; and the second VH chain comprises the VH chain of the 5F9 antibody.

42. The antibody molecule, or bispecific antibody molecule, according to any of the preceding aspects, wherein the antibody comprises a humanized light chain.

43. The antibody molecule, or bispecific antibody molecule, according to any of the preceding aspects, wherein the antibody comprises a humanized heavy chain.

44. The antibody molecule, or bispecific antibody molecule, according to any one of the preceding aspects for use in a method of treating cancer in a subject, the method comprising administering the antibody to the subject.

45. The antibody molecule, or bispecific antibody molecule, for use according to aspect 44, wherein the method comprising administering the antibody in combination with at least one additional active agent wherein the at least one additional active agent comprises a chemotherapeutic agent, an inhibitor of a multidrug resistance transporter, an immunotherapy agent, or a combination thereof.

46. The antibody molecule, or bispecific antibody molecule, for use according to aspect 45, wherein the at least one additional active agent is a chemotherapy agent, optionally wherein the chemotherapeutic agent is a taxol, a *vinca* alkaloid, or an anthracycline.

47. The antibody molecule, or bispecific antibody molecule for use according to aspect 46, wherein the subject being treated has a cancer which has been determined to be resistant to treatment with the chemotherapeutic agent.

48. A method of treating a subject for a cancer, the method comprising administering to the subject a therapeutically effective amount of the antibody molecule according to any one of aspects 1 to 21 or the bispecific antibody molecule according to any one of aspects 22 to 43.

49. The method according to aspect 48, wherein the method comprises administering the antibody molecule, or bispecific antibody molecule in combination with at least one additional active agent, wherein the at least one additional active agent comprises a chemotherapy agent, an inhibitor of a multidrug resistance transporter, an immunotherapy agent, or a combination thereof.

50. The method according to aspect 49, wherein the at least one additional active agent is a chemotherapy agent, optionally wherein the chemotherapy agent is a taxol, a *vinca* alkaloid, or an anthracycline.

51. The method according to aspect 50, wherein the subject being treated has a cancer that is classed as being resistant to the chemotherapy agent.

52. One or more nucleic acids comprising one or more sequences encoding the antibody molecule according to any one of aspects 1 to 21 or the bispecific antibody molecule according to any one of aspects 22 to 43.

53. One or more recombinant expression vectors comprising the one or more nucleic acids according to aspect 52.

54. A host cell genetically modified with the recombinant one or more recombinant expression vectors according to aspect 52.

55. An immune effector cell comprising a chimeric antigen receptor (CAR) comprising a MDR1 binding domain, a transmembrane domain, and an intracellular signaling domain, and wherein the MDR1 binding domain comprises heavy chain complementarity determining regions (HCDRs) and/or light chain CDRs (LCDRs) of a pair of variable heavy chain (VH) region and variable light chain (VL) region of an antibody listed in Table 2.

56. A method of inhibiting efflux activity of MDR1 expressed by a live cell, the method comprising contacting the cell with the antibody according molecule according to any one of aspects 1 to 21 or the bispecific antibody molecule according to any one of aspects 22 to 43.

57. The method of aspect 56, further comprising contacting the cell with an inhibitor of MDR1 mediated efflux.

58. The method according to aspect 56 or 57, further comprising contacting the cells with a chemotherapy agent.

59. The method according to any one of aspects 56 to 58, wherein the cell is a cancer cell.

60. The method according to aspect 59, wherein the cancer cell is a multidrug resistant cancer cell.

61. A method of assaying expression of MDR1 on cell surface of a cell, the method comprising contacting the cell with the antibody molecule according to any one of aspects 1 to 47.

62. The method of aspect 61, wherein the antibody is detectably labeled.

63. A method for diagnosing a disease or condition associated with MDR1 expression in a subject, the method comprising contacting a tissue sample or a cell sample from the subject with an antibody molecule as set forth in any one of aspects 1-47.

64. The method according to aspect 63, wherein the antibody molecule comprises an arrangement of the VH and VL chains as shown for an antibody molecule in FIG. 19.

65. An antibody that specifically binds to a multidrug resistance protein 1 (MDR1) wherein the antibody competes for binding to MDR1 with an antibody comprising: heavy chain complementarity determining regions 1-3 (HCDRs 1-3) and light chain CDRs 1-3 (LCDRs 1-3) of a pair of variable heavy chain (VH) region and variable light chain (VL) region of an antibody listed in Table 2, for use as a medicament.

66. Use of an antibody that specifically binds to a multidrug resistance protein 1 (MDR1) wherein the antibody competes for binding to MDR1 with an antibody comprising: heavy chain complementarity determining regions 1-3 (HCDRs 1-3) and light chain CDRs 1-3 (LCDRs 1-3) of a pair of variable heavy chain (VH) region and variable light chain (VL) region of an antibody listed in Table 2, for the manufacture of a medicament for the treatment of cancer.

67. A pharmaceutical composition comprising an antibody that specifically binds to a multidrug resistance protein 1 (MDR1) wherein the antibody competes for binding to MDR1 with an antibody comprising: heavy chain complementarity determining regions 1-3 (HCDRs 1-3) and light chain CDRs 1-3 (LCDRs 1-3) of a pair of variable heavy chain (VH) region and variable light chain (VL) region of an antibody listed in Table 2, for use in a method of treating cancer in a subject, the method comprising administering the antibody to the subject.

68. An antibody molecule that specifically binds to a multidrug resistance protein 1 (MDR1), wherein the antigen-binding site of the antibody molecule comprises:

heavy chain complementarity determining regions 1-3 (HCDRs 1-3) and light chain CDRs 1-3 (LCDRs 1-3) of a pair of variable heavy chain (VH) region and variable light chain (VL) region of an antibody listed in Table 2;

HCDRs 1-3 of a VH region of an antibody listed in Table 2; or LCDRs 1-3 of a VL region of an antibody listed in Table 2, for use as a medicament.

69. Use of an antibody molecule that specifically binds to a multidrug resistance protein 1 (MDR1), wherein the antigen-binding site of the antibody molecule comprises:

heavy chain complementarity determining regions 1-3 (HCDRs 1-3) and light chain CDRs 1-3 (LCDRs 1-3) of a pair of variable heavy chain (VH) region and variable light chain (VL) region of an antibody listed in Table 2; HCDRs 1-3 of a VH region of an antibody listed in Table 2; or LCDRs 1-3 of a VL region of an antibody listed in Table 2, for the manufacture of a medicament for the treatment of cancer.

70. A pharmaceutical composition comprising an antibody that specifically binds to a multidrug resistance protein 1 (MDR1) wherein the antigen-binding site of the antibody molecule comprises:

heavy chain complementarity determining regions 1-3 (HCDRs 1-3) and light chain CDRs 1-3 (LCDRs 1-3) of a pair of variable heavy chain (VH) region and variable light chain (VL) region of an antibody listed in Table 2; HCDRs 1-3 of a VH region of an antibody listed in Table 2; or LCDRs 1-3 of a VL region of an antibody listed in Table 2, use in a method of treating cancer in a subject, the method comprising administering the antibody to the subject.

71. An antibody molecule according to aspect 21, for use as a medicament.

72. Use of an antibody molecule according to aspect 21, for the manufacture of a medicament for the treatment of cancer.

73. A pharmaceutical composition comprising the antibody molecule of aspect 21, for use in a method of treating cancer in a subject, the method comprising administering the antibody to the subject.

74. A bispecific antibody molecule that binds multidrug resistance protein 1 (MDR1) and a tumor associated antigen (TAA), the antibody molecule comprising two identical variable light (VL) chains, a first variable heavy (VH) chain, and a second VH chain, wherein the VL chains each comprise an antigen-binding site for MDR1, the first VH chain comprises an antigen-binding site for MDR1, and the second VH chain comprises an antigen-binding site for the TAA, and wherein the second VH chain binds the TAA when paired with one of the light chains, for use as a medicament.

75. Use of a bispecific antibody molecule that binds multidrug resistance protein 1 (MDR1) and a tumor associated antigen (TAA), the antibody molecule comprising two identical variable light (VL) chains, a first variable heavy (VH) chain, and a second VH chain, wherein the VL chains each comprise an antigen-binding site for MDR1, the first VH chain comprises an antigen-binding site for MDR1, and the second VH chain comprises an antigen-binding site for the TAA, and wherein the second VH chain binds the TAA when paired with one of the light chains, for the manufacture of a medicament for the treatment of cancer.

76. A pharmaceutical composition comprising a bispecific antibody molecule that binds multidrug resistance protein 1 (MDR1) and a tumor associated antigen (TAA), the antibody molecule comprising two identical variable light (VL) chains, a first variable heavy (VH) chain, and a second VH chain, wherein the VL chains each comprise an antigen-binding site for MDR1, the first VH chain comprises an antigen-binding site for MDR1, and the second VH chain comprises an antigen-binding site for the TAA, and wherein the second VH chain binds the TAA when paired with one of the light chains, for the manufacture of a medicament for the treatment of cancer in a subject, the method comprising administering the antibody to the subject.

77. The bispecific molecule of aspect 74 for use as a medicament as, the use of aspect 75, or the pharmaceutical composition of aspect 76, wherein the bispecific molecule comprises a LCDRs 1-3 of a VL region of an antibody listed in Table 2.

The following example(s) is/are offered by way of illustration and not by way of limitation.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, cells, and kits for methods referred to in, or related to, this disclosure are available from commercial vendors such as BioRad, Agilent Technologies, Thermo Fisher Scientific, Sigma-Aldrich, New England Biolabs (NEB), Takara Bio USA, Inc., and the like, as well as repositories such as e.g., Addgene, Inc., American Type Culture Collection (ATCC), and the like.

Example 1: Generation of Antibodies that Bind Specifically to Cells Expressing High Levels of Pgp (MDR1) but Significantly Less or not at all to Cells Having Reduced or Absent Expression of MDR1

Materials and Methods

Antibody Production

Wilt type (WT) and mutant MDR1 were used for immunization. Mutant MDR1 that contains mutations that constrains the pump in an open configuration and another MDR1 mutant that contains mutations that constrains the pump in a closed configuration were generated. The mutations in the human and *Macaca fascicularis* MDR1 to generate MDR1 mutants that are constrained in an open configuration are as follows: E556Q and E1201Q. The mutations in the human MDR1 to generate MDR1 mutants that are constrained in closed configuration are as follows: (i) K433M, S434A, K1076M, S1077A; (ii) K433M, S434A, Q475A, K1076M, S1077A, Q1118A; and/or (iii) K433M, S434A, Q475A, R588E, K1076M, S1077A, Q1118A, R1233E. Additional MDR1 mutants included deletion in loop 1 of human MDR1, with deletion of amino acid residues 82-99 or 79-102. The numbering of the amino acid residues for the substituted positions is with reference to the sequence of the human MDR1.

Wild type (WT) and mutated MDR1 was expressed in 3T3 cells. Female mice were immunized with MDR1 (wild type or mutated) DNA and/or MDR1 (wild type or mutated) expressing cells using various prime-boost strategies for 8 weeks. In some instances, more than one antigen (one or more of WT or mutated MDR1) was used for immunization to increase diversity of the generated antibodies. Spleen and lymph nodes cells were fused with SP2/0 myeloma cells. Hybridomas were screened for the presence of anti-ABCB1 antibodies by flow cytometry, then for functional activity in cell killing assays. CDRs from select murine IgGs were cloned into mammalian IgG1 backbone expression vectors and transfected into a HEK 293 mammalian cell line for expression of the full length IgG1 antibodies.

DNA Sequence Determination

DNA sequences were determined by double strand sequencing.

DNA and Protein Sequence Analysis and Sequence Data Management

The Vector NTI (ThermoFisher) software package was used for sequence mapping, analysis, annotation and illustration.

Cell Culture and Antibody Production

Standard cell culture techniques are used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

Expression Vectors

For the generation of the antibody expression vectors, the variable regions of heavy and light chain DNA sequences were subcloned in frame with either the human IgG1 constant heavy chain or the human IgG1 kappa constant light chain pre-inserted into the respective generic recipient expression vector optimized for expression in mammalian cell lines. The genes to be expressed were cloned into the pCI-neo Mammalian Expression Vector (Promega) that uses the full-length human cytomegalovirus (CMV) immediate-early promoter for high level gene expression. The two antibody chains were cloned into two different vectors.

The N-terminal signal sequences from mouse IgG heavy chain and kappa light chain were used for the secreted expression of the heavy and light chain, respectively. The signal peptide was cleaved during expression, leaving intact N-terminus. In the Fab constructs, the C-terminus of the CH1 IgG1 constant region was fused with a 6×His tag for purification.

Monoclonal antibodies raised against Pgp were cloned as recombinant engineered antibodies into a Human IgG1/Kappa expression vector.

Variable heavy and light fragments from mouse hybridoma sequences were obtained and were cloned into the same background of leader sequence and constant region Production of mAb, Fab'2, Fab, and Bispecific mAb Antibody constructs were expressed using polymer-based co-transfection of Expi293 cells (A14527, ThermoFisher) cells growing in suspension with the mammalian expression vectors following the manufacturer's recommendations.

About six days after transfection the cells were harvested by centrifugation. In detail, 1 ug of total encoding DNA per 1 ml of transfected culture was diluted into of Opti-MEM® medium (Life Technologies), and incubated with Expifectamine reagent (Life Technologies) in the same medium for 20 min. The mixture was then added into the Expi293® cells growing in suspension in Expi293® Expression medium (Life Technologies) at 2.5 million cells/ml at 37° C. with and overlay of 8% of CO2 in air. After 6 days, the medium containing the antibody construct was harvested by centrifugation.

Purification of mAbs

To purify antibody formats containing the Fc, 10 μl of MabSelect™ SuRe™ (GE Healthcare) per 1 ml of supernatant were added to the harvested medium and kept stirring at 4° C. overnight. The next day, the protein A resin was applied in a 24 well filter plate using a vacuum manifold unit (Pall Lifesciences, USA). The resin was washed with PBS and the antibody eluted in 50 mM phosphate pH 3 and neutralized with 10×PBS pH 13.

Fabs were purified following the same procedure using Ni Sepharose 6 Fast Flow histidine-tagged protein purification resin (GE Healthcare). The beads were washed with PBS followed by washes with 25 mM phosphate buffer pH 7.4, 150 mM NaCl supplemented with 20 mM of imidazole. The complex was eluted with 2 volumes of 25 mM phosphate buffer pH 7.4, 150 mM NaCl supplemented with 500 mM of imidazole. Finally, purified Fab was buffer-exchanged into PBS. Chromatogram of an anti-Pgp monoclonal antibody is shown in FIG. 1.

Analytical Test for mAbs (GXII Educed and Non-Reduced)

Purity and monomer content of the final protein preparation was determined by high-throughput analysis on the Caliper's LabChip GXII using Protein Express LabChip Kit (Perkin-Elmer) as described by the manufacturer. The chip was automatically primed on the instrument with polymer solution containing 0.2% SDS and fluorescent staining dye. The destain channels were filled with polymer solution free of SDS and dye. Briefly, proteins in reducing and not reducing conditions were prepared by mixing a small volume (2-5 μL) of sample with the caliper sample buffer with or without DDT. The samples were denatured at 75° C. for 5 minutes, centrifuged at 2000 g for 3 minutes, and then run. Electropherograms were generated by LabChip GXII Touch software (Perkin Elmer).

Reagent Cell Lines Used to Test: Binding, Affinity, Efflux Blockade, Cell Sensitization to Chemotherapeutics Human embryonic kidney (HEK) cell line HEK 293FT (Life Technologies) was maintained in Dulbecco's modified Eagle's Medium (DMEM) supplemented with 10% fetal bovine serum (HyClone), 2 mM GlutaMAX (Life Technologies), 100 U/mL penicillin, and 100 g/mL streptomycin at 37° C. with 5% CO2 incubation.

293T cells were transiently transfected with the Human P Glycoprotein Tagged ORF Clone in pLenti-C-Myc-DDK-P2A-Puro plasmid using the optimized PEIPro™ transfection protocol (Polyplus). DNA and JetPEI® were respectively diluted in culture media before being gently mixed for approximately 10 min. This mixing led to the formation of a transfection complex, which was directly added to the cell culture. Efflux blockade was measure using the Multidrug Resistance Direct Dye Efflux Assay (Chemicon) following the manufacturer's protocol.

Detection of ABCB1 Specific Binding

Binding specificity of the mAbs, Fab and Fab'2 antibodies were tested by by FACS using 293T cell lines naturally expressing Pgp, 293T naïve cells overexpressing the human Pgp target, Pgp knock down 293T cells (after lentiviral iRNA treatment). Briefly, the different cell lines were incubated with various amounts of mAbs or bispecific mAbs, or a human IgG1 isotype control antibody on ice for 1 hr. The cells were washed three times with FACS buffer (PBS containing 0.5% BSA). Alexa647 labeled goat anti-human antibody was added as a secondary antibody, and the samples were incubated on ice for another 1 hour. Samples were washed and analyzed using a BD FACSCanto (BD Biosciences).

MDR1-Overexpressing Cell Line Generation

The MDR1 overexpressing HEK 293T cells or C6 cells were generated by transfection with human MDR1 cDNA in a mammalian expression vector, followed by a multistep selection of transfectants for resistance to hygromycin at 0.2 mg/ml or 0.5 mg/ml. A MDR1 high-expressing clone was isolated using a FACS Aria, after incubation with a detecting antibody, MRK16-PE.

Efflux Blockade Experimental Procedure

HEK 293T cells expressing human MDR1 or MES-SA/DX5 cells expressing human MDR1 were washed several times and aliquoted into 96-well plates as 50 μl aliquots/well at a cell density of 1×10e6 cells per ml in phenol red-free DMEM. Cells were mixed with 300 nM to 1 nM antibodies and incubated for 1 h at 37° C. To determine efflux blockade cells were incubated in the presence of B1 fluorescent substrates as follows: 0.6 μM Rhodamine; 5 μM Daunorubicin (DiOC2(3)) or 0.6 μM Calcein AM for 1.5 h at 37° C. The cells were then washed twice and finally resuspended in 200 ml PBS. Rhodamine, DiOC2(3) or Calcein AM fluorescence were measured by flow cytometry.

Cell Binding Assays

Antibody binding to cells was evaluated by flow cytometry. 293T cells stably transfected to express human ABCB1 (293T_KPB1_OX) were washed once in flow cytometry buffer (PBS+2% FBS+0.02% sodium azide), resuspended at 2×10^6 cells/mL in flow cytometry buffer, and dispensed into 96-well microtiter plates at 0.1 mL/well. In the figures, "B1" refers to ABCB1 (also known as MDR1 or Pgp). Recombinant antibodies were added to cells at 5 ug/mL for initial binding confirmation, or serially diluted from 100 ug/mL in flow cytometry buffer. After incubating cells on ice for 30 min, cells were washed twice with flow cytometry buffer. Bound antibody was detected with PE-labeled F(ab')$_2$ fragment goat anti-human IgG (Jackson ImmunoResearch) and evaluated on an Attune NxT flow cytometer.

Monoclonal Antibody Titration Binding to KPB1

Binding titration of recombinant antibodies to ABCB1 transfectants was performed by 3-fold serial dilution of antibodies from 666.7 nM. Diluted antibody in flow cytometry buffer was incubated with cells on ice for 30 min. After 2 washes with flow cytometry buffer, bound antibody was detected with PE-labeled F(ab')$_2$ fragment goat anti-human IgG (Jackson ImmunoResearch) diluted 1:200 in flow cytometry buffer and incubated with cells for 20 min on ice. After 2 washes with flow cytometry buffer fluorescence was measured on an Attune NxT flow cytometer. Data were analyzed with GraphPad Prism 8.0 software to determine EC50's.

Cytotoxicity Assays

The effect of antibodies on vincristine cytotoxicity was evaluated on N6/ADR, a doxorubicin-selected, ABCB1-positive variant of the human acute lymphoblastic leukemia (ALL) cell line, NALM6. Cells were plated in 0.05 mL of Assay Media (RPMI-1640+10% FBS) at 5000 cells/well in white flat bottom 96-well tissue culture plates. Vincristine was prepared at 2× final assay concentration by serial dilution from 200 uM in assay media containing test antibodies or control antibodies at 100 ug/mL (2× final concentration), or valspodar, a small molecule KPB1 inhibitor at 7 uM (2× final concentration). An equivalent volume (0.05 mL) of the vincristine/antibody mixture was added to the N6/ADR cells in 96-well plates. The plates were then incubated at 37° C., in 5% C02. After 72 hr plates were equilibrated to room temperature and cell viability assessed using Promega® CellTiter-Glo® Luminescent Cell Viability Assay according to the manufacturer's recommended protocol. Luminescence was measured on a Molecular Devices® FlexStation® 3 Multi-Mode Microplate Reader and data analyzed using GraphPad Prism 8.0 software.

Example 2: In Vivo Efficacy of Anti-ABCB1 Monoclonal Antibodies

Anti-ABCB1 antibodies B1.129, B1.261, B1.223, B1.225, B1.188, B1.28, and B1.226 were tested for effect on growth of tumors in immunodeficient mice. The following cancer cell lines were used for generating tumor models.

MES-SA DX5: The multi drug-resistant cell line MES-SA/Dx5 (Sigma. 95051031) was derived from the human uterine sarcoma cell line MES-SA (Sigma Catalogue number. 95051030) which was originally obtained from a tumour from a 56-year-old Caucasian female at the time of hysterectomy. The Dx5 variant exhibits a 100-fold resistance to doxorubicin and has a reported doubling time of 30 hours. MES-SA/Dx-5 cells exhibit marked cross-resistance to a number of chemotherapeutic agents (including daunorubicin, dactinomycin, vincristine, taxol, colchicine) and moderate cross-resistance to mitomycin C and melphalan. Cross resistance to bleomycin, cisplatin, carmustine, 5-fluorouracil or methotrexate was not observed.

A2780 ADR: The adriamycin-resistant cell line A2780ADR has been developed by exposure of the parent A2780 cell line (Sigma catalogue no. 93112519) to adriamycin. A2780ADR is cross-resistant to melphalan and vinblastine. To retain resistance adriamycin has to be added to the media. The cells grow as a monolayer and in suspension in spinner cultures and are tumorigenic in immune deficient mice. Together with the cisplatin-resistant variant A2780cis these lines only differ in their exposure to a single drug and should facilitate the search for molecular changes responsible for the expression of pleiotropic drug resistance in human ovarian cancer.

MES-SA DX5 and A2780ADR cells express the efflux pump ABCB1 and tumor target CD47. The bispecific antibody comprising 15D3VH:MRK16VL::MRK16VL:5F9VH chains (KB1-1401) shows binding to both MES-SA DX5 and A2780ADR. The KB1-1401 bispecific antibody sensitizes MES-SA DX5 and A2780ADR tumors to paclitaxel in in vivo studies. The KB1-1401 bispecific antibody is also referred to as KNJY Bis P1.1 or KBis1.1.

Ovarian Carcinoma

Figure 5A:
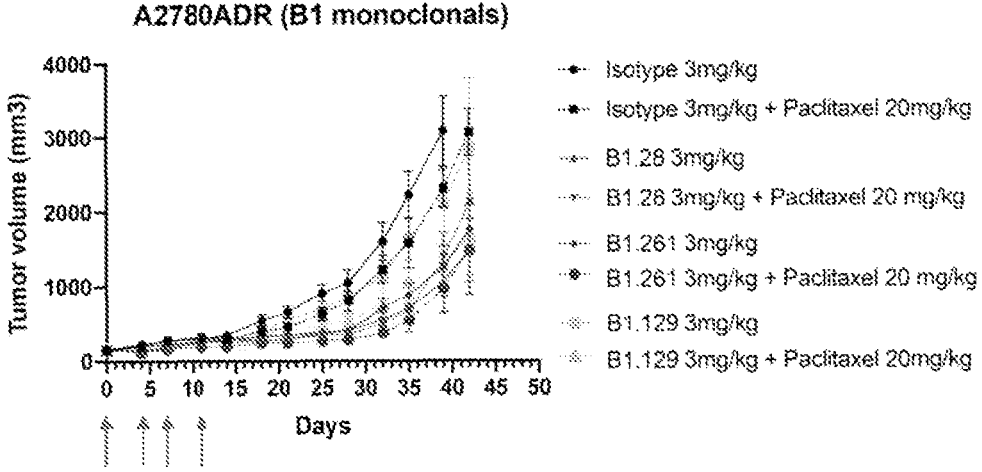
FIGS. 5A-5C show efficacy of the listed anti-MDR1 antibodies against drug-resistant ovarian carcinoma (A2780 ADR) model in nude mice.
Figure 5B:
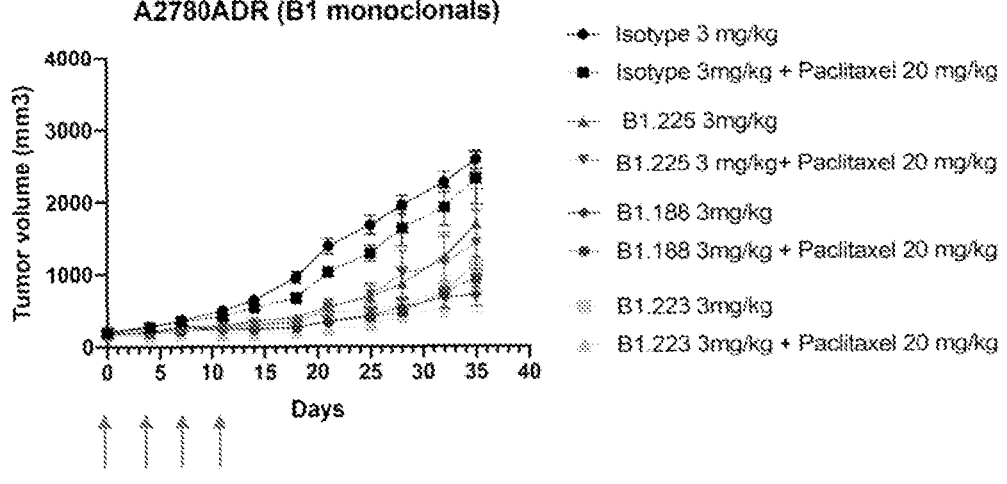

Nude mice were implanted with A2780 ADR cells to model ovarian carcinoma. Anti-B1 monoclonal antibodies are efficacious in A2780 ADR ovarian carcinoma model in nude mice. Anti-ABCB1 antibodies B1.28, B1.261, B1.129, B1.226, B1.223, B1.225, B1.188 decreased tumor volume in mice model of ovarian carcinoma (A2780 ADR) as a single agent and also in combination with paclitaxel. See FIGS. 5A-5C.

Uterine Sarcoma

Figure 6:
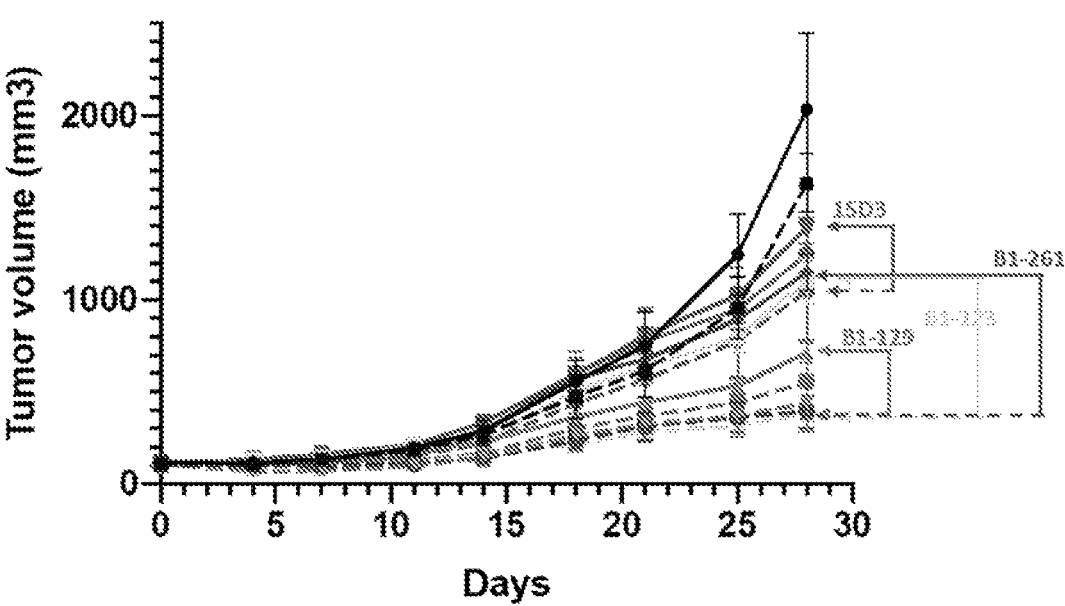
FIG. 6 show efficacy of the listed anti-MDR1 antibodies against drug-resistant MES-SA-DX5 uterine sarcoma model in nude mice.

Nude mice were implanted with MES-SA DX5 cells to model uterine sarcoma. Anti-B1 monoclonal antibodies are efficacious in MES-SA DX5 uterine sarcoma model in nude mice. Anti-ABCB1 antibodies B1.261, B1.129, and B1.223 decreased tumor volume in mice model of uterine sarcoma (MES-SA DX5) as a single agent and also in combination with paclitaxel. See FIG. 6.

Figure 5C:
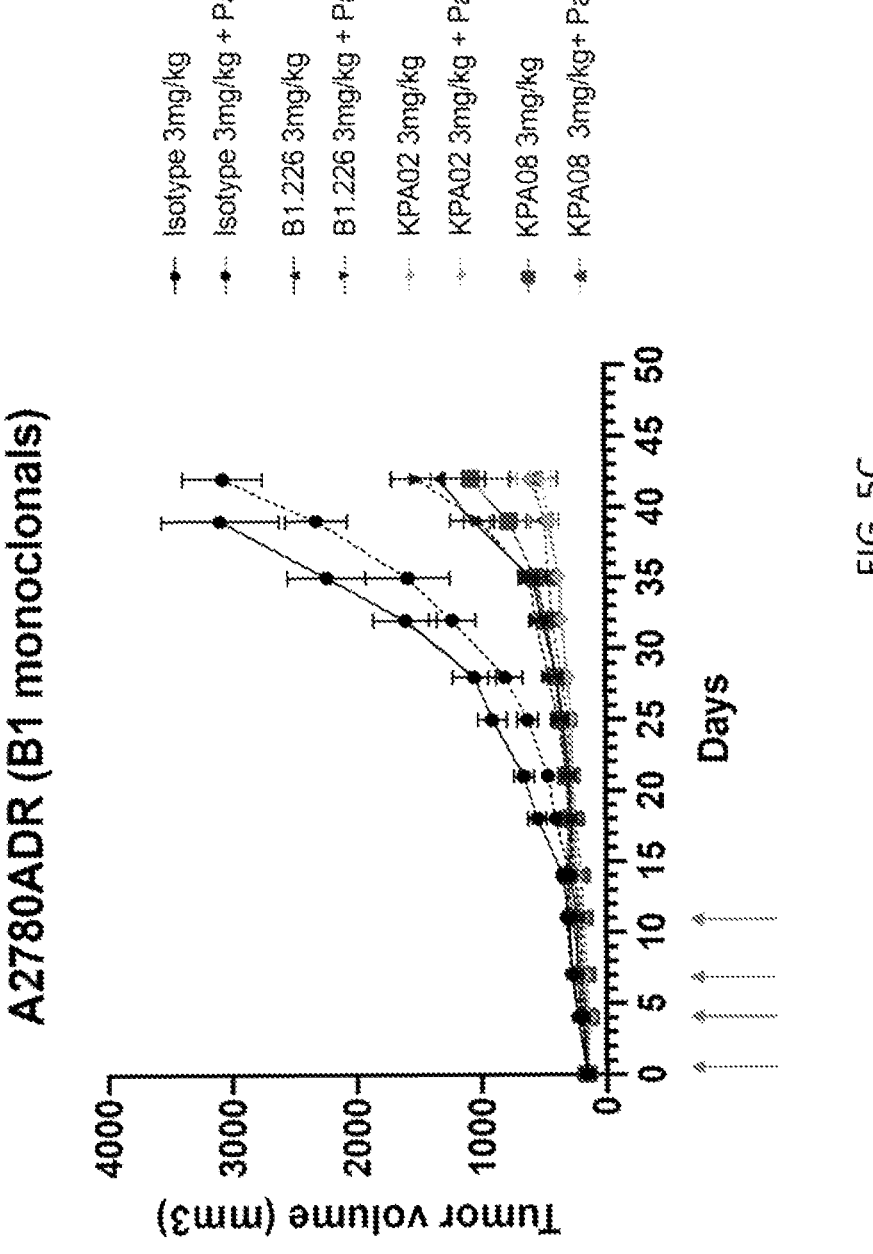

FIG. 5C. KPA02 is an anti-ABCB1 antibody known as MRK16. KPA08 is an anti-ABCB1 antibody generated by combining two anti-ABCB1 antibodies, MRK16 and 15D3. KPA08 antibody includes two heavy chains from 15D3 and two light chains from MRK16. KPA01 is an anti-ABCB1 antibody known as 15D3. KPA06 is the anti-CD47 antibody, 5F9.

15D3 antibody (KPA01) did not sensitize MES-SA DX5 uterine sarcoma to paclitaxel. B1.129 antibody was more effective in inhibiting tumor growth than 15D3 antibody (KPA01) as a single agent and with paclitaxel. B1. 261 and B.223 both sensitized MES-SA DX5 uterine sarcoma to paclitaxel. See FIG. 6.

Figure 7:
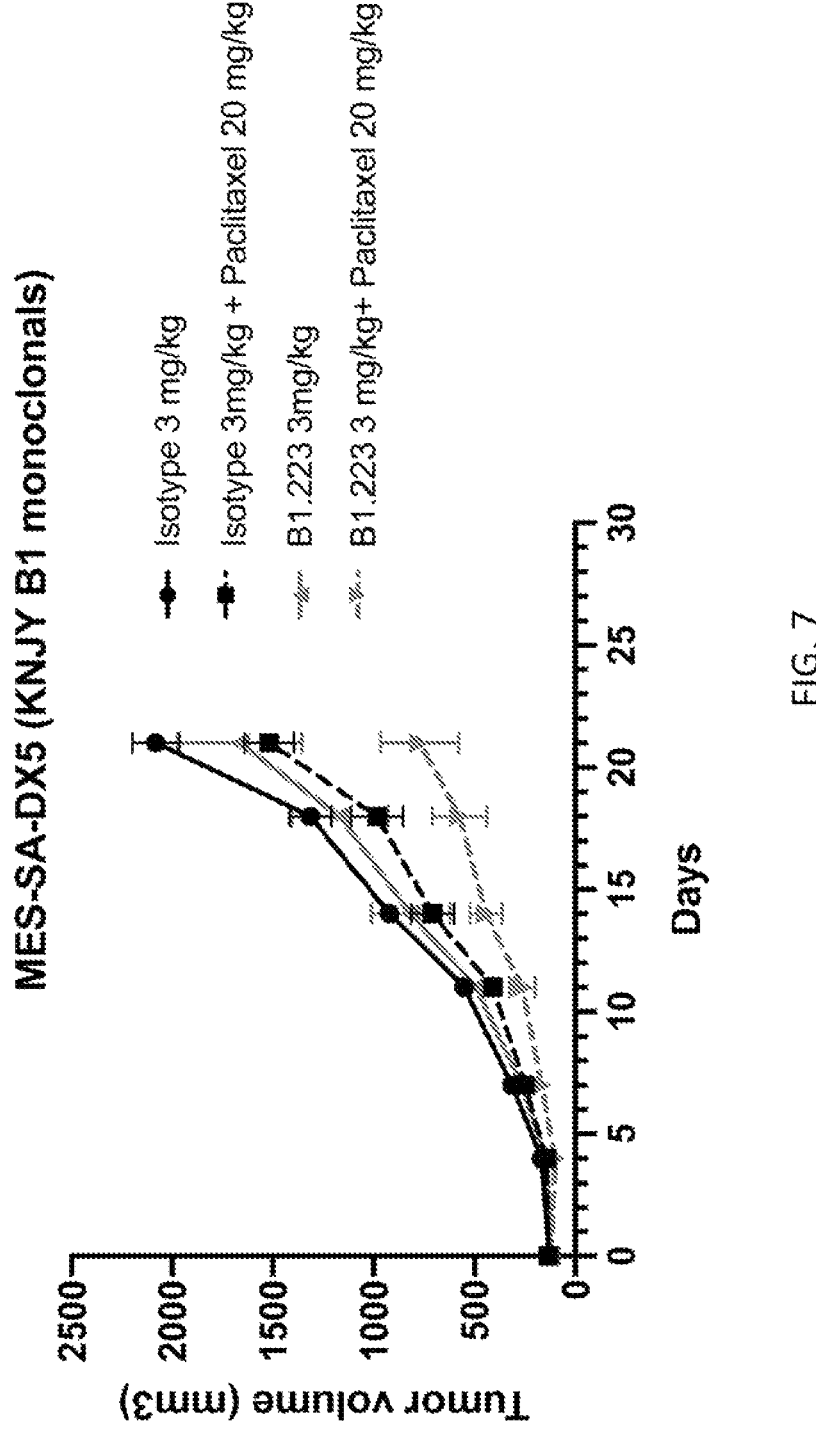
FIG. 7 shows efficacy of the anti-MDR1 antibody B1.223 against drug-resistant MES-SA-DX5 uterine sarcoma model in NSG mice.

NSG mice were implanted with MES-SA DX5 cells to model uterine sarcoma. Anti-B1 monoclonal antibodies are efficacious in MES-SA DX5 uterine sarcoma model in NSG mice. FIG. 7 shows that B1.223 sensitizes MES-SA DX5 uterine sarcoma to paclitaxel.

FIG. 8 shows that ABCB1 expression is required for resistance of MES-SA DX5 uterine sarcoma to paclitaxel. MES-SA DX5 uterine sarcoma formed using MES-SA DX5 cells lacking ABCB1 expression (DX5-B1 KO) is sensitive to paclitaxel.

Example 3: Epitope Mapping of Anti-MDR1 Antibodies

To determine binding of anti-MDR1 mAbs listed in Table 2 to the two major extracellular loops 1 and 4 of MDR1, various mutations were constructed to alter or substitute these two loops. To examine binding to cynomolgus extracellular loops, the extracellular loop 1 and/or loop 4 of cynomolgus MDR1 were grafted (with a C-terminal FLAG tag) to substitute for the human loops in the human MDR1 using standard techniques. To examine binding dependence on the normal human loops, MDR1 variants with deletion 79-102 and deletion 82-99 in loop 1 were also generated. Loop 1 is also referred to as ECD1. Loop 4 is also referred to as ECD4. These mutant MDR1 efflux pump variants were expressed on 293T cells using standard methods to generate cells that could be used to distinguish binding of various anti-MDR1 mAbs. The different cells were incubated with different anti-MDR1 mAbs for about 1 hour at 4° C. The cells were washed twice with FACS buffer (PBS containing 0.5% BSA). Alexa647 labeled goat anti-human antibody was added as a secondary antibody, and the samples were incubated on ice for another 1 hour. Samples were washed again and analyzed by flow cytometry.

FIG. 9 summarizes the findings from preliminary epitope mapping using mutant human MDR1. "+" indicates that the listed ECD was required for antibody binding, based on a significant reduced binding to a mutant ABCB1 lacking the ECD, as compared to a WT human ABCB1. "−" indicates that the listed ECD was not required for antibody binding, based on a lack significant change in binding to a mutant ABCB1 lacking the ECD, as compared to a WT human ABCB1. For example, anti-MDR1 mAb B1.129 requires ECD1 and ECD4 for binding to human MDR1. All of the anti-MDR1 antibodies contact ECD4. KPA01 and KPA08 antibodies do not require ECD1 for binding to ABCB1. This data suggests that many of the anti-B1 antibodies listed in FIG. 9 bind to an epitope that includes sequences present in ECD1 and ECD4, as indicated by "+" for both ECD1 and ECD4 binding. In contrast, KPA01 and KPA08 antibodies bind to an epitope that includes ECD4 sequences but not the ECD1 sequence. ECD1 refers to the first extracellular domain of human ABCB1, ECD4 refers to the fourth extracellular domain of human ABCB1 and "others" refers to the remainder of the extracellular domains 2-3 and 5-6 of human ABCB1. Only binding to ECD1 and ECD4 was tested.

Example 4: Characterization of Anti-MDR1 Antibodies

Anti-MDR1 mAb B1.129 and a humanized version thereof were assessed for binding to 293T cell line overexpressing human MDR1 or to 293T cells transfected with cynomolgus MDR1. FIGS. 10A-10B shows that B1.129 mAb binds to both human (hB1, FIG. 10A) and cynomolgus (cB1, FIG. 10B) MDR1. B1.129.hz1 also binds to both hB1 and cB1 with a lower affinity while B1.129.hz2 did not show significant binding to either hB1 or cB1. B1.129.hz1 and B1.129.hz2 antibodies are the same as the humanized versions B1.129.huH1-huL1(KV3) and B1.129.huH1-huL1 (KV1), respectively, listed in Table 2_FIG. 10C summarizes the binding data for the B1.129 antibody.

Figure 11:
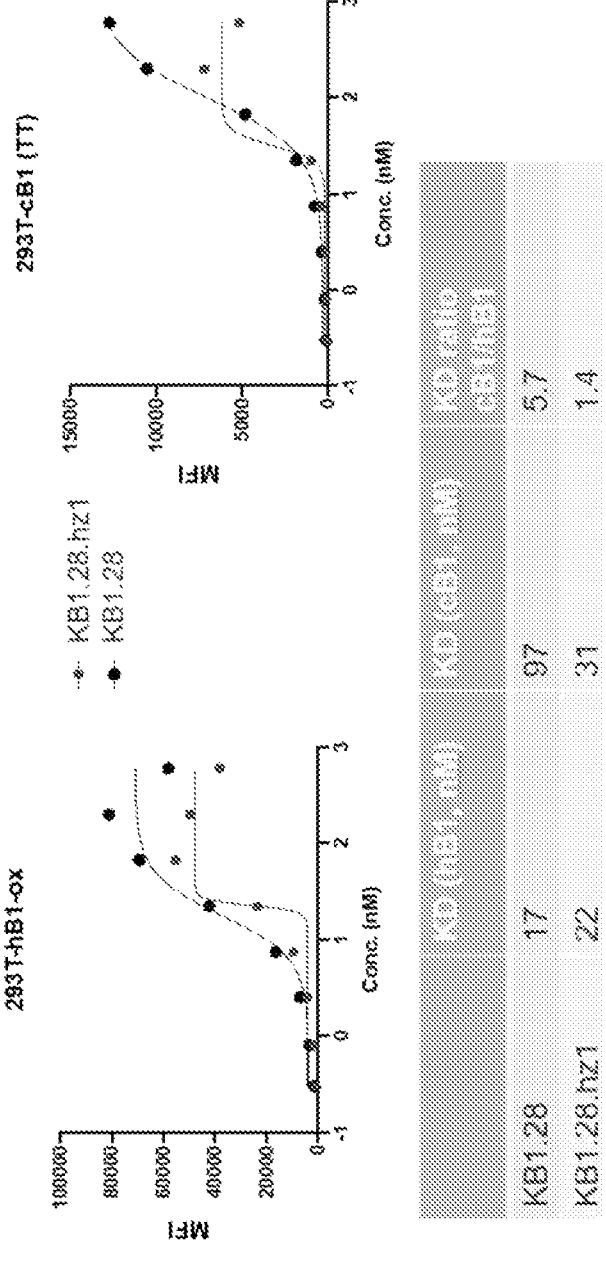
FIG. 11 shows binding of B1.28 antibody and a humanized version thereof to human and cynomolgus MDR1.

Anti-MDR1 mAb B1.28 and a humanized version thereof were assessed for binding to 293T cell line overexpressing human MDR1 or to 293T cells transfected with cynomolgus MDR1. FIG. 11 shows that B1.28 mAb binds to both hB1 and cB1. B1.28.hz1 mAb also binds to both hB1 and cB1 with a lower affinity as compared to the B1.28 mAb. B1.28.hz1 antibody is the same as the humanized version B1.28 human1 listed in Table 2.

Figure 12:
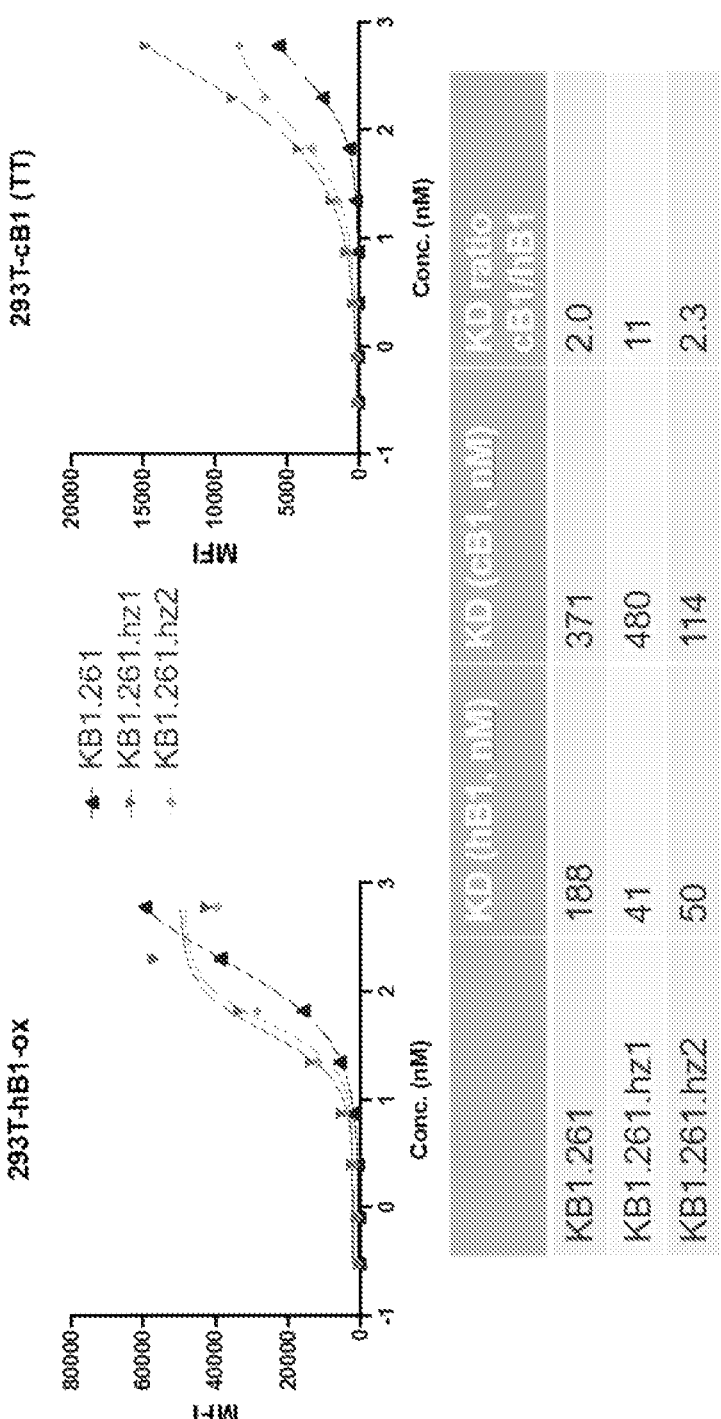
FIG. 12 shows binding of B1.261 antibody and humanized versions thereof to human and cynomolgus MDR1.

FIG. 12 shows binding of anti-MDR1 mAb B1.261 and two humanized versions thereof bind to hB1 and cB1.

Effect of anti-MDR1 antibodies on efflux of MDR1 substrates Calcein, DIOC2, and Rhodamine was assessed as described in efflux blockade experimental procedure. The data is summarized in FIG. 13.

Figure 13:
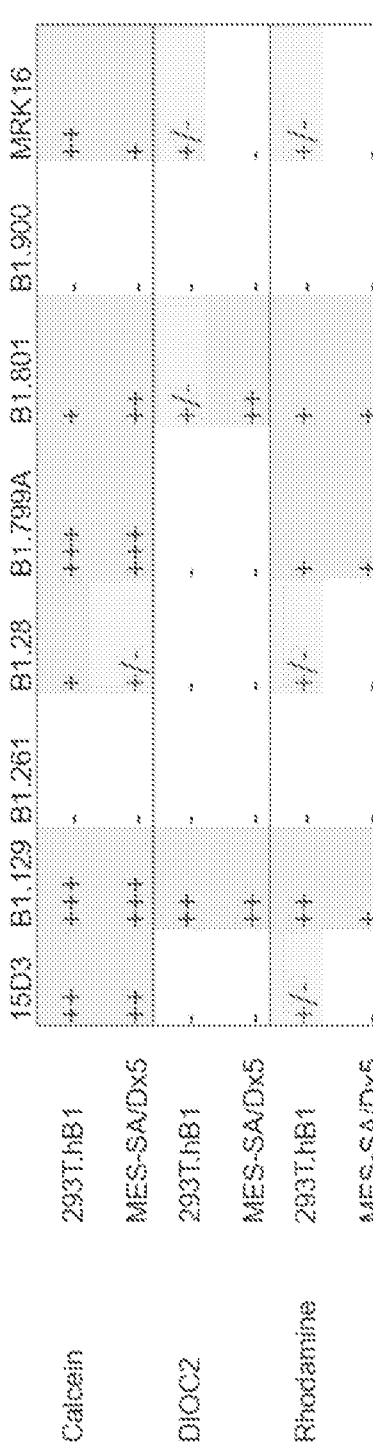
FIG. 13 summarizes effect of the listed antibodies on efflux of MDR1 substrates.

As seen in FIG. 13, B1.129 mAb inhibited efflux of Calcein to a greater extent than the anti-MDR1 antibody 15D3. B1.129 mAb also inhibited efflux of DIOC2 and Rhodamine in two different hB1 expressing cells lines. In contrast, 15D3 has no observable effect on DIOC2 efflux (−) in both cell lines and a low inhibition of rhodamine efflux (+/−) in 293T.hB1 cell line while having no effect on rhodamine efflux in the MES-SA/Dx5 cells.

Example 5: Chemosensitization of Cancer Cells by Anti-MDR1 Antibodies

Anti-MDR1 antibodies listed in Table 2 were tested for effect on chemotoxicity of vincristine on N6ADR cells. See FIGS. 4A-4D. Table 7 shows that a number of the anti-MDR1 mAbs increased the cytotoxicity of vincristine to a level similar to or even higher than achieved using another cytotoxic agent, valspodar. Many of the anti-MDR1 antibodies provided in Table 2 enhanced chemotoxicity of vincristine by a factor of 40 or more. These antibodies are italicized in Table 7.

TABLE 7

| Effect of listed anti-MDR1 antibodies on cytotoxicity to N6/ADR cells by vincristine | |
| --- | --- |
| Treatment | IC50 (pM) |
| Vincristine | 4118 |
| Vin + Valspodar | 128 |
| Vin + hIgG1 | 3989 |
| Vin + KPA08 | 2926 |
| Vin + KB1.27 | 2829 |
| Vin + B1-28 | 3343 |
| Vin + KB1.28 | 2872 |
| Vin + KB1.30 | 52.2 |
| Vin + KB1.39 | 90.9 |
| Vin + KB1.85 | 34.5 |
| Vin + KB1.99 | 61.9 |
| Vin + KB1.112 | 73.6 |
| Vin + KB1.178 | 52.8 |
| Vin + KB1.188 | 92.9 |
| Vin + KB1.197 | 17.6 |
| Vin + KB1.198 | 16.7 |
| Vin + KB1.201 | 21.6 |
| Vin + KB1.207 | 9.5 |
| Vin + KB1.217 | 38.6 |
| Vin + KB1.219 | 10.3 |
| Vin + KB1.223 | 6.8 |
| Vin + KB1.225 | 3.5 |
| Vin + B1-226 | 13.8 |
| Vin + B1-89 | 62.2 |
| Vin + KB1.129 | 13.2 |
| Vin + KB1.116 | 8.7 |
| Vin + KB1.80 | 3.7 |
| Vin + KB1.261 | 3.8 |
| Vin + KB1.263 | 6.2 |
| Vin + KB1.264 | 19.2 |
| Vin + KB1.269A | 32.3 |
| Vin + KB1.271A | 88.4 |
| Vin + KB1.276 | 29 |
| Vin + KB1.278 | 29 |
| Vin + KB1.273A | 29.9 |
| Vin + KB1.275 | 78.1 |

Example 6: Generation of Bispecific Antibodies that Bind MDR1 and CD47

15D3VH:B1-28VL::B1-28VL:5F9VH Bispecific Antibody

A bispecific antibody having a variable heavy chain (VH) of an anti-MDR1 antibody 15D3, a variable heavy chain of anti-CD47 antibody 5F9 and a common variable light chain from the anti-MDR1 antibody "B1-28" (see Table 2) was generated. A humanized version of the VH chain of 15D3 was generated which included framework regions from human IGHV3 group and included N56Q/N56S substitutions in the 15D3 CDR H2. These variable heavy chains (HCs) are referred to herein as 15D3 Hz0 (humanized 15D3 HC); 15D3 Hz1 (humanized 15D3 HC+ N56Q substitution in CDR H2); and 15D3 Hz2 (humanized 15D3 HC+ N56S substitution in CDR H2) and have the following amino acid sequences:

15D3 Hz0:

(SEQ ID NO: 350)
EVOLVESGGVVVQPGGSLRLSCAASGFTFSRYTMSWVRQAPGKGLEWVA

TISSGGGNTYYPDSVKGRFTVSRDNSKNSLYLQMNSLRTEDTALYYCAR

YGAGDAWFAYWGQGTLVTVSS

15D3 Hz1:

(SEQ ID NO: 351)
EVOLVESGGVVVQPGGSLRLSCAASGFTFSRYTMSWVRQAPGKGLEWVA

TISSGGGQTYYPDSVKGRFTVSRDNSKNSLYLQMNSLRTEDTALYYCAR

YGAGDAWFAYWGQGTLVTVSS

15D3 Hz2:

(SEQ ID NO: 352)
EVOLVESGGVVVQPGGSLRLSCAASGFTFSRYTMSWVRQAPGKGLEWVA

TISSGGGSTYYPDSVKGRFTVSRDNSKNSLYLQMNSLRTEDTALYYCAR

YGAGDAWFAYWGQGTLVTVSS

5F9 antibody variable heavy chain sequence is as follows:

(SEQ ID NO: 294)
QVQLVQSGAEVKKPGASVKVSCKASGYTFTNYNMHWVRQAPGQRLEWMG

TIYPGNDDTSYNQKFKDRVTITADTSASTAYMELSSLRSEDTAVYYCAR

GGYRAMDYWGQGTLVTVSS

Sequence of humanized B1-28 VL chain is as follows:

(SEQ ID NO: 20)
DVVLTQSPLSLPVTLGQPASISCRSSQNIVHSTGNTYLDWYQQRPGQSP

RLLIYKVSNRFSGVPDRFSGSGSGTDFTLKISRVEAEDVGVYFCFQGSH

IPRTFGQGTKLEIK

Sequence of humanized B1-28 VH chain is as follows:

(SEQ ID NO: 19)
EVQLVESGGGLVKPGGSLRLSCAASGFTFGLYTMSWVRQAPGKGLEWVA

TISSGGSNTYYPDSVKGRFTISRDNAKNSLYLQMNSLRAEDTAVYYCAR

YYRYDAWFAYWGQGTLVTVSS

The bispecific antibodies included either the 15D3Hz1 or the 15D3Hz2 variable region. 15D3 variable heavy region fused to human IgG1 Fc region with the charged pair substitutions K392D and K409D and 5F9 variable heavy region fused to human IgG1 Fc region with the charged pair substitutions E356K and D399K.

The bispecific antibodies were characterized by binding titration and chemotoxicity assay.

Cell Binding Assays. Antibody binding to cells was evaluated by flow cytometry. 293T cells stably transfected to express human ABCB1 (293T_ABCB1_OX) were washed once in flow cytometry buffer (PBS+2% FBS+0.02% sodium azide), resuspended at $2 \times 10^{\wedge}6$ cells/mL in flow cytometry buffer, and dispensed into 96-well microtiter plates at 0.1 mL/well. Recombinant antibodies were added to cells at 5 ug/mL for initial binding confirmation, or serially diluted from 100 ug/mL in flow cytometry buffer. After incubating cells on ice for 30 min, cells were washed twice with flow cytometry buffer. Bound antibody was detected with PE-labeled F(ab')$_2$ fragment goat anti-human IgG (Jackson ImmunoResearch) and evaluated on an Attune NxT flow cytometer. EC50 is calculated to be the concentration of antibody that gives half maximal response.

Cytotoxicity Assays. The effect of antibodies on vincristine cytotoxicity was evaluated on N6/ADR, a doxorubicin-selected, B1-positive variant of the human acute lymphoblastic leukemia (ALL) cell line, NALM6. Cells were plated in 0.05 mL of Assay Media (RPMI-1640+10% FBS) at 5000 cells/well in white flat bottom 96-well tissue culture plates. Vincristine was prepared at 2× final assay concentration by serial dilution from 200 uM in assay media containing test antibodies or control antibodies at 100 ug/mL (2× final concentration), or valspodar, a small molecule B1 inhibitor at 7 uM (2× final concentration). An equivalent volume (0.05 mL) of the vincristine/antibody mixture was added to the N6/ADR cells in 96-well plates. The plates were then incubated at 37° C., in 5% $CO_2$. After 72 hr plates were equilibrated to room temperature and cell viability assessed using Promega® CellTiter-Glo® Luminescent Cell Viability Assay according to the manufacturer's recommended protocol. Luminescence was measured on a Molecular Devices® FlexStation® 3 Multi-Mode Microplate Reader and data analyzed using GraphPad Prism 8.0 software. Half maximal inhibitory concentration (IC50) is the concentration of drug (vincristine or other chemotherapy cytotoxic agent) where the response (cell growth) is reduced by 50%.

Cell Binding of bispecific antibodies (BisAb-1 and BisAb-2) to 293T_ABCB1_OX cell is summarized in Table 3:

TABLE 3

| EC50 (nM) | Ab | HC1 | HC2 | LC |
|---|---|---|---|---|
| 118.4 | BisAb-1 | 15D3 HC-Hz1 DD hIgG1 | KT14 IgG1 KK | B1-28 VL humaniz |

TABLE 3-continued

| EC50 (nM) | Ab | HC1 | HC2 | LC |
|---|---|---|---|---|
| 75.3 | BisAb-2 | 15D3 HC-Hz2 DD hIgG1 | KT14 IgG1 KK | B1-28 VL humaniz |
| 14.6 | 15D3 | | | |
| 0.3 | KT14 | | | |

KT14 refers to CD47. KT14 antibody (Ab) in Table 3 is the anti-CD47 antibody 5F9 (see Table 5 for amino acid sequence). In both BisAb-1 and BisAb-2, the HC from anti-CD47 antibody 5F9 was used.

The effect of antibodies on vincristine cytotoxicity is summarized in Table 4. While hIgG1, 15D3 and MRK16 antibodies did not potentiate vincristine mediated cytotoxicity, both Bis-Ab-1 and BisAb-2 antibodies increased the cytotoxicity of vincristine.

TABLE 4

| treatment | IC50 (nM) |
|---|---|
| Vin | 0.5429 |
| Vin + hIgG1 | 0.7869 |
| Vin + 15D3 | 0.4663 |
| Vin + MRK16 | 0.7335 |
| Vin + BisAb-1 | 0.0064 |
| Vin + BisAb-2 | 0.1608 |

TABLE 5

Additional bispecific antibodies were generated:

| Antibody (VH/VH/VL) | VH/VL | Sequence | CDR1 | CDR2 | CDR3 |
|---|---|---|---|---|---|
| 15D3DD/ KT14KK/ G2.343 | 15D3DD VH | EVKVVESGGVLVRPGGSLKLSC AASGFTFSRYTMSWVRQTPEK RLEWVATISSGGGNTYYPDSVK GRFTVSRDNAMSSLYLQMSSL RSEDTALYYCARYGAGDAWFA YWGQGTLVTVSS (SEQ ID NO: 287) | GFTFSRY (SEQ ID NO: 343) | SSGGGN (SEQ ID NO: 344) | GAGDA WFAY (SEQ ID NO: 345) |
| | KT14KK VH | QVQLVQSGAEVKKPGASVKVSC KASGYTFTNYNMHWVRQAPG QRLEWMGTIYPGNDDTSYNQK FKDRVTITADTSASTAYMELSSL RSEDTAVYYCARGGYRAMDYW GQGTLVTVSS (SEQ ID NO: 294) | GYTFTNY (SEQ ID NO: 346) | YPGNDD (SEQ ID NO: 347) | GGYRAM DY (SEQ ID NO: 308) |
| | Common LC: G2.343 (anti-ABCG2 antibody LC) | DVVLAQTPPTLSATIGQSVSISCR SSQSLLHSSGNTYLNWLLQRPG QPPQLLIYLVSRLESRVPNRFSGS GSGTDFTLKISGVEAEDLGVYYC VQSTHAPRTFGGGTKLELKRTV (SEQ ID NO: 353) | RSSQSLLHS SGNTYLN (SEQ ID NO: 380) | LVSRLES (SEQ ID NO: 354) | VQSTHA PRT (SEQ ID NO: 355) |
| 15D3DD/ KT14KK/B1.27 | Common LC: B1.27 | DVLLTQTPLSLPVSLGDQASISCR SSQNIVHSTGNTYLDWYLQKPG QSPKLLIYKVSNRFSGVPDRFSG SGSGTDFTLKISRVEAEDLGVYF CFQGSHIPRTFGGGTKLEIK (SEQ ID NO: 18) | RSSQNIVHS TGNTYLD (SEQ ID NO: 11) | KVSNRFS (SEQ ID NO: 12) | FQGSHIP RT (SEQ ID NO: 13) |
| 15D3DD/ KT14KK/225v1 | Common LC: B1.225v1 (anti-MDR1 VL) | DVVMTQTPLSLPVSLGDQASIS CRFSQSIVHSNGNTYLEWYLQK PGQSPKLLIYKVSNRFFGVPDRF SGSGSGTDFTLKISRVEAEDLGV YYCFQASHFPRTFGGGTKLEIK (SEQ ID NO: 356) | RFSQSIVHS NGNTYLE (SEQ ID NO: 110) | KVSNRFF (SEQ ID NO: 78) | FQASHFP RT (SEQ ID NO: 329) |
| 15D3DD/ KT14KK/89v1 | Common LC: B1.89v1 | DVLMTQTPLSLPVSLGDQASISC RSSQTIVHSNGNTYLEWYLQKP GQSPKLLIYKVSKRFSGVPDRFS | RSSQTIVHS NGNTYLE (SEQ ID | KVSKRFS (SEQ ID | FQASHFP RT (SEQ ID |

TABLE 5-continued

Additional bispecific antibodies were generated:

| Antibody (VH/VH/VL) | VH/VL | Sequence | CDR1 | CDR2 | CDR3 |
|---|---|---|---|---|---|
| | (anti-MDR1 VL) | GSGSGTDFTLKISRVEAEDLGVY YCFQASHFPRTFGGGTKLEIK (SEQ ID NO: 313) | NO: 39) | NO: 40) | NO: 329) |
| 15D3DD/ KT14KK/VL6. CDR3mod | Common LC: VL6.CDR3mod (anti-MDR1 VL) | DVLMTQTPLSLPVSLGDQASISC RSSQSLVHSNGNTYLEWYLQKP GQSPKLLIYKVSNRFSGVPDRFS GSGSGTDFTLKISRVEAEDLGVY YCFQGSHFPRTFGGGTKLEIKRT VAAPSVFIF (SEQ ID NO: 357) | RSSQSLVHS NGNTYLE (SEQ ID NO: 290) | KVSNRFS (SEQ ID NO: 12) | FQGSHFP RT (SEQ ID NO: 42) |
| B1.261.huVH4 DD/KT14KK/B1. 261.huL1 | B1.261 VH | EVQLQESGPGLVKPSETLSLTCT VSGFSLTSYGVHWVRQPPGKGL EWLVVIWSDGSTTYNSALKSRL TISKDNSKNQVSLKLSSVTAADT AVYYCARHGRWLLQRGGAMD YWGQGTMVTVSS (SEQ ID NO: 126) | GFSLTSY (SEQ ID NO: 358) | WSDGS (SEQ ID NO: 359) | HGRWLL QRGGA MDY (SEQ ID NO: 121) |
| | Common LC: B1.261.huL1 | DVVMTQAPKFMSTSVGDRVSV TCRASQNVGSYIAWYQQKLGQ SPKALIYSASYRCSGVPDRFTGS GAGTDFTLTIRNVQSEDLAEYFC QQYNSYPLTFGGGTKLEIK (SEQ ID NO: 122) | RASQNVGS YIA (SEQ ID NO: 123) | SASYRCS (SEQ ID NO: 124) | QQYNSY PLT (SEQ ID NO: 125) |
| B1.261.huVH4 DD/KT14KK/M RK16.huLC | Common LC: MRK16.huLC | DIVMTQTPLSSPVTLGQPASISC RSSQSIVHSTGNTYLEWYQQRP GQPPRLLIYKISNRFSGVPDRFS GSGAGTDFTLKISRVEAEDVGVY YCFQASHFPRTFGGGTKLEIK (SEQ ID NO: 360) | RSSQSIVHS TGNTYLE (SEQ ID NO: 25) | KISNRFS (SEQ ID NO: 328) | QASHFPR T (SEQ ID NO: 364) |
| B1.28DD/KT14 KK/B1.28 | B1.28DD VH | DVLLTQTPLSLPVSLGDQASISC RSSQNIVHSTGNTYLDWYLQKP GQSPKLLIYKVSNRFSGVPDRFS GSGSGTDFTLKISRVEAEDLGVY FCFQGSHIPRTFGGGTKLEIK (SEQ ID NO: 18) | RSSQNIVHS TGNTYLD (SEQ ID NO: 11) | KVSNRFS (SEQ ID NO: 12) | FQGSHIP RT (SEQ ID NO: 13) |
| B1.188VH:MR K16VL::MRK16 VL:5F9VH | B1.188 VH | EVMLVESGGALVKPGGSLKLSC AASGFTFSNYAMSWVRQTPEK RLEWVATISSGGSYTYYPDSVKG RFTISRDNARNTLYLQMSSLRSE DTAMYYCARGYGNFAWFAYW GQGTLVTVSA (SEQ ID NO: 66) | NYAMS (SEQ ID NO: 35) | TISSGGSY TYYPDSVK G (SEQ ID NO: 52) | GYGNFA WFAY (SEQ ID NO: 32) |
| | 5F9 VH | QVQLVQSGAEVKKPGASVKVSC KASGYTFTNYNMHWVRQAPG QRLEWMGTIYPGNDDTSYNQK FKDRVTITADTSASTAYMELSSL RSEDTAVYYCARGGYRAMDYW GQGTLVTVSS (SEQ ID NO: 294) | NYNMH (SEQ ID NO: 306) | TIYPGNDD TSYNQKFK D (SEQ ID NO: 307) | GGYRAM DY (SEQ ID NO: 308) |
| | Common LC (MRK16) | DVLMTQTPVSLSVSLGDQASISC RSSQSIVHSTGNTYLEWYLQKP GQSPKLLIYKISNRFSGVPDRFSG SGSGTDFTLKISRVEAEDLGVYY CFQASHFPRTFGGGTKLEIK (SEQ ID NO: 283) | RSSQSIVHS TGNTYLE (SEQ ID NO: 25) | KISNRFS (SEQ ID NO: 328) | FQASHFP RT (SEQ ID NO: 329) |
| B1.225VH:MR K16VL::MRK16 VL:5F9VH | B1.225VH | EVQLVESGGALVKPGGSLKLSCA ASGFTFSNYGMSWVRQTPEKR LEWVATISSGGSYTYYPDTVKGR FTISRDNAKNTLHLQMSSLRSED TALYYCARRGTNDAWFGYWG QGTLVTVSA (SEQ ID NO: 105) | NYGMS (SEQ ID NO: 106) | TISSGGSY TYYPDTVK G (SEQ ID NO: 107) | RGTNDA WFGY (SEQ ID NO: 108) |
| | 5F9VH | QVQLVQSGAEVKKPGASVKVSC KASGYTFTNYNMHWVRQAPG QRLEWMGTIYPGNDDTSYNQK FKDRVTITADTSASTAYMELSSL RSEDTAVYYCARGGYRAMDYW GQGTLVTVSS (SEQ ID NO: 294) | NYNMH (SEQ ID NO: 306) | TIYPGNDD TSYNQKFK D (SEQ ID NO: 307) | GGYRAM DY (SEQ ID NO: 308) |
| | Common LC (MRK16) | DVLMTQTPVSLSVSLGDQASISC RSSQSIVHSTGNTYLEWYLQKP GQSPKLLIYKISNRFSGVPDRFSG | RSSQSIVHS TGNTYLE (SEQ ID | KISNRFS (SEQ ID NO: 328) | FQASHFP RT (SEQ ID |

TABLE 5-continued

| Antibody (VH/VH/VL) | VH/VL | Sequence | CDR1 | CDR2 | CDR3 |
|---|---|---|---|---|---|
| | | SGSGTDFTLKISRVEAEDLGVYY CFQASHFPRTFGGGTKLEIK (SEQ ID NO: 283) | NO: 25) | | NO: 329) |
| B1.28VH:B1.28 VL:: B1.28VL:5F9VH | B1.28VH | EVKLVESGGGLVKPGGSLKLSCA ASGFTFGLYTMSWVRQTPERRL EWVATISSGGSNTYYPDSVKGR FTISRDNAKNNLFLQMNSLRSE DTALYYCARYYRYDAWFAYWG QGTLVTVSS (SEQ ID NO: 14) | LYTMS (SEQ ID NO: 15) | TISSGGSN TYYPDSVK G (SEQ ID NO: 16) | YYRYDA WFAY (SEQ ID NO: 17) |
| | 5F9VH | QVQLVQSGAEVKKPGASVKVSC KASGYTFTNYNMHWVRQAPG QRLEWMGTIYPGNDDTSYNQK FKDRVTITADTSASTAYMELSSL RSEDTAVYYCARGGYRAMDYW GQGTLVTVSS (SEQ ID NO: 294) | NYNMH (SEQ ID NO: 306) | TIYPGNDD TSYNQFK D (SEQ ID NO: 307) | GGYRAM DY (SEQ ID NO: 308) |
| | B1.28LC | DVLLTQTPLSLPVSLGDQASISC RSS (SEQ ID NO: 361) | QNIVHSTG NTY (SEQ ID NO: 362) | LDWYLAK PGQSPKLL IY (SEQ ID NO: 363) | KVS |
| B1.28.huVH1:B 1.28.huVL::B1. 28.huVL: 5F9huVH3 | B1.28.huV H1 | EVQLVESGGGLVKPGGSLRLSC AASGFTFGLYTMSWVRQAPGK GLEWVATISSGGSNTYYPDSVK GRFTISRDNAKNSLYLQMNSLR AEDTAVYYCARYYRYDAWFAY WGQGTLVTVSS (SEQ ID NO: 19) | LYTMS (SEQ ID NO: 15) | TISSGGSN TYYPDSVK G (SEQ ID NO: 16) | YYRYDA WFAY (SEQ ID NO: 17) |
| | 5F9.huVH3 | EVQLVESGGGLVQPGGSLRLSC AASGYTFTNYNMHWVRQAPG KGLEWMGTIYPGNDDTSYNQK FKDRVTISRDNSKNTLYLQMNS LRAEDTAVYYCARGGYRAMDY WGQGTLVTVSS (SEQ ID NO: 365) | NYNMH (SEQ ID NO: 306) | TIYPGNDD TSYNQFK D (SEQ ID NO: 307) | GGYRAM DY (SEQ ID NO: 308) |
| | B1.28.huLC | DVVLTQSPLSLPVTLGQPASISC RSSQNIVHSTGNTYLDWYQQR PGQSPRLLIYKVSNRFSGVPDRF SGSGSGTDFTLKISRVEAEDVGV YFCFQGSHIPRTFGQGTKLEIK (SEQ ID NO: 20) | RSSQNIVHS TGNTYLD (SEQ ID NO: 11) | KVSNRFS (SEQ ID NO: 12) | FQGSHIP RT (SEQ ID NO: 13) |
| B1.28huVH1:B 1.28.huVL:: B1.28.huVL: 5F9huVH7 | B1.28.huV H1 | EVQLVESGGGLVKPGGSLRLSC AASGFTFGLYTMSWVRQAPGK GLEWVATISSGGSNTYYPDSVK GRFTISRDNAKNSLYLQMNSLR AEDTAVYYCARYYRYDAWFAY WGQGTLVTVSS (SEQ ID NO: 19) | LYTMS (SEQ ID NO: 15) | TISSGGSN TYYPDSVK G (SEQ ID NO: 16) | YYRYDA WFAY (SEQ ID NO: 17) |
| | 5F9.huVH7 | QVQLVQSGSELKKPGASVKVSC KASGYTFTNYNMHWVRQAPG QGLEWMGTIYPGNDDTSYNQ KFKDRFVFSLDTSVSTAYLQISSL KAEDTAVYYCARGGYRAMDY WGQGTTVTVSS (SEQ ID NO: 366) | NYNMH (SEQ ID NO: 306) | TIYPGNDD TSYNQFK D (SEQ ID NO: 307) | GGYRAM DY (SEQ ID NO: 308) |
| | B1.28.huLC | DVVLTQSPLSLPVTLGQPASIS CRSSQNIVHSTGNTYLDWYQ QRPGQSPRLLIYKVSNRFSGVP DRFSGSGSGTDFTLKISRVEAE DVGVYFCFQGSHIPRTFGQGT KLEIK (SEQ ID NO: 20) | RSSQNIVHS TGNTYLD (SEQ ID NO: 11) | KVSNRFS (SEQ ID NO: 12) | FQGSHIP RT (SEQ ID NO: 13) |
| B1.28VH:MRK 16VL:: MRK16VL: 5F9VH | B1.28VH | EVKLVESGGGLVKPGGSLKLSC AASGFTFGLYTMSWVRQTPE RRLEWVATISSGGSNTYYPDS VKGRFTISRDNAKNNLFLQMN SLRSEDTALYYCARYYRYDAW FAYWGQGTLVTVSS (SEQ ID NO: 14) | LYTMS (SEQ ID NO: 15) | TISSGGSN TYYPDSVK G (SEQ ID NO: 16) | YYRYDA WFAY (SEQ ID NO: 17) |
| | Common LC (MRK16) | DVLMTQTPVSLSVSLGDQASI SCRSSQSIVHSTGNTYLEWYLQ KPGQSPKLLIYKISNRFSGVPD RFSGSGSGTDFTLKISRVEAED | RSSQSIVHS TGNTYLE (SEQ ID NO: 25) | KISNRFS (SEQ ID NO: 328) | FQASHFP RT (SEQ ID NO: 329) |

TABLE 5-continued

Additional bispecific antibodies were generated:

| Antibody (VH/VH/VL) | VH/VL | Sequence | CDR1 | CDR2 | CDR3 |
|---|---|---|---|---|---|
| | 5F9VH | LGVYYCFQASHFPRTFGGGTK LEIK (SEQ ID NO: 283) QVQLVQSGAEVKKPGASVKV SCKASGYTFTNYNMHWVRQA PGQRLEWMGTIYPGNDDTSY NQKFKDRVTITADTSASTAYM ELSSLRSEDTAVYYCARGGYRA MDYWGQGTLVTVSS (SEQ ID NO: 294) | NYNMH (SEQ ID NO: 306) | TIYPGNDD TSYNQKFK D (SEQ ID NO: 307) | GGYRAM DY (SEQ ID NO: 308) |
| B1.261VH:MR K16VL:: MRK16VL: 5F9VH | B1.261VH | QVQLKESGPGLVAPSQSLSITC TVSGFSLTSYGVHWVRQPPGK GLEWLVVIWSDGSTTYNSALK SRLSISKDNSKSQVFLKMNSLQ IDDTAMYYCARHGRWLLQRG GAMDYWGQGTSVTVSS (SEQ ID NO: 118) | SYGVH (SEQ ID NO: 119) | VIWSDGS TTYNSALK S (SEQ ID NO: 120) | HGRWLL QRGGA MDY (SEQ ID NO: 121) |
| | Common LC (MRK16) | DVLMTQTPVSLSVSLGDQASI SCRSSQSIVHSTGNTYLEWYLQ KPGQSPKLLIYKISNRFSGVPD RFSGSGSGTDFTLKISRVEAED LGVYYCFQASHFPRTFGGGTK LEIK (SEQ ID NO: 283) | RSSQSIVHS TGNTYLE (SEQ ID NO: 25) | KISNRFS (SEQ ID NO: 328) | FQASHFP RT (SEQ ID NO: 329) |
| | 5F9VH | QVQLVQSGAEVKKPGASVKV SCKASGYTFTNYNMHWVRQA PGQRLEWMGTIYPGNDDTSY NQKFKDRVTITADTSASTAYM ELSSLRSEDTAVYYCARGGYRA MDYWGQGTLVTVSS (SEQ ID NO: 294) | NYNMH (SEQ ID NO: 306) | TIYPGNDD TSYNQKFK D (SEQ ID NO: 307) | GGYRAM DY (SEQ ID NO: 308) |

TABLE 6 summarizes the nomenclature used for antibodies used to generate the data in the figures:

| Antibody | Nomenclature |
|---|---|
| KNJY B1-129 | KB1.129 or B1.129 |
| KNJY B1-261 | KB1.261 or B1.261 |
| KNJY B1-223 | KB1.223 or B1.223 |
| KNJY B1-225 | KB1.225 or B1.225 |
| KNJY B1-188 | KB1.188 or B1.188 |
| KNJY B1-28 | KB1.28 or B1.28 |
| KNJY B1-226 | KB1.226 or B1.226 |
| MRK16/MRK16 | KPA02 |
| 15D3/MRK16 | KPA08 |
| 15D3 hybridoma | KPA01 |
| 5F9 | KT14 |
| 15D3VH:MRK16VL::MRK16VL:5F9VH | KPB1-1401 or KNJY Bis P1.1 |

Figure 14:
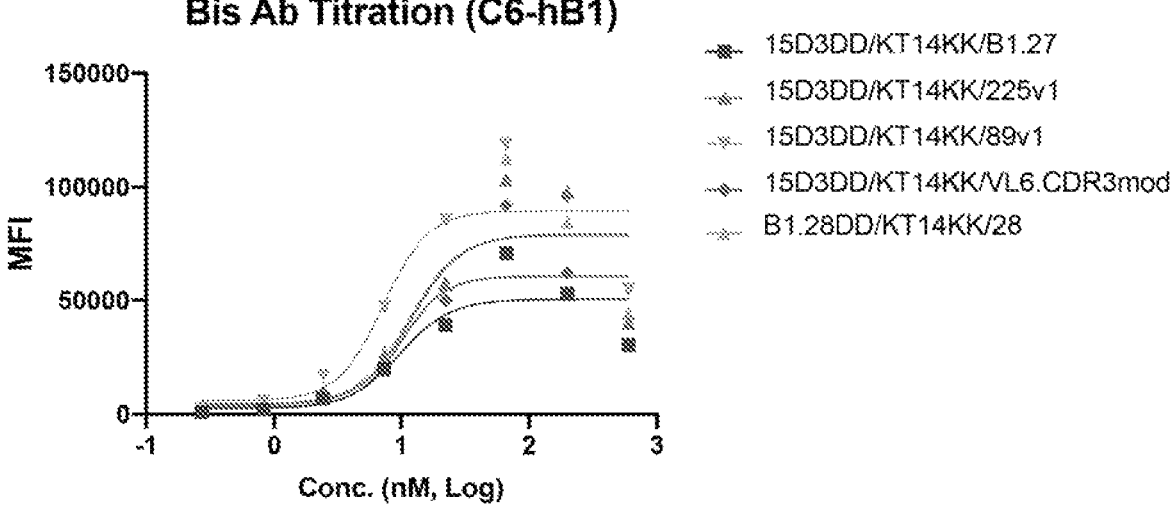
FIG. 14 shows binding of anti-MDR1 and anti-CD47 bispecific antibodies to human MDR1 expressed on the surface of C6 cells.

The heavy chain of anti-MDR1 antibody 15D3 was combined with the heavy chain of anti-CD47 antibody 5F9 and with different light chains from anti-MDR1 antibodies. Data for binding of these bispecific antibodies to C6 cells overexpressing human B1 is shown are FIG. 14.

Cells expressing hABCB1 or hKT14 in stable cell lines were generated by transfecting rat fibroblast C6 cells. Because 5F9 and anti-ABCB1 antibodies have little affinity respectively to murine KT14 or ABCB1, the C6 cell line was used to measure affinity to the human targets expressed in it. KT14/Fc/KT14 Ab refers to single arm format of 5F9, i.e., one heavy chain and one light only.

FIG. 15 shows binding of these bispecific antibodies to C6 cells overexpressing cynomolgus CD47 (cKT14) or human CD47 (hKT14). Binding was evaluated by flow cytometry and recombinant protein by Bio-Layer Interferometry (BLI). Octet KD− was calculated by measuring antibody binding to recombinant human CD47 (rhCD47) by Bio-Layer Interferometry (BLI) using a ForteBio Octet. Sensors were loaded with antibody before associating into 300 nM, 100 nM and 33 nM rhCD47. Binding constants were calculated for association and dissociation of each analyte. 1:1 Curve Fits were applied and global fits were generated. The binding of the BsAb appears to require high amount of B1 while increasing the amount of CD47 does not increase binding affinity. Thus, the BsAb is expected to be specific for cells that overexpress B1. Low affinity for CD47 is advantageous in reducing off-target effects since CD47 is expressed on many normal cells.

Binding selectivity of anti-MDR1 and anti-CD47 bispecific antibodies was assessed using B1+/CD47+ MES-SA-DX5 cells, hereafter referred to as DX5WT cells, B1 gene knockout and CD47 gene knockout cell lines derived from DXWT cells, hereafter referred to as DX5 B1 KO (B1−/CD47+) and DX5 CD47 KO (B1+/CD47−) cells, respectively.

Prior to addition of antibodies DX5WT cells and DX5 CD47 KO cells were stained with CellTrace™ Violet and CellTrace™ Far Red (Life Technologies, NY), respectively, and DX5 B1 KO cells were left unstained. The cells were combined at 1:1:1 ratio in FACS buffer at a final concentration of $6 \times 10^6$ cells/ml ($2 \times 10^6$ cells/ml of each cell population). $3 \times 10^6$ cells/well were then incubated with serial dilutions of antibodies for 1 h at room temperature. Cells were then washed 3 times with FACS buffer and cell-bound antibody was detected with PE-conjugated goat anti-human IgG Fcgamma-specific antibody (Jackson ImmunoResearch).

Flow cytometry was performed on an Attune NXT (Thermo Fisher Scientific) with individual cells populations gated based on tracer dye expression or exclusion and doublets excluded by physical scatter properties. Antibody binding was determined by mean fluorescence intensity (MFI).

Figure 16:
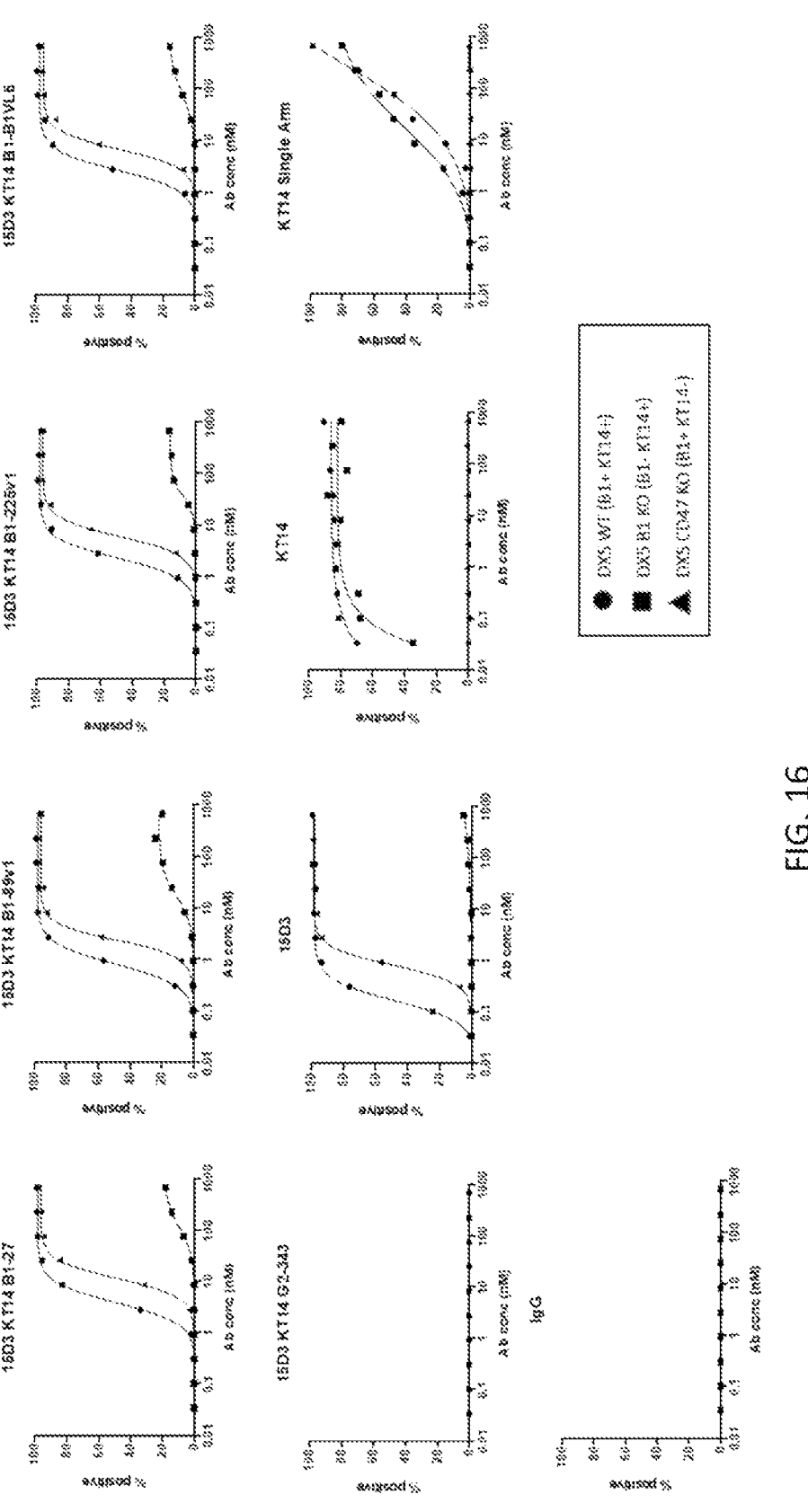
FIG. 16 shows binding selectivity titration of the listed bispecific antibodies on DX5 WT, DX5 B1 KO, DX5 CD47 KO cell lines.

FIG. 16 shows binding selectivity titration of the listed bispecific antibodies on DX5 WT, DX5 B1 KO, DX5 CD47 KO cell lines.

FIGS. 17A and 17B show binding of anti-MDR1 and anti-CD47 bispecific antibodies to human and to cynomolgus MDR1 expressing cells after the HC and LC were humanized. The amino acid sequences of the humanized HC and LC are as follows:

15D3 Hmz DD IgG1 (HC):

(SEQ ID NO: 350)
EVOLVESGGVVVQPGGSLRLSCAASGFTFSRYTMSWVRQAPGKGLEWVA

TISSGGGNTYYPDSVKGRFTVSRDNSKNSLYLQMNSLRTEDTALYYCAR

YGAGDAWFAYWGQGTLVTVSS

B1.28.huL1 (LC):

(SEQ ID NO: 20)
DVVLTQSPLSLPVTLGQPASISCRSSQNIVHSTGNTYLDWYQQRPGQSP

RLLIYKVSNRFSGVPDRFSGSGSGTDFTLKISRVEAEDVGVYFCFQGSH

IPRTFGQGTKLEIK

B1.28.huL2 (LC):

(SEQ ID NO: 21)
DVVLTQSPLSLPVTPGEPASISCRSSQNIVHSTGNTYLDWYLQKPGQSP

QLLIYKVSNRFSGVPDRFSGSGSGTDFTLKISRVEAEDVGVYYCFQGSH

IPRTFGQGTKLEIK

B1.28.huL3 (LC):

(SEQ ID NO: 22)
EVVLTQSPATLSLSPGERATLSCRSSQNIVHSTGNTYLDWYQQKPGQSP

RLLIYKVSNRFSGVPARFSGSGSGTDFTLTISSLEPEDFAVYYCFQGSH

IPRTFGGGTKLEIK

B1V6.CDRv1.hmzLC:

(SEQ ID NO: 367)
DIVMTQTPLSLPVTLGDPASISCRSSQSIVHSNGNTYLEWYLQKPGQSP

KLLIYKVSNRFSGVPDRFSGSGSGTDFTLKISRVEAEDVGVYYCFQGSH

FPRTFGGGTKLEIK

B1V6.CDRv2.hmzLC:

(SEQ ID NO: 311)
DIVMTQSPLSLPVSLGDPASISCRSSQSLVHSNGNTYLEYYLQKPGQSP

KLLIYKVSNRFSGVPDRFSGSGSGTDFTLKISRVEAEDLGVYYCFQGSH

FPRTFGGGTKLEIK

B1V6.CDRv3.hmzLC:

(SEQ ID NO: 368)
DIVLTQTPLSLPVSLGDPASISCRSSQSLVHSSGNTYLEWYLQKPGQSP

-continued

KLLIYKVSNRFSGVPDRFSGSGSGTDFTLKISRVEAEDLGVYYCFQGSH

FPRTFGGGTKLEIK

To find optimal bispecific antibodies, many of the heavy chains of anti-MDR1 antibodies listed in Table 2 were combined with heavy chains of anti-CD47 antibody 5F9 and with different light chains from anti-MDR1 antibodies. Some of the LCs were from anti-MDR1 antibodies listed in Table 2.

Results from assaying for binding of these various bispecific antibodies to CD47 using ELISA or cells expressing CD47 and using cells expressing ABCB1 are shown in FIGS. 18A and 18B.

KPB1 VL/CDR3 LC has been engineered from KJB1-6 light chain antibody introducing mutations in VH CDR3.

KPB1-6 LC Sequence:

KPB1-6 LC sequence:
(SEQ ID NO: 369)
DVLMTQTPLSLPVSLGDQASISCRSSQSLVHSNGNTYLEWYLQKPGQSP

KLLIYKVSNRFSGVPDRFSGSGSGTDFTLKISRVEAEDLGVYYCFQGSH

VPFTFGSGTKLEIK

VL CDR1:
(SEQ ID NO: 290)
RSSQSLVHSNGNTYLE

VL CDR2:
(SEQ ID NO: 12)
KVSNRFS

VL CDR3:
(SEQ ID NO: 370)
QGSHVPFT

KPB1 VL/CDR3 LC sequence:
(SEQ ID NO: 311)
DIVMTQSPLSLPVSLGDPASISCRSSQSLVHSNGNTYLEYYLQKPGQSP

KLLIYKVSNRFSGVPDRFSGSGSGTDFTLKISRVEAEDLGVYYCFQGSH

FPRTFGGGTKLEIK

VL CDR1:
(SEQ ID NO: 290)
RSSQSLVHSNGNTYLE

VL CDR2:
(SEQ ID NO: 12)
KVSNRFS

VL CDR3:
(SEQ ID NO: 348)
QGSHFPRT

Unless specified otherwise, all of the bispecific antibodies disclosed herein include a HC derived from an anti-MDR1 antibody, a HC derived from an anti-tumor associated antigen antibody (e.g., anti-CD47 Ab), and a common light derived from an anti-MDR1 antibody. These antibodies are listed in the format VH/VH/VL or VH:VL::VL:VH.

Example 7: Generation of Bispecific Antibodies Having Non-Traditional Arrangement of HC and LC The monospecific and bispecific antibodies disclosed herein may include the heavy and light chains in a format illustrated in FIG. 19.

Figure 20:
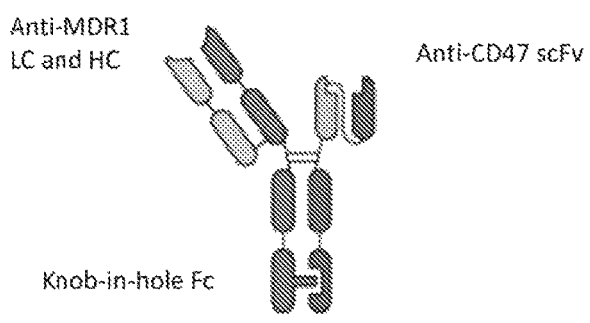
FIG. 20 illustrates an anti-MDR1 and anti-CD47 bispecific antibody having a scFv-Fab-Fc format.

Anti-MDR1 and anti-CD47 bispecific antibodies were generated in a scFv-Fab-Fc format as depicted in FIG. 20.

The Fc region of the anti-CD47 arm of the bispecific antibody is depicted as having a "hole" created by amino acid substitution and the Fc region of the anti-MDR-1 arm includes a "knob" created by amino acid substitution. However, the knob and hole mutations may be reversed such that the anti-CD47 arm contains the knob and the anti-MDR1 arm contains the hole. Four bispecific antibodies were generated:

KT14.5F9hu scFv-B1.28.hu13

KT14.B6H12hu scFv-B1.28.hu13

KT14.5F9hu scFv-B1.261.hu1

KT14.B6H12hu scFv-B1.261.hu1

KT14.5F9hu scFv and KT14.B6H12hu scFv include a human IgG1 Fc region with a "knob" mutation to facilitate pairing the Fc region of anti-MDR1 antibody which included a "hole" mutation.

KT14.5F9hu scFv-hIgG1_knob has the following amino acid sequence:

(SEQ ID NO: 371)
EVQLVESGGGLVQPGGSLRLSCAASGYTFTNYNMHWVRQAPGKGLEWMG

TIYPGNDDTSYNQKFKDRVTISRDNSKNTLYLQMNSLRAEDTAVYYCAR

GGYRAMDYWGQGTLVTVSSGGGGSGGGGSGGGGSDIQMTQSPSSLSASV

GDRVTITCRSSQSIVYSNGNTYLGWYQQKPGKSPKLLIYKVSNRFSGVP

SRFSGSGSGTDFTLTISSLQPEDVATYYCFQGSHVPYTFGQGTKLEIKG

GGGTDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWL

NGKEYKCKVSNKALPAPIEKTISKAKGQPREPQVYTLPPCREEMTKNQV

SLWCLVKGFYPSDIAVEWESNGQPENNYKTTPPVLDSDGSFFLYSKLTV

DKSRWQQGNVFSCSVMHEALHNHYTQKSLSLSPGK

HCDRs1-3 are indicated in bold. LCDRs1-3 are in bold and are underlined.

KT14.B6H12hu scFv-hIgG1_knob has the following amino acid sequence:

(SEQ ID NO: 372)
EVQLVQSGAEVKKPGASVKVSCKASGFTFSGYGMSWVRQAPGQRLEWVA

TITSGGTYTYYPDSVKGRFTITRDNSASTLYMELSSLRSEDTAVYYCAR

SLAGNAMDYWGQGTMVTVSSGGGGSGGGGSGGGGSDIVMTQSPLSLPVT

PGEPASISCRASQTISDYLHWYLQKPGQSPQLLIKFASQSISGIPDRFS

GSGSGSDFTLKISRVEAEDVGVYYCQNGHGFPRTFGGGTKLEIKGGGGT

DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPCREEMTKNQVSLWC

LVKGFYPSDIAVEWESNGQPENNYKTTPPVLDSDGSFFLYSKLTVDKSR

WQQGNVFSCSVMHEALHNHYTQKSLSLSPGK

HCDRs1-3 are indicated in bold. LCDRs1-3 are in bold and are underlined.

B1.28.hu13-hIgG1_hole has the following amino acid sequence:

(SEQ ID NO: 373)
EVQLVESGGGLVKPGGSLRLSCAASGFTFGLYTMSWVRQAPGKGLEWVA

TISSGGSNTYYPDSVKGRFTISRDNAKNSLYLQMNSLRAEDTAVYYCAR

YYRYDAWFAYWGQGTLVTVSSASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKRVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVCTLPPSREEMTKNQVSLSCAVKGFYPSDIAVEWESNGQPENN

YKTTPPVLDSDGSFFLVSKLTVDKSRWQQGNVFSCSVMHEALHNHYTQK

SLSLSPGK

HCDRs1-3 are indicated in bold.

B1.28.LC used has the following amino acid sequence:

(SEQ ID NO: 374)
EVVLTQSPATLSLSPGERATLSCRSSQNIVHSTGNTYLDWYQQKPGQSP

RLLIYKVSNRFSGVPARFSGSGSGTDFTLTISSLEPEDFAVYYCFQGSH

IPRTFGGGTKLEIKRTVAAPSVFIFPPSDEQLKSGTASVVCLLNNFYPR

EAKVQWKVDNALQSGNSQESVTEQDSKDSTYSLSSTLTLSKADYEKHKV

YACEVTHQGLSSPVTKSFNRGEC

LCDRs1-3 are indicated in bold and are underlined.

B1.261.huH1.hIgG1_hole has the following amino acid sequence:

(SEQ ID NO: 375)
EVQLQESGPGLVKPSETLSLTCTVSGFSLTSYGVHWVRQPPGKGLEWLV

VIWSDGSTTYNSALKSRLTISKDNSKNQVSLKLSSVTAADTAVYYCARH

GRWLLQRGGAMDYWGQGTMVTVSSASTKGPSVFPLAPSSKSTSGGTAAL

GCLVKDYFPEPVTVSWNSGALTSGVHTFPAVLQSSGLYSLSSVVTVPSS

SLGTQTYICNVNHKPSNTKVDKRVEPKSCDKTHTCPPCPAPELLGGPSV

FLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISK

AKGQPREPQVCTLPPSREEMTKNQVSLSCAVKGFYPSDIAVEWESNGQP

ENNYKTTPPVLDSDGSFFLVSKLTVDKSRWQQGNVFSCSVMHEALHNHY

TQKSLSLSPGK

HCDRs1-3 are indicated in bold.

B1.261.huL1 has the following amino acid sequence:

(SEQ ID NO: 319)
DVQMTQSPSSLSASVGDRVTITCRASQNVGSYIAWYQQKPGKSPKALIY

SASYRSSGVPSRFSGSGAGTDFTLTISSLQPEDFATYFCQQYNSYPLTF

GGGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

LCDRs1-3 are indicated in bold and are underlined.

Figure 21:
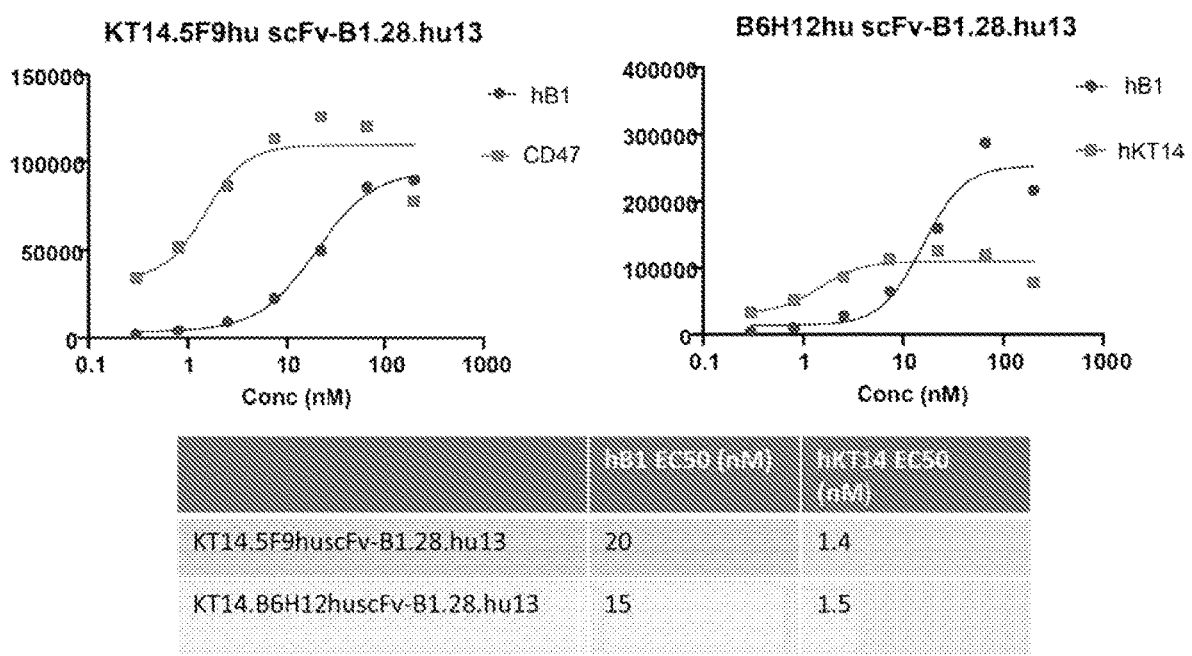
FIG. 21 shows that KT14.5F9hu scFv-B1.28.hu13 and KT14.B6H12hu scFv-B1.28.hu13 antibodies bind to both human CD47 and to human MDR1 expressed on the surface of C6 cells.

FIG. 21 shows that KT14.5F9hu scFv-B1.28.hu13 and KT14.B6H12hu scFv-B1.28.hu13 antibodies bind to both human CD47 and to human MDR1 expressed on the surface of C6 cells.

FIG. 22 shows that KT14.5F9hu scFv-B1.261.hu1 and KT14.B6H12hu scFv-B1.261.hu1 antibodies bind to both human CD47 and to human MDR1 expressed on the surface of C6 cells.

Example 8: In Vivo Efficacy of Anti-MDR1 and Anti-CD47 Antibodies

Figure 23A:
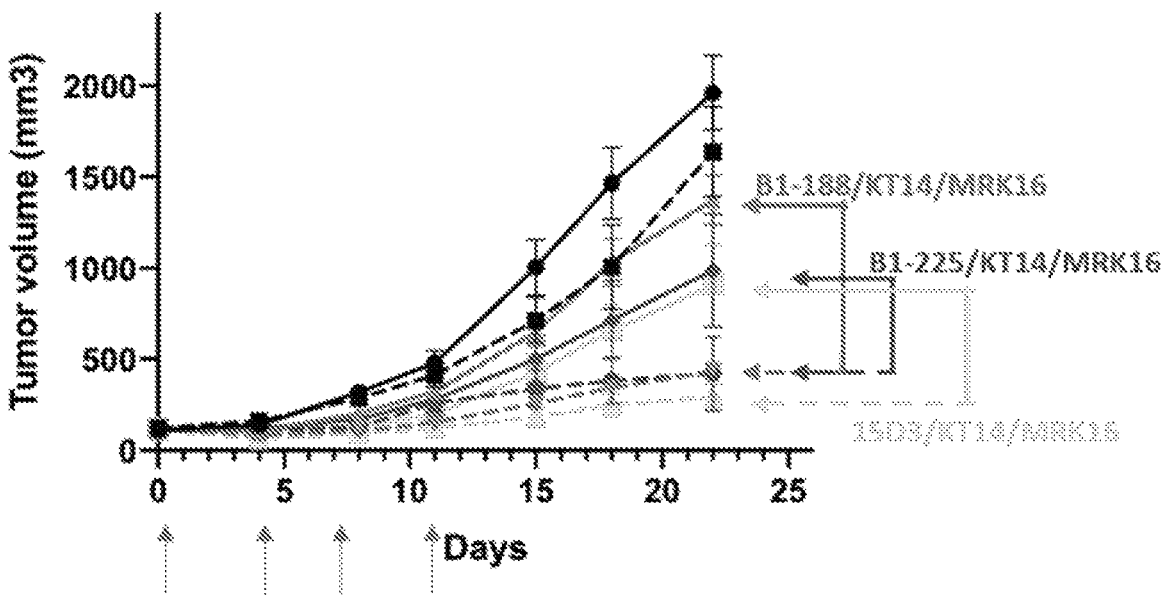

FIGS. 23A-23C show in vivo efficacy of anti-MDR1 and anti-CD47 bispecific antibodies in reducing tumor volume in MES-SA-DX5 models. FIG. 23A shows that B1-188 VH:MRK16LC::MRK16LC:5F9 HC antibody (B1-188/KT14/MRK16) and B1-225 VH:MRK16 LC::MRK16 LC:5F9 HC antibody (B1-225/KT14/MRK16) reduced tumor volume alone and in combination with paclitaxel treatment. B1-225/KT14/MRK16 has an efficacy similar to that of the KBisP1.1 antibody that includes 15D3 VH:MRK16LC::MRK16LC:5F9 HC antibody (15D3/KT14/MRK16).

FIG. 23B shows that each of the bispecific antibodies reduce tumor volume as a single agent and in combination with paclitaxel to a level lower than that observed with paclitaxel and a negative control antibody.

FIG. 23C shows that replacing the MRK16 LC with the LC from the anti-MDR1 antibodies B1.VL6, B1.225v1, or B1.27 enhances the efficacy of the bispecific antibody either as a single agent or in combination with paclitaxel.

Example 9: Generation of Bispecific Antibodies that Bind to MDR-1 and Her2

Heavy chains of anti-MDR1 antibodies listed in Table 2 were combined with heavy chains of anti-Her2 antibodies Trastuzumab or Pertuzumab.
Trastuzumab Light Chain Sequence:

```
                                    (SEQ ID NO: 376)
DIQMTQSPSSLSASVGDRVTITCRASQDVNTAVAWYQQKPGKAPKLLIY
SASFLYSGVPSRFSGSRSGTDFTLTISSLQPEDFATYYCQQHYTTPPTF
GQGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC
```

Trastuzumab Heavy Chain Sequence:

```
                                    (SEQ ID NO: 320)
EVQLVESGGGLVQPGGSLRLSCAASGFNIKDTYIHWVRQAPGKGLEWVA
RIYPTNGYTRYADSVKGRFTISADTSKNTAYLQMNSLRAEDTAVYYCSR
WGGDGFYAMDYWGQGTLVTVSSASTKGPSVFPLAPSSKSTSGGTAALGC
LVKDYFPEPVTVSWNSGALTSGVHTFPAVLQSSGLYSLSSVVTVPSSSL
GTQTYICNVNHKPSNTKVDKKVEPKSCDKTHTCPPCPAPELLGGPSVFL
FPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAK
GQPREPQVYTLPPSREEMTKNQVSLTCLVKGFYPSDIAVEWESNGQPEN
```

```
-continued
NYKTTPPVLDSDGSFFLYSKLTVDKSRWQQGNVFSCSVMHEALHNHYTQ
KSLSLSPGK
```

Pertuzumab Heavy Chain Sequence:

```
                                    (SEQ ID NO: 324)
EVQLVESGGGLVQPGGSLRLSCAASGFTFTDYTMDWVRQAPGKGLEWVA
DVNPNSGGSIYNQRFKGRFTLSVDRSKNTLYLQMNSLRAEDTAVYYCAR
NLGPSFYFDYWGQGTLVTVSSASTKGPSVFPLAPSSKSTSGGTAALGCL
VKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLF
PPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKG
QPREPQVYTLPPSREEMTKNQVSLTCLVKGFYPSDIAVEWESNGQPENN
YKTTPPVLDSDGSFFLYSKLTVDKSRWQQGNVFSCSVMHEALHNHYTQK
SLSLSPG
```

Pertuzumab Light Chain Sequence:

```
                                    (SEQ ID NO: 377)
DIQMTQSPSSLSASVGDRVTITCKASQDVSIGVAWYQQKPGKAPKLLIY
SASYRYTGVPSRFSGSGSGTDFTLTISSLQPEDFATYYCQQYYIYPYTF
GQGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC
```

The notation "KT-1" is used herein to refer to the antibody Trastuzumab. The notation "KT-1-2" is used herein to refer to the antibody Pertuzumab. FIG. 24 lists the various combinations of anti-MDR1 heavy chains, anti-HER2 heavy chains, and anti-MDR1 common light chains tested in a bispecific antibody format to identify a combination that binds to both antigens. Binding to HER2 was determined using the SKBR cell line that expresses HER2.

Example 10: Generation of Bispecific Antibodies that Bind to MDR-1 and PDL1

Heavy chains of anti-MDR1 antibodies listed in Table 2 were combined with heavy chains of anti-PDL1 antibody Atezolizumab.

Atezolizumab Light Chain Sequence:

```
                                    (SEQ ID NO: 378)
DIQMTQSPSSLSASVGDRVTITCRASQDVSTAVAWYQQKPGKAPKLLIY
SASFLYSGVPSRFSGSGSGTDFTLTISSLQPEDFATYYCQQYLYHPATF
GQGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC
```

123

Atezolizumab Heavy Chain Sequence:

(SEQ ID NO: 318)
EVQLVESGGGLVQPGGSLRLSCAASGFTFSDSWIHWVRQAPGKGLEWVA

WISPYGGSTYYADSVKGRFTISADTSKNTAYLQMNSLRAEDTAVYYCAR

RHWPGGFDYWGQGTLVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPRE

EQYASTYRVVSVLTVLHQDWLNGKEYKCKVSNKALPAPIEKTISKAKGQ

PREPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQKS

LSLSPGK

FIG. 25 lists the various combinations of anti-MDR1 heavy chains, anti-PDL1 heavy chains, and anti-MDR1 common light chains tested in a bispecific antibody format to identify a combination that binds to both antigens.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. An anti-multidrug resistance protein 1 (MDR1) antibody, wherein the antibody comprises: a variable heavy chain (VH) region comprising heavy chain complementarity determining region (HCDR) 1 comprising SEQ ID NO: 35; HCDR2 comprising SEQ ID NO: 36; and HCDR3 comprising SEQ ID NO: 37; and a variable light chain (VL) region comprising light chain complementarity determining region (LCDR) 1 comprising SEQ ID NO: 39; LCDR2 comprising SEQ ID NO: 40; and LCDR3 comprising SEQ ID NO: 329 or SEQ ID NO: 42.

2. The anti-MDR1 antibody of claim 1, wherein the VH region comprises SEQ ID NO: 34 and the VL region comprises SEQ ID NO: 313 or SEQ ID NO: 38.

3. The anti-MDR1 antibody of claim 1, wherein the antibody is humanized.

4. The anti-MDR1 antibody of claim 1, wherein the antibody is a bispecific antibody or a single chain Fv antibody.

5. The anti-MDR1 antibody of claim 1, wherein the antibody is conjugated to a toxic moiety.

6. The anti-MDR1 antibody of claim 5, wherein the toxic moiety is a chemotherapeutic agent.

7. A pharmaceutical composition comprising the antibody of claim 1, and a carrier or an excipient.

8. A bispecific antibody that binds to MDR1 and CD47, the antibody comprising:

a common variable light chain (VL) region that binds to MDR1 and CD47 and comprises LCDRs 1-3 comprising SEQ ID NO:39, SEQ ID NO:40, and SEQ ID NO:329 or SEQ ID NO:42, respectively;

a first variable heavy chain (VH) region that binds to MDR1 and comprises HCDRs 1-3 comprising SEQ ID NO: 343; SEQ ID NO: 344; and SEQ ID NO: 345, respectively; and a second VH region that binds to CD47 and comprises HCDRs 1-3 comprising SEQ ID NO: 346; SEQ ID NO: 347; and SEQ ID NO: 308, respectively.

9. A method of treating a subject for a cancer expressing MDR1 and CD47, the method comprising administering to the subject a therapeutically effective amount of the antibody of claim 8.

10. The method of claim 9, wherein the method comprises administering the antibody and at least one additional active agent to the subject, wherein the at least one additional active agent comprises a chemotherapy agent, an inhibitor of a multidrug resistance transporter, an immunotherapy agent, or a combination thereof.

11. The method of claim 10, wherein the at least one additional active agent is a chemotherapy agent.

12. The method of claim 11, wherein the chemotherapy agent is a taxol, a *vinca* alkaloid, or an anthracycline.

13. The method of claim 10, wherein the subject being treated has a cancer that is classified as being resistant to the chemotherapy agent.

14. A method for inhibiting efflux activity of MDR1 expressed by a live cell, the method comprising contacting the cell with the antibody of claim 1.

15. The method of claim 14, wherein the cell is a cancer cell.

16. The method of claim 15, wherein the cancer cell is a multidrug resistant cancer cell.

\* \* \* \* \*